US008367825B2

(12) United States Patent
Guozhang et al.

(10) Patent No.: US 8,367,825 B2
(45) Date of Patent: *Feb. 5, 2013

(54) SUBSTITUTED PYRIMIDINYL OXIME KINASE INHIBITORS

(75) Inventors: Xu Guozhang, Bensalem, PA (US); Lily Lee, Yonkers, NY (US); Terry V. Hughes, Blue Bell, PA (US); Steven K. Wetter, Flemington, NJ (US); Peter J. Connolly, New Providence, NJ (US); Marta C. Abad, Downington, PA (US); Stuart L. Emanuel, Doylestown, PA (US); Prabha S. Kamachi, Hillsborough, NJ (US); Steven A. Middleton, Flemington, NJ (US); Kathleen A. Battista, Williamstown, NJ (US); Gilles C. Bignan, Bridgewater, NJ (US)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/406,822

(22) Filed: Feb. 28, 2012

(65) Prior Publication Data

US 2012/0157412 A1 Jun. 21, 2012

Related U.S. Application Data

(63) Continuation of application No. 11/609,450, filed on Dec. 12, 2006, now Pat. No. 8,153,791.

(60) Provisional application No. 60/752,633, filed on Dec. 21, 2005.

(51) Int. Cl.
| C07D 239/48 | (2006.01) |
| C07D 239/50 | (2006.01) |
| C07D 401/12 | (2006.01) |
| C07D 401/14 | (2006.01) |
| C07D 403/12 | (2006.01) |
| C07D 403/14 | (2006.01) |
| A61K 31/505 | (2006.01) |
| A61K 31/506 | (2006.01) |
| A61P 19/02  | (2006.01) |

(52) U.S. Cl. .......................... 544/326; 544/328; 514/256
(58) Field of Classification Search .................. 544/326, 544/328; 514/256
See application file for complete search history.

(56) References Cited

U.S. PATENT DOCUMENTS

| 6,080,750 A | 6/2000 | Hisaki et al. |
| 6,107,301 A | 8/2000 | Aldrich et al. |
| 6,833,378 B2 | 12/2004 | Chen et al. |
| 7,253,174 B2 | 8/2007 | Ahmed et al. |
| 8,013,153 B2 * | 9/2011 | Butler et al. ................ 544/298 |
| 8,153,791 B2 * | 4/2012 | Xu et al. .................... 544/326 |
| 2003/0060466 A1 | 3/2003 | Binggeli et al. |
| 2003/0139435 A1 | 7/2003 | Ahmed et al. |
| 2005/0256111 A1 | 11/2005 | Kath et al. |
| 2005/0261313 A1 | 11/2005 | Askew et al. |
| 2005/0277652 A1 | 12/2005 | Matsushima et al. |
| 2006/0052604 A1 | 3/2006 | Newton et al. |
| 2008/0249304 A1 | 10/2008 | Chen et al. |

OTHER PUBLICATIONS

Abdel-Razik, H. et al., "Synthesis of Some New 2,6-Diamino-4-(P-Arylazo) Anilinopyrimidine and Some Related 5-Arylazopyrimidine Derivatives for Dyeing Synthetic Fibres," Heterocyclic Communications, 2001; 7(3):263-270.
Banker, G.S. et al., "Modern Pharmaceutice, $3^{rd}$ Edition," Marcel Dekker, Inc., New York, 1996, pp. 451 and 596.
Barillari, C. et al., "Solid Phase Synthesis of Diamino-Substituted Pyrimidines," Eur. J. Org. Chem, 2001; 4737-4741.
Bennett, J.C. and Plum F., "Cecil Textbook of Medicine," $20^{th}$ Edition, vol. 1, 1996, 1004-1010.
Bertino et al., "Horizons in Cancer Therapeutics: From Bench to Bedside," Signal Transduction Inhibitors, Oct. 30, 2001: 2(2):1-39.
Boyden, S., "The Chemotactic Effect of Mixtures of Antibody and Antigen on Polymorphonuclear Leucocytes," Exp. Med, Aug. 21, 1961; 453-466.
Brooks, E. et al., "CVY-313, a Specific and Potent Inhibitor of CDK2 That Prevents Neointima Proliferation", J. Bio Chem., Nov. 14, 1997; 272:46, 29207-29211.
Bundgaard H., "Design of Prodrugs,", 1985, Elsevier, New York, Table of Contents, 3 pgs.
CAS Registry No. 109831-69-8, "5-Pyrimidinecarboxaldehyde, 4,6-diamino-, oxime", 1 pg.
CAS Registry No. 14160-97-5, 4,6-Pyrimidinediamine, N,N'-dimethyl-5-[(methylimino)methyl]-(9CI), 1 pg.
Chapman, N. et al., "Nucleophilic Displacement Reactions in Aromatic Systems," J. Chem. Soc., 1954; 1190-1996.
Cohen et al., "The development and therapeutic potential of protein kinase inhibitors," Current Opinion in Chemical Biology, 1999; 3, 459-465.
Cross, F. et al., "Simple and Complex Cell Cycles,", Annual Rev. Cell Biol., 1989; 5:341-395.

(Continued)

*Primary Examiner* — Venkataraman Balasubramanian
(74) *Attorney, Agent, or Firm* — Woodcock Washburn LLP

(57) ABSTRACT

The present invention is directed to substituted pyrimidine compounds of formula (I):

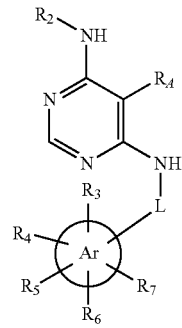

and forms thereof, their synthesis and use for treating, preventing or ameliorating a chronic or acute protein kinase mediated disease, disorder or condition.

13 Claims, No Drawings

OTHER PUBLICATIONS

Davis, S. et al., "Prevention of Chemotherapy-Induced Alopecia in Rats by CDT Inhibitors," Science, Jan. 5, 2001; 291:5501, 134-137.

DelSal, G. et al., "Cell Cycle and Cancer: Critical Events at the G1 Restriction Point," Critical Reviews in Ongogenesis, 1996; 7:1&2, 127-142.

Dermer et al., "Another Anniversary for the War on Cancer," Bio/Technology, 1994; 12:320.

Draetta, G., "Cell cycle control in eukaryotes: molecular mechanisms of cdc2 activation," Trends in Biochem. Science, Oct. 1990; 15:378-382.

Eckstrand A.J. et al., "Amplified and Rearranged Epidermal Growth Factor Receptor Genes in Human Glioblastomas Reveal Deletions of Sequences Encoding Portions of the N-and/or C-Terminal Tails," Proc. Acad. Natl. Sci. USA, 1992; 89:4309-4313.

Edgar, B. et al., "Developmental Control of Cell Cycle Regulators: A Fly's Perspective," Science, Dec. 6, 1996; 274:1646-1652.

Ekstrand, A. et al., "Amplified and rearranged epidermal growth factor receptor genes in humn glioblastomas reveal deletions of sequences encoding portions of the N- and/or C-terminal tails," Proc. Natl. Acad. Sci. USA, May 1992; 89:4309-4313.

Elledge S., "Cell Cycle Checkpoints: Preventing an Identity Crisis," Science, Dec. 6, 1996; 274:1664-1672.

Emanuel, S. et al., "A Vascular Endothelial Growth Factor Receptor-2 Kinase Inhibitor Potentiates the Activity of the Conventional Chemotherapeutic Agents Paclitaxel and Doxorubicin in Tumor Xenograft Models," Molecular Pharmacology, 2004: 66:3, 635-647.

Fabbro et al., "Protein kinases as targets for anticancer agents: from inhibitors to useful drugs," Pharmacology & Therapeutics, 2002; 93, 79-98.

Freshney et al., "Culture of Animal Cells, A Manual of Basic Technique," Alan R. Liss, Inc., 1983, New York, p. 4.

Gerber, H. et al., "Vascular Endothelial Growth Factor Regulations Endothelial Cell Survival through the Phosphatidylinositol 3'-Kinase/Akt Signal Transduction Pathway," J. Bio Chem., Nov. 13, 1998; 273:46, 30336-30343.

Giard, D. et al., "In Vitro Cultivation of Human Tumors: Establishment of Cell Lines Derived From a Series of Solid Tumors," J. Natl. Cancer Inst., 1973; 51:1417-1423.

Golub et al., "Molecular Classification of Cancer: Class Discovery and Class Prediction by Gene Expression Monitoring," Science, 1999; 286, 531-537.

Gomtsyan, A et al., "Design, Synthesis, and Structure-Activity Relationship of 6-Alkynlpyrimidines as Potent Adenosine Kinase Inhibitors," J. Med. Chem., 2002; 45:3639-3648.

Greene, T. et al., "Protective Groups in Organic Synthesis," $3^{rd}$ Edition, Title Page, Table of Contents, John Wiley & Sons, 1999; 3 pgs.

Grossi, P. et al., "Efficacy of Intracerebral microinfusion of Trastuzumab in an Athymic Rat Model of Intracerebral Metastic Breast Cancer," Clin. Can. Res., Nov. 15, 2003; 9:5514-5520.

Hall, M. et al., "Genetic Alterations of Cyclins, Cyclin-Dependent Kinases, and Cdk Inhibitors in Cancer," n. Human Cancer,' Adv. Cancer Res., 1996; 68:67-108.

Harper, J. Wade, "Cyclin Dependent Kinase Inhibitors," Cancer Surveys, 1997; 29:91-107.

Hartung, C. et al., "Efficient Microwave-Assisted Synthesis of Highly Functionalized Pyrimidine Derivatives," Tetrahedron, 2006; 62:10055-10064.

Hetzel, D. et al., "HER-2/neu Expression: A Major Prognostic Factor in Endometrial Cancer," Gynecol. Oncol., 1992; 47:179-185.

Hunt, T., "Maturation promoting factor, cyclin and the control of M-phase," Current Opinion Cell Biol., 1989; 1:268-274.

In the U.S. Patent and Trademark Office U.S. Appl. No. 11/766,257 Final Office Action dated Oct. 14, 2010, 11 pages.

In the U.S. Patent and Trademark Office U.S. Appl. No. 11/766,257 Non-Final Office Action dated Apr. 7, 2010, 9 pages.

International Patent Application No. PCT/US2006/061890: International Search Report dated Oct. 3, 2007, 5 pgs.

Kamb, A. et al., "A Cell Cycle Regulator Potentially Involved in Genesis of Many Tumor Types," Science, 1994; 264:438-440.

Kasprzyk, P.et al., "Therapy of an Animal Model of Human Gastric Cancer Using a Combination of Anti-*erb*B-2 Monoclonal Antibodies," Cancer Res., May 15, 1992; 52:2771-2776.

Kawamoto, T. et al., "Growth stimulationo f A431 cells by epidermal growth factor: Identification of high-affinity receptors for epidermal growth factor by an anti-receptor monoclonal antibody," Proc. Natl. Acad. Sci. USA, Mar. 1983; 80:1337-1341.

Kenyon, B. et al., "A Model of Angiogenesis in the Mouse Cornea," Invest. Opthalmol. Vis. Sci., 1996: 37:1625-1632.

King, R. et al., "How Proteolysis Drives the Cell Cycle," Science, 1996: 274:1652-1659.

Kirsch, D. et al., "Targeting HER2 in Brain Metastases from Breast Cancer," Clin. Can. Res., Nov. 15, 2003; 9:5435-5436.

Kitamura, T. et al., "Combined Effects of Cyclooxygenase-1 and Cyclooxygenase-2 Selective Inhibitors on Intestinal Tumorigenesis in *Adenomatous Polyposis coli* Gene Knockout Mice," Int. J. Cancer, 2004; 109:576-580.

Klign, J.G.M. et al., "The Clinical Significance of Epidermal Growth Factor Receptor (EGF-R) in Human Breast Cancer: A Review on 5232 Patients," Endocr. Rev., 1992; 13:3-17.

Koprivica V. et al., "EGFR Activation Mediates Inhibition of Axon Regeneration by Myelin and Chondroitin Sulfate Proteoglycans," Science, Oct. 7, 2005; 310:106.

LaMontagne K. et al., "Antagonism of Spingosine-1-Phospate Receptors by FTY720 Inhibits Angiogenesis and Tumor Vascularization," Cancer Res., 2006; 66(1):221-231.

Liu B. et al., "Melanoma Cell Lines Express VEGF Receptor KDR and Respond to Exogenously Added VEGF," Biochem Biophys Res Comm., Dec. 26, 1995; 217(3):721-727.

Loda M. et al., "Increased proteasome-dependent degradation of the cyclin-dependent kinase inhibitor p27 in aggressive colorectal carcinomas," Nature Medicine, 1997: 3(2):231-234.

Lukas J. et al., "Cyclin E-induced S phase without activation of the pRb/E2F pathway," Genes & Dev., 1997: 11:1479-1492.

Maggiolo, A. et al., "Synthesis of 2-Methyl-4-Amino-6-Substituted Aminopyrimidines," J. Americ. Chem. Society, 1951; vol. 73, 106-107.

Maggiolo, A. et al., "The Reaction of alkylamines With Chloroheterocyclic Compounds II.$^1$2-Amino-4-Chlor-6-Methylprimdine," J. Am. Chem Soc. P., 1950; 376-382.

Marx J., "Preventing Hair Loss From Chemotherapy," Science, Jan. 5, 2001; 291:25-26.

Mass, R.D., "The HER Receptor Family: A Rich Target for Therapeutic Development," Int. J. Radiation Oncology Bio. Phys., 2004, vol. 58(3):932-940.

McOmie, J.F.W., "Protective Groups in Organic Chemistry," Plenum Press, 1973: Table of Contents, 3 pgs.

Morgan, D.O., "Cyclin-Dependent Kniases: Engines, Clocks, and Microprocessors," Annu. Rev. Cel Dev. Biol., 1997: 13:261-91.

Nasmyth, K., "Viewpoint: Putting the Cell Cycle in Order," Science, 1996; 274:1643-1645.

Noble et al., "Protein Kinase Inhibitors: Insights into Drug Design from Structure," Science, Mar. 19, 2004; 303, 1800-1805.

Nobori T. et al., "Deletions of the cyclin-dependent kinase-4 Inhibitor gene in multiple human cancers," Letters to Nature, 1994; 368:753-756.

Nurse P., "Universal control mechanism regulating onset of M-phase," Nature, 1990; 344:503-508.

O'Brien, D. et al., "Pyrimidines, VII.2-Amino-4-(Substituted Anilino) Pyrimidines," J. of Organic Chemistry, 1962; 27(3), 1104-1107.

Okada F. et al., "Impact of oncogenes in tumor angiogenesis: Mutant K-*ras*up-regulation of vascular endothelial growth factor/vascular permeability factor is necessary, but not sufficient for tumorigenicity of human colorectal carcinoma cells," Proc. Natl. Acad. Sci. USA, Mar. 1998; 95:3609-3614.

Powell et al., "Growth inhibition of psoriatic keratinocytes by quinazoline tyrosine kinase inhibitors," British Journal of Dermatology, 1999; 141:802-810.

Rabindran, S. et al., "Antitumor Activity of HKI-272, an Orally Active, Irreversible Inhibitor of the HER-2 Tyrosine Kinase," Cancer Res., Jun. 1, 2004; 64:3958-3965.

Ross, R., "The pathogenesis of atherosclerosis: a perspective for the 1990s," Nature, 1993; 362:801-809.

Rousseau, S. et al., "Integrating the VEGF Singals Leading to Actin-Based Motility in Vascular Endothelial Cells," Trends Cardiovasc Med, 2000; 10(8):321-327.

Schueneman, A. et al., "SU11248 Maintenance Therapy Prevents Tumor Regrowth After Fractionated Irradiation of Murine Tumor Models," Cancer Research, Jul. 15, 2003; 63:4009-4016.

Sherr, C.J., "Cancer Cell Cycles," Science, 1996; 274:1672-1677.

Sherr, C.J., "Mammalian $G_1$ Cyclins," Cell, Jun. 18, 1993; 73:1059-1065.

Slamon, D. et al., "Human Breast Cancer: Correlation of Relapse and Survival with Amplification of the Her-2/*neu* Oncogene," Science, 1989; 244:707-712.

Slamon, D. et al., "Studies of the Her-2/*neu* Proto-oncogene in Human Breast and Ovarian Cancer," Science, 1989; 244:707-712.

Stillman, B., "Cell Cycle Control of DNA Replication," Science, 1996; 274:1659-1664.

Taylor, E. et al., "A Novel 'Ring-Switching' Amination: Conversion of 4-Amino-5-Cyanopyrimidine to 4,6-Diamono-5-Cyanopyrimidine," Heterocycles, 1987; 25(1):343-345.

Viloria-Petit, A. et al., "Acquired Resistance to the Antitumor Effect of Epidermal Growth Factor Receptor-blocking Antibodies in Vivo: A Role for Altered Tumor Angiogenesis," Cancer Research, Jul. 1, 2001, 61:5090-5101.

Vippagunta et al., "Crystalline Solids," Advanced Drug Delivery Reviews, 2001; 48:3-26.

Wang, X. et al., "Epidermal Growth Factor is a Cellular Receptor for Human Cytomegalovirus," Nature, 2003; 424:456-561.

Wei, G.L. et al., "Temporally and Spatially Coordinated Expression of Cell Cycle Regulatory Factors After Angioplasty," Cir. Res., 1997; 80(3):418-426.

West, Anthony R., "Solid State Chemistry and its Appications,", Wiley, New York, 1998, pp. 358 and 365.

Wikstrand, C. et al., "Monoclonal Antibodies Against EGFRvIII Are Tumor Specific and React with Breast and Lung Carcinomas and Malignant Gliomas," Cancer Res., Jul. 15, 1995; 55:3140-3148.

Wolff, Manfred E., "Burger's Medicinal Chemistry, $5^{th}$ Edition, vol. I: Principles and Practice," John Wiley & Sons, 1995, 975-977.

Yang, K. et al., "A Mouse Model of Human Familial Adenomatous Polyposis," J. Exp. Zool., 1997; 277:245-254.

\* cited by examiner

SUBSTITUTED PYRIMIDINYL OXIME KINASE INHIBITORS

CROSS REFERENCE TO RELATED APPLICATIONS

This application is a continuation of U.S. application Ser. No. 11/609,450, filed Dec. 12, 2006, which claims the benefit of U.S. Provisional Patent Application Ser. No. 60/752,633, filed Dec. 21, 2005, the entireties of which are incorporated herein by reference for all purposes.

FIELD OF THE INVENTION

The present invention is in the area of substituted pyrimidine compounds and forms thereof and methods of preparation and use thereof as kinase inhibitors.

BACKGROUND OF THE INVENTION

In general, protein kinases are the largest set of structurally related phosphoryl transferases, have highly conserved structures and catalytic functions and may be categorized into families by the substrates they phosphorylate (e.g., protein-tyrosine, protein-serine/threonine, histidine and the like) and are responsible for the control of a wide variety of cellular signal transduction processes.

Examples of protein-tyrosine kinases include, but are not limited to, Irk, IGFR-1, Zap-70, Bmx, Btk, CHK (Csk homologous kinase), CSK (C-terminal Src Kinase), Itk-1, Src (c-Src, Lyn, Fyn, Lck, Syk, Hck, Yes, Blk, Fgr and Frk), Tec, Txk/Rlk, Abl, EGFR (EGFR-1/ErbB-1, ErbB-2/NEU/HER-2, ErbB-3 and ErbB-4), FAK, FGF1R (also FGFR1 or FGR-1), FGF2R (also FGR-2), MET (also Met-1 or c-MET), PDGFR (α and β), Tie-1, Tie-2 (also Tek-1 or Tek), VEGFR1 (also FLT-1), VEGFR2 (also KDR), FLT-3, FLT-4, c-KIT, JAK1, JAK2, JAK3, TYK2, LOK, RET, TRKA, PYK2, ALK (Anaplastic Lymphoma Kinase), EPHA (1-8), EPHB (1-6), RON, Fes, Fer or EPHB4 (also EPHB4-1).

Examples of protein-serine/threonine kinases include, but are not limited to, Ark, ATM (1-3), CamK (1-IV), CamKK, Chk1 and 2 (Checkpoint kinases), CK1, CK2, Erk, IKK-I (also IKK-ALPHA or CHUK), IKK-2 (also IKK-BETA), Ilk, Jnk (1-3), LimK (1 and 2), MLK3Raf (A, B, and C), CDK (1-10), PKC (including all PKC subtypes), Plk (1-3), NIK, Pak (1-3), PDK1, PKR, RhoK, RIP, RIP-2, GSK3 (α and β), PKA, P38, Erk (1-3), PKB (including all PKB subtypes) (also AKT-1, AKT-2, AKT-3 or AKT3-1), IRAK1, FRK, SGK, TAK1 or Tp1-2 (also COT).

Protein kinases play very important roles in the normal regulation of cell growth. However, as a result of dysregulation of the tyrosine kinases (receptor or non-receptor) or the ligands of the receptor tyrosine kinases, signaling can become deregulated, resulting in uncontrolled cell proliferation leading to cancer or a related disease, disorder or syndrome.

Protein kinases catalyze and regulate the process of phosphorylation, whereby the kinases covalently attach phosphate groups to proteins or lipid targets in response to a variety of extracellular signals: hormones, neurotransmitters, growth and differentiation factors, cell cycle events, environmental stresses, nutritional stresses and the like.

Phosphorylation modulates or regulates a variety of cellular processes such as proliferation, growth, differentiation, metabolism, apoptosis, motility, transcription, translation and other signaling processes. Defective control of protein phosphorylation due to unregulated cellular mitosis, unregulated cell proliferation and upregulated kinase activity has been implicated in a number of diseases and disease conditions, such as osteoarthritis, rheumatoid arthritis, synovial pannus invasion in arthritis, multiple sclerosis, myasthenia gravis, diabetes mellitus, diabetic angiopathy, diabetic retinopathy, retinal vessel proliferation, inflammatory bowel disease, Crohn's disease, ulcerative colitis, bone diseases, transplant or bone marrow transplant rejection, lupus, chronic pancreatitis, cachexia, septic shock, fibroproliferative and differentiative skin diseases or disorders, central nervous system diseases, neurodegenerative diseases, disorders or conditions related to nerve damage and axon degeneration subsequent to a brain or spinal cord injury, acute or chronic cancer, ocular diseases, viral infections, heart disease, lung or pulmonary diseases or kidney or renal diseases. Therefore, kinase inhibitors have potential use as therapeutic agents.

The term "myasthenia gravis" means a disease having the characteristic feature of easy fatigue of certain voluntary muscle groups on repeated use. Muscles of the face or upper trunk are especially likely to be affected. In most and perhaps all cases, the disease is due to the development of autoantibodies against the acetylcholine receptor in neuromuscular junctions. Immunization of animals with this receptor protein leads to a disease with the features of myasthenia gravis.

In reference to "synovial pannus invasion in arthritis", the term "pannus" means a disease whereby vascularised granulation tissue rich in fibroblasts, lymphocytes and macrophages, derived from synovial tissue, overgrows the bearing surface of the joint in rheumatoid arthritis and is associated with the breakdown of the articular surface.

The tyrosine kinases can further be categorized by whether they are receptor tyrosine kinases or non-receptor tyrosine kinases. The receptor tyrosine kinases span the cell membrane with a ligand interacting domain protruding from the cell, with a hydrophobic trans-membrane domain, and a cytoplasmic domain that contains the catalytic kinase domain and other regulatory sequences. Non-receptor tyrosine kinases are often myristylated or modified by the addition of other hydrophobic moieties that allow them to be anchored to the cell membrane.

The epidermal growth factor receptor (EGFR) tyrosine-kinase family includes the receptors EGFR (also referred to as EGFR-1 or Erb-B1), HER-2 (or neu), EGFR3 and EGFR4. Epidermal Growth Factor (EGF), Transforming Growth Factor-α (TGF-α) and the HER-2 ligand heregulin are three of the ligands that bind to the EGFR receptors.

For example, EGFR overexpression or mutation of one or more EGFR kinase family members has been commonly involved in cancer and other diseases characterized by uncontrolled or abnormal cell growth. Deregulation of EGFR has also been associated with epidermoid tumors, head and neck tumors, breast tumors and tumors involving other major organs, such as the lungs and gastrointestinal tract. The clinically prevalent cancers related to EGFR include lung, gastric and head and neck cancer (Klijn J G, Berns P M, Schmitz P I and Foekens J A; The clinical significance of epidermal growth factor receptor (EGF-R) in human breast cancer: a review on 5232 patients, *Endocr. Rev.*, 1992, 13, 3-17; Salomon D and Gullick W; The erbB family of receptors and their ligands: Multiple targets for therapy, *Signal,* 2001, 2, 4-11).

In treating cancers of the head such as brain cancers and the like, the ability of small molecule EGFR inhibitors to penetrate the blood brain barrier could have therapeutic advantages since EGFR is often overexpressed in primary brain tumors and also in breast and non-small cell lung carcinomas that frequently metastasize to the brain (Eckstrand A J, Sugawa N, James C D and Collins V P; Amplified and rearranged epidermal growth factor receptor genes in human glioblastomas reveal deletions of sequences encoding portions of the N- and/or C-terminal tails, *Proc. Acad. Natl. Sci. USA,* 1992, 89, 4309-4313; and, Wickstrand C J, Hale L P, Batra S K, Hill M L, Humphrey P A, Kurpad S N, McLendon R E, Moscatello D, Pegram C N, Reist C J, Traweek S T, Wong A J, Zalutsky M R and Bigner, D D; Monoclonal antibodies against EGFRvIII are tumor specific and react with breast and lung carcinomas and malignant gliomas, *Cancer Res.,* 1995, 55, 3140-3148).

Diseases associated with increased EGFR expression include proliferative glomerulonephritis, diabetes-induced renal disease and chronic pancreatitis.

EGFR inhibitors tested in neurite outgrowth assays have activity in promoting neurite outgrowth in both cerebellar granule cells and dorsal root ganglion neurons, likely by acting directly on neurons to block neuronal inhibitory responses to myelin inhibitors, and thus an EGFR inhibitor may have potential use for promoting axon regeneration after brain and spinal cord injury (V. Koprivica, et al, EGFR activation mediates inhibition of axon regeneration by myelin and chondroitin sulfate proteoglycans, *Science,* 2005, 310, 106).

HER1 and HER2 overexpression has been implicated in a variety of cancers, such as bladder, breast, colorectal, endometrial, esophageal, gastric (stomach), glioma head and neck, lung (non-small cell lung cancer), ovarian, pancreatic, renal and prostate cancer.

Comparing the overexpression of HER1 and HER2 in tumors, according to order of prevalence, HER1 overexpression is found in breast, renal cell, lung, colorectal, head and neck, ovarian, pancreatic, glioma, bladder, esophageal, gastric, endometrial and cervical cancer tumors; in contrast, HER2 overexpression is found in esophageal, head and neck, lung, gastric, renal cell, breast, bladder, ovarian and colorectal, prostate and endometrial cancer tumors (Horizons in Cancer Therapeutics: From Bench to Bedside, Signal Transduction Inhibitors, 2001, 2(2), ISSN 1532-3048).

While the degree of HER2 overexpression in breast and ovarian cancer is not as great as in some other cancers, HER2 has been found to be responsible for these clinically prevalent cancers (Slamon D J, Clark G M, Wong S G, Levin W J, Ullrich A and McGuire W L; Human breast cancer: Correlation of relapse and survival with amplification of HER-2/neu oncogene, *Science,* 1987, 235, 177-82; Slamon D J, Godolphin W, Jones L A, Holt J A, Wong S G, Keith D E, et al; Studies of the HER-2/neu proto-oncogene in human breast and ovarian cancer, *Science,* 1989, 244, 707-712; Hetzel D J, Wilson T O, Keeney G L, Roche P C, Cha S S and Podrantz K C; HER-2/neu expression: A major prognostic factor in endometrial cancer, *Gynecol. Oncol.,* 1992, 47, 179-85).

Furthermore, patients with HER-2 overexpressing breast cancer frequently experience metastases to the brain (Kirsch D G and Hochberg F H; Targeting HER-2 in brain metastases from breast cancer, *Clin. Can. Res.,* 2003, 9, 5435-5436). These patients have an extremely poor prognosis and intracerebral tumors are often the cause of death. Autopsy revealed that 20-30% of patients who die of breast cancer have brain metastases (Grossi P M, Ochiai H, Archer G E, McLendon R E, Zalutsky M R, Friedman A H, Friedman H S, Bigner D D and Sampson J H; Efficacy of intracerebral microinfusion of trastuzumab in an athymic rat model of intracerebral metastatic breast cancer, *Clin. Can. Res.,* 2003, 9, 5514-5520).

Human cytomegalovirus (CMV) is a widespread opportunistic human herpes virus that causes severe and fatal diseases in those who are immune compromised and in transplant recipients. CMV is also a leading cause of atherosclerosis and virally mediated birth defects. The human CMV uses the EGFR receptor to enter cells during infection, EGFR is autophosphorylated and the downstream signal transduction pathway components are activated; however, the EGFR specific inhibitor tyrphostin AG1478 has been shown to reduce the viral load in cells that were infected in the presence of the tyrphostin (Wang X, et al., Nature, 24 Jul. 2003, Vol. 424, 456-461). Accordingly, potent EGFR selective inhibitors may be useful in anti-CMV therapy.

Certain oxime substituted pyrimidines are registered by the Chemical Abstracts Society (CAS) such as 4,6-diamino-5-pyrimidinecarboxaldehyde oxime (CAS Registry No.: 109831-69-8) and N,N-dimethyl-5-[(methylimino)methyl]-4,6-pyrimidinediamine (CAS Registry No.: 14160-97-5) and described in *Heterocycles,* 1987, 25(1), 343-5. Certain references describe substituted pyrimidine compounds such as United States patents: U.S. Pat. No. 6,080,750, U.S. Pat. No. 6,107,301 and U.S. Pat. No. 6,833,378.

There is a need for potent small-molecule kinase inhibitors of one or more of the EGFR, HER-1, HER-2 kinase proteins and the like possessing anti-tumor cell proliferation activity, and as such are useful for treating or ameliorating a EGFR, HER-1 or HER-2 kinase receptor mediated, angiogenesis-mediated or hyperproliferative disorder.

SUMMARY OF THE INVENTION

The present invention is directed to a compound of formula (I):

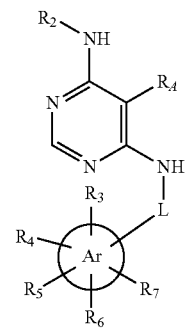

and forms thereof, wherein $R_A$, $R_2$, $R_3$, $R_4$, $R_5$, $R_6$, $R_7$, L and Ar are as defined herein.

An example of the present invention includes a compound of formula (I) and forms thereof as a protein kinase inhibitor.

An example of the present invention includes a prodrug form of a compound of formula (I) and forms thereof as a protein kinase inhibitor.

An example of the present invention includes a metabolite form of a compound of formula (I) and forms thereof as a protein kinase inhibitor.

An example of the present invention includes use of a compound of formula (I) and forms thereof as an inhibitor of a protein kinase such as EGFR, HER-1, HER-2 and the like comprising contacting the protein kinase domain or receptor with the compound.

An example of the present invention includes the use of a compound of formula (I) and forms thereof as a pharmaceutical composition, medicine or medicament for treating, preventing or ameliorating a kinase mediated disease, disorder or condition.

An example of the present invention includes the use of a compound of formula (I) and forms thereof as a medicament.

An example of the present invention includes the use of a prodrug of a compound of formula (I) and forms thereof as a pharmaceutical composition, medicine or medicament for treating, preventing or ameliorating a kinase mediated disease, disorder or condition.

An example of the present invention includes the use of a prodrug of a compound of formula (I) and forms thereof as a medicament.

The present invention is further directed to a method for treating, preventing or ameliorating a chronic or acute protein kinase mediated disease, disorder or condition in a subject in need thereof comprising administering to the subject an effective amount of a compound of formula (I) and forms thereof.

An example of the present invention includes a method for treating, preventing or ameliorating a chronic or acute protein kinase mediated disease, disorder or condition in a subject in need thereof comprising administering to the subject an effective amount of a prodrug of a compound of formula (I) and forms thereof.

These and other aspects and advantages of the invention, which will become apparent in light of the detailed description below, are achieved through use of the compounds of this invention.

DETAILED DESCRIPTION OF THE INVENTION

The present invention is directed to a compound of formula (I):

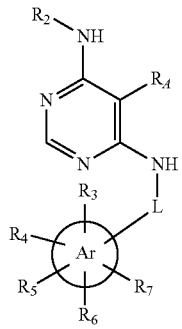

and forms thereof, wherein

L is selected from a bond, $C_{1-6}$alkyl or halo-$C_{1-6}$alkyl;

Ar is selected from aryl, heteroaryl, benzofused-heterocyclyl or benzofused-$C_{3-12}$cycloalkyl;

$R_A$ is selected from C=N—O—$R_1$, cyano or an $R_1$ substituted oxadiazole;

$R_1$ is selected from hydrogen, $C_{1-8}$alkyl, $C_{1-8}$alkenyl, $C_{1-8}$alkoxy, $C_{1-8}$alkoxy-$C_{1-8}$alkyl, hydroxy-$C_{1-8}$alkyl, hydroxy-$C_{1-8}$alkoxy, amino-$C_{1-8}$alkyl, $C_{1-8}$alkyl-amino-$C_{1-8}$alkyl, $C_{1-8}$alkoxy-$C_{1-8}$alkyl-amino-$C_{1-8}$alkyl, $C_{1-8}$alkyl-sulfonyl-$C_{1-8}$alkyl, $C_{1-8}$alkyl-sulfonyloxy-$C_{1-8}$alkyl, aryl, aryl-$C_{1-8}$alkyl, aryloxy-$C_{1-8}$alkyl, heterocyclyl-$C_{1-8}$alkyl, heterocyclyl-carbonyl-$C_{1-8}$alkyl, benzofused-heterocyclyl-$C_{1-8}$alkyl or heteroaryl-$C_{1-8}$alkyl, wherein aryl-$C_{1-8}$alkyl is optionally substituted on aryl with one, two, three, four or five substituents each selected from hydroxy, $C_{1-8}$alkyl, $C_{1-8}$alkoxy, amino, $C_{1-8}$alkyl-amino or $C_{1-8}$alkoxycarbonyl, and wherein heterocyclyl-$C_{1-8}$alkyl is optionally substituted on heterocyclyl with one, two, three or four substituents each selected from hydroxy, $C_{1-8}$alkyl, $C_{1-8}$alkoxy, amino, $C_{1-8}$alkyl-amino or $C_{1-8}$alkoxycarbonyl;

$R_2$ is selected from hydrogen, $C_{1-8}$alkyl or $C_{1-8}$alkoxy; and $R_3$, $R_4$, $R_5$, $R_6$ and $R_7$ is each selected from hydrogen, halogen, hydroxy, $C_{1-8}$alkyl, $C_{1-8}$alkoxy, $C_{1-8}$alkoxy-$C_{1-8}$alkyl, hydroxy-$C_{1-8}$alkyl, halo-$C_{1-8}$alkyl, hydroxy-$C_{1-8}$alkoxy, halo-$C_{1-8}$alkoxy, cyano-$C_{1-8}$alkyl, amino, $C_{1-8}$alkyl-amino, amino-$C_{1-8}$alkyl, $C_{1-8}$alkyl-amino-$C_{1-8}$alkyl, $C_{1-8}$alkyl-amino-$C_{1-8}$alkyl-amino-carbonyl, $C_{1-8}$alkoxy-imino-$C_{1-8}$alkyl, $C_{1-8}$alkoxy-imino-(aryl)$C_{1-8}$alkyl, carboxy, $C_{1-8}$acyl, $C_{1-8}$acyl-amino, $C_{1-8}$alkoxycarbonyl, thio-$C_{1-8}$alkyl, substituted phosphonic acid, $C_{3-12}$cycloalkyl, aryl, aryloxy, aryl-amino, aryl-$C_{1-8}$alkyl, aryl-$C_{1-8}$alkoxy, aryl-carbonyl-$C_{1-8}$alkyl, aryl-amido, heteroaryl, heteroaryloxy, heteroaryl-$C_{1-8}$alkoxy, heteroaryl-amino-sulfonyl, benzofused-heterocyclyl or heterocyclyl, wherein phosphonic acid is substituted on the phosphorous atom with two substituents selected from hydroxy or $C_{1-8}$alkoxy, wherein aryl, aryloxy, aryl-amino, aryl-$C_{1-8}$alkyl and aryl-$C_{1-8}$alkoxy is each optionally substituted on aryl with one, two, three, four or five substituents each selected from cyano, halogen, hydroxy, $C_{1-8}$alkyl, $C_{1-8}$alkoxy, amino, $C_{1-8}$alkyl-amino, amino-$C_{1-8}$alkyl, $C_{1-8}$alkyl-amino-$C_{1-8}$alkyl or $C_{1-8}$alkoxycarbonyl, wherein benzofused-heterocyclyl is optionally substituted on the heterocyclyl portion with one or two oxo substituents, and wherein heteroaryl, heteroaryl-amino-sulfonyl and heteroaryloxy is each optionally substituted on heteroaryl with one, two, three, four or five substituents each selected from $C_{1-8}$alkyl, amino-$C_{1-8}$alkyl, $C_{1-8}$alkyl-amino-$C_{1-8}$alkyl, carboxy, $C_{1-8}$acyl or $C_{1-8}$alkoxycarbonyl.

The present invention is directed to a compound of formula (II):

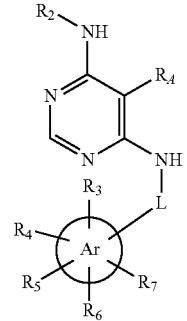

and forms thereof, wherein

L is selected from a bond, $C_{1-6}$alkyl or halo-$C_{1-6}$alkyl;

Ar is selected from aryl, heteroaryl, benzofused-heterocyclyl or benzofused-$C_{3-12}$cycloalkyl, wherein the benzene ring portion of the benzofused ring system is attached to the L variable;

$R_A$ is selected from C=N—O—$R_1$ or cyano;

$R_1$ is selected from hydrogen, $C_{1-8}$alkyl, $C_{1-8}$alkenyl, $C_{1-8}$alkoxy, $C_{1-8}$alkoxy-$C_{1-8}$alkyl, hydroxy-$C_{1-8}$alkyl, hydroxy-$C_{1-8}$alkoxy, amino-$C_{1-8}$alkyl, $C_{1-8}$alkyl-amino-$C_{1-8}$alkyl, $C_{1-8}$alkoxy-$C_{1-8}$alkyl-amino-$C_{1-8}$alkyl, $C_{1-8}$alkyl-sulfonyl-$C_{1-8}$alkyl, $C_{1-8}$alkyl-sulfonyloxy-$C_{1-8}$alkyl, aryl, aryl-$C_{1-8}$alkyl, aryloxy-$C_{1-8}$alkyl, heterocyclyl-$C_{1-8}$alkyl, heterocyclyl-carbonyl-$C_{1-8}$alkyl or heteroaryl-$C_{1-8}$alkyl, wherein aryl-$C_{1-8}$alkyl is optionally substituted on aryl with one, two, three, four or five substituents each selected from hydroxy, $C_{1-8}$alkyl, $C_{1-8}$alkoxy, amino, $C_{1-8}$alkyl-amino or $C_{1-8}$alkoxycarbonyl, and wherein heterocyclyl-$C_{1-8}$alkyl is optionally substituted on heterocyclyl with one, two, three or four substituents each selected from hydroxy, $C_{1-8}$alkyl, $C_{1-8}$alkoxy, amino, $C_{1-8}$alkyl-amino or $C_{1-8}$alkoxycarbonyl;

$R_2$ is selected from hydrogen, $C_{1-8}$alkyl or $C_{1-8}$alkoxy; and $R_3$, $R_4$, $R_5$, $R_6$ and $R_7$ is each selected from hydrogen, halogen, hydroxy, $C_{1-8}$alkyl, $C_{1-8}$alkoxy, $C_{1-8}$alkoxy-$C_{1-8}$alkyl, hydroxy-$C_{1-8}$alkyl, halo-$C_{1-8}$alkyl, hydroxy-$C_{1-8}$alkoxy, halo-$C_{1-8}$alkoxy, amino, $C_{1-8}$alkyl-amino, amino-$C_{1-8}$alkyl, $C_{1-8}$alkyl-amino-$C_{1-8}$alkyl, carboxy, $C_{1-8}$acyl, $C_{1-8}$alkoxycarbonyl, $C_{3-12}$cycloalkyl, aryl, aryloxy, aryl-$C_{1-8}$alkyl, aryl-$C_{1-8}$alkoxy, aryl-amido, heteroaryl, heteroaryloxy, heteroaryl-$C_{1-8}$alkoxy or heterocyclyl, wherein aryl, aryloxy, aryl-$C_{1-8}$alkyl and aryl-$C_{1-8}$alkoxy is each optionally substituted on aryl with one, two, three, four or five substituents each selected from cyano, halogen, hydroxy, $C_{1-8}$alkyl, $C_{1-8}$alkoxy, amino, $C_{1-8}$alkyl-amino, amino-$C_{1-8}$alkyl, $C_{1-8}$alkyl-amino-$C_{1-8}$alkyl or $C_{1-8}$alkoxycarbonyl, and wherein heteroaryl and heteroaryloxy is each optionally substituted on heteroaryl with one, two, three, four or five substituents each selected from $C_{1-8}$alkyl, amino-$C_{1-8}$alkyl, $C_{1-8}$alkyl-amino-$C_{1-8}$alkyl, carboxy, $C_{1-8}$acyl or $C_{1-8}$alkoxycarbonyl.

An example of a compound of formula (I) and forms thereof includes a compound wherein $R_4$ is C=N—O—$R_1$.

An example of a compound of formula (I) and forms thereof includes a compound wherein $R_4$ is cyano.

An example of a compound of formula (I) and forms thereof includes a compound wherein $R_4$ is an $R_1$ substituted oxadiazole.

An example of a compound of formula (I) and forms thereof includes a compound wherein $R_1$ is selected from hydrogen, $C_{1-8}$alkyl, $C_{1-8}$alkenyl, $C_{1-8}$alkoxy, $C_{1-8}$alkoxy-$C_{1-8}$alkyl, hydroxy-$C_{1-8}$alkyl, hydroxy-$C_{1-8}$alkoxy, amino-$C_{1-8}$alkyl, $C_{1-8}$alkyl-amino-$C_{1-8}$alkyl, $C_{1-8}$alkoxy-$C_{1-8}$alkyl-amino-$C_{1-8}$alkyl, $C_{1-8}$alkyl-sulfonyl-$C_{1-8}$alkyl, $C_{1-8}$alkyl-sulfonyloxy-$C_{1-8}$alkyl, aryl, aryl-$C_{1-8}$alkyl, aryloxy-$C_{1-8}$alkyl, heterocyclyl-$C_{1-8}$alkyl, heterocyclyl-carbonyl-$C_{1-8}$alkyl, benzofused-heterocyclyl-$C_{1-8}$alkyl or heteroaryl-$C_{1-8}$alkyl, wherein aryl-$C_{1-8}$alkyl is optionally substituted on aryl with a substituent selected from hydroxy, $C_{1-8}$alkyl, $C_{1-8}$alkoxy, amino, $C_{1-8}$alkyl-amino or $C_{1-8}$alkoxycarbonyl, and wherein heterocyclyl-$C_{1-8}$alkyl is optionally substituted on heterocyclyl with a substituent selected from hydroxy, $C_{1-8}$alkyl, $C_{1-8}$alkoxy, amino, $C_{1-8}$alkyl-amino or $C_{1-8}$alkoxycarbonyl.

An example of a compound of formula (I) and forms thereof includes a compound wherein $R_1$ is selected from hydrogen, $C_{1-8}$alkyl, $C_{1-8}$alkenyl, $C_{1-8}$alkoxy, $C_{1-8}$alkoxy-$C_{1-8}$alkyl, hydroxy-$C_{1-8}$alkyl, hydroxy-$C_{1-8}$alkoxy, amino-$C_{1-8}$alkyl, $C_{1-8}$alkyl-amino-$C_{1-8}$alkyl, $C_{1-8}$alkoxy-$C_{1-8}$alkyl-amino-$C_{1-8}$alkyl, $C_{1-8}$alkyl-sulfonyl-$C_{1-8}$alkyl, $C_{1-8}$alkyl-sulfonyloxy-$C_{1-8}$alkyl, aryl, aryl-$C_{1-8}$alkyl, aryloxy-$C_{1-8}$alkyl, heterocyclyl-$C_{1-8}$alkyl, heterocyclyl-carbonyl-$C_{1-8}$alkyl, benzofused-heterocyclyl-$C_{1-8}$alkyl or heteroaryl-$C_{1-8}$alkyl, wherein aryl-$C_{1-8}$alkyl is optionally substituted on aryl with $C_{1-8}$alkoxy, and wherein heterocyclyl-$C_{1-8}$alkyl is optionally substituted on heterocyclyl with hydroxy or $C_{1-8}$alkoxycarbonyl.

An example of a compound of formula (I) and forms thereof includes a compound wherein $R_1$ is selected from hydrogen, $C_{1-8}$alkyl, $C_{1-8}$alkenyl, $C_{1-8}$alkoxy-$C_{1-8}$alkyl, hydroxy-$C_{1-8}$alkyl, hydroxy-$C_{1-8}$alkoxy, $C_{1-8}$alkyl-amino-$C_{1-8}$alkyl, $C_{1-8}$alkoxy-$C_{1-8}$alkyl-amino-$C_{1-8}$alkyl, $C_{1-8}$alkylsulfonyloxy-$C_{1-8}$alkyl, aryl, aryl-$C_{1-8}$alkyl, aryloxy-$C_{1-8}$alkyl, heterocyclyl-$C_{1-8}$alkyl, heterocyclyl-carbonyl-$C_{1-8}$alkyl, benzofused-heterocyclyl-$C_{1-8}$alkyl or heteroaryl-$C_{1-8}$alkyl, wherein aryl-$C_{1-8}$alkyl is optionally substituted on aryl with $C_{1-8}$alkoxy, and wherein heterocyclyl-$C_{1-8}$alkyl is optionally substituted on heterocyclyl with hydroxy or $C_{1-8}$alkoxycarbonyl.

An example of a compound of formula (I) and forms thereof includes a compound wherein $R_2$ is selected from hydrogen.

An example of a compound of formula (I) and forms thereof includes a compound wherein $R_2$ is selected from $C_{1-8}$alkyl.

An example of a compound of formula (I) and forms thereof includes a compound wherein $R_2$ is selected from $C_{1-8}$alkoxy.

An example of a compound of formula (I) and forms thereof includes a compound wherein $R_3$, $R_4$, $R_5$, $R_6$ and $R_7$ is each selected from hydrogen, halogen, hydroxy, $C_{1-8}$alkyl, $C_{1-8}$alkoxy, $C_{1-8}$alkoxy-$C_{1-8}$alkyl, hydroxy-$C_{1-8}$alkyl, halo-$C_{1-8}$alkyl, hydroxy-$C_{1-8}$alkoxy, halo-$C_{1-8}$alkoxy, cyano-$C_{1-8}$alkyl, amino, $C_{1-8}$alkyl-amino, amino-$C_{1-8}$alkyl, $C_{1-8}$alkyl-amino-$C_{1-8}$alkyl, $C_{1-8}$alkyl-amino-$C_{1-8}$alkyl-amino-carbonyl, $C_{1-8}$alkoxy-imino-$C_{1-8}$alkyl, $C_{1-8}$alkoxy-imino-(aryl)$C_{1-8}$alkyl, carboxy, $C_{1-8}$acyl, $C_{1-8}$acyl-amino, $C_{1-8}$alkoxycarbonyl, thio-$C_{1-8}$alkyl, substituted phosphonic acid, $C_{3-12}$cycloalkyl, aryl, aryloxy, aryl-amino, aryl-$C_{1-8}$alkyl, aryl-$C_{1-8}$alkoxy, aryl-carbonyl-$C_{1-8}$alkyl, aryl-amido, heteroaryl, heteroaryloxy, heteroaryl-$C_{1-8}$alkoxy, heteroaryl-amino-sulfonyl, benzofused-heterocyclyl or heterocyclyl, wherein phosphonic acid is substituted on the phosphorous atom with two $C_{1-8}$alkoxy substituents, wherein aryl, aryl-amino, aryl-$C_{1-8}$alkyl and aryl-$C_{1-8}$alkoxy is each optionally substituted on aryl with one or two substituents each selected from cyano, halogen, hydroxy, $C_{1-8}$alkyl, $C_{1-8}$alkoxy, amino, $C_{1-8}$alkyl-amino, amino-$C_{1-8}$alkyl, $C_{1-8}$alkyl-amino-$C_{1-8}$alkyl or $C_{1-8}$alkoxycarbonyl, wherein benzofused-heterocyclyl is optionally substituted on the heterocyclyl portion with two oxo substituents, and wherein heteroaryl-amino-sulfonyl and heteroaryloxy is each optionally substituted on heteroaryl with one or two substituents each selected from $C_{1-8}$alkyl, amino-$C_{1-8}$alkyl, $C_{1-8}$alkyl-amino-$C_{1-8}$alkyl, carboxy, $C_{1-8}$acyl or $C_{1-8}$alkoxycarbonyl.

An example of a compound of formula (I) and forms thereof includes a compound wherein $R_3$, $R_4$, $R_5$, $R_6$ and $R_7$ is each selected from hydrogen, halogen, hydroxy, $C_{1-8}$alkyl, $C_{1-8}$alkoxy, $C_{1-8}$alkoxy-$C_{1-8}$alkyl, hydroxy-$C_{1-8}$alkyl, halo-$C_{1-8}$alkyl, hydroxy-$C_{1-8}$alkoxy, halo-$C_{1-8}$alkoxy, cyano-$C_{1-8}$alkyl, amino, $C_{1-8}$alkyl-amino, amino-$C_{1-8}$alkyl, $C_{1-8}$alkyl-amino-$C_{1-8}$alkyl, $C_{1-8}$alkyl-amino-$C_{1-8}$alkyl-amino-carbonyl, $C_{1-8}$alkoxy-imino-$C_{1-8}$alkyl, $C_{1-8}$alkoxy-imino-(aryl)$C_{1-8}$alkyl, carboxy, $C_{1-8}$acyl, $C_{1-8}$acyl-amino, $C_{1-8}$alkoxycarbonyl, thio-$C_{1-8}$alkyl, substituted phosphonic acid, $C_{3-12}$cycloalkyl, aryl, aryloxy, aryl-amino, aryl-$C_{1-8}$alkyl, aryl-$C_{1-8}$alkoxy, aryl-carbonyl-$C_{1-8}$alkyl, aryl-amido, heteroaryl, heteroaryloxy, heteroaryl-$C_{1-8}$alkoxy, heteroaryl-amino-sulfonyl, benzofused-heterocyclyl or heterocyclyl, wherein phosphonic acid is substituted on the phosphorous atom with two $C_{1-8}$alkoxy substituents, wherein aryl, aryl-amino, aryl-$C_{1-8}$alkyl and aryl-$C_{1-8}$alkoxy is each optionally substituted on aryl with one or two substituents each selected from cyano, halogen, $C_{1-8}$alkoxy or $C_{1-8}$alkoxycarbonyl, wherein benzofused-heterocyclyl is optionally substituted on the heterocyclyl portion with two oxo substituents, and wherein heteroaryl-amino-sulfonyl and heteroaryloxy is each optionally substituted on heteroaryl with one or two $C_{1-8}$alkyl substituents.

An example of a compound of formula (I) and forms thereof includes a compound wherein $R_3$, $R_4$, $R_5$, $R_6$ and $R_7$ is each selected from hydrogen, halogen, hydroxy, $C_{1-8}$alkyl, $C_{1-8}$alkoxy, halo-$C_{1-8}$alkyl, halo-$C_{1-8}$alkoxy, cyano-$C_{1-8}$alkyl, $C_{1-8}$alkyl-amino, $C_{1-8}$alkyl-amino-$C_{1-8}$alkyl-amino-carbonyl, $C_{1-8}$alkoxy-imino-$C_{1-8}$alkyl, $C_{1-8}$alkoxy-imino-(aryl)$C_{1-8}$alkyl, $C_{1-8}$acyl, $C_{1-8}$acyl-amino, $C_{1-8}$alkoxycarbonyl, thio-$C_{1-8}$alkyl, substituted phosphonic acid, $C_{3-12}$cycloalkyl, aryl, aryloxy, aryl-amino, aryl-$C_{1-8}$alkyl, aryl-$C_{1-8}$alkoxy, aryl-carbonyl-$C_{1-8}$alkyl, aryl-amido, heteroaryloxy, heteroaryl-$C_{1-8}$alkoxy, heteroaryl-amino-sulfonyl, benzofused-heterocyclyl or heterocyclyl, wherein phosphonic acid is substituted on the phosphorous atom with two $C_{1-8}$alkoxy substituents, wherein aryl, aryl-amino, aryl-$C_{1-8}$alkyl and aryl-$C_{1-8}$alkoxy is each optionally substituted on aryl with one or two substituents each selected from cyano, halogen, $C_{1-8}$alkoxy or $C_{1-8}$alkoxycarbonyl, wherein benzofused-heterocyclyl is optionally substituted on the heterocyclyl portion with two oxo substituents, and wherein heteroaryl-amino-sulfonyl and heteroaryloxy is each optionally substituted on heteroaryl with one or two $C_{1-8}$alkyl substituents.

An example of a compound of formula (I) and forms thereof includes a compound wherein L is selected from a bond, $C_{1-6}$alkyl or halo-$C_{1-6}$alkyl;

Ar is selected from aryl, heteroaryl, benzofused-heterocyclyl or benzofused-$C_{3-12}$cycloalkyl;

$R_A$ is selected from C=N—O—$R_1$, cyano or an $R_1$ substituted oxadiazole;

$R_1$ is selected from hydrogen, $C_{1-8}$alkyl, $C_{1-8}$alkenyl, $C_{1-8}$alkoxy-$C_{1-8}$alkyl, hydroxy-$C_{1-8}$alkyl, hydroxy-$C_{1-8}$alkoxy, $C_{1-8}$alkyl-amino-$C_{1-8}$alkyl, $C_{1-8}$alkoxy-$C_{1-8}$ alkyl-amino-$C_{1-8}$alkyl, $C_{1-8}$alkyl-sulfonyloxy-$C_{1-8}$alkyl, aryl, aryl-$C_{1-8}$alkyl, aryloxy-$C_{1-8}$alkyl, heterocyclyl-$C_{1-8}$ alkyl, heterocyclyl-carbonyl-$C_{1-8}$alkyl, benzofused-heterocyclyl-$C_{1-8}$alkyl or heteroaryl-$C_{1-8}$alkyl, wherein aryl-$C_{1-8}$alkyl is optionally substituted on aryl with $C_{1-8}$alkoxy, and wherein heterocyclyl-$C_{1-8}$alkyl is optionally substituted on heterocyclyl with hydroxy or $C_{1-8}$alkoxycarbonyl;

$R_2$ is selected from hydrogen, $C_{1-8}$alkyl or $C_{1-8}$alkoxy; and $R_3$, $R_4$, $R_5$, $R_6$ and $R_7$ is each selected from hydrogen, halogen, hydroxy, $C_{1-8}$alkyl, $C_{1-8}$alkoxy, halo-$C_{1-8}$alkyl, halo-$C_{1-8}$alkoxy, cyano-$C_{1-8}$alkyl, $C_{1-8}$alkyl-amino, $C_{1-8}$alkyl-amino-$C_{1-8}$alkyl-amino-carbonyl, $C_{1-8}$alkoxy-imino-$C_{1-8}$ alkyl, $C_{1-8}$alkoxy-imino-(aryl)$C_{1-8}$alkyl, $C_{1-8}$acyl, $C_{1-8}$acyl-amino, $C_{1-8}$alkoxycarbonyl, thio-$C_{1-8}$alkyl, substituted phosphonic acid, $C_{3-12}$cycloalkyl, aryl, aryloxy, aryl-amino, aryl-$C_{1-8}$alkyl, aryl-$C_{1-8}$alkoxy, aryl-carbonyl-$C_{1-8}$alkyl, aryl-amido, heteroaryloxy, heteroaryl-$C_{1-8}$ alkoxy, heteroaryl-amino-sulfonyl, benzofused-heterocyclyl or heterocyclyl, wherein phosphonic acid is substituted on the phosphorous atom with two $C_{1-8}$alkoxy substituents, wherein aryl, aryl-amino, aryl-$C_{1-8}$alkyl and aryl-$C_{1-8}$alkoxy is each optionally substituted on aryl with one or two substituents each selected from cyano, halogen, $C_{1-8}$alkoxy or $C_{1-8}$alkoxycarbonyl, wherein benzofused-heterocyclyl is optionally substituted on the heterocyclyl portion with two oxo substituents, and wherein heteroaryl-amino-sulfonyl and heteroaryloxy is each optionally substituted on heteroaryl with one or two $C_{1-8}$alkyl substituents.

An example of a compound of formula (I) and forms thereof includes a compound wherein L is selected from a bond, $C_{1-6}$alkyl or halo-$C_{1-6}$alkyl;

Ar is selected from phenyl, naphthalenyl, 1,2,3,4-tetrahydro-naphthalenyl, 5,6,7,8-tetrahydro-naphthalenyl, pyridinyl, pyridiminyl, indazolyl, indolyl, benzofuranyl, benzoimidazolyl, benzothiazolyl, benzo[1,3]dioxolyl, 2,3-dihydro-indolyl, 1,2,3,4-tetrahydro-phthalazinyl or indanyl;

$R_A$ is selected from C=N—O—$R_1$, cyano or an $R_1$ substituted oxadiazole;

$R_1$ is selected from hydrogen, $C_{1-8}$alkyl, $C_{1-8}$alkenyl, $C_{1-8}$alkoxy-$C_{1-8}$alkyl, hydroxy-$C_{1-8}$alkyl, hydroxy-$C_{1-8}$ alkoxy, $C_{1-8}$alkyl-amino-$C_{1-8}$alkyl, $C_{1-8}$alkoxy-$C_{1-8}$ alkyl-amino-$C_{1-8}$alkyl, $C_{1-8}$alkyl-sulfonyloxy-$C_{1-8}$alkyl, aryl, phenyl-$C_{1-8}$alkyl, phenoxy-$C_{1-8}$alkyl, morpholin-4-yl-$C_{1-8}$ alkyl, piperidinyl-$C_{1-8}$alkyl, morpholin-4-yl-carbonyl-$C_{1-8}$alkyl, benzofused-heterocyclyl-$C_{1-8}$alkyl or pyridinyl-$C_{1-8}$alkyl, wherein phenyl-$C_{1-8}$alkyl is optionally substituted on phenyl with $C_{1-8}$alkoxy, and wherein piperidinyl-$C_{1-8}$alkyl is optionally substituted on piperidinyl with hydroxy or $C_{1-8}$alkoxycarbonyl;

$R_2$ is selected from hydrogen, $C_{1-8}$alkyl or $C_{1-8}$alkoxy; and $R_3$, $R_4$, $R_5$, $R_6$ and $R_7$ is each selected from hydrogen, halogen, hydroxy, $C_{1-8}$alkyl, $C_{1-8}$alkoxy, halo-$C_{1-8}$alkyl, halo-$C_{1-8}$alkoxy, cyano-$C_{1-8}$alkyl, $C_{1-8}$alkyl-amino, $C_{1-8}$alkyl-amino-$C_{1-8}$alkyl-amino-carbonyl, $C_{1-8}$alkoxy-imino-$C_{1-8}$ alkyl, $C_{1-8}$alkoxy-imino-(aryl)$C_{1-8}$alkyl, $C_{1-8}$acyl, $C_{1-8}$acyl-amino, $C_{1-8}$alkoxycarbonyl, thio-$C_{1-8}$alkyl, substituted phosphonic acid, cyclohexyl, phenyl, phenoxy, phenyl-amino, phenyl-$C_{1-8}$alkyl, phenyl-$C_{1-8}$alkoxy, aryl-carbonyl-$C_{1-8}$alkyl, phenyl-amido, pyridinyloxy, heteroaryl-$C_{1-8}$alkoxy, pyridimin-2-yl-amino-sulfonyl, pyrazin-2-yl-amino-sulfonyl, benzofused-heterocyclyl or morpholin-4-yl, wherein phosphonic acid is substituted on the phosphorous atom with two $C_{1-8}$alkoxy substituents, wherein phenyl, phenyl-amino, phenyl-$C_{1-8}$alkyl and phenyl-$C_{1-8}$alkoxy is each optionally substituted on aryl with one or two substituents each selected from cyano, halogen, $C_{1-8}$alkoxy or $C_{1-8}$alkoxycarbonyl, wherein benzofused-heterocyclyl is optionally substituted on the heterocyclyl portion with two oxo substituents, and wherein pyridimin-2-yl-amino-sulfonyl, pyrazin-2-yl-amino-sulfonyl and pyridinyloxy is each optionally substituted with one or two $C_{1-8}$alkyl substituents.

An example of a compound of formula (I) and forms thereof includes a compound wherein L is a bond;

Ar is selected from phenyl, 1,2,3,4-tetrahydro-naphthalenyl, pyridinyl, indazolyl or indolyl;

$R_A$ is selected from C=N—O—$R_1$ or cyano;

$R_1$ is selected from hydrogen, $C_{1-8}$alkyl, $C_{1-8}$alkenyl, hydroxy-$C_{1-8}$alkyl, morpholin-4-yl-$C_{1-8}$alkyl or piperidinyl-$C_{1-8}$alkyl;

$R_2$ is hydrogen; and $R_3$, $R_4$, $R_5$, $R_6$ and $R_7$ is each selected from hydrogen, halogen, phenoxy, phenyl-$C_{1-8}$alkyl or phenyl-$C_{1-8}$alkoxy, wherein phenyl-$C_{1-8}$alkyl is optionally substituted on phenyl with halogen.

The present invention is further directed to a compound of formula (Ia):

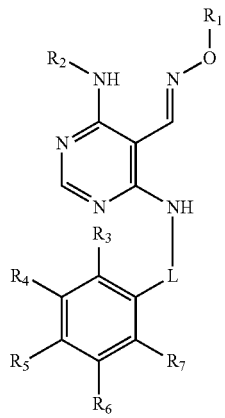

and forms thereof, wherein
L is selected from a bond, $C_{1-6}$alkyl or halo-$C_{1-6}$alkyl;
$R_1$ is selected from hydrogen, $C_{1-8}$alkyl, $C_{1-8}$alkenyl, $C_{1-8}$alkoxy, $C_{1-8}$alkoxy-$C_{1-8}$alkyl, hydroxy-$C_{1-8}$alkyl, hydroxy-$C_{1-8}$alkoxy, amino-$C_{1-8}$alkyl, $C_{1-8}$alkyl-amino-$C_{1-8}$alkyl, $C_{1-8}$alkoxy-$C_{1-8}$alkyl-amino-$C_{1-8}$alkyl, $C_{1-8}$alkyl-sulfonyl-$C_{1-8}$alkyl, $C_{1-8}$alkyl-sulfonyloxy-$C_{1-8}$alkyl, aryl, aryl-$C_{1-8}$alkyl, aryloxy-$C_{1-8}$alkyl, heterocyclyl-$C_{1-8}$alkyl, heterocyclyl-carbonyl-$C_{1-8}$alkyl, benzofused-heterocyclyl-$C_{1-8}$alkyl or heteroaryl-$C_{1-8}$alkyl,
wherein aryl-$C_{1-8}$alkyl is optionally substituted on aryl with one, two, three, four or five substituents each selected from hydroxy, $C_{1-8}$alkyl, $C_{1-8}$alkoxy, amino, $C_{1-8}$alkyl-amino or $C_{1-8}$alkoxycarbonyl, and
wherein heterocyclyl-$C_{1-8}$alkyl is optionally substituted on heterocyclyl with one, two, three or four substituents each selected from hydroxy, $C_{1-8}$alkyl, $C_{1-8}$alkoxy, amino, $C_{1-8}$alkyl-amino or $C_{1-8}$alkoxycarbonyl;
$R_2$ is selected from hydrogen, $C_{1-8}$alkyl or $C_{1-8}$alkoxy; and
$R_3$, $R_4$, $R_5$, $R_6$ and $R_7$ is each selected from hydrogen, halogen, hydroxy, $C_{1-8}$alkyl, $C_{1-8}$alkoxy, $C_{1-8}$alkoxy-$C_{1-8}$alkyl, hydroxy-$C_{1-8}$alkyl, halo-$C_{1-8}$alkyl, hydroxy-$C_{1-8}$alkoxy, halo-$C_{1-8}$alkoxy, cyano-$C_{1-8}$alkyl, amino, $C_{1-8}$alkyl-amino, amino-$C_{1-8}$alkyl, $C_{1-8}$alkyl-amino-$C_{1-8}$alkyl, $C_{1-8}$alkyl-amino-$C_{1-8}$alkyl-amino-carbonyl, $C_{1-8}$alkoxy-imino-$C_{1-8}$alkyl, $C_{1-8}$alkoxy-imino-(aryl)$C_{1-8}$alkyl, carboxy, $C_{1-8}$acyl, $C_{1-8}$acyl-amino, $C_{1-8}$alkoxycarbonyl, thio-$C_{1-8}$alkyl, substituted phosphonic acid, $C_{3-12}$cycloalkyl, aryl, aryloxy, aryl-amino, aryl-$C_{1-8}$alkyl, aryl-$C_{1-8}$alkoxy, aryl-carbonyl-$C_{1-8}$alkyl, aryl-amido, heteroaryl, heteroaryloxy, heteroaryl-$C_{1-8}$alkyl, heteroaryl-amino-sulfonyl, benzofused-heterocyclyl or heterocyclyl,
wherein phosphonic acid is substituted on the phosphorous atom with two substituents selected from hydroxy or $C_{1-8}$alkoxy,
wherein aryl, aryl-amino, aryloxy, aryl-$C_{1-8}$alkyl and aryl-$C_{1-8}$alkoxy is each optionally substituted on aryl with one, two, three, four or five substituents each selected from cyano, halogen, hydroxy, $C_{1-8}$alkyl, $C_{1-8}$alkoxy, amino, $C_{1-8}$alkyl-amino, amino-$C_{1-8}$alkyl, $C_{1-8}$alkyl-amino-$C_{1-8}$alkyl or $C_{1-8}$alkoxycarbonyl,
wherein benzofused-heterocyclyl is optionally substituted on the heterocyclyl portion with one or two oxo substituents, and
wherein heteroaryl, heteroaryl-amino-sulfonyl and heteroaryloxy is each optionally substituted on heteroaryl with one, two, three, four or five substituents each selected from $C_{1-8}$alkyl, amino-$C_{1-8}$alkyl, $C_{1-8}$alkyl-amino-$C_{1-8}$alkyl, carboxy, $C_{1-8}$acyl or $C_{1-8}$alkoxycarbonyl.

The present invention is further directed to a compound of formula (Ib):

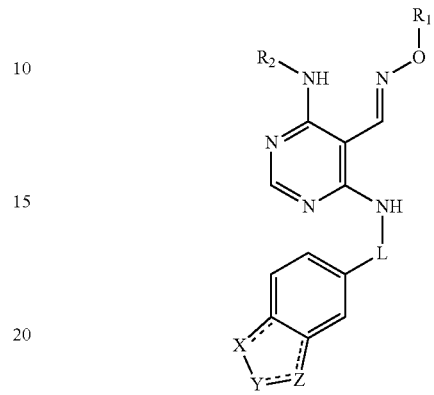

and forms thereof, wherein
L is selected from a bond, $C_{1-6}$alkyl or halo-$C_{1-6}$alkyl;
-X-Y-Z- is a moiety selected from —N($R_3$)—N=C($R_3$)—, =N—N($R_3$)—C($R_3$)=, —N($R_3$)—C($R_3$)=C($R_3$)—, —C($R_3$)$_2$—C($R_3$)$_2$—C($R_3$)$_2$—, —O—C($R_3$)$_2$—O—, —N($R_3$)—C($R_3$)=N—, —O—C($R_3$)=C($R_3$)—, —N($R_3$)—C($R_3$)$_2$—C($R_3$)$_2$— or —S—C($R_3$)=N—;
wherein the dashed lines in formula (Ib) represent the locations for one or two double bonds when present in the moiety;
$R_1$ is selected from hydrogen, $C_{1-8}$alkyl, $C_{1-8}$alkenyl, $C_{1-8}$alkoxy, $C_{1-8}$alkoxy-$C_{1-8}$alkyl, hydroxy-$C_{1-8}$alkyl, hydroxy-$C_{1-8}$alkoxy, amino-$C_{1-8}$alkyl, $C_{1-8}$alkyl-amino-$C_{1-8}$alkyl, $C_{1-8}$alkoxy-$C_{1-8}$alkyl-amino-$C_{1-8}$alkyl, $C_{1-8}$alkyl-sulfonyl-$C_{1-8}$alkyl, $C_{1-8}$alkyl-sulfonyloxy-$C_{1-8}$alkyl, aryl, aryl-$C_{1-8}$alkyl, aryloxy-$C_{1-8}$alkyl, heterocyclyl-$C_{1-8}$alkyl, heterocyclyl-carbonyl-$C_{1-8}$alkyl, benzofused-heterocyclyl-$C_{1-8}$alkyl or heteroaryl-$C_{1-8}$alkyl,
wherein aryl-$C_{1-8}$alkyl is optionally substituted on aryl with one, two, three, four or five substituents each selected from hydroxy, $C_{1-8}$alkyl, $C_{1-8}$alkoxy, amino, $C_{1-8}$alkyl-amino or $C_{1-8}$alkoxycarbonyl, and
wherein heterocyclyl-$C_{1-8}$alkyl is optionally substituted on heterocyclyl with one, two, three or four substituents each selected from hydroxy, $C_{1-8}$alkyl, $C_{1-8}$alkoxy, amino, $C_{1-8}$alkyl-amino or $C_{1-8}$alkoxycarbonyl;
$R_2$ is selected from hydrogen, $C_{1-8}$alkyl or $C_{1-8}$alkoxy; and
$R_3$ is selected from hydrogen, halogen, hydroxy, $C_{1-8}$alkyl, $C_{1-8}$alkoxy, $C_{1-8}$alkoxy-$C_{1-8}$alkyl, hydroxy-$C_{1-8}$alkyl, halo-$C_{1-8}$alkyl, hydroxy-$C_{1-8}$alkoxy, halo-$C_{1-8}$alkoxy, cyano-$C_{1-8}$alkyl, amino, $C_{1-8}$alkyl-amino, amino-$C_{1-8}$alkyl, $C_{1-8}$alkyl-amino-$C_{1-8}$alkyl, $C_{1-8}$alkyl-amino-$C_{1-8}$alkyl-amino-carbonyl, $C_{1-8}$alkoxy-imino-$C_{1-8}$alkyl, $C_{1-8}$alkoxy-imino-(aryl)$C_{1-8}$alkyl, carboxy, $C_{1-8}$acyl, $C_{1-8}$acyl-amino, $C_{1-8}$alkoxycarbonyl, thio-$C_{1-8}$alkyl, substituted phosphonic acid, $C_{3-12}$cycloalkyl, aryl, aryloxy, aryl-amino, aryl-$C_{1-8}$alkyl, aryl-$C_{1-8}$alkoxy, aryl-carbonyl-$C_{1-8}$alkyl, aryl-amido, heteroaryl, heteroaryloxy, heteroaryl-$C_{1-8}$alkoxy, heteroaryl-amino-sulfonyl, benzofused-heterocyclyl or heterocyclyl,
wherein phosphonic acid is substituted on the phosphorous atom with two substituents selected from hydroxy or $C_{1-8}$alkoxy, wherein aryl, aryl-amino, aryloxy, aryl-$C_{1-8}$alkyl and aryl-$C_{1-8}$alkoxy is each optionally substituted on aryl with one, two, three, four or five substituents each selected from cyano, halogen, hydroxy, $C_{1-8}$alkyl, $C_{1-8}$alkoxy, amino, $C_{1-8}$alkyl-amino, amino-$C_{1-8}$alkyl, $C_{1-8}$alkyl-amino-$C_{1-8}$alkyl or $C_{1-8}$alkoxycarbonyl, wherein benzofused-heterocyclyl is optionally substituted on the heterocyclyl portion with one or two oxo substituents, and wherein heteroaryl, heteroaryl-amino-sulfonyl and heteroaryloxy is each optionally substituted on heteroaryl with one, two, three, four or five substituents each selected from $C_{1-8}$alkyl, amino-$C_{1-8}$alkyl, $C_{1-8}$alkyl-amino-$C_{1-8}$alkyl, carboxy, $C_{1-8}$acyl or $C_{1-8}$alkoxycarbonyl.

The present invention is further directed to a compound of formula (Ic):

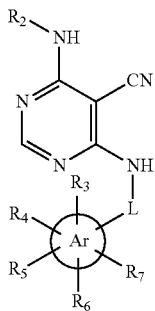

and forms thereof, wherein

L is selected from a bond, $C_{1-6}$alkyl or halo-$C_{1-6}$alkyl;

Ar is selected from aryl, heteroaryl, benzofused-heterocyclyl or benzofused-$C_{3-12}$cycloalkyl;

$R_2$ is selected from hydrogen, $C_{1-8}$alkyl or $C_{1-8}$alkoxy; and $R_3$, $R_4$, $R_5$, $R_6$ and $R_7$ is each selected from hydrogen, halogen, hydroxy, $C_{1-8}$alkyl, $C_{1-8}$alkoxy, $C_{1-8}$alkoxy-$C_{1-8}$alkyl, hydroxy-$C_{1-8}$alkyl, halo-$C_{1-8}$alkyl, hydroxy-$C_{1-8}$alkoxy, halo-$C_{1-8}$alkoxy, cyano-$C_{1-8}$alkyl, amino, $C_{1-8}$alkyl-amino, amino-$C_{1-8}$alkyl, $C_{1-8}$alkyl-amino-$C_{1-8}$alkyl, $C_{1-8}$alkyl-amino-$C_{1-8}$alkyl-amino-carbonyl, $C_{1-8}$alkoxy-imino-$C_{1-8}$alkyl, $C_{1-8}$alkoxy-imino-(aryl)$C_{1-8}$alkyl, carboxy, $C_{1-8}$acyl, $C_{1-8}$acyl-amino, $C_{1-8}$alkoxycarbonyl, thio-$C_{1-8}$alkyl, substituted phosphonic acid, $C_{3-12}$cycloalkyl, aryl, aryloxy, aryl-amino, aryl-$C_{1-8}$alkyl, aryl-$C_{1-8}$alkoxy, aryl-carbonyl-$C_{1-8}$alkyl, aryl-amido, heteroaryl, heteroaryloxy, heteroaryl-$C_{1-8}$alkoxy, heteroaryl-amino-sulfonyl, benzofused-heterocyclyl or heterocyclyl, wherein phosphonic acid is substituted on the phosphorous atom with two substituents selected from hydroxy or $C_{1-8}$alkoxy, wherein aryl, aryloxy, aryl-amino, aryl-$C_{1-8}$alkyl and aryl-$C_{1-8}$alkoxy is each optionally substituted on aryl with one, two, three, four or five substituents each selected from cyano, halogen, hydroxy, $C_{1-8}$alkyl, $C_{1-8}$alkoxy, amino, $C_{1-8}$alkyl-amino, amino-$C_{1-8}$alkyl, $C_{1-8}$alkyl-amino-$C_{1-8}$alkyl or $C_{1-8}$alkoxycarbonyl, wherein benzofused-heterocyclyl is optionally substituted on the heterocyclyl portion with one or two oxo substituents, and wherein heteroaryl, heteroaryl-amino-sulfonyl and heteroaryloxy is each optionally substituted on heteroaryl with one, two, three, four or five substituents each selected from $C_{1-8}$alkyl, amino-$C_{1-8}$alkyl, $C_{1-8}$alkyl-amino-$C_{1-8}$alkyl, carboxy, $C_{1-8}$acyl or $C_{1-8}$alkoxycarbonyl.

An example of a compound of formula (Ic) and forms thereof includes a compound wherein $R_2$ is selected from hydrogen.

An example of a compound of formula (Ic) and forms thereof includes a compound wherein $R_3$, $R_4$, $R_5$, $R_6$ and $R_7$ is each selected from hydrogen, halogen, hydroxy, $C_{1-8}$alkyl, $C_{1-8}$alkoxy, $C_{1-8}$alkoxy-$C_{1-8}$alkyl, hydroxy-$C_{1-8}$alkyl, halo-$C_{1-8}$alkyl, hydroxy-$C_{1-8}$alkoxy, halo-$C_{1-8}$alkoxy, cyano-$C_{1-8}$alkyl, amino, $C_{1-8}$alkyl-amino, amino-$C_{1-8}$alkyl, $C_{1-8}$alkyl-amino-$C_{1-8}$alkyl, $C_{1-8}$alkyl-amino-$C_{1-8}$alkyl-amino-carbonyl, $C_{1-8}$alkoxy-imino-$C_{1-8}$alkyl, $C_{1-8}$alkoxy-imino-(aryl)$C_{1-8}$alkyl, carboxy, $C_{1-8}$acyl, $C_{1-8}$acyl-amino, $C_{1-8}$alkoxycarbonyl, thio-$C_{1-8}$alkyl, substituted phosphonic acid, $C_{3-12}$cycloalkyl, aryl, aryloxy, aryl-amino, aryl-$C_{1-8}$alkyl, aryl-$C_{1-8}$alkoxy, aryl-carbonyl-$C_{1-8}$alkyl, aryl-amido, heteroaryl, heteroaryloxy, heteroaryl-$C_{1-8}$alkoxy, heteroaryl-amino-sulfonyl, benzofused-heterocyclyl or heterocyclyl, wherein phosphonic acid is substituted on the phosphorous atom with two $C_{1-8}$alkoxy substituents, wherein aryl, aryl-amino, aryl-$C_{1-8}$alkyl and aryl-$C_{1-8}$alkoxy is each optionally substituted on aryl with one or two substituents each selected from cyano, halogen, hydroxy, $C_{1-8}$alkyl, $C_{1-8}$alkoxy, amino, $C_{1-8}$alkyl-amino, amino-$C_{1-8}$alkyl, $C_{1-8}$alkyl-amino-$C_{1-8}$alkyl or $C_{1-8}$alkoxycarbonyl, wherein benzofused-heterocyclyl is optionally substituted on the heterocyclyl portion with two oxo substituents, and wherein heteroaryl-amino-sulfonyl and heteroaryloxy is each optionally substituted on heteroaryl with one or two $C_{1-8}$alkyl substituents.

An example of a compound of formula (Ic) and forms thereof includes a compound wherein $R_3$, $R_4$, $R_5$, $R_6$ and $R_7$ is each selected from hydrogen, halogen, hydroxy, $C_{1-8}$alkyl, $C_{1-8}$alkoxy, $C_{1-8}$alkoxy-$C_{1-8}$alkyl, hydroxy-$C_{1-8}$alkyl, halo-$C_{1-8}$alkyl, hydroxy-$C_{1-8}$alkoxy, halo-$C_{1-8}$alkoxy, cyano-$C_{1-8}$alkyl, amino, $C_{1-8}$alkyl-amino, amino-$C_{1-8}$alkyl, $C_{1-8}$alkyl-amino-$C_{1-8}$alkyl, $C_{1-8}$alkyl-amino-$C_{1-8}$alkyl-amino-carbonyl, $C_{1-8}$alkoxy-imino-$C_{1-8}$alkyl, $C_{1-8}$alkoxy-imino-(aryl)$C_{1-8}$alkyl, carboxy, $C_{1-8}$acyl, $C_{1-8}$acyl-amino, $C_{1-8}$alkoxycarbonyl, thio-$C_{1-8}$alkyl, substituted phosphonic acid, $C_{3-12}$cycloalkyl, aryl, aryloxy, aryl-amino, aryl-$C_{1-8}$alkyl, aryl-$C_{1-8}$alkoxy, aryl-carbonyl-$C_{1-8}$alkyl, aryl-amido, heteroaryl, heteroaryloxy, heteroaryl-$C_{1-8}$alkoxy, heteroaryl-amino-sulfonyl, benzofused-heterocyclyl or heterocyclyl, wherein phosphonic acid is substituted on the phosphorous atom with two $C_{1-8}$alkoxy substituents, wherein aryl, aryl-amino, aryl-$C_{1-8}$alkyl and aryl-$C_{1-8}$alkoxy is each optionally substituted on aryl with one or two substituents each selected from cyano, halogen, $C_{1-8}$alkoxy or $C_{1-8}$alkoxycarbonyl, wherein benzofused-heterocyclyl is optionally substituted on the heterocyclyl portion with two oxo substituents, and wherein heteroaryl-amino-sulfonyl and heteroaryloxy is each optionally substituted on heteroaryl with one or two $C_{1-8}$alkyl substituents.

An example of a compound of formula (Ic) and forms thereof includes a compound wherein $R_3$, $R_4$, $R_5$, $R_6$ and $R_7$ is each selected from hydrogen, halogen, hydroxy, $C_{1-8}$alkyl, $C_{1-8}$alkoxy, halo-$C_{1-8}$alkyl, halo-$C_{1-8}$alkoxy, cyano-$C_{1-8}$alkyl, $C_{1-8}$alkyl-amino, $C_{1-8}$alkyl-amino-$C_{1-8}$alkyl-amino-carbonyl, $C_{1-8}$alkoxy-imino-$C_{1-8}$alkyl, $C_{1-8}$alkoxy-imino-(aryl)$C_{1-8}$alkyl, $C_{1-8}$acyl, $C_{1-8}$acyl-amino, $C_{1-8}$alkoxycarbonyl, thio-$C_{1-8}$alkyl, substituted phosphonic acid, $C_{3-12}$cycloalkyl, aryl, aryloxy, aryl-amino, aryl-$C_{1-8}$alkyl, aryl-$C_{1-8}$alkoxy, aryl-carbonyl-$C_{1-8}$alkyl, aryl-amido, heteroaryloxy, heteroaryl-$C_{1-8}$alkoxy, heteroaryl-amino-sulfonyl, benzofused-heterocyclyl or heterocyclyl, wherein phosphonic acid is substituted on the phosphorous atom with two $C_{1-8}$alkoxy substituents, wherein aryl, aryl-amino, aryl-$C_{1-8}$alkyl and aryl-$C_{1-8}$alkoxy is each optionally substituted on aryl with one or two substituents each selected from cyano, halogen, $C_{1-8}$alkoxy or $C_{1-8}$alkoxycarbonyl, wherein benzofused-heterocyclyl is optionally substituted on the heterocyclyl portion with two oxo substituents, and wherein heteroaryl-amino-sulfonyl and heteroaryloxy is each optionally substituted on heteroaryl with one or two $C_{1-8}$alkyl substituents.

An example of a compound of formula (Ic) and forms thereof includes a compound wherein L is selected from a bond, $C_{1-6}$alkyl or halo-$C_{1-6}$alkyl;

Ar is selected from aryl, heteroaryl, benzofused-heterocyclyl or benzofused-$C_{3-12}$cycloalkyl;

$R_2$ is selected from hydrogen, $C_{1-8}$alkyl or $C_{1-8}$alkoxy; and $R_3$, $R_4$, $R_5$, $R_6$ and $R_7$ is each selected from hydrogen, halogen, hydroxy, $C_{1-8}$alkyl, $C_{1-8}$alkoxy, halo-$C_{1-8}$alkyl, halo-$C_{1-8}$alkoxy, cyano-$C_{1-8}$alkyl, $C_{1-8}$alkyl-amino, $C_{1-8}$alkyl-amino-$C_{1-8}$alkyl-amino-carbonyl, $C_{1-8}$alkoxy-imino-$C_{1-8}$alkyl, $C_{1-8}$alkoxy-imino-(aryl)$C_{1-8}$alkyl, $C_{1-8}$acyl, $C_{1-8}$acyl-amino, $C_{1-8}$alkoxycarbonyl, thio-$C_{1-8}$alkyl, substituted phosphonic acid, $C_{3-12}$cycloalkyl, aryl, aryloxy, aryl-amino, aryl-$C_{1-8}$alkyl, aryl-$C_{1-8}$alkoxy, aryl-carbonyl-$C_{1-8}$alkyl, aryl-amido, heteroaryloxy, heteroaryl-$C_{1-8}$alkoxy, heteroaryl-amino-sulfonyl, benzofused-heterocyclyl or heterocyclyl, wherein phosphonic acid is substituted on the phosphorous atom with two $C_{1-8}$alkoxy substituents, wherein aryl, aryl-amino, aryl-$C_{1-8}$alkyl and aryl-$C_{1-8}$alkoxy is each optionally substituted on aryl with one or two substituents each selected from cyano, halogen, $C_{1-8}$alkoxy or $C_{1-8}$alkoxycarbonyl, wherein benzofused-heterocyclyl is optionally substituted on the heterocyclyl portion with two oxo substituents, and wherein heteroaryl-amino-sulfonyl and heteroaryloxy is each optionally substituted on heteroaryl with one or two $C_{1-8}$alkyl substituents.

The present invention is further directed to a compound of formula (Id):

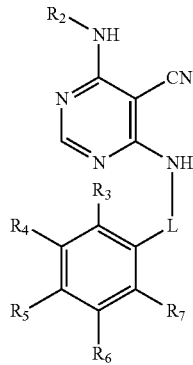

and forms thereof, wherein

L is selected from a bond, $C_{1-6}$alkyl or halo-$C_{1-6}$alkyl;

$R_2$ is selected from hydrogen, $C_{1-8}$alkyl or $C_{1-8}$alkoxy; and $R_3$, $R_4$, $R_5$, $R_6$ and $R_7$ is each selected from hydrogen, halogen, hydroxy, $C_{1-8}$alkyl, $C_{1-8}$alkoxy, $C_{1-8}$alkoxy-$C_{1-8}$alkyl, hydroxy-$C_{1-8}$alkyl, halo-$C_{1-8}$alkyl, hydroxy-$C_{1-8}$alkoxy, halo-$C_{1-8}$alkoxy, cyano-$C_{1-8}$alkyl, amino, $C_{1-8}$alkyl-amino, amino-$C_{1-8}$alkyl, $C_{1-8}$alkyl-amino-$C_{1-8}$alkyl, $C_{1-8}$alkyl-amino-$C_{1-8}$alkyl-amino-carbonyl, $C_{1-8}$alkoxy-imino-$C_{1-8}$alkyl, $C_{1-8}$alkoxy-imino-(aryl)$C_{1-8}$alkyl, carboxy, $C_{1-8}$acyl, $C_{1-8}$acyl-amino, $C_{1-8}$alkoxycarbonyl, thio-$C_{1-8}$alkyl, substituted phosphonic acid, $C_{3-12}$cycloalkyl, aryl, aryloxy, aryl-amino, aryl-$C_{1-8}$alkyl, aryl-$C_{1-8}$alkoxy, aryl-carbonyl-$C_{1-8}$alkyl, aryl-amido, heteroaryl, heteroaryloxy, heteroaryl-$C_{1-8}$alkoxy, heteroaryl-amino-sulfonyl, benzofused-heterocyclyl or heterocyclyl, wherein phosphonic acid is substituted on the phosphorous atom with two substituents selected from hydroxy or $C_{1-8}$alkoxy, wherein aryl, aryl-amino, aryloxy, aryl-$C_{1-8}$alkyl and aryl-$C_{1-8}$alkoxy is each optionally substituted on aryl with one, two, three, four or five substituents each selected from cyano, halogen, hydroxy, $C_{1-8}$alkyl, $C_{1-8}$alkoxy, amino, $C_{1-8}$alkyl-amino, amino-$C_{1-8}$alkyl, $C_{1-8}$alkyl-amino-$C_{1-8}$alkyl or $C_{1-8}$alkoxycarbonyl, wherein benzofused-heterocyclyl is optionally substituted on the heterocyclyl portion with one or two oxo substituents, and wherein heteroaryl, heteroaryl-amino-sulfonyl and heteroaryloxy is each optionally substituted on heteroaryl with one, two, three, four or five substituents each selected from $C_{1-8}$alkyl, amino-$C_{1-8}$alkyl, $C_{1-8}$alkyl-amino-$C_{1-8}$alkyl, carboxy, $C_{1-8}$acyl or $C_{1-8}$alkoxycarbonyl.

The present invention is further directed to a compound of formula (Ie):

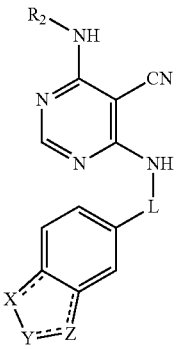

and forms thereof, wherein

L is selected from a bond, $C_{1-6}$alkyl or halo-$C_{1-6}$alkyl;

-X-Y-Z- is a moiety selected from —N($R_3$)—N=C($R_3$)—, =N—N($R_3$)—C($R_3$)=, —N($R_3$)—C($R_3$)=C($R_3$)—, —C($R_3$)$_2$—C($R_3$)$_2$—C($R_3$)$_2$—, —O—C($R_3$)$_2$—O—, —N($R_3$)—C($R_3$)=N—, —O—C($R_3$)=C($R_3$)—, —N($R_3$)—C($R_3$)$_2$—C($R_3$)$_2$— or —S—C($R_3$)=N—;

wherein the dashed lines in formula (Ie) represent the locations for one or two double bonds when present in the moiety;

$R_2$ is selected from hydrogen, $C_{1-8}$alkyl or $C_{1-8}$alkoxy; and $R_3$ is selected from hydrogen, halogen, hydroxy, $C_{1-8}$alkyl, $C_{1-8}$alkoxy, $C_{1-8}$alkoxy-$C_{1-8}$alkyl, hydroxy-$C_{1-8}$alkyl, halo-$C_{1-8}$alkyl, hydroxy-$C_{1-8}$alkoxy, halo-$C_{1-8}$alkoxy, cyano-$C_{1-8}$alkyl, amino, $C_{1-8}$alkyl-amino, amino-$C_{1-8}$alkyl, $C_{1-8}$alkyl-amino-$C_{1-8}$alkyl, $C_{1-8}$alkyl-amino-$C_{1-8}$alkyl-amino-carbonyl, $C_{1-8}$alkoxy-imino-$C_{1-8}$alkyl, $C_{1-8}$alkoxy-imino-(aryl)$C_{1-8}$alkyl, carboxy, $C_{1-8}$acyl, $C_{1-8}$acyl-amino, $C_{1-8}$alkoxycarbonyl, thio-$C_{1-8}$alkyl, substituted phosphonic acid, $C_{3-12}$cycloalkyl, aryl, aryloxy, aryl-amino, aryl-$C_{1-8}$alkyl, aryl-$C_{1-8}$alkoxy, aryl-carbonyl-$C_{1-8}$alkyl, aryl-amido, heteroaryl, heteroaryloxy, heteroaryl-$C_{1-8}$alkoxy, heteroaryl-amino-sulfonyl, benzofused-heterocyclyl or heterocyclyl, wherein phosphonic acid is substituted on the phosphorous atom with two substituents selected from hydroxy or $C_{1-8}$alkoxy, wherein aryl, aryl-amino, aryloxy, aryl-$C_{1-8}$alkyl and aryl-$C_{1-8}$alkoxy is each optionally substituted on aryl with one, two, three, four or five substituents each selected from cyano, halogen, hydroxy, $C_{1-8}$alkyl, $C_{1-8}$alkoxy, amino, $C_{1-8}$alkyl-amino, amino-$C_{1-8}$alkyl, $C_{1-8}$alkyl-amino-$C_{1-8}$alkyl or $C_{1-8}$alkoxycarbonyl, wherein benzofused-heterocyclyl is optionally substituted on the heterocyclyl portion with one or two oxo substituents, and wherein heteroaryl, heteroaryl-amino-sulfonyl and heteroaryloxy is each optionally substituted on heteroaryl with one, two, three, four or five substituents each selected from $C_{1-8}$alkyl, amino-$C_{1-8}$alkyl, $C_{1-8}$alkyl-amino-$C_{1-8}$alkyl, carboxy, $C_{1-8}$acyl or $C_{1-8}$alkoxycarbonyl.

The present invention is further directed to a compound of formula (If):

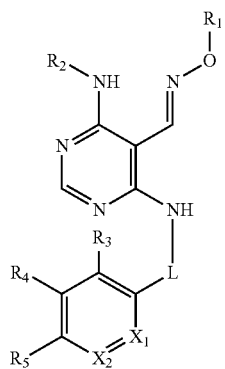

and forms thereof, wherein $X_1$ and $X_2$ is each selected from —$C(R_6)$— or —N—, wherein $X_1$ and $X_2$ are not the same;

L is selected from a bond, $C_{1-6}$alkyl or halo-$C_{1-6}$alkyl;

$R_1$ is selected from hydrogen, $C_{1-8}$alkyl, $C_{1-8}$alkenyl, $C_{1-8}$alkoxy, $C_{1-8}$alkoxy-$C_{1-8}$alkyl, hydroxy-$C_{1-8}$alkyl, hydroxy-$C_{1-8}$alkoxy, amino-$C_{1-8}$alkyl, $C_{1-8}$alkyl-amino-$C_{1-8}$alkyl, $C_{1-8}$alkoxy-$C_{1-8}$alkyl-amino-$C_{1-8}$alkyl, $C_{1-8}$alkyl-sulfonyl-$C_{1-8}$alkyl, $C_{1-8}$alkyl-sulfonyloxy-$C_{1-8}$alkyl, aryl, aryl-$C_{1-8}$alkyl, aryloxy-$C_{1-8}$alkyl, heterocyclyl-$C_{1-8}$alkyl, heterocyclyl-carbonyl-$C_{1-8}$alkyl, benzofused-heterocyclyl-$C_{1-8}$alkyl or heteroaryl-$C_{1-8}$alkyl, wherein aryl-$C_{1-8}$alkyl is optionally substituted on aryl with one, two, three, four or five substituents each selected from hydroxy, $C_{1-8}$alkyl, $C_{1-8}$alkoxy, amino, $C_{1-8}$alkyl-amino or $C_{1-8}$alkoxycarbonyl, and wherein heterocyclyl-$C_{1-8}$alkyl is optionally substituted on heterocyclyl with one, two, three or four substituents each selected from hydroxy, $C_{1-8}$alkyl, $C_{1-8}$alkoxy, amino, $C_{1-8}$alkyl-amino or $C_{1-8}$alkoxycarbonyl;

$R_2$ is selected from hydrogen, $C_{1-8}$alkyl or $C_{1-8}$alkoxy; and $R_3$, $R_4$, and $R_5$ is each selected from hydrogen, halogen, hydroxy, $C_{1-8}$alkyl, $C_{1-8}$alkoxy, $C_{1-8}$alkoxy-$C_{1-8}$alkyl, hydroxy-$C_{1-8}$alkyl, halo-$C_{1-8}$alkyl, hydroxy-$C_{1-8}$alkoxy, halo-$C_{1-8}$alkoxy, cyano-$C_{1-8}$alkyl, amino, $C_{1-8}$alkyl-amino, amino-$C_{1-8}$alkyl, $C_{1-8}$alkyl-amino-$C_{1-8}$alkyl, $C_{1-8}$alkyl-amino-$C_{1-8}$alkyl-amino-carbonyl, $C_{1-8}$alkoxy-imino-$C_{1-8}$alkyl, $C_{1-8}$alkoxy-imino-(aryl)$C_{1-8}$alkyl, carboxy, $C_{1-8}$acyl, $C_{1-8}$acyl-amino, $C_{1-8}$alkoxycarbonyl, thio-$C_{1-8}$alkyl, substituted phosphonic acid, $C_{3-12}$cycloalkyl, aryl, aryloxy, aryl-amino, aryl-$C_{1-8}$alkyl, aryl-$C_{1-8}$alkoxy, aryl-carbonyl-$C_{1-8}$alkyl, aryl-amido, heteroaryl, heteroaryloxy, heteroaryl-$C_{1-8}$alkoxy, heteroaryl-amino-sulfonyl, benzofused-heterocyclyl or heterocyclyl, wherein phosphonic acid is substituted on the phosphorous atom with two substituents selected from hydroxy or $C_{1-8}$alkoxy, wherein aryl, aryl-amino, aryloxy, aryl-$C_{1-8}$alkyl and aryl-$C_{1-8}$alkoxy is each optionally substituted on aryl with one, two, three, four or five substituents each selected from cyano, halogen, hydroxy, $C_{1-8}$alkyl, $C_{1-8}$alkoxy, amino, $C_{1-8}$alkyl-amino, amino-$C_{1-8}$alkyl, $C_{1-8}$alkyl-amino-$C_{1-8}$alkyl or $C_{1-8}$alkoxycarbonyl, wherein benzofused-heterocyclyl is optionally substituted on the heterocyclyl portion with one or two oxo substituents, and wherein heteroaryl, heteroaryl-amino-sulfonyl and heteroaryloxy is each optionally substituted on heteroaryl with one, two, three, four or five substituents each selected from $C_{1-8}$alkyl, amino-$C_{1-8}$alkyl, $C_{1-8}$alkyl-amino-$C_{1-8}$alkyl, carboxy, $C_{1-8}$acyl or $C_{1-8}$alkoxycarbonyl; and $R_6$ is selected from hydrogen, halogen, hydroxy, $C_{1-8}$alkyl, $C_{1-8}$alkoxy, $C_{1-8}$alkoxy-$C_{1-8}$alkyl, hydroxy-$C_{1-8}$alkyl, halo-$C_{1-8}$alkyl, hydroxy-$C_{1-8}$alkoxy, halo-$C_{1-8}$alkoxy, cyano-$C_{1-8}$alkyl, amino, $C_{1-8}$alkyl-amino, amino-$C_{1-8}$alkyl or $C_{1-8}$alkyl-amino-$C_{1-8}$alkyl.

An example of a compound of Formula (I) includes a compound and forms thereof, wherein (*)-$R_4$, $R_2$, $R_3$, $R_4$, $R_5$, $R_6$, $R_7$, L and Ar are dependently selected from (wherein * represents the configuration of the oxime portion in relationship to the double bond; further, when one or more of $R_3$, $R_4$, $R_5$, $R_6$ or $R_7$ is hydrogen, the hydrogen is omitted from the following table):

| Cpd | (*)-$R_4$ | $R_2$ | L | ($R_3$—$R_4$—$R_5$—$R_6$—$R_7$)Ar |
|---|---|---|---|---|
| 1 | (E)-CH=N—OCH$_3$ | H | bond | (3-Cl-4-F)phenyl |
| 2 | (E)-CH=N—OCH$_3$ | H | bond | 1-(3-F-benzyl)indazol-5-yl |
| 3 | (E)-CH=N—OCH$_3$ | H | bond | (3-Cl-4-F)benzyl |
| 4 | (E)-CH=N—OCH$_3$ | H | bond | [3-Cl-4-(3-F-benzyloxy)]phenyl |
| 5 | (E)-CH=N—OCH$_3$ | H | bond | 2-(3-F-benzyl)indazol-5-yl |
| 6 | (E)-CH=N—OCH$_2$C(O)-morpholin-4-yl | H | bond | 1-(3-F-benzyl)indazol-5-yl |
| 7 | (E)-CH=N—OCH$_3$ | H | bond | (3-OCH$_3$-4-phenoxy)phenyl |
| 8 | (E)-CH=N—OCH$_2$C(O)-morpholin-4-yl | H | bond | (3-OCH$_3$-4-phenoxy)phenyl |
| 9 | (E)-CH=N—OCH$_3$ | H | bond | (3-Cl-4-benzyloxy)phenyl |
| 10 | (E)-CH=N—OCH$_2$CH$_3$ | H | bond | 1-(3-F-benzyl)indazol-5-yl |
| 11 | (E)-CH=N—OCH$_2$CH=CH$_2$ | H | bond | 1-(3-F-benzyl)indazol-5-yl |
| 12 | (E)-CH=N—O—C(CH$_3$)$_3$ | H | bond | 1-(3-F-benzyl)indazol-5-yl |

-continued

| Cpd | (*)-R$_4$ | R$_2$ | L | (R$_3$—R$_4$—R$_5$—R$_6$—R$_7$)Ar |
|---|---|---|---|---|
| 13 | (E)-CH=N—OCH$_3$ | H | bond | (3-CH$_3$-4-pyridin-3-yloxy)phenyl |
| 14 | (E)-CH=N—OCH$_2$CH$_3$ | H | —CH(R—CH$_3$)— | phenyl |
| 15 | (Z)—CH=N—OH | H | bond | 1-(3-F-benzyl)indazol-5-yl |
| 16 | (E)-CH=N—OCH$_2$CH$_3$ | H | —CH(S—CH$_3$)— | phenyl |
| 17 | (E)-CH=N—OCH$_3$ | H | bond | indol-5-yl |
| 18 | (E)-CH=N—OCH$_2$CH$_3$ | H | bond | [3-Cl-4-(3-F-benzyloxy)]phenyl |
| 19 | (E)-CH=N—O(CH$_2$)$_2$-morpholin-4-yl | H | bond | 1-(3-F-benzyl)indazol-5-yl |
| 20 | (E)-CH=N—OCH$_3$ | H | bond | indan-5-yl |
| 21 | (E)-CH=N—OCH$_3$ | H | bond | 4-OCHF$_2$-phenyl |
| 22 | (E)-CH=N—OCH$_3$ | H | bond | indazol-5-yl |
| 23 | (E)-CH=N—OCH$_3$ | H | bond | benzo[1,3]dioxol-5-yl |
| 24 | (E)-CH=N—OCH$_3$ | H | bond | (4-phenoxy)phenyl |
| 25 | (E)-CH=N—OCH$_3$ | H | bond | (4-benzyloxy)phenyl |
| 26 | (E)-CH=N—OCH$_3$ | H | bond | 4-CH(CH$_3$)CH$_2$CH$_3$-phenyl |
| 27 | (E)-CH=N—OCH$_3$ | H | bond | 4-C(CH$_3$)$_3$-phenyl |
| 28 | (E)-CH=N—OCH$_3$ | H | bond | (3-benzyloxy)phenyl |
| 29 | (E)-CH=N—OCH$_3$ | H | bond | [3-CH$_3$-4-(6-CH$_3$-pyridin-3-yloxy)]phenyl |
| 30 | (E)-CH=N—OCH$_2$CH(CH$_3$)$_2$ | H | bond | 1-(3-F-benzyl)indazol-5-yl |
| 31 | (E)-CH=N—O(CH$_2$)$_2$-phenoxy | H | bond | 1-(3-F-benzyl)indazol-5-yl |
| 32 | (E)-CH=N—OCH$_3$ | H | bond | (3-Cl-4-pyridin-2-yloxy)phenyl |
| 33 | (E)-CH=N—OCH$_2$CH$_3$ | H | bond | 1-(3-F-benzyl)indol-5-yl |
| 34 | (E)-CH=N—OCH$_3$ | H | bond | 1-(3-F-benzyl)indol-5-yl |
| 35 | (E)-CH=N—OCH$_3$ | H | —CH$_2$CF$_2$— | 6-CH$_3$-pyridin-2-yl |
| 36 | (E)-CH=N—OCH$_3$ | H | bond | 3-Br-phenyl |
| 37 | (E)-CH=N—OCH$_2$CH$_3$ | H | bond | (3-Cl-4-benzyloxy)phenyl |
| 38 | (E)-CH=N—OCH$_3$ | H | bond | (3-Cl-4-pyridin-3-yloxy)phenyl |
| 39 | (E)-CH=N—OCH$_3$ | CH$_3$ | bond | [3-Cl-4-(3-F-benzyloxy)]phenyl |
| 40 | (E)-CH=N—OCH$_3$ | CH$_2$CH$_3$ | bond | 1-(3-F-benzyl)indazol-5-yl |
| 41 | (E)-CH=N—OCH$_2$CH$_3$ | CH$_2$CH$_3$ | bond | 1-(3-F-benzyl)indazol-5-yl |
| 42 | (E)-CH=N—OCH$_3$ | CH$_2$CH$_3$ | bond | [3-Cl-4-(3-F-benzyloxy)]phenyl |
| 43 | (E)-CH=N—OCH$_2$CH$_3$ | CH$_2$CH$_3$ | bond | [3-Cl-4-(3-F-benzyloxy)]phenyl |
| 44 | (E)-CH=N—(4-OCH$_3$-benzyloxy) | H | bond | 1-(3-F-benzyl)indazol-5-yl |
| 45 | (E)-CH=N—(2-OCH$_3$-benzyloxy) | H | bond | 1-(3-F-benzyl)indazol-5-yl |
| 46 | (E)-CH=N—benzyloxy | H | bond | 1-(3-F-benzyl)indazol-5-yl |
| 47 | (E)-CH=N—OCH(CH$_3$)$_2$ | H | bond | 1-(3-F-benzyl)indazol-5-yl |
| 48 | (E)-CH=N—OCH$_3$ | H | bond | 1-benzyl-indazol-5-yl |
| 49 | (E)-CH=N—OCH$_2$CH$_3$ | H | bond | 1-benzyl-indazol-5-yl |
| 50 | (E)-CH=N—OCH$_3$ | H | bond | 1-(3-CN-benzyl)indazol-5-yl |
| 51 | (E)-CH=N—OCH$_2$CH$_3$ | H | bond | 1-(3-CN-benzyl)indazol-5-yl |
| 52 | (E)-CH=N—OCH$_2$CH$_3$ | H | bond | 2-benzyl-indazol-5-yl |
| 53 | (E)-CH=N—OCH$_3$ | CH$_3$ | bond | 1-(3-F-benzyl)indazol-5-yl |
| 54 | (E)-CH=N—OCH$_3$ | H | bond | 1-(3-Cl-benzyl)indazol-5-yl |
| 55 | (E)-CH=N—OCH$_2$CH$_3$ | H | bond | 1-(3-Cl-benzyl)indazol-5-yl |
| 56 | (E)-CH=N—OCH$_3$ | H | bond | 1-(3-OCH$_3$-benzyl)indazol-5-yl |
| 57 | (E)-CH=N—OCH$_2$CH$_3$ | H | bond | 1-(3-OCH$_3$-benzyl)indazol-5-yl |
| 58 | (E)-CH=N—OCH$_2$CH$_3$ | H | bond | 2-(3-F-benzyl)benzoimidazol-5-yl |
| 59 | (E)-CH=N—OCH$_3$ | H | bond | 3-Cl-phenyl |
| 60 | (E)-CH=N—OCH$_3$ | H | bond | 2-(3-F-benzyl)benzoimidazol-5-yl |
| 61 | (E)-CH=N—OCH$_3$ | H | bond | [3-OCH$_3$-4-(3-F-benzyloxy)]phenyl |
| 62 | (E)-CH=N—OCH$_2$CH$_3$ | H | bond | [3-OCH$_3$-4-(3-F-benzyloxy)]phenyl |
| 63 | (E)-CH=N—OCH$_3$ | H | bond | (3-Cl-4-OCH$_3$)phenyl |
| 64 | (E)-CH=N—OCH$_3$ | H | bond | (3-Cl-4-morpholin-4-yl)phenyl |
| 65 | (E)-CH=N—phenoxy | H | bond | 1-(3-F-benzyl)indazol-5-yl |
| 66 | (E)-CH=N—OCH$_3$ | H | bond | 1-(4-F-benzyl)indazol-5-yl |
| 67 | (E)-CH=N—OCH$_2$CH$_3$ | H | bond | 1-(4-F-benzyl)indazol-5-yl |
| 68 | (E)-CH=N—O(CH$_2$)$_2$OCH$_3$ | H | bond | 1-(3-F-benzyl)indazol-5-yl |
| 69 | (Z)—CH=N—O(CH$_2$)$_3$OH | H | bond | 1-(3-F-benzyl)indazol-5-yl |
| 70 | (E)-CH=N—O(CH$_2$)$_3$N(CH$_3$)$_2$ | H | bond | 1-(3-F-benzyl)indazol-5-yl |
| 71 | (E)-CH=N—O(CH$_2$)$_2$OCH$_3$ | H | bond | (3-Cl-4-benzyloxy)phenyl |
| 72 | (E)-CH=N—OCH$_3$ | H | bond | 2-(3-F-phenyl)benzofuran-5-yl |
| 73 | (E)-CH=N—OCH$_3$ | H | bond | 2-benzyl-benzofuran-5-yl |
| 74 | (E)-CH=N—OCH$_3$ | H | bond | 1-(3-F-benzyl)-2,3-dihydro-indol-5-yl |
| 75 | (E)-CH=N—O(CH$_2$)$_3$OH | H | bond | [3-Cl-4-(3-F-benzyloxy)]phenyl |
| 76 | (E)-CH=N—O(CH$_2$)$_3$OH | H | bond | (3-Cl-4-benzyloxy)phenyl |
| 77 | (E)-CH=N—OH | H | bond | (3-Cl-4-benzyloxy)phenyl |
| 78 | (E)-CH=N—O(CH$_2$)$_2$-morpholin-4-yl | H | bond | (3-Cl-4-benzyloxy)phenyl |
| 79 | (E)-CH=N—OH | H | bond | [3-Cl-4-(3-F-benzyloxy)]phenyl |
| 80 | (E)-CH=N—OCH$_3$ | H | bond | (2-F-4-Cl)phenyl |
| 81 | (Z)—CH=N—OCH$_3$ | H | bond | (2-F-4-Cl)phenyl |
| 82 | (E)-CH=N—OCH$_3$ | H | bond | (2-F-4-Br)phenyl |
| 83 | (Z)—CH=N—OCH$_3$ | H | bond | (2-F-4-Br)phenyl |
| 84 | (E)—CH=N—OH | H | bond | 1-(3-F-benzyl)indazol-5-yl |
| 85 | (E)-CH=N—O(CH$_2$)$_3$OH | H | bond | 1-(3-F-benzyl)indazol-5-yl |

-continued

| Cpd | (*)-R$_A$ | R$_2$ | L | (R$_3$—R$_4$—R$_5$—R$_6$—R$_7$)Ar |
|---|---|---|---|---|
| 86 | (E)-CH=N—OCH$_3$ | CH$_3$ | bond | (2-F-4-Br)phenyl |
| 87 | (E)-CH=N—O(CH$_2$)$_3$-morpholin-4-yl | H | bond | 1-(3-F-benzyl)indazol-5-yl |
| 88 | (E)-CH=N—OH | H | bond | 1-(3-F-benzyl)indol-5-yl |
| 89 | (E)-CH=N—OCH$_3$ | H | bond | (4-Cl-2-F-5-OH)phenyl |
| 90 | (Z)—CH=N—OCH$_3$ | H | bond | (4-Cl-2-F-5-OH)phenyl |
| 91 | (E)-CH=N—O(CH$_2$)$_3$OH | H | bond | 1-(3-F-benzyl)indol-5-yl |
| 92 | (E)-CH=N—O(CH$_2$)$_3$-piperidin-1-yl | H | bond | 1-(3-F-benzyl)indazol-5-yl |
| 93 | (E)-CH=N—O(CH$_2$)$_2$-morpholin-4-yl | H | bond | [3-Cl-4-(3-F-benzyloxy)]phenyl |
| 94 | (E)-CH=N—O(CH$_2$)$_2$-morpholin-4-yl | H | bond | [3-Cl-4-(3-F-benzyloxy)]phenyl |
| 95 | (E)-CH=N—O(CH$_2$)$_2$-piperidin-1-yl | H | bond | (3-Cl-4-benzyloxy)phenyl |
| 96 | (E)-CH=N—O(CH$_2$)$_2$-piperidin-1-yl | H | bond | [1-(3-F-benzyl)]indazol-5-yl |
| 97 | (E)-CH=N—OCH$_3$ | H | bond | [3-Cl-4-(3,5-F$_2$-benzyloxy)]phenyl |
| 98 | (E)-CH=N—OH | H | bond | [3-Cl-4-(3,5-F$_2$-benzyloxy)]phenyl |
| 99 | (E)-CH=N—O(CH$_2$)$_2$-morpholin-4-yl | H | bond | [3-Cl-4-(3,5-F$_2$-benzyloxy)]phenyl |
| 100 | (E)-CH=N—OH | H | —CH(S—CH$_3$)— | phenyl |
| 101 | (E)-CH=N—O(CH$_2$)$_2$-morpholin-4-yl | H | bond | 1-(3-F-benzyl)indol-5-yl |
| 102 | (E)-CH=N—O(CH$_2$)$_2$-piperidin-1-yl | H | bond | 1-(3-F-benzyl)indol-5-yl |
| 103 | (E)-CH=N—O(CH$_2$)$_2$-morpholin-4-yl | H | —CH(S—CH$_3$)— | phenyl |
| 104 | (E)-CH=N—OCH$_3$ | H | bond | [4-NHC(O)-phenyl]phenyl |
| 105 | (E)-CH=N—OH | H | bond | [4-NHC(O)-phenyl]phenyl |
| 106 | (E)-CH=N—O(CH$_2$)$_2$-piperidin-1-yl | H | —CH(S—CH$_3$)— | phenyl |
| 107 | (E)-CH=N—O(CH$_2$)$_2$-morpholin-4-yl | H | bond | [4-NHC(O)-phenyl]phenyl |
| 108 | (E)-CH=N—O(CH$_2$)$_2$-morpholin-4-yl | H | bond | (3-Cl-4-F)phenyl |
| 109 | (E)-CH=N—O(CH$_2$)$_2$-morpholin-4-yl | H | bond | (4-phenoxy)phenyl |
| 110 | (E)-CH=N—OCH$_3$ | H | bond | [2-NHC(O)-phenyl]pyrimidin-5-yl |
| 111 | (E)-CH=N—OH | H | bond | (4-phenoxy)phenyl |
| 112 | (E)-CH=N—O(CH$_2$)$_3$-morpholin-4-yl | H | bond | (3-Cl-4-benzyloxy)phenyl |
| 113 | (E)-CH=N—OCH$_2$)$_3$O—SO$_2$CH$_3$ | H | bond | (3-Cl-4-benzyloxy)phenyl |
| 114 | (E)-CH=N—OCH$_2$-pyridin-2-yl | H | bond | (3-Cl-4-benzyloxy)phenyl |
| 115 | (E)-CH=N—O(CH$_2$)$_3$—NH(CH$_2$)$_2$—OCH$_3$ | H | bond | (3-Cl-4-benzyloxy)phenyl |
| 116 | (E)-CH=N—O(CH$_2$)$_3$-(4-OH-piperidin-1-yl) | H | bond | (3-Cl-4-benzyloxy)phenyl |
| 117 | (E)-CH=N—OCH$_2$-(1-C(O)O—C(CH$_3$)$_3$-piperidin-4-yl) | H | bond | (3-Cl-4-benzyloxy)phenyl |
| 118 | CN | H | bond | (3-Cl-4-benzyloxy)phenyl |
| 119 | (E)-CH=N—CH$_2$-benzo[1,3]dioxol-5-yl | H | —CH$_2$— | benzo[1,3]dioxol-5-yl |
| 120 | (E)-CH=N—OCH$_3$ | H | bond | (4-OCH$_3$)phenyl |
| 121 | (E)-CH=N—OCH$_3$ | H | —CH$_2$— | benzo[1,3]dioxol-5-yl |
| 122 | (E)-CH=N—OCH$_3$ | H | bond | [3,4-OCH$_3$)$_2$]benzyl |
| 123 | (E)-CH=N—OCH$_3$ | H | bond | (4-phenoxy)benzyl |
| 124 | (E)-CH=N—OCH$_3$ | H | bond | (1R)-indan-1-yl |
| 125 | (E)-CH=N—OCH$_3$ | H | bond | 1,2,3,4-tetrahydro-naphthalen-1-yl |
| 126 | (E)-CH=N—OCH$_3$ | H | —CH(CH$_3$)— | (4-Cl)phenyl |
| 127 | (E)-CH=N—OCH$_3$ | H | —CH[(S)—CH$_3$)]— | (4-OCH$_3$)phenyl |
| 128 | (E)-CH=N—OCH$_3$ | H | bond | (2-phenoxy)pyridin-5-yl |
| 129 | (E)-CH=N—OCH$_3$ | H | bond | (2-morpholin-4-yl)pyridin-5-yl |
| 130 | (E)-CH=N—OCH$_3$ | H | bond | 1,4-dioxo-1,2,3,4-tetrahydro-phthalazin-5-yl |
| 131 | (E)-CH=N—OCH$_3$ | H | bond | (2-F-5-CH$_3$)phenyl |
| 132 | (E)-CH=N—OCH$_3$ | H | bond | [2,4,6-(CH$_3$)$_3$]phenyl |
| 133 | (E)-CH=N—OCH$_3$ | H | bond | (2-CH$_3$-3-Cl)phenyl |
| 134 | (E)-CH=N—OCH$_3$ | H | bond | (3-SCH$_3$)phenyl |
| 135 | (E)-CH=N—OCH$_3$ | H | bond | [3-C(CH$_3$)=N(OCH$_3$)]phenyl |
| 136 | (E)-CH=N—OCH$_3$ | H | bond | [3,5-(CH$_3$)$_2$]phenyl |
| 137 | (E)-CH=N—OCH$_3$ | H | bond | [4-NHC(O)CH$_3$]phenyl |
| 138 | (E)-CH=N—OCH$_3$ | H | bond | phenyl |
| 139 | (E)-CH=N—OCH$_3$ | H | bond | (4-morpholin-4-yl)phenyl |
| 140 | (E)-CH=N—OCH$_3$ | H | bond | (2-CH$_3$)phenyl |
| 141 | (E)-CH=N—OCH$_3$ | H | bond | (3,4-F$_2$)phenyl |
| 142 | (E)-CH=N—OCH$_3$ | H | bond | (3-F-4-CH$_3$)phenyl |
| 143 | (E)-CH=N—OCH$_3$ | H | bond | (3,4-Cl$_2$)phenyl |
| 144 | (E)-CH=N—OCH$_3$ | H | bond | (3-Cl-4-CH$_3$)phenyl |
| 145 | (E)-CH=N—OCH$_3$ | H | bond | {2-CH$_3$-4-[CH$_2$C(O)-phenyl]-5-Cl}phenyl |
| 146 | (E)-CH=N—OCH$_3$ | H | bond | (3-CH$_2$CH$_3$)phenyl |
| 147 | (E)-CH=N—OCH$_3$ | H | bond | [4-CH(CH$_3$)$_2$]phenyl |
| 148 | (E)-CH=N—OCH$_3$ | H | bond | indazol-5-yl |
| 149 | (E)-CH=N—OCH$_3$ | H | bond | (3-CF$_3$)phenyl |
| 150 | (E)-CH=N—OCH$_3$ | H | bond | (3-CH$_3$)phenyl |
| 151 | (E)-CH=N—OCH$_3$ | H | bond | (4-Cl)phenyl |

-continued

| Cpd | (*)-R$_4$ | R$_2$ | L | (R$_3$—R$_4$—R$_5$—R$_6$—R$_7$)Ar |
|---|---|---|---|---|
| 152 | (E)-CH=N—OCH$_3$ | H | bond | (2-CH$_3$-4-Cl)phenyl |
| 153 | (E)-CH=N—OCH$_3$ | H | bond | (4-NH-phenyl)phenyl |
| 154 | (E)-CH=N—OCH$_3$ | H | bond | [4-N(CH$_2$CH$_3$)$_2$]phenyl |
| 155 | (E)-CH=N—OCH$_3$ | H | bond | [4-C(O)OCH$_3$]phenyl |
| 156 | (E)-CH=N—OCH$_3$ | H | bond | [4-C(phenyl)=N(OCH$_3$)]phenyl |
| 157 | (E)-CH=N—OCH$_3$ | H | bond | [4-C(O)CH$_3$]phenyl |
| 158 | (E)-CH=N—OCH$_3$ | H | bond | [4-C(CH$_3$)=N(OCH$_3$)]phenyl |
| 159 | (E)-CH=N—OCH$_3$ | H | bond | (4-CH$_2$CN)phenyl |
| 160 | (E)-CH=N—OCH$_3$ | H | bond | [2-OCH$_3$-4-(NH-phenyl)]phenyl |
| 161 | (E)-CH=N—OCH$_3$ | H | bond | [2-OCH$_3$-4-NHC(O)CH$_3$]phenyl |
| 162 | (E)-CH=N—OCH$_3$ | H | bond | (4-cyclohexyl)phenyl |
| 163 | (E)-CH=N—OCH$_3$ | H | bond | naphthalen-1-yl |
| 164 | (E)-CH=N—OCH$_3$ | H | bond | (4-Cl)naphthalen-1-yl |
| 165 | (E)-CH=N—OCH$_3$ | H | bond | (2,4-F$_2$)phenyl |
| 166 | (E)-CH=N—OCH$_3$ | H | bond | (2-SCH$_3$)phenyl |
| 167 | (E)-CH=N—OCH$_3$ | H | bond | (3-F)phenyl |
| 168 | (E)-CH=N—OCH$_3$ | H | bond | (2-CH$_3$-5-F)phenyl |
| 169 | (E)-CH=N—OCH$_3$ | H | bond | (3,5-Cl$_2$)phenyl |
| 170 | (E)-CH=N—OCH$_3$ | H | bond | (2-OCH$_3$-5-Cl)phenyl |
| 171 | (E)-CH=N—OCH$_3$ | H | bond | (2-CH$_3$-5-Cl)phenyl |
| 172 | (E)-CH=N—OCH$_3$ | H | bond | (4-F)phenyl |
| 173 | (E)-CH=N—OCH$_3$ | H | bond | biphenyl |
| 174 | (E)-CH=N—OCH$_3$ | H | bond | (4-SCH$_3$)phenyl |
| 175 | (E)-CH=N—OCH$_3$ | H | bond | [3,5-(OCH$_3$)$_2$]phenyl |
| 176 | (E)-CH=N—OCH$_3$ | H | bond | [3,4,5-(OCH$_3$)$_3$]phenyl |
| 177 | (E)-CH=N—OCH$_3$ | H | bond | [3,4-(OCH$_3$)$_2$]phenyl |
| 178 | (E)-CH=N—OCH$_3$ | H | bond | 5,6,7,8-tetrahydro-naphthalen-1-yl |
| 179 | (E)-CH=N—OCH$_3$ | H | bond | (4-SO$_2$NH-pyrimidin-2-yl)phenyl |
| 180 | (E)-CH=N—OCH$_3$ | H | bond | [3-C(O)OCH$_2$CH$_3$]phenyl |
| 181 | (E)-CH=N—OCH$_3$ | H | bond | [4-CH$_2$P(=O)—(OCH$_2$CH$_3$)$_2$]phenyl |
| 182 | (E)-CH=N—OCH$_3$ | H | bond | (4-CH$_2$CH$_3$)phenyl |
| 183 | (E)-CH=N—OCH$_3$ | H | bond | (4-{SO$_2$NH-[3,5-(CH$_3$)$_2$-pyrazin-2-yl]})phenyl |
| 184 | (E)-CH=N—OCH$_3$ | H | bond | (2-CH$_3$)benzothiazol-5-yl |
| 185 | (E)-CH=N—OCH$_3$ | H | bond | [4-NH-(4-OCH$_3$-phenyl)]phenyl |
| 186 | (E)-CH=N—OCH$_3$ | H | bond | [4-N(CH$_3$)$_2$]phenyl |
| 187 | (E)-CH=N—OCH$_3$ | H | bond | [4-C(O)NH(CH$_2$)$_2$—N(CH$_2$CH$_3$)$_2$]phenyl |
| 188 | (E)-CH=N—OCH$_3$ | H | bond | [4-C(O)O(CH$_2$)$_3$CH$_3$]phenyl |
| 189 | (E)-CH=N—OCH$_3$ | H | bond | indan-4-yl |
| 190 | (E)-CH=N—OCH$_3$ | H | bond | (4'-Cl)biphenyl |
| 191 | (E)-CH=N—OCH$_3$ | H | bond | [2-(4-F-phenoxy)]pyridin-5-yl |
| 192 | (E)-CH=N—OCH$_3$ | H | bond | [4'-C(O)OCH$_3$]biphenyl |
| 193 | [5-(CH$_2$)$_2$-morpholin-4-yl]-[1,3,4]oxadiazol-2-yl | H | bond | (3-Cl-4-benzyloxy)phenyl |

Examples of a compound of Formula (I) include compounds selected from the group consisting of:

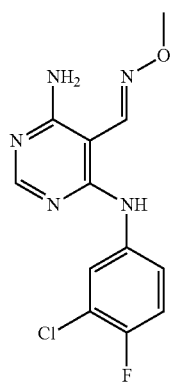

Cpd 1

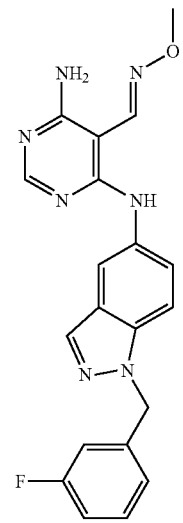

Cpd 2

Cpd 3
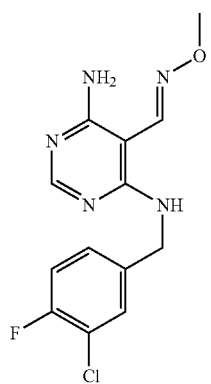
Cpd 4
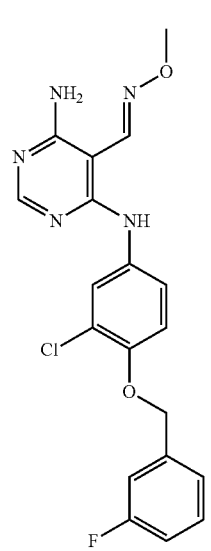
Cpd 5
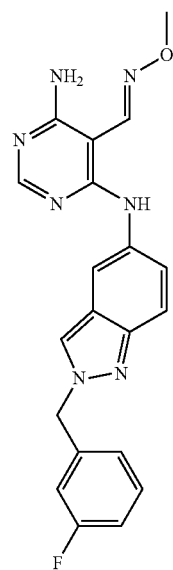
Cpd 6
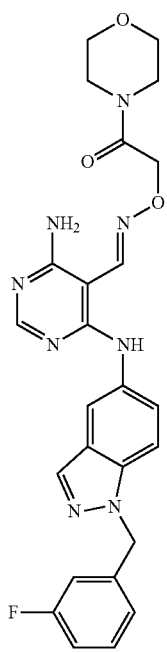
Cpd 7
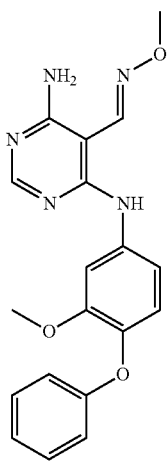

Cpd 8
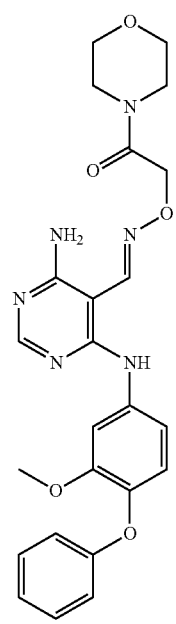
Cpd 9
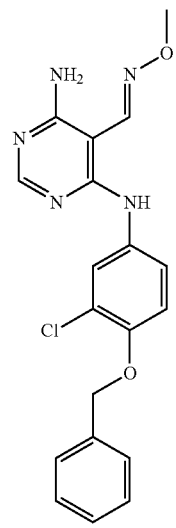
Cpd 10
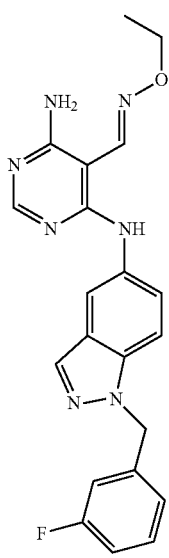
Cpd 11
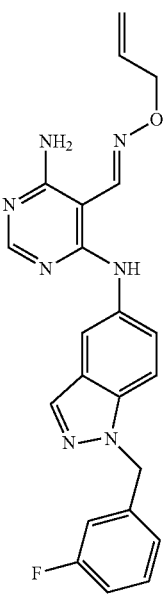

Cpd 12
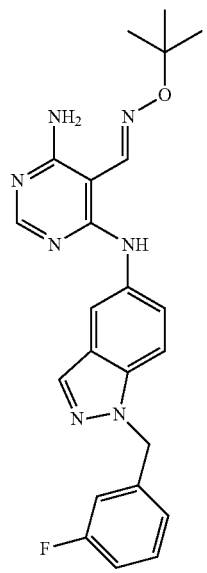
Cpd 15
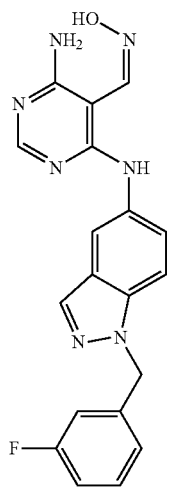
Cpd 13
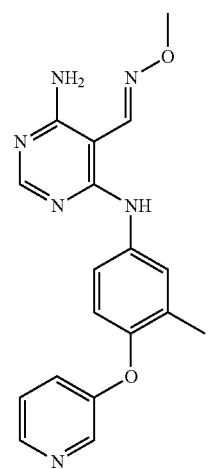
Cpd 16
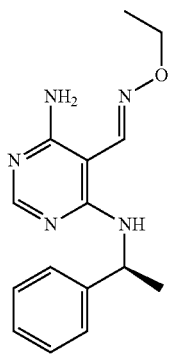
Cpd 14
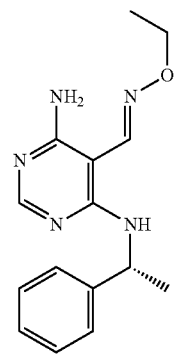
Cpd 17
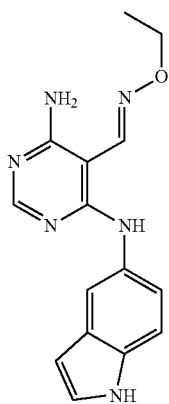

Cpd 18
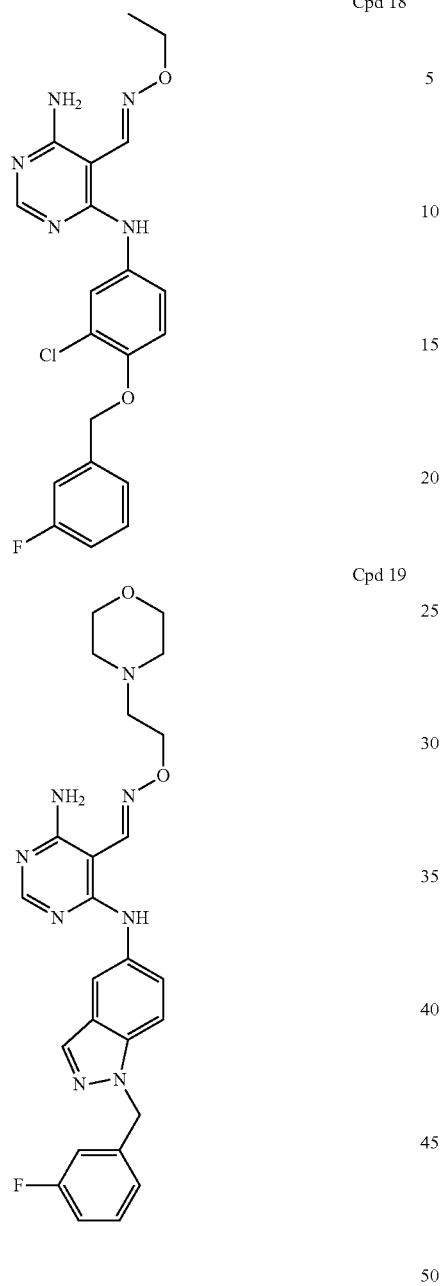
Cpd 19
Cpd 20
Cpd 21
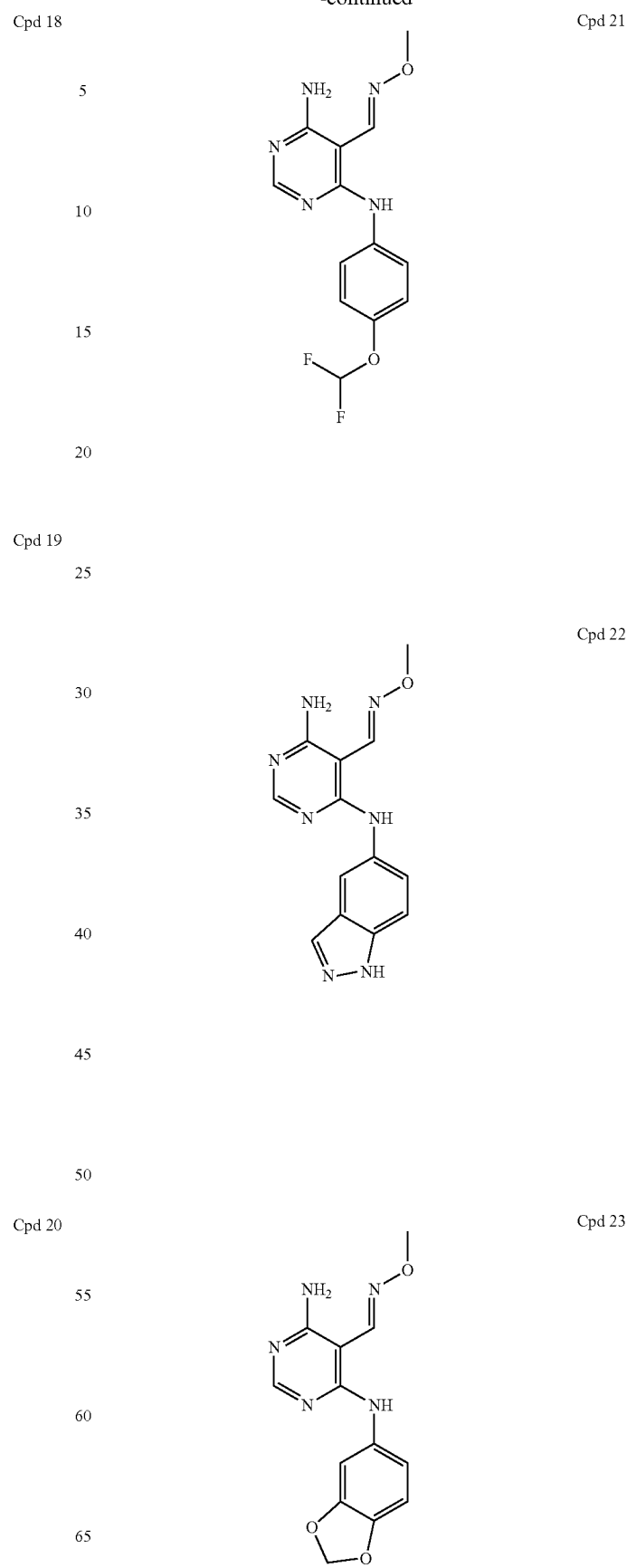
Cpd 22
Cpd 23

Cpd 24
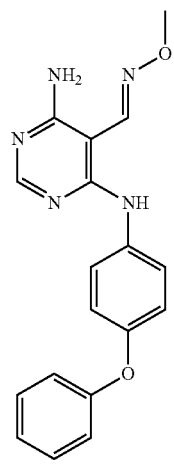
Cpd 25
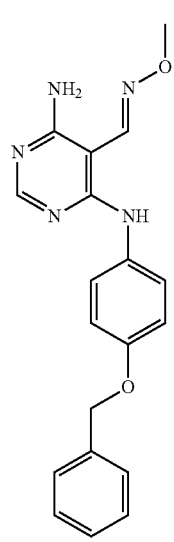
Cpd 26
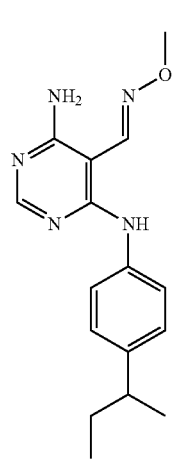
Cpd 27
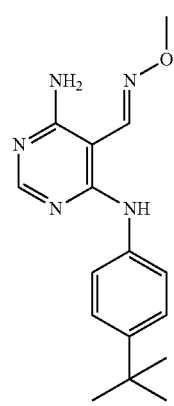
Cpd 28
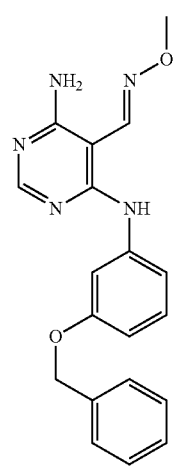
Cpd 29
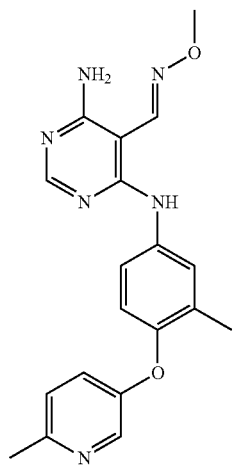

Cpd 30
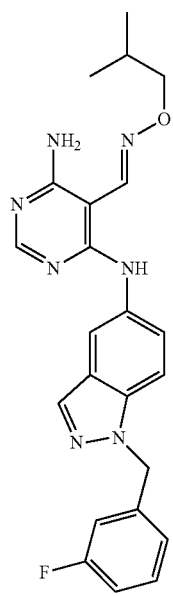
Cpd 31
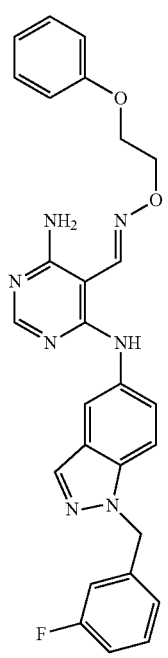
Cpd 32
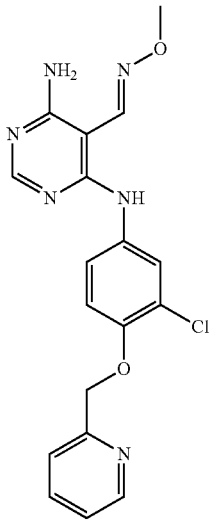
Cpd 33
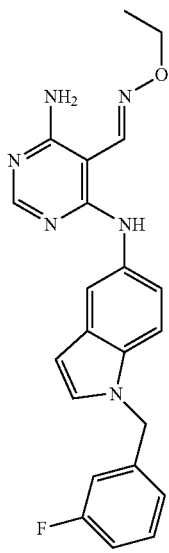
Cpd 34
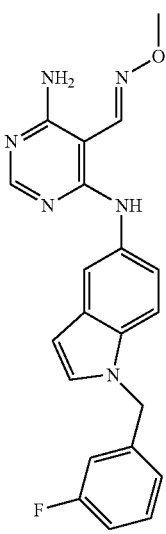

Cpd 35
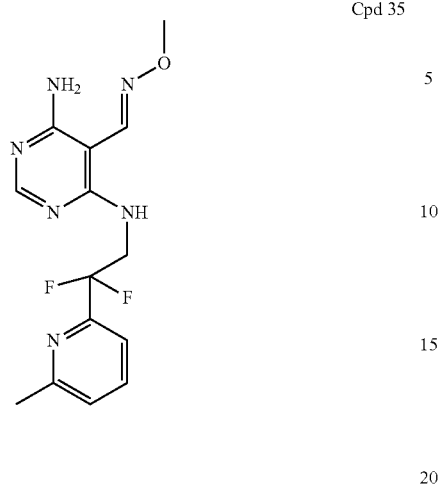
Cpd 38
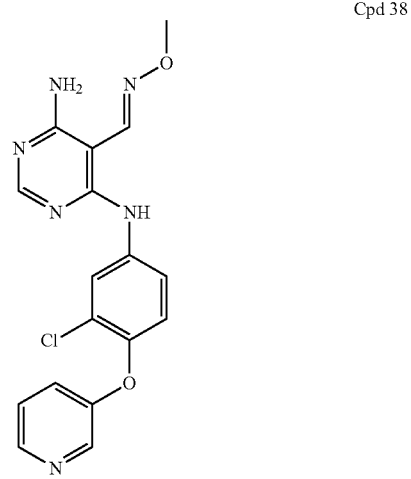
Cpd 36
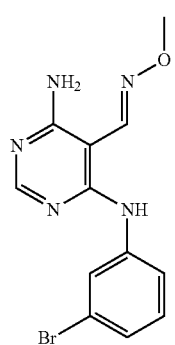
Cpd 39
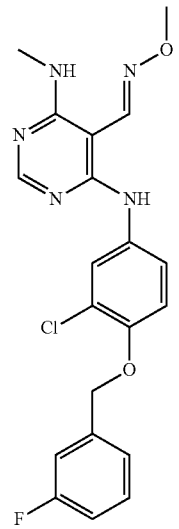
Cpd 37
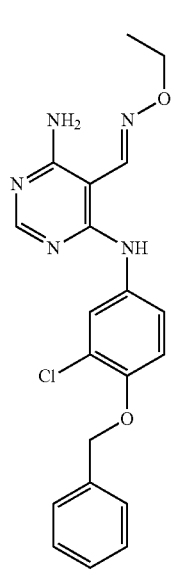
Cpd 40
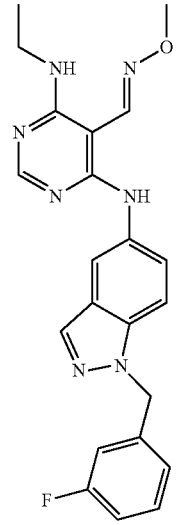

Cpd 41
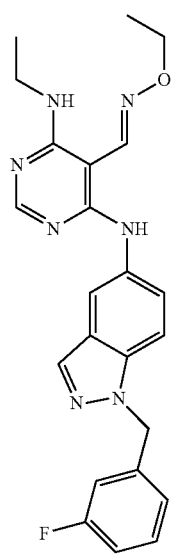
Cpd 42
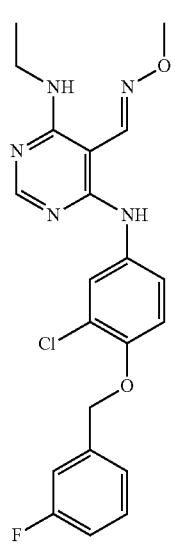
Cpd 43
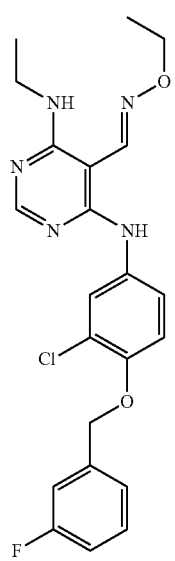
Cpd 44
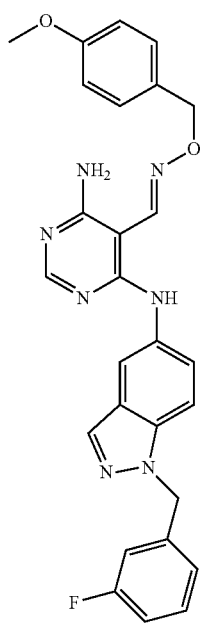
Cpd 45
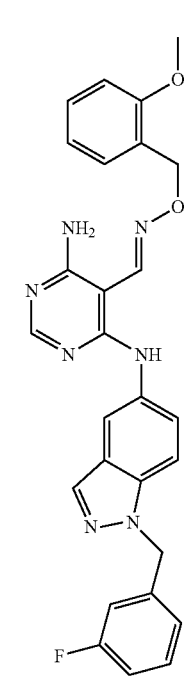

-continued
Cpd 46
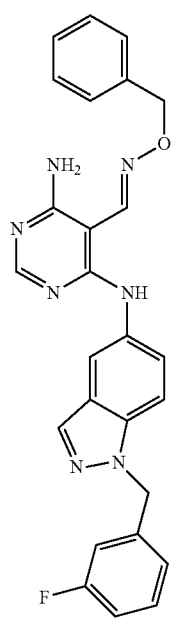
Cpd 47
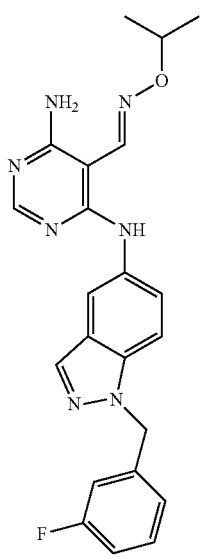
-continued
Cpd 48
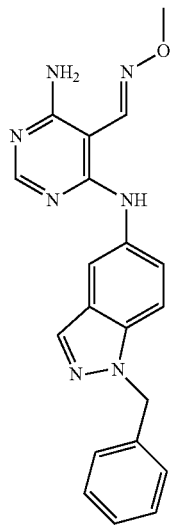
Cpd 49
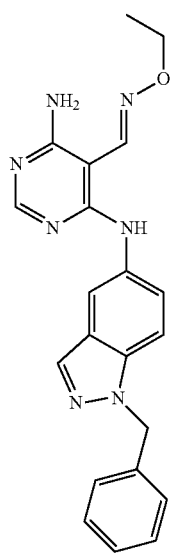
Cpd 50
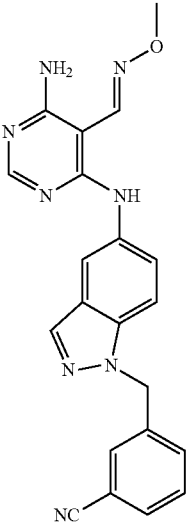

Cpd 51
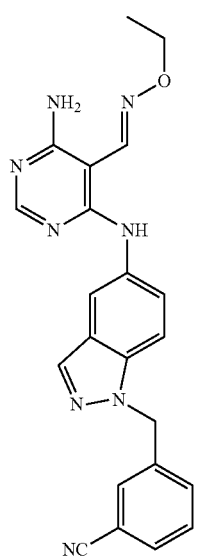
Cpd 52
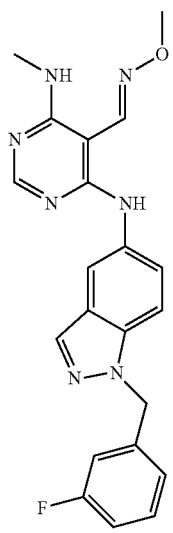
Cpd 53
Cpd 54
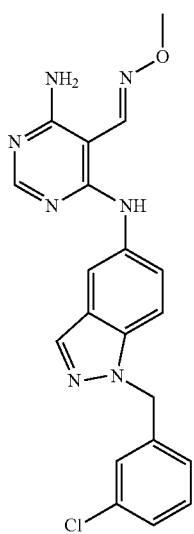
Cpd 55
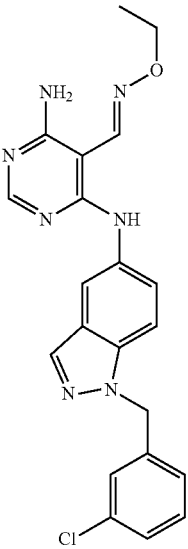

Cpd 56
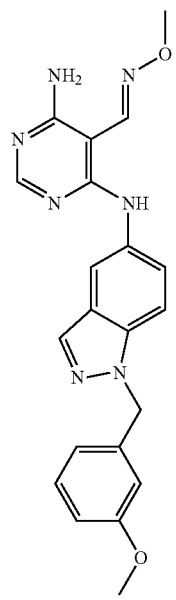
Cpd 57
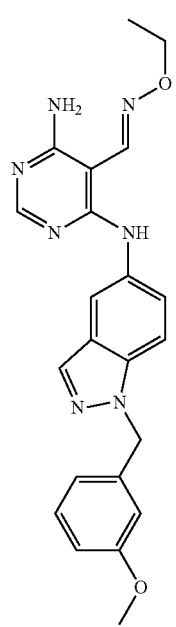
Cpd 58
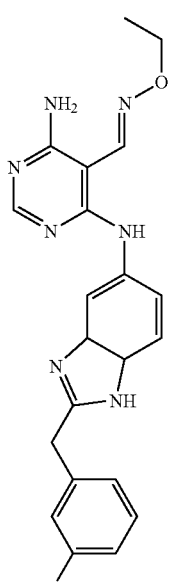
Cpd 59
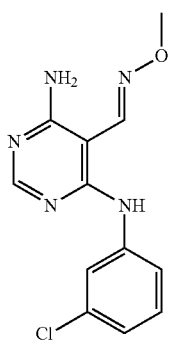
Cpd 60
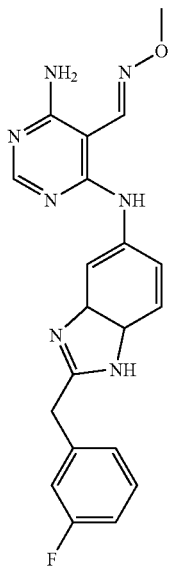

Cpd 61
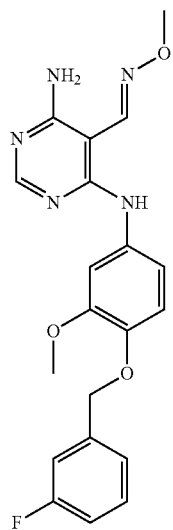
Cpd 62
Cpd 63
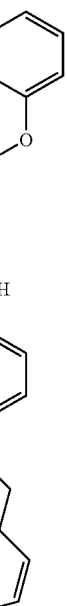
Cpd 64
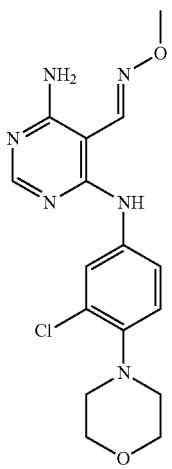
Cpd 65
Cpd 66
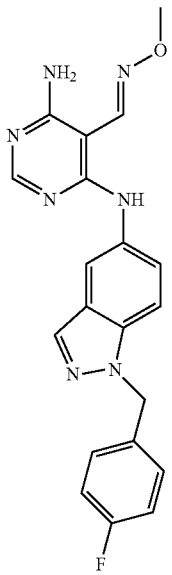

Cpd 67
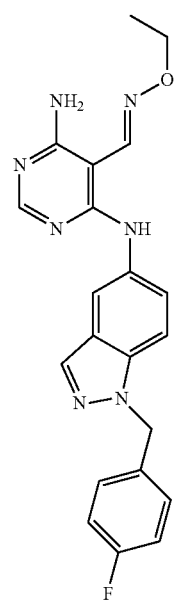
Cpd 68
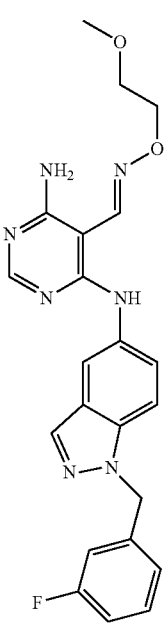
Cpd 69
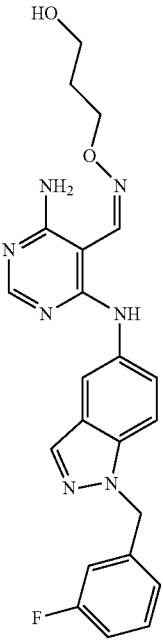
Cpd 70
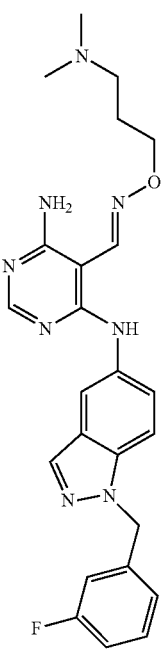

Cpd 71
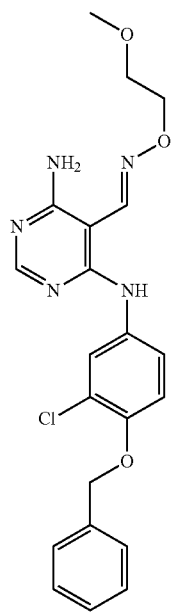
Cpd 72
Cpd 73
Cpd 74
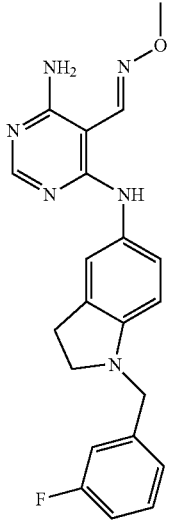
Cpd 75
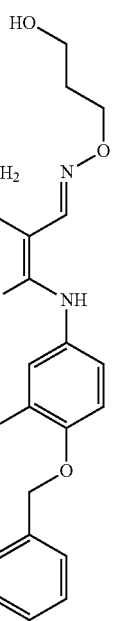

Cpd 76
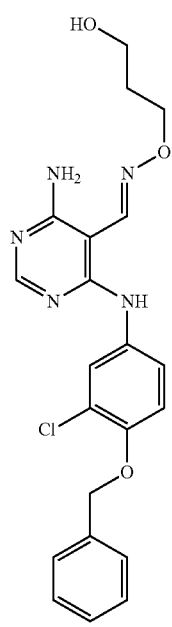
Cpd 77
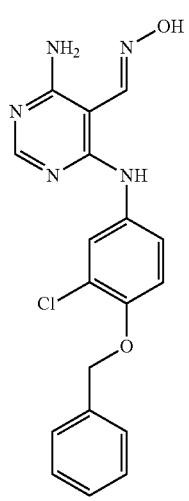
Cpd 78
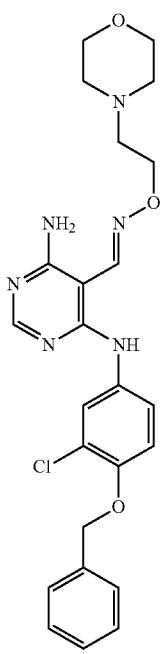
Cpd 79
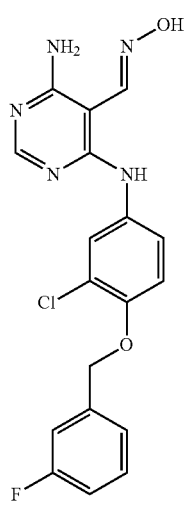
Cpd 80
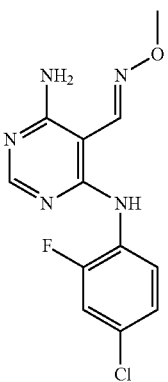

Cpd 81
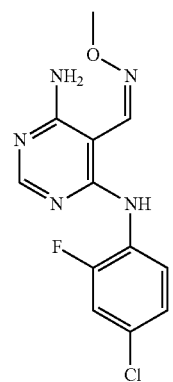
Cpd 82
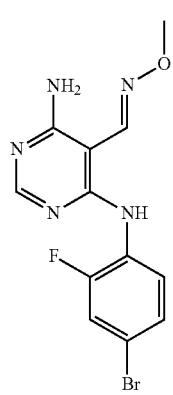
Cpd 83
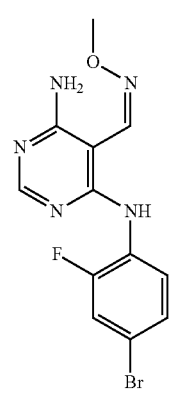
Cpd 84
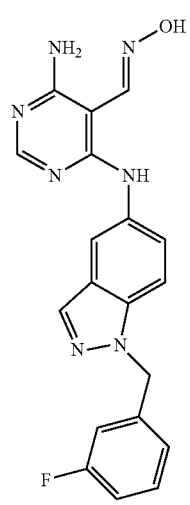
Cpd 85
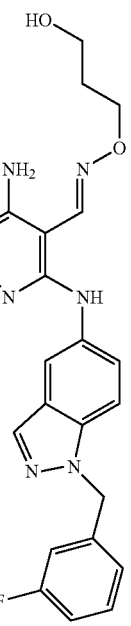
Cpd 86
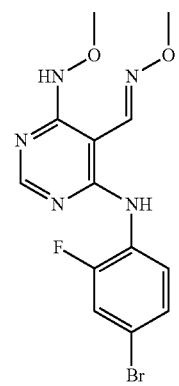
Cpd 87
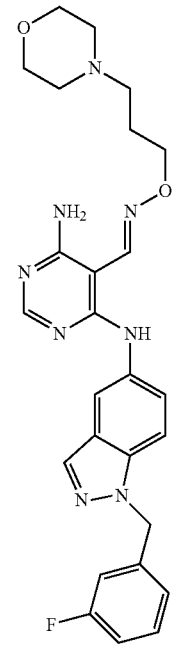

Cpd 88
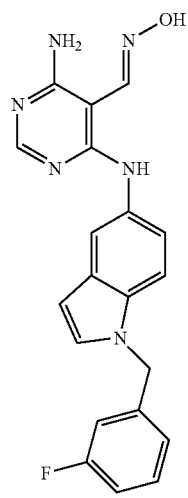
Cpd 89
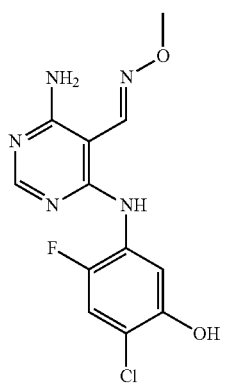
Cpd 90
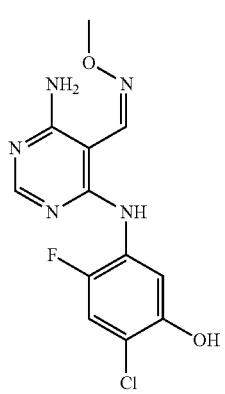
Cpd 91
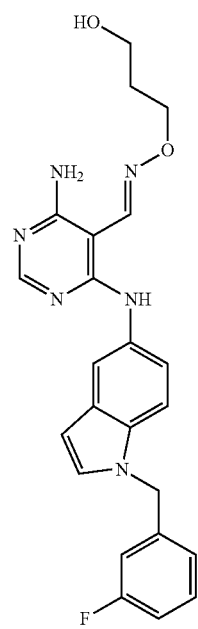
Cpd 92
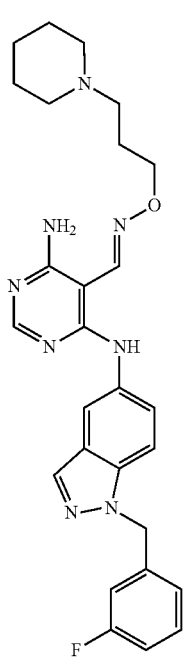

Cpd 93
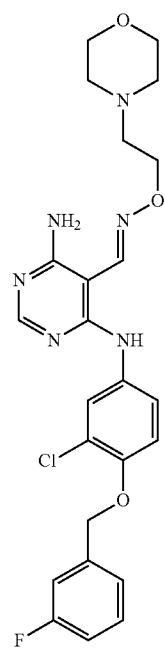
Cpd 94
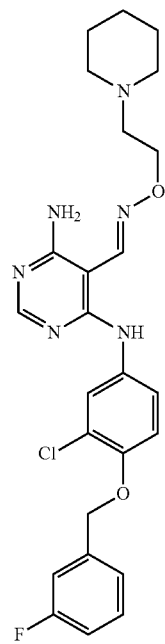
Cpd 95
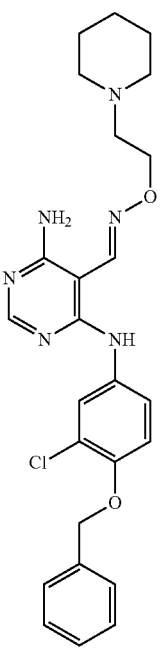
Cpd 96
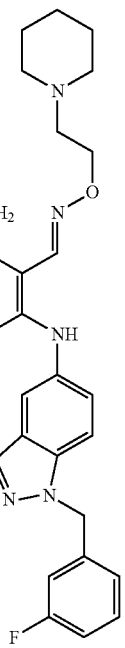

Cpd 97
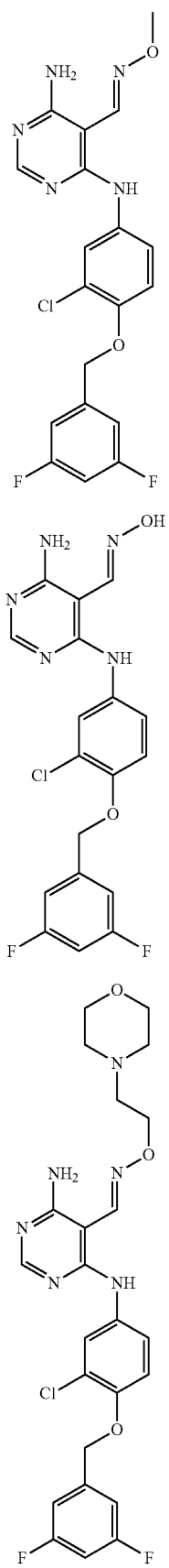
Cpd 98
Cpd 99
Cpd 100
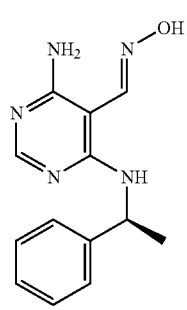
Cpd 101
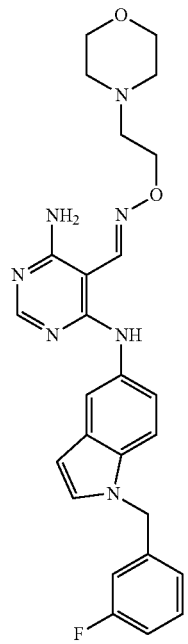
Cpd 102
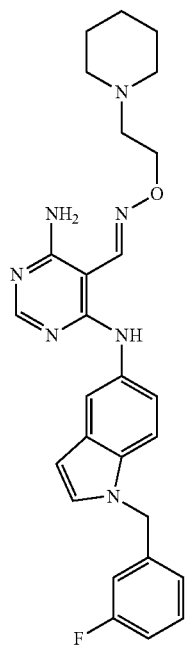

Cpd 103
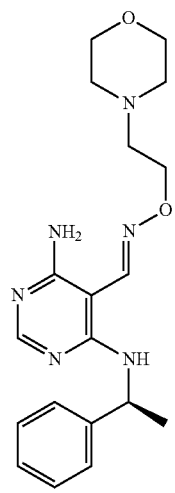
Cpd 104
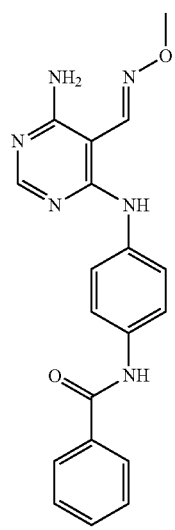
Cpd 105
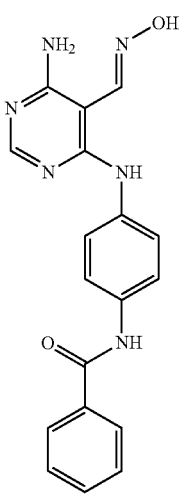
Cpd 106
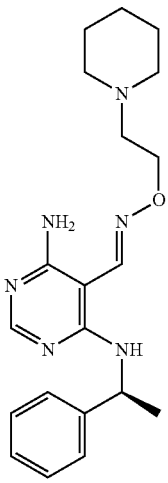
Cpd 107
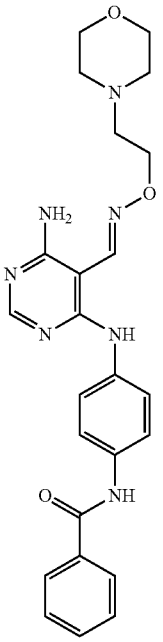
Cpd 108
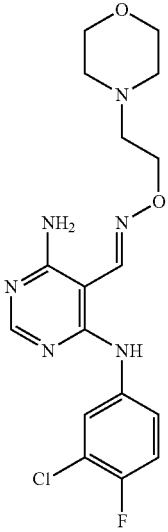

Cpd 109
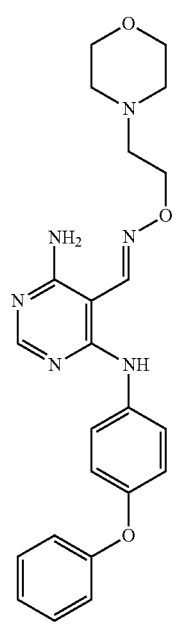
Cpd 110
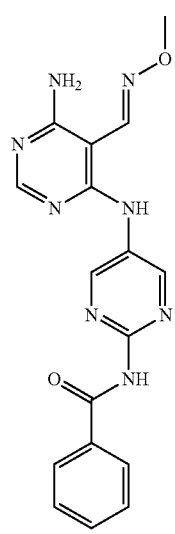
Cpd 111
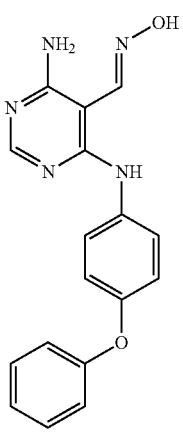
Cpd 112
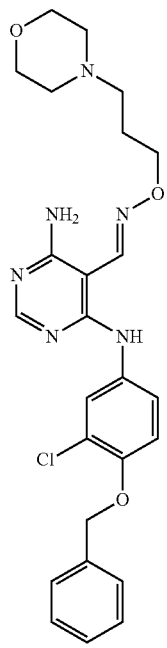
Cpd 113
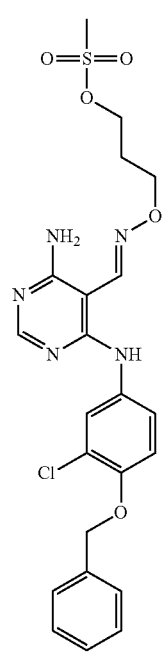

Cpd 114
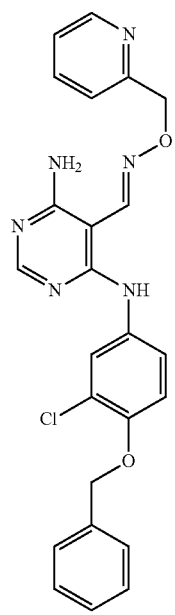
Cpd 115
Cpd 116
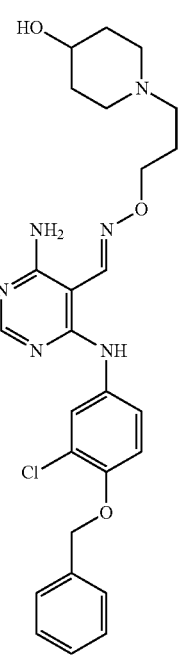
Cpd 117

Cpd 118
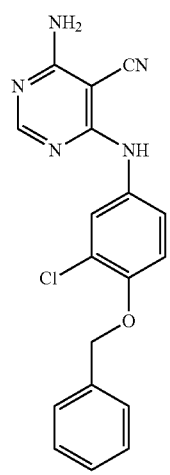
Cpd 119
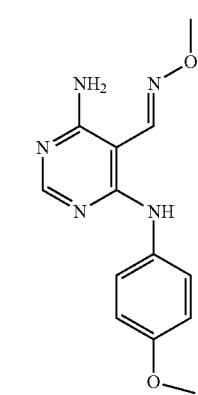
Cpd 120
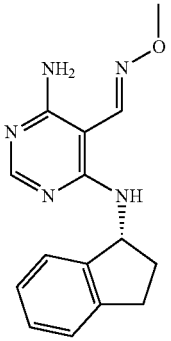
Cpd 121
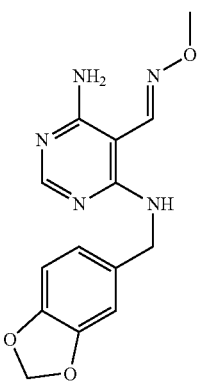
Cpd 122
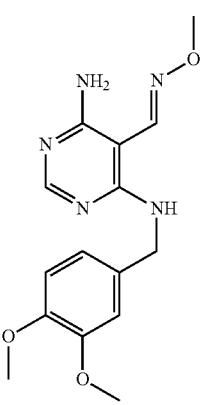
Cpd 123
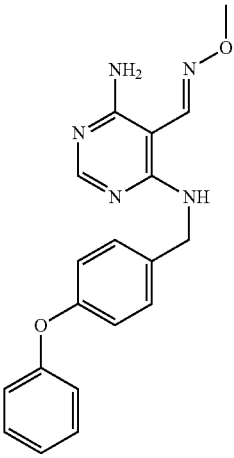
Cpd 124
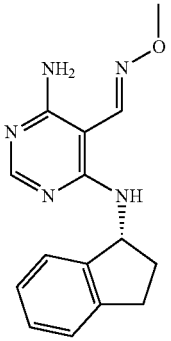

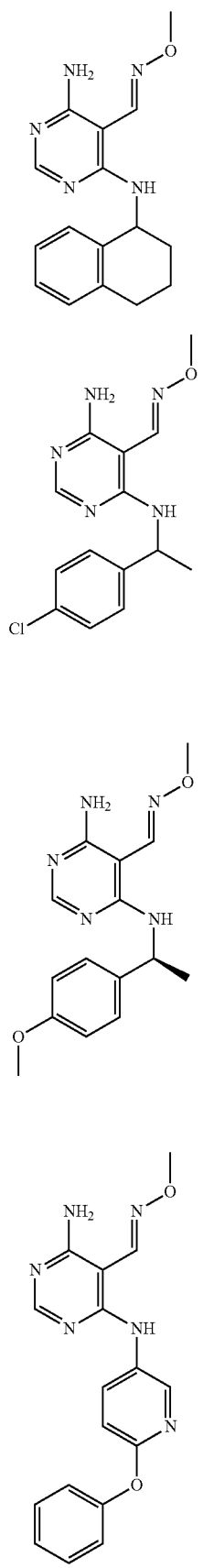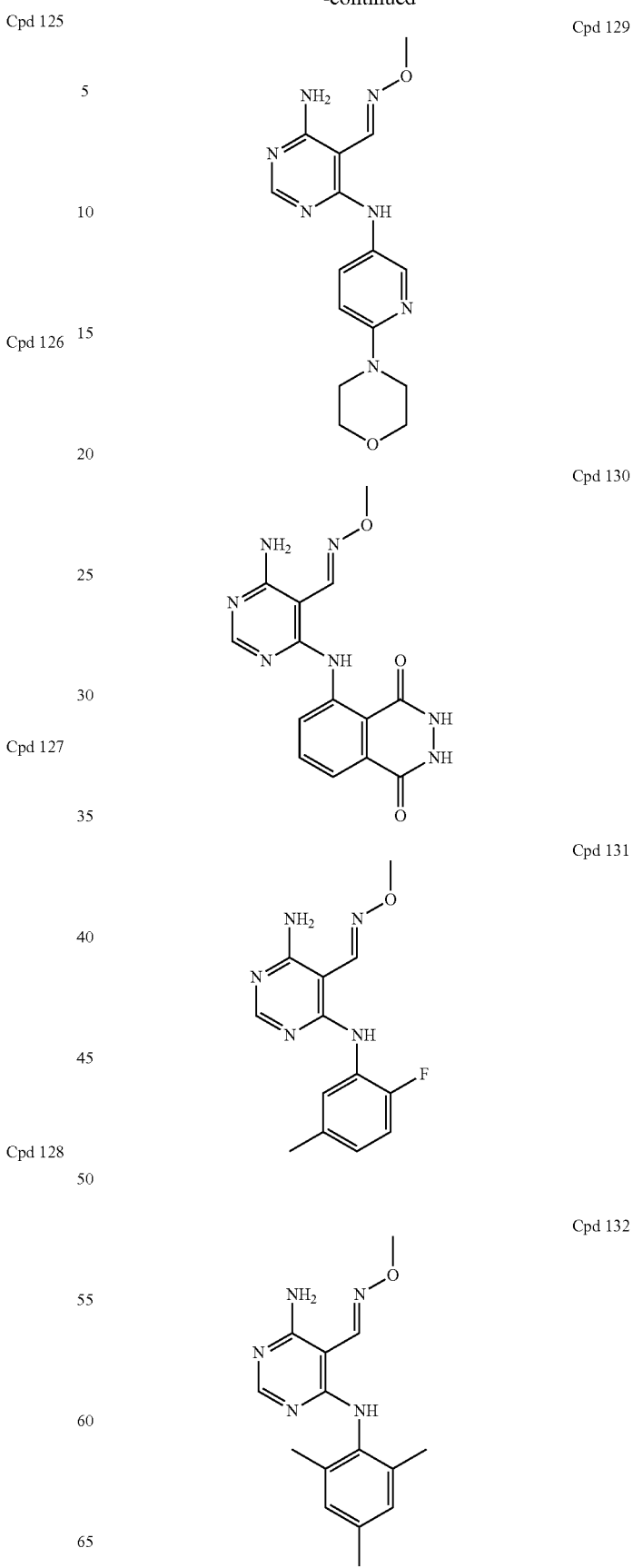

Cpd 133
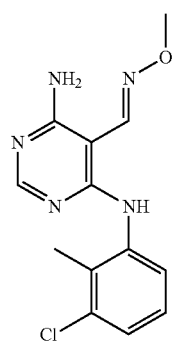
Cpd 134
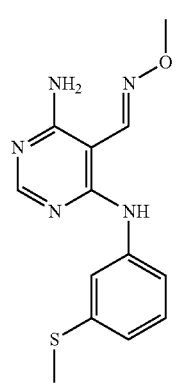
Cpd 135
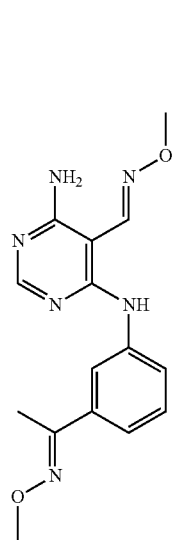
Cpd 136
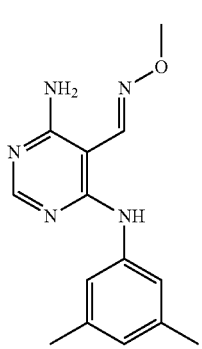
Cpd 137
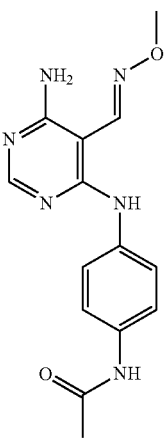
Cpd 138
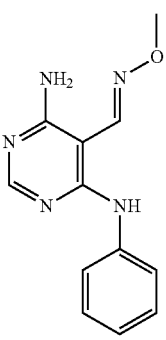
Cpd 139
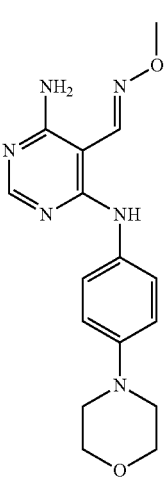
Cpd 140
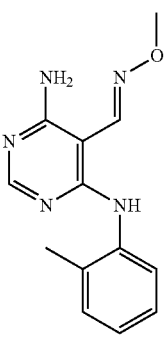

Cpd 141
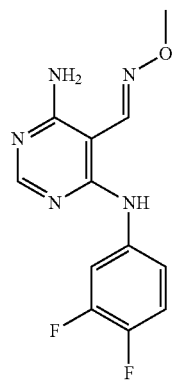
Cpd 142
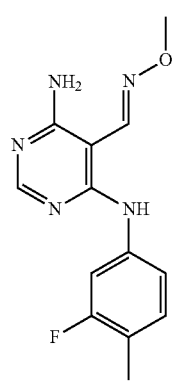
Cpd 143
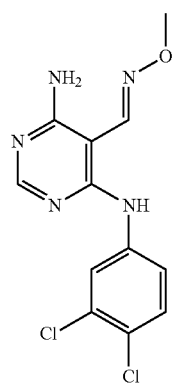
Cpd 144
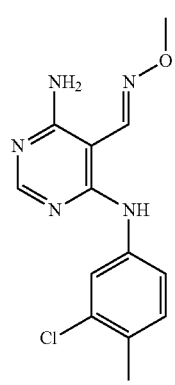
Cpd 145
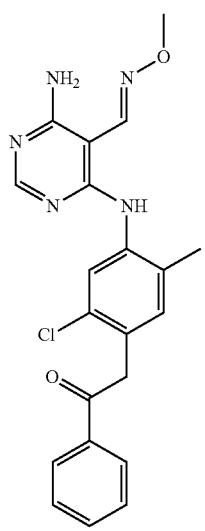
Cpd 146
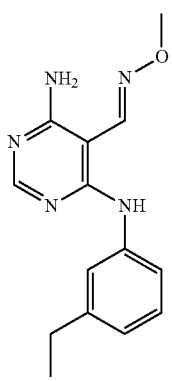
Cpd 147
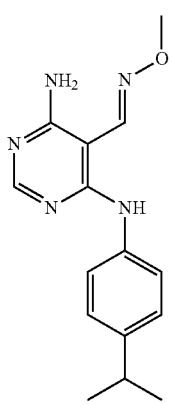

Cpd 148
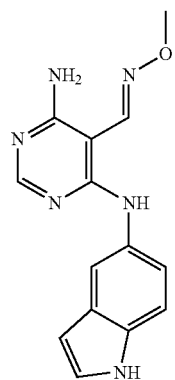
Cpd 149
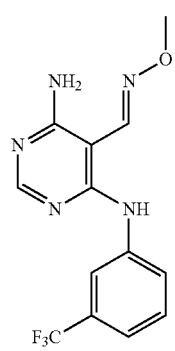
Cpd 150
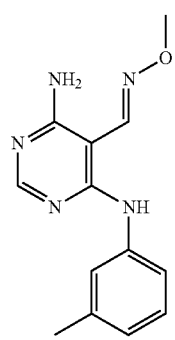
Cpd 151
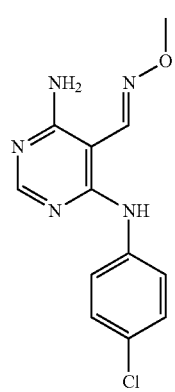
Cpd 152
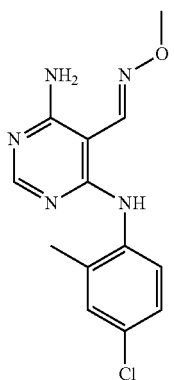
Cpd 153
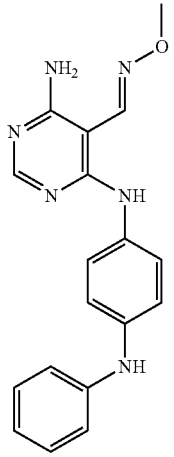
Cpd 154
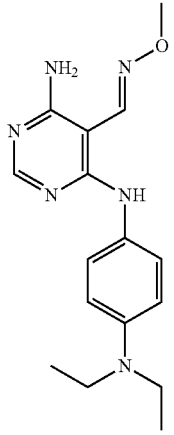

Cpd 155
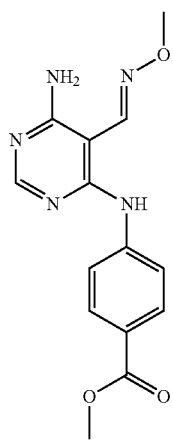
Cpd 156
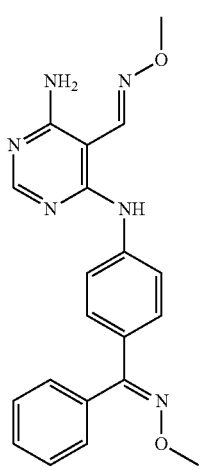
Cpd 157
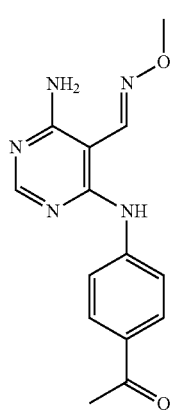
Cpd 158
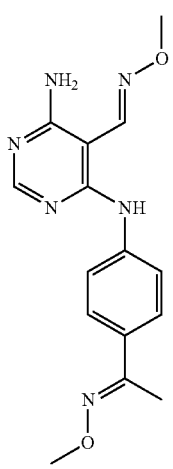
Cpd 159
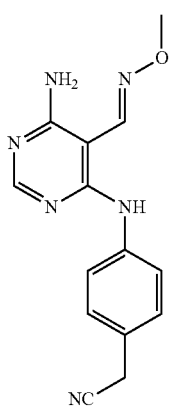
Cpd 160
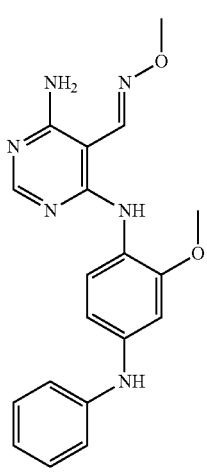

-continued
Cpd 161
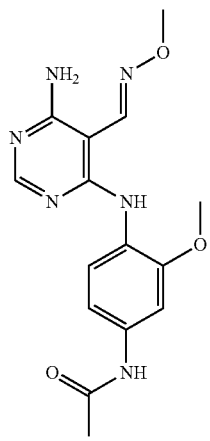
Cpd 162
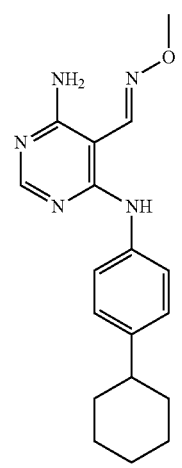
Cpd 163
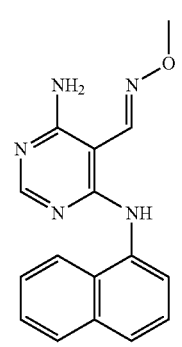
Cpd 164
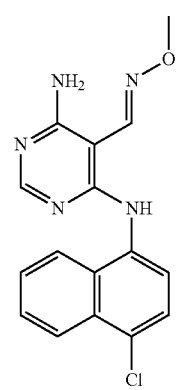
Cpd 165
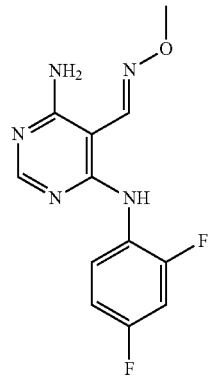
Cpd 166
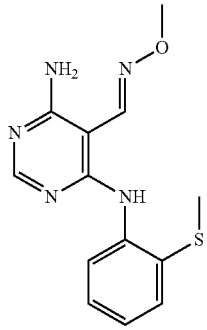
Cpd 167
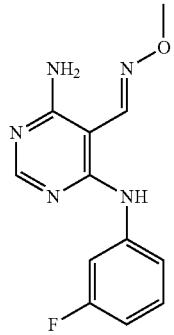
Cpd 168
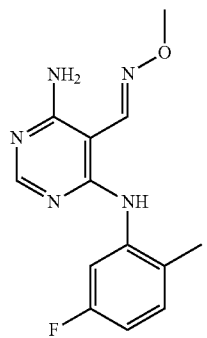

Cpd 169
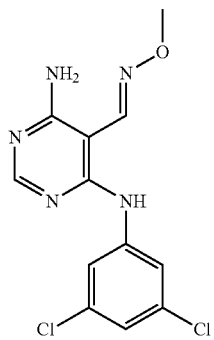
Cpd 170
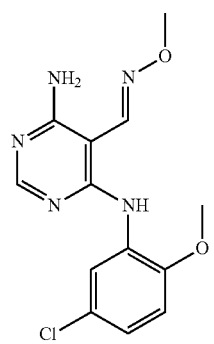
Cpd 171
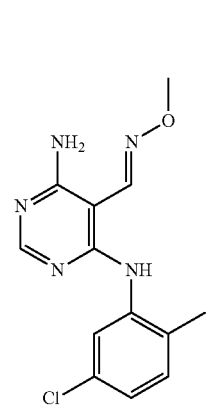
Cpd 172
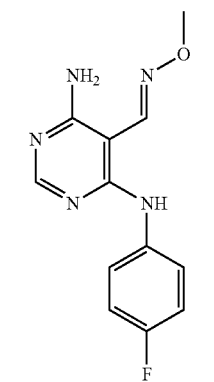
Cpd 173
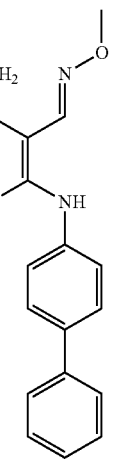
Cpd 174
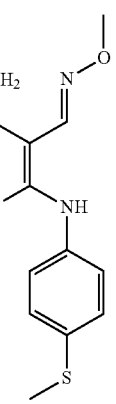
Cpd 175
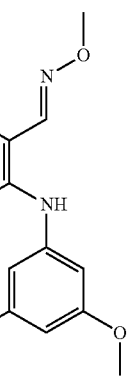
Cpd 176
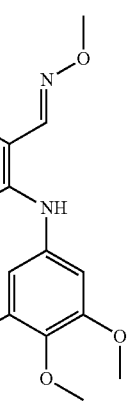

Cpd 177
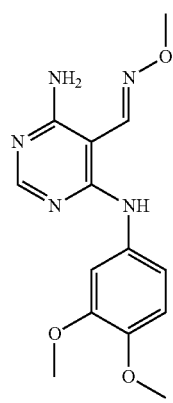
Cpd 178
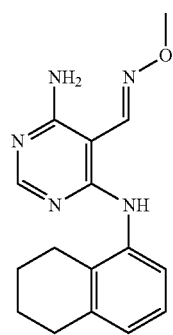
Cpd 179
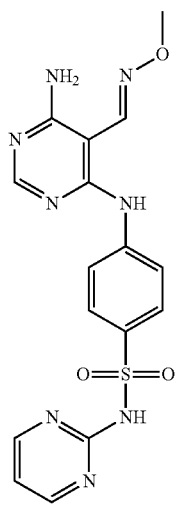
Cpd 180
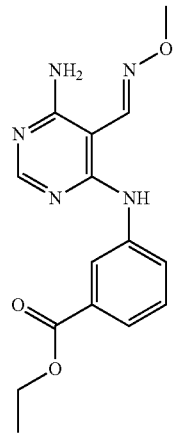
Cpd 181
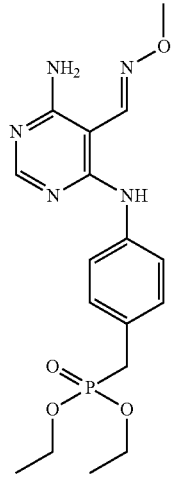
Cpd 182
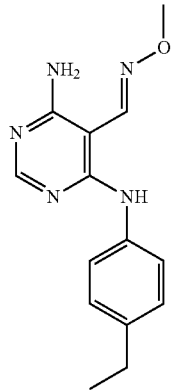

-continued
Cpd 183
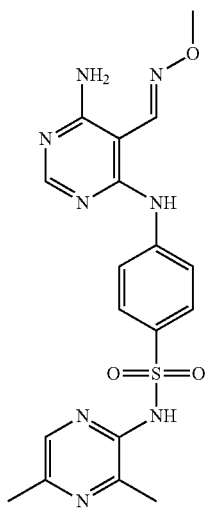
Cpd 184
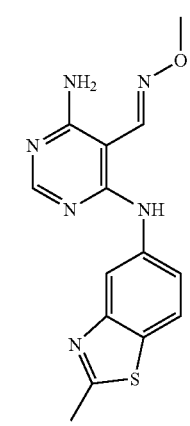
Cpd 185
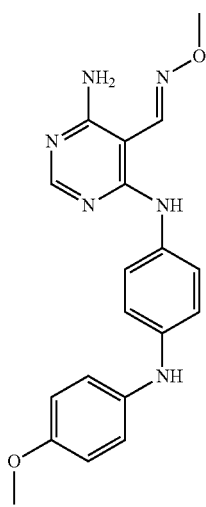
-continued
Cpd 186
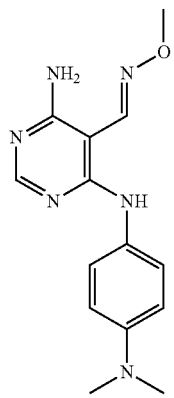
Cpd 187
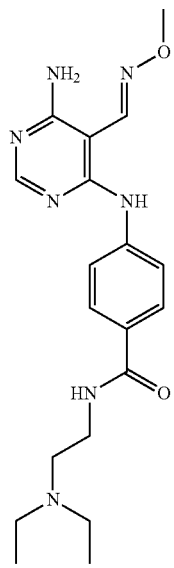
Cpd 188
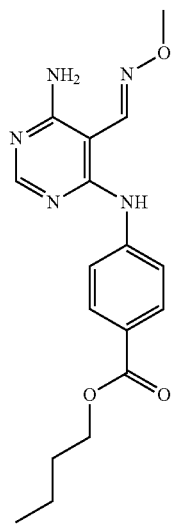

Cpd 189

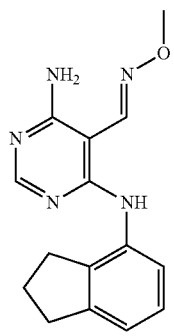

Cpd 190

Cpd 191

Cpd 192

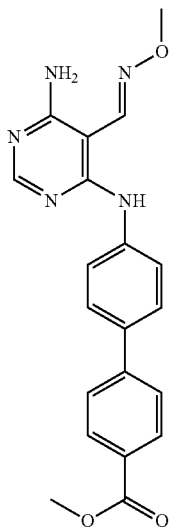

Cpd 193

Chemical Definitions & Nomenclature

Bond lines drawn into a ring system from a substituent variable indicate that the substituent may be attached to any of the substitutable ring atoms.

As used herein, the following terms are intended to have the following definitions. The definitions herein may specify that a chemical term has an indicated formula. The particular formula provided is not intended to limit the scope of the invention, but is provided as an illustration of the term. The scope of the per se definition of the term is intended to include the plurality of variations expected to be included by one of ordinary skill in the art. Chemical terms are to be read from right to left, wherein the right-most group is attached to the core molecule and the left-most group is the terminal group. The formula (s) illustrating a term are to be read from left to right, wherein the left-most group is attached to the core molecule, as indicated by the dash, and the right-most group is the terminal group.

The term "$C_{1-8}$alkyl" means a saturated aliphatic branched or straight-chain hydrocarbon radical or linking group having from 1 up to 8 carbon atoms in a linear or branched arrangement, wherein the radical is derived by the removal of one hydrogen atom from a carbon atom and the linking group is derived by the removal of one hydrogen atom from each of two carbon atoms in the chain. The term "$C_{1-8}$alkyl" also includes a "$C_{1-6}$alkyl" and "$C_{1-4}$alkyl" radical or linking group having from 1 up to 6 carbon atoms and 1 up to 4 carbon atoms respectively, such as methyl, ethyl, 1-propyl, 2-propyl, 1-butyl, 2-butyl, tert-butyl, 1-pentyl, 2-pentyl, 3-pentyl, 1-hexyl, 2-hexyl, 3-hexyl, 1-heptyl, 2-heptyl, 3-heptyl, 1-octyl, 2-octyl, 3-octyl and the like. Alkyl radicals may be attached to a core molecule via a terminal carbon atom or via a carbon atom within the chain. Similarly, substituent variables may be attached to an alkyl linking group when allowed by available valences.

The term "$C_{2-8}$alkenyl" means an alkyl radical or linking group having from 2 up to 8 carbon atoms in a linear or branched arrangement having at least one carbon-carbon double bond. The term "$C_{2-8}$alkenyl" also includes a "$C_{2-4}$alkenyl" radical or linking group having from 2 up to 4 carbon atoms, such as ethenyl (also referred to as vinyl), iso-propenyl, allyl (also referred to as propenyl), propylidene and the like.

The term "$C_{1-8}$alkoxy" means an alkyl radical or linking group having from 1 up to 8 carbon atoms in a linear or branched arrangement, wherein the radical or linking group is attached through an oxygen linking atom, as in the formula: —O—$C_{1-8}$alkyl. The term "$C_{1-8}$alkoxy" also includes a "$C_{1-6}$alkoxy" and "$C_{1-4}$alkoxy" radical or linking group having from 1 up to 6 carbon atoms and from 1 up to 4 carbon atoms respectively, such as methoxy, ethoxy, propoxy, butoxy and the like. An alkoxy radical may be attached to a core molecule and further substituted as a linking group where indicated.

The term "$C_{3-12}$cycloalkyl" means a saturated or partially unsaturated cyclic hydrocarbon ring system radical. The term "$C_{3-12}$cycloalkyl" also includes a $C_{3-8}$cycloalkyl, $C_{3-10}$cycloalkyl, $C_{5-6}$cycloalkyl, $C_{5-8}$cycloalkyl, $C_{5-12}$cycloalkyl, $C_{9-13}$cycloalkyl or benzofused-$C_{3-12}$cycloalkyl ring system radical and the like, such as cyclopropyl, cyclobutyl, cyclopentyl, cyclohexyl, cycloheptyl, cyclooctyl, 1H-indenyl, indanyl, 9H-fluorenyl, 1,2,3,4-tetrahydro-naphthalenyl, acenaphthenyl, adamantanyl and the like.

The term "benzofused-$C_{3-12}$cycloalkyl" means a $C_{3-12}$cycloalkyl ring system radical having a benzene ring fused on the ring system on adjacent carbons. Examples of benzofused-$C_{3-12}$cycloalkyl in compounds representative of the present invention include a benzofused-$C_{5-6}$cycloalkyl ring system radical and the like, such as 1H-indenyl, indanyl and the like.

The term "aryl" means an unsaturated aromatic hydrocarbon ring system radical. Aryl ring systems include phenyl, naphthalenyl, azulenyl, anthracenyl and the like. Examples of aryl in compounds representative of the present invention include phenyl or naphthalenyl.

The term "hetero", when used as a prefix for a ring system, refers to the replacement of at least one carbon atom member in the ring system with a heteroatom selected from N, O, S, S(O), or $SO_2$. A hetero ring may have 1, 2, 3 or 4 carbon atom members replaced by a nitrogen atom. Alternatively, a ring may have 1, 2 or 3 nitrogen atom members and 1 oxygen or sulfur atom member. Alternatively, a ring may have 1 oxygen or sulfur atom member. Alternatively, up to two adjacent ring members may be heteroatoms, wherein one heteroatom is nitrogen and the other heteroatom is selected from N, S or O.

The term "heterocyclyl" means a saturated or partially unsaturated "hetero" ring system radical. Heterocyclyl ring systems include azetidinyl, 2H-pyrrole, 2-pyrrolinyl, 3-pyrrolinyl, pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, tetrazolidinyl, piperidinyl, 1,4-dioxanyl, morpholinyl, 1,4-dithianyl, thiomorpholinyl, piperazinyl, azepanyl, hexahydro-1,4-diazepinyl, hexahydro-1,4-oxazepanyl, tetrahydro-furanyl, tetrahydro-thienyl, tetrahydro-pyranyl, tetrahydro-pyridazinyl and the like. The term "heterocyclyl" also includes a benzofused-heterocyclyl ring system radical and the like, such as indolinyl (also referred to as 2,3-dihydro-indolyl), benzo[1,3]dioxolyl, 2,3-dihydro-1,4-benzodioxinyl, 2,3-dihydro-benzofuranyl, 1,2-dihydro-phthalazinyl and the like.

The term "benzofused-heterocyclyl" means a heterocyclyl ring system radical having a benzene ring fused on the ring system on adjacent carbons. Examples of benzofused-heterocyclyl in compounds representative of the present invention include benzo[1,3]dioxolyl and 2,3-dihydro-indolyl.

The term "heteroaryl" means a monovalent, unsaturated aromatic "hetero" ring system radical. Heteroaryl ring systems include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl and the like.

The term "heteroaryl" also includes a benzofused-heteroaryl ring system radical and the like, such as indolizinyl, indolyl, azaindolyl, isoindolyl, benzofuranyl, benzothienyl, indazolyl, azaindazolyl, benzoimidazolyl, benzothiazolyl, benzoxazolyl, benzoisoxazolyl, benzothiadiazolyl, benzotriazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl and the like.

The term "benzofused-heteroaryl" means a heteroaryl ring system radical having a benzene ring fused on the ring system on adjacent carbons. Examples of benzofused-heteroaryl in compounds representative of the present invention include indazolyl, indolyl, benzofuranyl and benzoimidazolyl.

The term "$C_{1-8}$acyl" means a radical of the formula: —C(O)H or —C(O)—$C_{1-8}$alkyl, or a linking group of the formula: —C(O)—$C_{1-8}$alkyl-terminal group.

The term "$C_{1-8}$acyl-amino" means a radical of the formula: —NH—C(O)H or —NH—C(O)—$C_{1-8}$alkyl, or a linking group of the formula: —NH—C(O)—$C_{1-8}$alkyl-terminal group.

The term "$C_{1-8}$alkoxy-$C_{1-8}$alkyl" means a radical of the formula: —$C_{1-8}$alkyl-O—$C_{1-8}$alkyl, or a linking group of the formula: —$C_{1-8}$alkyl-O—$C_{1-8}$alkyl-terminal group.

The term "$C_{1-8}$alkoxy-$C_{1-8}$alkyl-amino-$C_{1-8}$alkyl" means a radical of the formula: —$C_{1-8}$alkyl-NH—$C_{1-8}$alkyl-O—$C_{1-8}$alkyl, —$C_{1-8}$alkyl-N[($C_{1-8}$alkyl)($C_{1-8}$alkyl-O—$C_{1-8}$alkyl)] or —$C_{1-8}$alkyl-N($C_{1-8}$alkyl-O—$C_{1-8}$alkyl)$_2$, or a linking group of the formula: —$C_{1-8}$alkyl-NH—$C_{1-8}$alkyl-O—$C_{1-8}$alkyl-terminal group, —$C_{1-8}$alkyl-N[($C_{1-8}$alkyl)($C_{1-8}$alkyl-O—$C_{1-8}$alkyl-terminal group)], —$C_{1-8}$alkyl-N[($C_{1-8}$alkyl-terminal group)($C_{1-8}$alkyl-O—$C_{1-8}$alkyl)] or —$C_{1-8}$alkyl-N[($C_{1-8}$alkyl)($C_{1-8}$alkyl-O—$C_{1-8}$alkyl-terminal group)].

The term "$C_{1-8}$alkoxycarbonyl" means a radical of the formula: —C(O)—O—$C_{1-8}$alkyl, or a linking group of the formula: —C(O)—O—$C_{1-8}$alkyl-terminal group.

The term "$C_{1-8}$alkoxy-imino-$C_{1-8}$alkyl" means a radical of the formula: —$C_{1-8}$alkyl=N($C_{1-8}$alkoxy).

The term "$C_{1-8}$alkoxy-imino-(aryl)$C_{1-8}$alkyl" means a radical of the formula: —$C_{1-8}$alkyl(aryl)=N($C_{1-8}$alkoxy); wherein the aryl and imino portion is substituted on the same or different $C_{1-8}$alkyl carbon atom.

The term "$C_{1-8}$alkyl-amino" means a radical of the formula: —NH—$C_{1-8}$alkyl or —N($C_{1-8}$alkyl)$_2$.

The term "$C_{1-8}$alkyl-amino-$C_{1-8}$alkyl" means a radical of the formula: —$C_{1-8}$alkyl-NH—$C_{1-8}$alkyl or —$C_{1-8}$alkyl-N($C_{1-8}$alkyl)$_2$, or a linking group of the formula: —$C_{1-8}$alkyl-NH—$C_{1-8}$alkyl-terminal group or —$C_{1-8}$alkyl-N($C_{1-8}$alkyl)-$C_{1-8}$alkyl-terminal group.

The term "$C_{1-8}$alkyl-amino-$C_{1-8}$alkyl-amino-carbonyl" means a radical of the formula: —C(O)—NH—$C_{1-8}$alkyl-NH—$C_{1-8}$alkyl or —C(O)—NH—$C_{1-8}$alkyl-N($C_{1-8}$alkyl)$_2$.

The term "$C_{1-8}$alkyl-sulfonyl-$C_{1-8}$alkyl" means a radical of the formula: —$C_{1-8}$alkyl-SO$_2$—$C_{1-8}$alkyl, or a linking group of the formula: —$C_{1-8}$alkyl-SO$_2$—$C_{1-8}$alkyl-terminal group.

The term "$C_{1-8}$alkyl-sulfonyloxy-$C_{1-8}$alkyl" means a radical of the formula: —$C_{1-8}$alkyl-O—SO$_2$—$C_{1-8}$alkyl, or a linking group of the formula: —$C_{1-8}$alkyl-O—SO$_2$—$C_{1-8}$alkyl-terminal group.

The term "amino" means a radical of the formula: —NH$_2$.

The term "amino-$C_{1-8}$alkyl" means a radical of the formula: —$C_{1-8}$alkyl-NH$_2$, or a linking group of the formula: —$C_{1-8}$alkyl-NH-terminal group or —$C_{1-8}$alkyl-N(terminal group)$_2$.

The term "aryl-amido" means a radical of the formula: —NHC(O)-aryl.

The term "aryl-amino" means a radical of the formula: —NH-aryl.

The term "aryl-$C_{1-8}$alkyl" means a radical of the formula: —$C_{1-8}$alkyl-aryl.

The term "aryl-carbonyl-$C_{1-8}$alkyl" means a radical of the formula: —$C_{1-8}$alkyl-C(O)-aryl.

The term "aryl-$C_{1-8}$alkoxy" means a radical of the formula: —O—$C_{1-8}$alkyl-aryl.

The term "aryloxy" means a radical of the formula: —O-aryl.

The term "aryloxy-$C_{1-8}$alkyl" means a radical of the formula: —$C_{1-8}$alkyl-O-aryl.

The term "carboxy" means a radical of the formula: —C(O)OH.

The term "cyano-$C_{1-8}$alkyl" means a radical of the formula: —$C_{1-8}$alkyl-C≡N.

The term "halogen" or "halo" means the group chloro, bromo, fluoro or iodo.

The term "halo-$C_{1-8}$alkoxy" means a radical of the formula: —$C_{1-8}$alkoxy(halo)$_{1-17}$, wherein one or more halogen atoms may be substituted on $C_{1-8}$alkoxy when allowed by available valences and includes monofluoromethoxy, difluoromethoxy, trifluoromethoxy, trifluoroethoxy and the like.

The term "halo-$C_{1-6}$alkoxy" means a radical of the formula: —$C_{1-6}$alkoxy(halo)$_{1-13}$, wherein one or more halogen atoms may be substituted on $C_{1-6}$alkoxy when allowed by available valences.

The term "halo-$C_{1-8}$alkyl" means a radical of the formula: —$C_{1-8}$alkyl(halo)$_{1-17}$, wherein one or more halogen atoms may be substituted on $C_{1-8}$alkyl when allowed by available valences and includes monofluoromethyl, difluoromethyl, trifluoromethyl, trifluoroethyl and the like.

The term "halo-$C_{1-6}$alkyl" means a radical of the formula: —$C_{1-6}$alkyl(halo)$_{1-13}$, wherein one or more halogen atoms may be substituted on $C_{1-6}$alkyl when allowed by available valences.

The term "heterocyclyl-$C_{1-8}$alkyl" means a radical of the formula: —$C_{1-8}$alkyl-heterocyclyl.

The term "heterocyclyl-carbonyl-$C_{1-8}$alkyl" means a radical of the formula: —$C_{1-8}$alkyl-C(O)-heterocyclyl.

The term "heteroaryl-$C_{1-8}$alkoxy" means a radical of the formula: —O—$C_{1-8}$alkyl-heteroaryl.

The term "heteroaryl-$C_{1-8}$alkyl" means a radical of the formula: —$C_{1-8}$alkyl-heteroaryl.

The term "heteroaryl-amino-sulfonyl" means a radical of the formula: —SO$_2$—NH-heteroaryl.

The term "heteroaryloxy" means a radical of the formula: —O-heteroaryl.

The term "hydroxy-$C_{1-8}$alkoxy" means a radical wherein $C_{1-8}$alkoxy is substituted on an available carbon chain atom with one or more hydroxy radicals.

The term "hydroxy-$C_{1-8}$alkyl" means a radical wherein $C_{1-8}$alkyl is substituted on an available carbon chain atom with one or more hydroxy radicals.

The term "substituted phosphonic acid" means a radical of the formula: —P(=O)—(O—$C_{1-8}$alkyl)$_2$, —P(=O)—(OH)$_2$ or —P(=O)(OH)—O—$C_{1-8}$alkyl.

The term "thio-$C_{1-8}$alkyl" means a radical of the formula: —S—$C_{1-8}$alkyl.

The term "substituted" means the independent replacement of one or more hydrogen atoms within a radical with that amount of substituents allowed by available valences.

The term "dependently selected" means that the structure variables are specified in an indicated combination.

The term "terminal group" means a moiety attached to a linking group substituent at a position other than the point of attachment of the linking group to the core molecule. The moiety functions to terminate the structure variable.

In general, IUPAC nomenclature rules are used herein.

Compound Forms

The term "form" means, in reference to compounds of the present invention, such may exist as, without limitation, a salt, stereoisomer, tautomer, crystalline, polymorph, amorphous, solvate, hydrate, ester, prodrug or metabolite form. The present invention encompasses all such compound forms and mixtures thereof.

The term "isolated form" means, in reference to compounds of the present invention, such may exist in an essentially pure state such as, without limitation, an enantiomer, a racemic mixture, a geometric isomer (such as a cis or trans stereoisomer), a mixture of geometric isomers, and the like. The present invention encompasses all such compound forms and mixtures thereof.

The compounds of the invention may be present in the form of pharmaceutically acceptable salts. For use in medicines, the "pharmaceutically acceptable salts" of the compounds of this invention refer to non-toxic acidic/anionic or basic/cationic salt forms.

Suitable salt forms include acid addition salts which may, for example, be formed by mixing a solution of the compound according to the invention with a solution of an acid such as acetic acid, adipic acid, benzoic acid, carbonic acid, citric acid, fumaric acid, glycolic acid, hydrochloric acid, maleic acid, malonic acid, phosphoric acid, saccharinic acid, succinic acid, sulphuric acid, tartaric acid, trifluoroacetic acid and the like.

Furthermore when the compounds of the present invention carry an acidic moiety, suitable salts thereof may include alkali metal salts, e.g. sodium or potassium salts; alkaline earth metal salts, e.g. calcium or magnesium salts; and salts formed with suitable organic ligands, e.g. quaternary ammonium salts.

Thus, representative salts include the following: acetate, adipate, benzenesulfonate, benzoate, bicarbonate, bisulfate, bitartrate, borate, bromide, calcium, camsylate (or camphorsulphonate), carbonate, chloride, clavulanate, citrate, dihydrochloride, edetate, fumarate, gluconate, glutamate, glyconate, hydrabamine, hydrobromine, hydrochloride, iodide, isothionate, lactate, malate, maleate, malonate, mandelate, mesylate, nitrate, oleate, pamoate, palmitate, phosphate/diphosphate, saccharinate, salicylate, stearate, sulfate, succinate, tartrate, tosylate, trichloroacetate, trifluoroacetate and the like.

Examples of salt forms of compounds representative of the present invention include the monohydrochloride salt.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, $3^{rd}$ Edition, John Wiley & Sons, 1999. The protecting groups may be removed at a convenient subsequent stage using methods known in the art. The scope of the present invention encompasses all such protected compound forms and mixtures thereof.

The invention includes compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (optical isomers).

The term "optical isomer" means isomers of identical constitution that differ only in the spatial arrangement of their groups. Optical isomers rotate the plane of polarized light in different directions. The term "optical activity" means the degree to which an optical isomer rotates the plane of polarized light.

The term "racemate" or "racemic mixture" means an equimolar mixture of two enantiomeric species, wherein each of isolated specie rotates the plane of polarized light in the opposite direction such that the mixture is devoid of optical activity.

The term "enantiomer" means an isomer having a nonsuperimposable mirror image. The term "diastereomer" means stereoisomers that are not enantiomers.

The term "chiral" means a molecule which, in a given configuration, cannot be superimposed on its mirror image. This is in contrast to achiral molecules which can be superimposed on their mirror images.

The two distinct mirror image versions of the chiral molecule are also known as levo (left-handed), abbreviated L, or dextro (right handed), abbreviated D, depending on which way they rotate polarized light. The symbols "R" and "S" represent the configuration of groups around a stereogenic carbon atom(s).

An example of an isolated form of an achiral mixture includes a dextrorotatory enantiomer, wherein the mixture is substantially free of the levorotatory isomer. In this context, substantially free means the levorotatory isomer may, in a range, comprise less than 25% of the mixture, less than 10%, less than 5%, less than 2% or less than 1% of the mixture according to the formula:

$$\% \text{ levorotatory} = \frac{(\text{mass lavorotatory})}{(\text{mass dextrorotatory}) + (\text{mass levorotatory})} \times 100$$

Similarly, an example of an isolated form of an achiral mixture includes a levorotatory enantiomer, wherein the mixture is substantially free of the dextrorotatory isomer. In this context, substantially free means the dextrorotatory isomer may, in a range, comprise less than 25% of the mixture, less than 10%, less than 5%, less than 2% or less than 1% of the mixture according to the formula:

$$\% \text{ dextrorotatory} = \frac{(\text{mass dextrorotatory})}{(\text{mass dextrorotatory}) + (\text{mass levorotatory})} \times 100$$

The term "geometric isomer" means isomers that differ in the orientation of substituent atoms in relationship to a carbon-carbon double bond, to a cycloalkyl ring, or to a bridged bicyclic system. Substituent atoms (other than hydrogen) on each side of a carbon-carbon double bond may be in an E or Z configuration. In the "E" configuration, the substituents are on opposite sides in relationship to the carbon-carbon double bond. In the "Z" configuration, the substituents are oriented on the same side in relationship to the carbon-carbon double bond.

Substituent atoms (other than hydrogen) attached to a ring system may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

The isomeric descriptors ("R", "S", "E", and "Z") indicate atom configurations and are intended to be used as defined in the literature.

The compounds of the invention may be prepared as individual isomers by either isomer-specific synthesis or resolved from an isomeric mixture. Conventional resolution techniques include combining the free base (or free acid) of each isomer of an isomeric pair using an optically active acid (or base) to form an optically active salt (followed by fractional crystallization and regeneration of the free base), forming an ester or amide of each of the isomers of an isomeric pair by reaction with an appropriate chiral auxiliary (followed by fractional crystallization or chromatographic separation and removal of the chiral auxiliary), or separating an isomeric mixture of either an intermediate or a final product using various well known chromatographic methods.

Furthermore, compounds of the present invention may have one or more polymorph or amorphous crystalline forms and, as such, are intended to be included in the scope of the invention. In addition, some of the compounds may form solvates with water (i.e., hydrates) or common organic solvents (e.g., organic esters such as ethanolate and the like) and, as such, are also intended to be encompassed within the scope of this invention.

Methods of Use

The compounds of formula (I) are inhibitors of a protein kinase such as EGFR, HER-1, HER-2 and the like, having an $IC_{50}$ (50% inhibition concentration) or an $EC_{50}$ (50% effective concentration) in a range of about 50 µM or less, of about 25 µM or less, of about 15 µM or less, of about 10 µM or less, of about 5 µM or less, of about 1 µM or less, of about 0.5 µM or less, of about 0.25 µM or less or of about 0.1 µM or less.

The present invention includes a compound of formula (I) and forms thereof as a protein kinase inhibitor, wherein the protein kinase is selected from EGFR, HER-1 or HER-2.

The present invention includes a prodrug form of a compound of formula (I) and forms thereof as a protein kinase inhibitor.

The present invention includes a metabolite form of a compound of formula (I) and forms thereof as a protein kinase inhibitor.

The present invention includes an isolated form of a compound of formula (I) and forms thereof as a protein kinase inhibitor.

The present invention includes a compound of formula (I) or a form thereof, wherein the compound is labeled with a ligand for use as a marker, and wherein the ligand is a radioligand selected from deuterium, tritium and the like.

The present invention includes use of a compound of formula (I) and forms thereof as an inhibitor of a protein kinase such as EGFR, HER-1, HER-2 and the like comprising contacting the protein kinase domain or receptor with the compound.

The present invention includes the use of a compound of formula (I) and forms thereof as a pharmaceutical composition, medicine or medicament for treating, preventing or ameliorating a kinase mediated disease, disorder or condition.

The present invention includes the use of a compound of formula (I) and forms thereof as a medicament.

The present invention includes the use of a prodrug of a compound of formula (I) and forms thereof as a pharmaceutical composition, medicine or medicament for treating, preventing or ameliorating a kinase mediated disease, disorder or condition.

The present invention includes the use of a prodrug of a compound of formula (I) and forms thereof as a medicament.

The present invention is directed to a method for treating, preventing or ameliorating a chronic or acute protein kinase mediated disease, disorder or condition in a subject in need thereof comprising administering to the subject an effective amount of a compound of formula (I) and forms thereof.

The method of the present invention further comprises administering to the subject an effective amount of a prodrug of a compound of formula (I) and forms thereof.

The method of the present invention further comprises treating, preventing or ameliorating a chronic or acute EGFR, HER-1 or HER-2 mediated disease, disorder or condition.

The method of the present invention wherein the disease, disorder or condition is associated with increased or unregulated protein kinase activity, expression or signaling and the like in the subject.

The method of the present invention further comprises administering to the subject an effective amount of a compound of formula (I) as a pharmaceutical composition, medicine or medicament thereof.

The method of the present invention wherein the disease, disorder or condition is an EGFR kinase mediated head or brain cancer in the subject, and wherein the compound penetrates the blood brain barrier.

The method of the present invention further comprises treating or ameliorating nerve damage and promoting axon regeneration subsequent to a brain or spinal cord injury in the subject, wherein the compound is an EGFR inhibitor.

The method of the present invention further comprises treating, preventing or ameliorating viral infection by an EGFR kinase mediated cytomegalovirus in the subject.

The term "chronic or acute protein kinase mediated disease, disorder or condition" as used herein, includes, and is not limited to diseases, disorders or conditions associated with unregulated kinase activity and conditions that accompany such activity.

The term "unregulated protein kinase activity, expression or signaling" refers to 1) increased or unregulated kinase expression or signaling, 2) increased kinase expression leading to unregulated cell proliferation, 3) increased kinase signaling leading to unregulated cell proliferation, or 4) mutations leading to constitutive kinase activation. The existence of unregulated kinase activity may be determined by procedures well known in the art.

The term "unregulated cell proliferation" refers to cell proliferation of one or more subset of cells in a multicellular organism resulting in harm (such as discomfort or decreased life expectancy) to the multicellular organism.

Tumor cells which result from unregulated cell proliferation use many mechanisms to enhance their survival and spread and often have high rates of proliferation because growth control signals that keep normal cells in check are defective. Many tumor cells secrete autocrine growth factors that increase proliferation rates or they induce other cells to secrete growth factors that they utilize.

Tumor cells grow and spread by dislodging from a primary tumor site, using proteases to digest the extracellular matrix, spreading in response to migration cues, allowing them to migrate to certain tissues preferentially where overexpressed adhesion molecules allow attachment and growth at the new site. The totality of these and other biological processes are responsible for the lethal effects of a tumor. A kinase inhibitor may affect one or more aspects of tumor survival mechanisms and thus be therapeutically useful. Alternatively, a kinase inhibitor may not affect one particular tumor survival mechanism but may still be therapeutically useful by affecting tumor survival by an unknown or as yet unelucidated mechanism of action.

The foregoing methods contemplate that a compound of formula (I) or a form thereof is useful for treating, preventing or ameliorating diseases, disorders or conditions such as, without limitation, osteoarthritis, rheumatoid arthritis, synovial pannus invasion in arthritis, multiple sclerosis, myasthenia gravis, diabetes mellitus, diabetic angiopathy, diabetic retinopathy, retinal vessel proliferation, inflammatory bowel disease, Crohn's disease, ulcerative colitis, bone diseases, transplant or bone marrow transplant rejection, lupus, chronic pancreatitis, cachexia, septic shock, fibroproliferative and differentiative skin diseases or disorders, central nervous system diseases, neurodegenerative diseases, disorders or conditions related to nerve damage and axon degeneration subsequent to a brain or spinal cord injury, acute or chronic cancer, ocular diseases, viral infections, heart disease, lung or pulmonary diseases or kidney or renal diseases.

Certain diseases, disorders or conditions further include, without limitation, acute or chronic cancer selected from bladder cancer, brain, head or neck cancer, breast cancer, colorectal cancer, endometrial cancer, epidermoid cancer, esophageal cancer, gastric cancer, glioma cancer, lung cancer, ovarian cancer, pancreatic cancer, prostate cancer, renal cell cancer, Kaposi's sarcoma, leukemia, lymphoma or papillocarcinoma; and, cancer-associated pathologies selected from abnormal cell proliferation, unregulated cell proliferation, tumor growth, tumor angiopathy, tumor angiogenesis, tumor vascularization or metastatic cancer cell invasion and migration.

Certain diseases, disorders or conditions further include, without limitation, fibroproliferative and differentiative skin diseases or disorders selected from papilloma formation, psoriasis, dermatitis, eczema, seborrhea or chemotherapy-induced alopecia; central nervous system diseases selected from Alzheimer's disease, Parkinson's disease or depression; ocular diseases selected from macular degeneration, diseases of the cornea or glaucoma; viral infections selected from mycotic infection, autoimmune disease or cytomegalovirus; heart disease selected from atherosclerosis, neointima formation or transplantation-induced vasculopathies such as arterial restenosis; lung or pulmonary diseases selected from allergic-asthma, lung fibrosis, pulmonary fibrosis or chronic obstructive pulmonary disorder; and, kidney or renal diseases selected from acute, subacute or chronic forms of glomerulonephritis or membranoproliferative glomerulonephritis, glomerulosclerosis, congenital multicystic renal dysplasia or kidney fibrosis.

Certain HER1 kinase mediated cancer includes, without limitation, bladder cancer, brain, head or neck cancer, breast cancer, cervical cancer, colorectal cancer, gastric cancer, glioma cancer, endometrial cancer, esophageal cancer, lung cancer, ovarian cancer, pancreatic cancer or renal cell cancer.

Certain HER2 kinase mediated cancer includes, without limitation, bladder cancer, brain, head or neck cancer, breast cancer, colorectal cancer, gastric cancer, endometrial cancer, esophageal cancer, lung cancer, ovarian cancer, prostate cancer or renal cell cancer.

The term "administering", with respect to the methods of the present invention, refers to a means for treating, ameliorating or preventing a disease, disorder or syndrome as described herein with a compound of formula (I) or a form thereof, which would obviously be included within the scope of the invention albeit not specifically disclosed for certain of said compounds.

Such methods include therapeutically or prophylactically administering an effective amount of compound of formula (I) or a form thereof at different times during the course of a therapy or concurrently in a combination form. Such methods further include administering an effective amount of said compound with one or more agents at different times during the course of a therapy or concurrently in a combination form.

The term "prodrug" means a compound of formula (I) or a form thereof that is converted in vivo into a functional derivative form that may contribute to therapeutic biological activity, wherein the converted form may be: 1) a relatively active form; 2) a relatively inactive form; 3) a relatively less active form; or, 4) any form which results, directly or indirectly, from such in vivo conversions.

Prodrugs are useful when said compound may be either too toxic to administer systemically, absorbed poorly by the digestive tract or broken down by the body before it reaches its target. Conventional procedures for the selection and preparation of suitable prodrug derivatives are described in, for example, "Design of Prodrugs", ed. H. Bundgaard, Elsevier, 1985.

The term "metabolite" means a prodrug form of a compound of formula (I) or a form thereof converted by in vivo metabolism or a metabolic process to a relatively less active functional derivative of said compound.

The term "subject" as used herein, refers to a patient, such as an animal, a mammal or a human, who has been the object of treatment, observation or experiment and is at risk of (or susceptible to) developing a disease or disorder or having a disease or disorder related to unregulated kinase activity.

The term "effective amount" refers to that amount of a compound of formula (I) or a form, pharmaceutical composition, medicine or medicament thereof that elicits the biological or medicinal response (such as inhibiting activation of unregulated kinase activity) in a tissue system, animal or human, that is being sought by a researcher, veterinarian, medical doctor, or other clinician, which includes alleviation of the symptoms of the disease or disorder being treated.

The effective amount of said compound is from about 0.001 mg/kg/day to about 300 mg/kg/day.

The term "pharmaceutical composition" refers to a product containing a compound of formula (I) or a form thereof, such as a product comprising the specified ingredients in the specified amounts, as well as any product which results, directly or indirectly, from such combinations of the specified ingredients in the specified amounts.

The term "medicament" or "medicine" refers to a product containing a compound of formula (I) or a form thereof. The present invention includes use of such a medicament for treating, preventing or ameliorating a chronic or acute kinase mediated disease, disorder or condition.

The term "pharmaceutically acceptable" refers to molecular entities and compositions that are of sufficient purity and quality for use in the formulation of a pharmaceutical composition, medicine or medicament of the present invention and that, when appropriately administered to an animal or a human, do not produce an adverse, allergic or other untoward reaction. Since both human use (clinical and over-the-counter) and veterinary use are equally included within the scope of the present invention, a pharmaceutically acceptable formulation would include a pharmaceutical composition, medicine or medicament for either human or veterinary use.

The term "combination form" refers to the use of a combination product comprising a compound of formula (I) or a form, pharmaceutical composition, medicine or medicament thereof and at least one therapeutic agent for treating, preventing or ameliorating a chronic or acute protein kinase mediated disease, disorder or condition.

Advantageously, the effective amount of a combination product for treating, preventing or ameliorating a chronic or acute protein kinase mediated disease, disorder or condition may be a reduced amount of either or both the compound or therapeutic agent compared to the effective amount of the compound or therapeutic agent otherwise recommended for treating, preventing or ameliorating the disease, disorder or condition. Therefore, it is contemplated that the compound is administered to the subject before, during or after the time the agent is administered.

The term "therapeutic agent" refers to chemotherapeutic agents used to treat a kinase mediated cancer or antiviral agents used to treat cytomegalovirus. Chemotherapeutic agents include and are not limited to anti-angiogenic agents, anti-tumor agents, cytotoxic agents, inhibitors of cell proliferation, radiation therapy and the like or a combination thereof.

The term "treating, preventing or ameliorating" refers, without limitation, to facilitating the eradication of, inhibiting the progression of or promoting stasis of a chronic or acute kinase mediated disease, disorder or condition.

The term "radiation therapy" refers to a therapy that comprises exposing the subject in need thereof to radiation. The present invention includes a method for administering a compound of formula (I) or a form, pharmaceutical composition, medicine or medicament thereof in combination with radiation therapy. Procedures for administering such therapy are known to those skilled in the art. The appropriate scheme of radiation therapy will be similar to those already employed in clinical therapies wherein the radiation therapy is used alone or in combination with other chemotherapeutic agents.

The present invention includes a pharmaceutical composition comprising an admixture of a compound of formula (I) or a form thereof and one or more pharmaceutically acceptable excipients.

The present invention includes a process for making a pharmaceutical composition, medicine or medicament comprising mixing a compound of formula (I) or a form thereof and an optional pharmaceutically acceptable carrier. The present invention includes a pharmaceutical composition, medicine or medicament resulting from the process of mixing a compound of formula (I) or a form thereof and an optional pharmaceutically acceptable carrier. Contemplated processes include both conventional and unconventional pharmaceutical techniques.

Said pharmaceutical composition, medicine or medicament may take a wide variety of forms to effectuate mode of administration, wherein the mode includes, and is not limited to, intravenous (both bolus and infusion), oral, nasal, transdermal, topical with or without occlusion, and via injection intraperitoneally, subcutaneously, intramuscularly, intratumorally, intracerebrally or intracranially. The composition, medicine or medicament may be in a dosage unit such as a tablet, pill, capsule, powder, granule, sterile parenteral solution or suspension, metered aerosol or liquid spray, drop, ampoule, auto-injector device or suppository for such administration modes.

Pharmaceutical compositions, medicines or medicaments suitable for oral administration include solid forms such as pills, tablets, caplets, capsules (each including immediate release, timed release and sustained release formulations), granules and powders; and, liquid forms such as solutions, syrups, elixirs, emulsions and suspensions. Forms useful for parenteral administration include sterile solutions, emulsions and suspensions. Alternatively, the pharmaceutical composition, medicine or medicament may be presented in a form suitable for once-weekly or once-monthly administration; for example, an insoluble salt of the active compound, such as the decanoate salt, may be adapted to provide a depot preparation for intramuscular injection.

The dosage form (tablet, capsule, powder, injection, suppository, teaspoonful and the like) containing the pharmaceutical composition, medicine or medicament contains an effective amount of the active ingredient necessary to be therapeutically or prophylactically effective as described above. The pharmaceutical composition, medicine or medicament may contain from about 0.001 mg to about 5000 mg (preferably, from about 0.001 to about 500 mg) of a compound of formula (I) or a form thereof and may be constituted into any form suitable for the mode of administration selected for a subject in need.

An example of a contemplated effective amount for a pharmaceutical composition, medicine or medicament of the present invention may range from about 0.001 mg to about 300 mg/kg of body weight per day. In another example, the range is from about 0.003 to about 100 mg/kg of body weight per day. In another example, the range is from about 0.005 to about 15 mg/kg of body weight per day. The pharmaceutical composition, medicine or medicament may be administered according to a dosage regimen of from about 1 to about 5 times per day.

For oral administration, the pharmaceutical composition, medicine or medicament is preferably in the form of a tablet containing, e.g., 0.01, 0.05, 0.1, 0.5, 1.0, 2.5, 5.0, 10.0, 15.0, 25.0, 50.0, 100, 150, 200, 250 and 500 milligrams of a compound of formula (I) or a form thereof for the symptomatic adjustment of the dosage to the patient to be treated.

Optimal dosages will vary depending on factors associated with the particular patient being treated (e.g., age, weight, diet and time of administration), the severity of the condition being treated, the particular compound being used, the mode of administration and the strength of the preparation. The use of either daily administration or post-periodic dosing may be employed.

A representative compound of formula (I) includes a compound selected from:

| Cpd | Names |
|---|---|
| 1 | (5E)-4-amino-6-(3-chloro-4-fluoro-phenylamino)-pyrimidine-5-carbaldehyde O-methyl-oxime, |
| 2 | (5E)-4-amino-6-[1-(3-fluoro-benzyl)-1H-indazol-5-ylamino]-pyrimidine-5-carbaldehyde O-methyl-oxime, |
| 4 | (5E)-4-amino-6-[3-chloro-4-(3-fluoro-benzyloxy)-phenylamino)-pyrimidine-5-carbaldehyde O-methyl-oxime, |
| 6 | (5E)-4-amino-6-[1-(3-fluoro-benzyl)-1H-indazol-5-ylamino]-pyrimidine-5-carbaldehyde O-(2-morpholin-4-yl-2-oxo-ethyl)-oxime, |
| 7 | (5E)-4-amino-6-(3-methoxy-4-phenoxy-phenylamino)-pyrimidine-5-carbaldehyde O-methyl-oxime, |
| 8 | (5E)-4-amino-6-(3-methoxy-4-phenoxy-phenylamino)-pyrimidine-5-carbaldehyde O-(2-morpholin-4-yl-2-oxo-ethyl)-oxime, |
| 9 | (5E)-4-amino-6-(4-benzyloxy-3-chloro-phenylamino)-pyrimidine-5-carbaldehyde O-methyl-oxime, |
| 10 | (5E)-4-amino-6-[1-(3-fluoro-benzyl)-1H-indazol-5-ylamino]-pyrimidine-5-carbaldehyde O-ethyl-oxime, |
| 11 | (5E)-4-amino-6-[1-(3-fluoro-benzyl)-1H-indazol-5-ylamino]-pyrimidine-5-carbaldehyde O-allyl-oxime, |
| 12 | (5E)-4-amino-6-[1-(3-fluoro-benzyl)-1H-indazol-5-ylamino]-pyrimidine-5-carbaldehyde O-tert-butyl-oxime, |
| 13 | (5E)-4-amino-6-[3-methyl-4-(pyridin-3-yloxy)-phenylamino]-pyrimidine-5-carbaldehyde O-methyl-oxime, |
| 16 | (5E)-4-amino-6-[(1S)-1-phenyl-ethylamino]-pyrimidine-5-carbaldehyde O-ethyl-oxime, |
| 17 | (5E)-4-amino-6-(1H-indol-5-ylamino)-pyrimidine-5-carbaldehyde O-ethyl-oxime, |
| 18 | (5E)-4-amino-6-[3-chloro-4-(3-fluoro-benzyloxy)-phenylamino)-pyrimidine-5-carbaldehyde O-ethyl-oxime, |
| 19 | (5E)-4-amino-6-[1-(3-fluoro-benzyl)-1H-indazol-5-ylamino]-pyrimidine-5-carbaldehyde O-(2-morpholin-4-yl-ethyl)-oxime, |
| 24 | (5E)-4-amino-6-(4-phenoxy-phenylamino)-pyrimidine-5-carbaldehyde O-methyl-oxime, |
| 25 | (5E)-4-amino-6-(4-benzyloxy-phenylamino)-pyrimidine-5-carbaldehyde O-methyl-oxime, |
| 29 | (5E)-4-amino-6-[3-methyl-4-(6-methyl-pyridin-3-yloxy)-phenylamino]-pyrimidine-5-carbaldehyde O-methyl-oxime, |

| Cpd | Names |
|---|---|
| 30 | (5E)-4-amino-6-[1-(3-fluoro-benzyl)-1H-indazol-5-ylamino]-pyrimidine-5-carbaldehyde O-isobutyl-oxime, |
| 31 | (5E)-4-amino-6-[1-(3-fluoro-benzyl)-1H-indazol-5-ylamino]-pyrimidine-5-carbaldehyde O-(2-phenoxy-ethyl)-oxime, |
| 32 | (5E)-4-amino-6-[3-chloro-4-(pyridin-2-ylmethoxy)-phenylamino]-pyrimidine-5-carbaldehyde O-methyl-oxime, |
| 33 | (5E)-4-amino-6-[1-(3-fluoro-benzyl)-1H-indol-5-ylamino]-pyrimidine-5-carbaldehyde O-ethyl-oxime, |
| 34 | (5E)-4-amino-6-[1-(3-fluoro-benzyl)-1H-indol-5-ylamino]-pyrimidine-5-carbaldehyde O-methyl-oxime, |
| 36 | (5E)-4-amino-6-(3-bromo-phenylamino)-pyrimidine-5-carbaldehyde O-methyl-oxime, |
| 37 | (5E)-4-amino-6-(4-benzyloxy-3-chloro-phenylamino)-pyrimidine-5-carbaldehyde O-ethyl-oxime, |
| 38 | (5E)-4-amino-6-[3-chloro-4-(pyridin-3-yloxy)-phenylamino]-pyrimidine-5-carbaldehyde O-methyl-oxime, |
| 44 | (5E)-4-amino-6-[1-(3-fluoro-benzyl)-1H-indazol-5-ylamino]-pyrimidine-5-carbaldehyde O-(4-methoxy-benzyl)-oxime, |
| 45 | (5E)-4-amino-6-[1-(3-fluoro-benzyl)-1H-indazol-5-ylamino]-pyrimidine-5-carbaldehyde O-(2-methoxy-benzyl)-oxime, |
| 46 | (5E)-4-amino-6-[1-(3-fluoro-benzyl)-1H-indazol-5-ylamino]-pyrimidine-5-carbaldehyde O-benzyl-oxime, |
| 47 | (5E)-4-amino-6-[1-(3-fluoro-benzyl)-1H-indazol-5-ylamino]-pyrimidine-5-carbaldehyde O-isopropyl-oxime, |
| 48 | (5E)-4-amino-6-(1-benzyl-1H-indazol-5-ylamino)-pyrimidine-5-carbaldehyde O-methyl-oxime, |
| 49 | (5E)-4-amino-6-(1-benzyl-1H-indazol-5-ylamino)-pyrimidine-5-carbaldehyde O-ethyl-oxime, |
| 50 | 3-{5-[6-amino-(5E)-5-(methoxyimino-methyl)-pyrimidin-4-ylamino]-indazol-1-ylmethyl}-benzonitrile, |
| 51 | 3-{5-[6-amino-(5E)-5-(ethoxyimino-methyl)-pyrimidin-4-ylamino]-indazol-1-ylmethyl}-benzonitrile, |
| 54 | (5E)-4-amino-6-[1-(3-chloro-benzyl)-1H-indazol-5-ylamino]-pyrimidine-5-carbaldehyde O-methyl-oxime, |
| 55 | (5E)-4-amino-6-[1-(3-chloro-benzyl)-1H-indazol-5-ylamino]-pyrimidine-5-carbaldehyde O-ethyl-oxime, |
| 58 | (5E)-4-amino-6-[2-(3-fluoro-benzyl)-1H-benzoimidazol-5-ylamino]-pyrimidine-5-carbaldehyde O-ethyl-oxime, |
| 59 | (5E)-4-amino-6-(3-chloro-phenylamino)-pyrimidine-5-carbaldehyde O-methyl-oxime, |
| 60 | (5E)-4-amino-6-[2-(3-fluoro-benzyl)-1H-benzoimidazol-5-ylamino]-pyrimidine-5-carbaldehyde O-methyl-oxime, |
| 65 | (5E)-4-amino-6-[1-(3-fluoro-benzyl)-1H-indazol-5-ylamino]-pyrimidine-5-carbaldehyde O-phenyl-oxime, |
| 66 | (5E)-4-amino-6-[1-(4-fluoro-benzyl)-1H-indazol-5-ylamino]-pyrimidine-5-carbaldehyde O-methyl-oxime, |
| 67 | (5E)-4-amino-6-[1-(4-fluoro-benzyl)-1H-indazol-5-ylamino]-pyrimidine-5-carbaldehyde O-ethyl-oxime, |
| 68 | (5E)-4-amino-6-[1-(3-fluoro-benzyl)-1H-indazol-5-ylamino]-pyrimidine-5-carbaldehyde O-(2-methoxy-ethyl)-oxime, |
| 69 | (5Z)-4-amino-6-[1-(3-fluoro-benzyl)-1H-indazol-5-ylamino]-pyrimidine-5-carbaldehyde O-(3-hydroxy-propyl)-oxime, |
| 70 | (5E)-4-amino-6-[1-(3-fluoro-benzyl)-1H-indazol-5-ylamino]-pyrimidine-5-carbaldehyde O-(3-dimethylamino-propyl)-oxime, |
| 71 | (5E)-4-amino-6-(4-benzyloxy-3-chloro-phenylamino)-pyrimidine-5-carbaldehyde O-(2-methoxy-ethyl)-oxime, |
| 74 | (5E)-4-amino-6-[1-(3-fluoro-benzyl)-2,3-dihydro-1H-indol-5-ylamino]-pyrimidine-5-carbaldehyde O-methyl-oxime, |
| 75 | (5E)-4-amino-6-[3-chloro-4-(3-fluoro-benzyloxy)-phenylamino]-pyrimidine-5-carbaldehyde O-(3-hydroxy-propyl)-oxime, |
| 76 | (5E)-4-amino-6-(4-benzyloxy-3-chloro-phenylamino)-pyrimidine-5-carbaldehyde O-(3-hydroxy-propyl)-oxime, |
| 77 | (5E)-4-amino-6-(4-benzyloxy-3-chloro-phenylamino)-pyrimidine-5-carbaldehyde oxime, |
| 78 | (5E)-4-amino-6-(4-benzyloxy-3-chloro-phenylamino)-pyrimidine-5-carbaldehyde O-(2-morpholin-4-yl-ethyl)-oxime, |
| 78* | (5E)-4-amino-6-(4-benzyloxy-3-chloro-phenylamino)-pyrimidine-5-carbaldehyde O-(2-morpholin-4-yl-ethyl)-oxime monohydrochloride salt, |
| 79 | (5E)-4-amino-6-[3-chloro-4-(3-fluoro-benzyloxy)-phenylamino]-pyrimidine-5-carbaldehyde oxime, |
| 84 | (5E)-4-amino-6-[1-(3-fluoro-benzyl)-1H-indazol-5-ylamino]-pyrimidine-5-carbaldehyde oxime, |
| 85 | (5E)-4-amino-6-[1-(3-fluoro-benzyl)-1H-indazol-5-ylamino]-pyrimidine-5-carbaldehyde O-(3-hydroxy-propyl)-oxime, |
| 87 | (5E)-4-amino-6-[1-(3-fluoro-benzyl)-1H-indazol-5-ylamino]-pyrimidine-5-carbaldehyde O-(3-morpholin-4-yl-propyl)-oxime, |
| 88 | (5E)-4-amino-6-[1-(3-fluoro-benzyl)-1H-indol-5-ylamino]-pyrimidine-5-carbaldehyde oxime, |

| Cpd | Names |
|---|---|
| 91 | (5E)-4-amino-6-[1-(3-fluoro-benzyl)-1H-indol-5-ylamino]-pyrimidine-5-carbaldehyde O-(3-hydroxy-propyl)-oxime, |
| 92 | (5E)-4-amino-6-[1-(3-fluoro-benzyl)-1H-indazol-5-ylamino]-pyrimidine-5-carbaldehyde O-(3-piperidin-1-yl-propyl)-oxime, |
| 93 | (5E)-4-amino-6-[3-chloro-4-(3-fluoro-benzyloxy)-phenylamino]-pyrimidine-5-carbaldehyde O-(2-morpholin-4-yl-ethyl)-oxime, |
| 94 | (5E)-4-amino-6-[3-chloro-4-(3-fluoro-benzyloxy)-phenylamino]-pyrimidine-5-carbaldehyde O-(2-piperidin-1-yl-ethyl)-oxime, |
| 95 | (5E)-4-amino-6-(4-benzyloxy-3-chloro-phenylamino)-pyrimidine-5-carbaldehyde O-(2-piperidin-1-yl-ethyl)-oxime, |
| 96 | (5E)-4-amino-6-[1-(3-fluoro-benzyl)-1H-indazol-5-ylamino]-pyrimidine-5-carbaldehyde O-(2-piperidin-1-yl-ethyl)-oxime, |
| 97 | (5E)-4-amino-6-[3-chloro-4-(3,5-difluoro-benzyloxy)-phenylamino]-pyrimidine-5-carbaldehyde O-methyl-oxime, |
| 98 | (5E)-4-amino-6-[3-chloro-4-(3,5-difluoro-benzyloxy)-phenylamino]-pyrimidine-5-carbaldehyde oxime, |
| 99 | (5E)-4-amino-6-[3-chloro-4-(3,5-difluoro-benzyloxy)-phenylamino]-pyrimidine-5-carbaldehyde O-(2-morpholin-4-yl-ethyl)-oxime, |
| 100 | (5E)-4-amino-6-[(1S)-1-phenyl-ethylamino]-pyrimidine-5-carbaldehyde oxime, |
| 101 | (5E)-4-amino-6-[1-(3-fluoro-benzyl)-1H-indol-5-ylamino]-pyrimidine-5-carbaldehyde O-(2-morpholin-4-yl-ethyl)-oxime, |
| 102 | (5E)-4-amino-6-[1-(3-fluoro-benzyl)-1H-indol-5-ylamino]-pyrimidine-5-carbaldehyde O-(2-piperidin-1-yl-ethyl)-oxime, |
| 111 | (5E)-4-amino-6-(4-phenoxy-phenylamino)-pyrimidine-5-carbaldehyde oxime, |
| 112 | (5E)-4-amino-6-(4-benzyloxy-3-chloro-phenylamino)-pyrimidine-5-carbaldehyde O-(3-morpholin-4-yl-propyl)-oxime, |
| 114 | (5E)-4-amino-6-(4-benzyloxy-3-chloro-phenylamino)-pyrimidine-5-carbaldehyde O-pyridin-2-ylmethyl-oxime, |
| 115 | (5E)-4-amino-6-(4-benzyloxy-3-chloro-phenylamino)-pyrimidine-5-carbaldehyde O-[3-(2-methoxy-ethylamino)-propyl]-oxime, |
| 118 | 4-amino-6-(4-benzyloxy-3-chloro-phenylamino)-pyrimidine-5-carbonitrile, |
| 119 | N-benzo[1,3]dioxol-5-ylmethyl-5-[(benzo[1,3]dioxol-5-ylmethylimino)-methyl]-pyrimidine-4,6-diamine, |
| 120 | 4-amino-6-(4-methoxy-phenylamino)-pyrimidine-5-carbaldehyde O-methyl-oxime, |
| 121 | 4-amino-6-[(benzo[1,3]dioxol-5-ylmethyl)-amino]-pyrimidine-5-carbaldehyde O-methyl-oxime, |
| 122 | 4-amino-6-(3,4-dimethoxy-benzylamino)-pyrimidine-5-carbaldehyde O-methyl-oxime, |
| 123 | 4-amino-6-(4-phenoxy-benzylamino)-pyrimidine-5-carbaldehyde O-methyl-oxime, |
| 124 | 4-amino-6-(indan-1-ylamino)-pyrimidine-5-carbaldehyde O-methyl-oxime, |
| 125 | 4-amino-6-(1,2,3,4-tetrahydro-naphthalen-1-ylamino)-pyrimidine-5-carbaldehyde O-methyl-oxime, |
| 126 | 4-amino-6-[1-(4-chloro-phenyl)-ethylamino]-pyrimidine-5-carbaldehyde O-methyl-oxime, |
| 127 | 4-amino-6-[1-(4-methoxy-phenyl)-ethylamino]-pyrimidine-5-carbaldehyde O-methyl-oxime, |
| 128 | 4-amino-6-(6-phenoxy-pyridin-3-ylamino)-pyrimidine-5-carbaldehyde O-methyl-oxime, |
| 129 | 4-amino-6-(6-morpholin-4-yl-pyridin-3-ylamino)-pyrimidine-5-carbaldehyde O-methyl-oxime, |
| 130 | 4-amino-6-(1,4-dioxo-1,2,3,4-tetrahydro-phthalazin-5-ylamino)-pyrimidine-5-carbaldehyde O-methyl-oxime, |
| 131 | 4-amino-6-(2-fluoro-5-methyl-phenylamino)-pyrimidine-5-carbaldehyde O-methyl-oxime, |
| 132 | 4-amino-6-(2,4,6-trimethyl-phenylamino)-pyrimidine-5-carbaldehyde O-methyl-oxime, |
| 133 | 4-amino-6-(3-chloro-2-methyl-phenylamino)-pyrimidine-5-carbaldehyde O-methyl-oxime, |
| 134 | 4-amino-6-(3-methylsulfanyl-phenylamino)-pyrimidine-5-carbaldehyde O-methyl-oxime, |
| 135 | 4-amino-6-[3-(1-methoxyimino-ethyl)-phenylamino]-pyrimidine-5-carbaldehyde O-methyl-oxime, |
| 136 | 4-amino-6-(3,5-dimethyl-phenylamino)-pyrimidine-5-carbaldehyde O-methyl-oxime, |
| 137 | N-{4-[6-amino-5-(methoxyimino-methyl)-pyrimidin-4-ylamino]-phenyl}-acetamide, |
| 138 | 4-amino-6-phenylamino-pyrimidine-5-carbaldehyde O-methyl-oxime, |
| 139 | 4-amino-6-(4-morpholin-4-yl-phenylamino)-pyrimidine-5-carbaldehyde O-methyl-oxime, |
| 140 | 4-amino-6-o-tolylamino-pyrimidine-5-carbaldehyde O-methyl-oxime, |
| 141 | 4-amino-6-(3,4-difluoro-phenylamino)-pyrimidine-5-carbaldehyde O-methyl-oxime, |
| 142 | 4-amino-6-(3-fluoro-4-methyl-phenylamino)-pyrimidine-5-carbaldehyde O-methyl-oxime, |

| Cpd | Names |
|---|---|
| 143 | 4-amino-6-(3,4-dichloro-phenylamino)-pyrimidine-5-carbaldehyde O-methyl-oxime, |
| 144 | 4-amino-6-(3-chloro-4-methyl-phenylamino)-pyrimidine-5-carbaldehyde O-methyl-oxime, |
| 145 | 4-amino-6-[5-chloro-2-methyl-4-(2-oxo-2-phenyl-ethyl)-phenylamino]-pyrimidine-5-carbaldehyde O-methyl-oxime, |
| 146 | 4-amino-6-(3-ethyl-phenylamino)-pyrimidine-5-carbaldehyde O-methyl-oxime, |
| 147 | 4-amino-6-(4-isopropyl-phenylamino)-pyrimidine-5-carbaldehyde O-methyl-oxime, |
| 148 | 4-amino-6-(1H-indol-5-ylamino)-pyrimidine-5-carbaldehyde O-methyl-oxime, |
| 149 | 4-amino-6-(3-trifluoromethyl-phenylamino)-pyrimidine-5-carbaldehyde O-methyl-oxime, |
| 150 | 4-amino-6-m-tolylamino-pyrimidine-5-carbaldehyde O-methyl-oxime, |
| 151 | 4-amino-6-(4-chloro-phenylamino)-pyrimidine-5-carbaldehyde O-methyl-oxime, |
| 152 | 4-amino-6-(4-chloro-2-methyl-phenylamino)-pyrimidine-5-carbaldehyde O-methyl-oxime, |
| 153 | 4-amino-6-(4-phenylamino-phenylamino)-pyrimidine-5-carbaldehyde O-methyl-oxime, |
| 154 | 4-amino-6-(4-diethylamino-phenylamino)-pyrimidine-5-carbaldehyde O-methyl-oxime, |
| 155 | 4-[6-amino-5-(methoxyimino-methyl)-pyrimidin-4-ylamino]-benzoic acid methyl ester, |
| 156 | 4-amino-6-[4-(methoxyimino-phenyl-methyl)-phenylamino]-pyrimidine-5-carbaldehyde O-methyl-oxime, |
| 157 | 4-(4-acetyl-phenylamino)-6-amino-pyrimidine-5-carbaldehyde O-methyl-oxime, |
| 158 | 4-amino-6-[4-(1-methoxyimino-ethyl)-phenylamino]-pyrimidine-5-carbaldehyde O-methyl-oxime, |
| 159 | {4-[6-amino-5-(methoxyimino-methyl)-pyrimidin-4-ylamino]-phenyl}-acetonitrile, |
| 160 | 4-amino-6-(2-methoxy-4-phenylamino-phenylamino)-pyrimidine-5-carbaldehyde O-methyl-oxime, |
| 161 | N-{4-[6-amino-5-(methoxyimino-methyl)-pyrimidin-4-ylamino]-3-methoxy-phenyl}-acetamide, |
| 162 | 4-amino-6-(4-cyclohexyl-phenylamino)-pyrimidine-5-carbaldehyde O-methyl-oxime, |
| 163 | 4-amino-6-(naphthalen-1-ylamino)-pyrimidine-5-carbaldehyde O-methyl-oxime, |
| 164 | 4-amino-6-(4-chloro-naphthalen-1-ylamino)-pyrimidine-5-carbaldehyde O-methyl-oxime, |
| 165 | 4-amino-6-(2,4-difluoro-phenylamino)-pyrimidine-5-carbaldehyde O-methyl-oxime, |
| 166 | 4-amino-6-(2-methylsulfanyl-phenylamino)-pyrimidine-5-carbaldehyde O-methyl-oxime, |
| 167 | 4-amino-6-(3-fluoro-phenylamino)-pyrimidine-5-carbaldehyde O-methyl-oxime, |
| 168 | 4-amino-6-(3,5-dichloro-phenylamino)-pyrimidine-5-carbaldehyde O-methyl-oxime, |
| 169 | 4-amino-6-(3,5-dichloro-phenylamino)-pyrimidine-5-carbaldehyde O-methyl-oxime, |
| 170 | 4-amino-6-(5-chloro-2-methoxy-phenylamino)-pyrimidine-5-carbaldehyde O-methyl-oxime, |
| 171 | 4-amino-6-(5-chloro-2-methyl-phenylamino)-pyrimidine-5-carbaldehyde O-methyl-oxime, |
| 172 | 4-amino-6-(4-fluoro-phenylamino)-pyrimidine-5-carbaldehyde O-methyl-oxime, |
| 173 | 4-amino-6-(biphenyl-4-ylamino)-pyrimidine-5-carbaldehyde O-methyl-oxime, |
| 174 | 4-amino-6-(4-methylsulfanyl-phenylamino)-pyrimidine-5-carbaldehyde O-methyl-oxime, |
| 175 | 4-amino-6-(3,5-dimethoxy-phenylamino)-pyrimidine-5-carbaldehyde O-methyl-oxime, |
| 176 | 4-amino-6-(3,4,5-trimethoxy-phenylamino)-pyrimidine-5-carbaldehyde O-methyl-oxime, |
| 177 | 4-amino-6-(3,4-dimethoxy-phenylamino)-pyrimidine-5-carbaldehyde O-methyl-oxime, |
| 178 | 4-amino-6-(5,6,7,8-tetrahydro-naphthalen-1-ylamino)-pyrimidine-5-carbaldehyde O-methyl-oxime, |
| 179 | 4-[6-amino-5-(methoxyimino-methyl)-pyrimidin-4-ylamino]-N-pyrimidin-2-yl-benzenesulfonamide, |
| 180 | 3-[6-amino-5-(methoxyimino-methyl)-pyrimidin-4-ylamino]-benzoic acid ethyl ester, |
| 181 | {4-[6-amino-5-(methoxyimino-methyl)-pyrimidin-4-ylamino]-benzyl}-phosphonic acid diethyl ester, |

-continued

| Cpd | Names |
|---|---|
| 182 | 4-amino-6-(4-ethyl-phenylamino)-pyrimidine-5-carbaldehyde O-methyl-oxime, |
| 183 | 4-[6-amino-5-(methoxyimino-methyl)-pyrimidin-4-ylamino]-N-(3,5-dimethyl-pyrazin-2-yl)-benzenesulfonamide, |
| 184 | 4-amino-6-(2-methyl-benzothiazol-5-ylamino)-pyrimidine-5-carbaldehyde O-methyl-oxime, |
| 185 | 4-amino-6-[4-(4-methoxy-phenylamino)-phenylamino]-pyrimidine-5-carbaldehyde O-methyl-oxime, |
| 186 | 4-amino-6-(4-dimethylamino-phenylamino)-pyrimidine-5-carbaldehyde O-methyl-oxime, |
| 187 | 4-[6-amino-5-(methoxyimino-methyl)-pyrimidin-4-ylamino]-N-(2-diethylamino-ethyl)-benzamide, |
| 188 | 4-[6-amino-5-(methoxyimino-methyl)-pyrimidin-4-ylamino]-benzoic acid butyl ester, |
| 189 | 4-amino-6-(indan-4-ylamino)-pyrimidine-5-carbaldehyde O-methyl-oxime, |
| 190 | 4-amino-6-(4'-chloro-biphenyl-4-ylamino)-pyrimidine-5-carbaldehyde O-methyl-oxime, |
| 191 | 4-amino-6-[6-(4-fluoro-phenoxy)-pyridin-3-ylamino]-pyrimidine-5-carbaldehyde O-methyl-oxime, |
| 192 | 4'-[6-amino-5-(methoxyimino-methyl)-pyrimidin-4-ylamino]-biphenyl-4-carboxylic acid methyl ester, and |
| 193 | N-(4-benzyloxy-3-chloro-phenyl)-5-[5-(2-morpholin-4-yl-ethyl)-[1,3,4]oxadiazol-2-yl]-pyrimidine-4,6-diamine. |

A representative compound of formula (I) includes a compound selected from:

| Cpd | Names |
|---|---|
| 1 | (5E)-4-amino-6-(3-chloro-4-fluoro-phenylamino)-pyrimidine-5-carbaldehyde O-methyl-oxime, |
| 2 | (5E)-4-amino-6-[1-(3-fluoro-benzyl)-1H-indazol-5-ylamino]-pyrimidine-5-carbaldehyde O-methyl-oxime, |
| 4 | (5E)-4-amino-6-[3-chloro-4-(3-fluoro-benzyloxy)-phenylamino]-pyrimidine-5-carbaldehyde O-methyl-oxime, |
| 7 | (5E)-4-amino-6-(3-methoxy-4-phenoxy-phenylamino)-pyrimidine-5-carbaldehyde O-methyl-oxime, |
| 9 | (5E)-4-amino-6-(4-benzyloxy-3-chloro-phenylamino)-pyrimidine-5-carbaldehyde O-methyl-oxime, |
| 10 | (5E)-4-amino-6-[1-(3-fluoro-benzyl)-1H-indazol-5-ylamino]-pyrimidine-5-carbaldehyde O-ethyl-oxime, |
| 11 | (5E)-4-amino-6-[1-(3-fluoro-benzyl)-1H-indazol-5-ylamino]-pyrimidine-5-carbaldehyde O-allyl-oxime, |
| 12 | (5E)-4-amino-6-[1-(3-fluoro-benzyl)-1H-indazol-5-ylamino]-pyrimidine-5-carbaldehyde O-tert-butyl-oxime, |
| 16 | (5E)-4-amino-6-[(1S)-1-phenyl-ethylamino]-pyrimidine-5-carbaldehyde O-ethyl-oxime, |
| 17 | (5E)-4-amino-6-(1H-indol-5-ylamino)-pyrimidine-5-carbaldehyde O-ethyl-oxime, |
| 18 | (5E)-4-amino-6-[3-chloro-4-(3-fluoro-benzyloxy)-phenylamino]-pyrimidine-5-carbaldehyde O-ethyl-oxime, |
| 19 | (5E)-4-amino-6-[1-(3-fluoro-benzyl)-1H-indazol-5-ylamino]-pyrimidine-5-carbaldehyde O-(2-morpholin-4-yl-ethyl)-oxime, |
| 24 | (5E)-4-amino-6-(4-phenoxy-phenylamino)-pyrimidine-5-carbaldehyde O-methyl-oxime, |
| 25 | (5E)-4-amino-6-(4-benzyloxy-phenylamino)-pyrimidine-5-carbaldehyde O-methyl-oxime, |
| 30 | (5E)-4-amino-6-[1-(3-fluoro-benzyl)-1H-indazol-5-ylamino]-pyrimidine-5-carbaldehyde O-isobutyl-oxime, |
| 31 | (5E)-4-amino-6-[1-(3-fluoro-benzyl)-1H-indazol-5-ylamino]-pyrimidine-5-carbaldehyde O-(2-phenoxy-ethyl)-oxime, |
| 32 | (5E)-4-amino-6-[3-chloro-4-(pyridin-2-ylmethoxy)-phenylamino]-pyrimidine-5-carbaldehyde O-methyl-oxime, |
| 33 | (5E)-4-amino-6-[1-(3-fluoro-benzyl)-1H-indol-5-ylamino]-pyrimidine-5-carbaldehyde O-ethyl-oxime, |
| 34 | (5E)-4-amino-6-[1-(3-fluoro-benzyl)-1H-indol-5-ylamino]-pyrimidine-5-carbaldehyde O-methyl-oxime, |
| 36 | (5E)-4-amino-6-(3-bromo-phenylamino)-pyrimidine-5-carbaldehyde O-methyl-oxime, |
| 37 | (5E)-4-amino-6-(4-benzyloxy-3-chloro-phenylamino)-pyrimidine-5-carbaldehyde O-ethyl-oxime, |
| 44 | (5E)-4-amino-6-[1-(3-fluoro-benzyl)-1H-indazol-5-ylamino]-pyrimidine-5-carbaldehyde O-(4-methoxy-benzyl)-oxime, |

-continued

| Cpd | Names |
|---|---|
| 45 | (5E)-4-amino-6-[1-(3-fluoro-benzyl)-1H-indazol-5-ylamino]-pyrimidine-5-carbaldehyde O-(2-methoxy-benzyl)-oxime, |
| 46 | (5E)-4-amino-6-[1-(3-fluoro-benzyl)-1H-indazol-5-ylamino]-pyrimidine-5-carbaldehyde O-benzyl-oxime, |
| 47 | (5E)-4-amino-6-[1-(3-fluoro-benzyl)-1H-indazol-5-ylamino]-pyrimidine-5-carbaldehyde O-isopropyl-oxime, |
| 48 | (5E)-4-amino-6-(1-benzyl-1H-indazol-5-ylamino)-pyrimidine-5-carbaldehyde O-methyl-oxime, |
| 49 | (5E)-4-amino-6-(1-benzyl-1H-indazol-5-ylamino)-pyrimidine-5-carbaldehyde O-ethyl-oxime, |
| 50 | 3-{5-[6-amino-(5E)-5-(methoxyimino-methyl)-pyrimidin-4-ylamino]-indazol-1-ylmethyl}-benzonitrile, |
| 51 | 3-{5-[6-amino-(5E)-5-(ethoxyimino-methyl)-pyrimidin-4-ylamino]-indazol-1-ylmethyl}-benzonitrile, |
| 54 | (5E)-4-amino-6-[1-(3-chloro-benzyl)-1H-indazol-5-ylamino]-pyrimidine-5-carbaldehyde O-methyl-oxime, |
| 55 | (5E)-4-amino-6-[1-(3-chloro-benzyl)-1H-indazol-5-ylamino]-pyrimidine-5-carbaldehyde O-ethyl-oxime, |
| 60 | (5E)-4-amino-6-[2-(3-fluoro-benzyl)-1H-benzoimidazol-5-ylamino]-pyrimidine-5-carbaldehyde O-methyl-oxime, |
| 70 | (5E)-4-amino-6-[1-(3-fluoro-benzyl)-1H-indazol-5-ylamino]-pyrimidine-5-carbaldehyde O-(3-dimethylamino-propyl)-oxime, |
| 71 | (5E)-4-amino-6-(4-benzyloxy-3-chloro-phenylamino)-pyrimidine-5-carbaldehyde O-(2-methoxy-ethyl)-oxime, |
| 75 | (5E)-4-amino-6-[3-chloro-4-(3-fluoro-benzyloxy)-phenylamino]-pyrimidine-5-carbaldehyde O-(3-hydroxy-propyl)-oxime, |
| 76 | (5E)-4-amino-6-(4-benzyloxy-3-chloro-phenylamino)-pyrimidine-5-carbaldehyde O-(3-hydroxy-propyl)-oxime, |
| 78 | (5E)-4-amino-6-(4-benzyloxy-3-chloro-phenylamino)-pyrimidine-5-carbaldehyde O-(2-morpholin-4-yl-ethyl)-oxime, |
| 78* | (5E)-4-amino-6-(4-benzyloxy-3-chloro-phenylamino)-pyrimidine-5-carbaldehyde O-(2-morpholin-4-yl-ethyl)-oxime monohydrochloride salt, |
| 79 | (5E)-4-amino-6-[3-chloro-4-(3-fluoro-benzyloxy)-phenylamino]-pyrimidine-5-carbaldehyde oxime, |
| 84 | (5E)-4-amino-6-[1-(3-fluoro-benzyl)-1H-indazol-5-ylamino]-pyrimidine-5-carbaldehyde oxime, |
| 85 | (5E)-4-amino-6-[1-(3-fluoro-benzyl)-1H-indazol-5-ylamino]-pyrimidine-5-carbaldehyde O-(3-hydroxy-propyl)-oxime, |
| 87 | (5E)-4-amino-6-[1-(3-fluoro-benzyl)-1H-indazol-5-ylamino]-pyrimidine-5-carbaldehyde O-(3-morpholin-4-yl-propyl)-oxime, |
| 88 | (5E)-4-amino-6-[1-(3-fluoro-benzyl)-1H-indol-5-ylamino]-pyrimidine-5-carbaldehyde oxime, |
| 91 | (5E)-4-amino-6-[1-(3-fluoro-benzyl)-1H-indol-5-ylamino]-pyrimidine-5-carbaldehyde O-(3-hydroxy-propyl)-oxime, |
| 92 | (5E)-4-amino-6-[1-(3-fluoro-benzyl)-1H-indazol-5-ylamino]-pyrimidine-5-carbaldehyde O-(3-piperidin-1-yl-propyl)-oxime, |
| 93 | (5E)-4-amino-6-[3-chloro-4-(3-fluoro-benzyloxy)-phenylamino]-pyrimidine-5-carbaldehyde O-(2-morpholin-4-yl-ethyl)-oxime, |
| 94 | (5E)-4-amino-6-[3-chloro-4-(3-fluoro-benzyloxy)-phenylamino]-pyrimidine-5-carbaldehyde O-(2-piperidin-1-yl-ethyl)-oxime, |
| 101 | (5E)-4-amino-6-[1-(3-fluoro-benzyl)-1H-indol-5-ylamino]-pyrimidine-5-carbaldehyde O-(2-morpholin-4-yl-ethyl)-oxime, |
| 102 | (5E)-4-amino-6-[1-(3-fluoro-benzyl)-1H-indol-5-ylamino]-pyrimidine-5-carbaldehyde O-(2-piperidin-1-yl-ethyl)-oxime, |
| 118 | 4-amino-6-(4-benzyloxy-3-chloro-phenylamino)-pyrimidine-5-carbonitrile, |
| 120 | 4-amino-6-(4-methoxy-phenylamino)-pyrimidine-5-carbaldehyde O-methyl-oxime, |
| 124 | 4-amino-6-(indan-1-ylamino)-pyrimidine-5-carbaldehyde O-methyl-oxime, |
| 125 | 4-amino-6-(1,2,3,4-tetrahydro-naphthalen-1-ylamino)-pyrimidine-5-carbaldehyde O-methyl-oxime, |
| 126 | 4-amino-6-[1-(4-chloro-phenyl)-ethylamino]-pyrimidine-5-carbaldehyde O-methyl-oxime, and |
| 128 | 4-amino-6-(6-phenoxy-pyridin-3-ylamino)-pyrimidine-5-carbaldehyde O-methyl-oxime. |

A representative compound of formula (I) includes a compound selected from:

| Cpd | Names |
|---|---|
| 2 | (5E)-4-amino-6-[1-(3-fluoro-benzyl)-1H-indazol-5-ylamino]-pyrimidine-5-carbaldehyde O-methyl-oxime, |
| 10 | (5E)-4-amino-6-[1-(3-fluoro-benzyl)-1H-indazol-5-ylamino]-pyrimidine-5-carbaldehyde O-ethyl-oxime, |

-continued

| Cpd | Names |
|---|---|
| 11 | (5E)-4-amino-6-[1-(3-fluoro-benzyl)-1H-indazol-5-ylamino]-pyrimidine-5-carbaldehyde O-allyl-oxime, |
| 75 | (5E)-4-amino-6-[3-chloro-4-(3-fluoro-benzyloxy)-phenylamino]-pyrimidine-5-carbaldehyde O-(3-hydroxy-propyl)-oxime, |

| Cpd | Names |
|---|---|
| 78 | (5E)-4-amino-6-(4-benzyloxy-3-chloro-phenylamino)-pyrimidine-5-carbaldehyde O-(2-morpholin-4-yl-ethyl)-oxime, |
| 78* | (5E)-4-amino-6-(4-benzyloxy-3-chloro-phenylamino)-pyrimidine-5-carbaldehyde O-(2-morpholin-4-yl-ethyl)-oxime monohydrochloride salt, |
| 79 | (5E)-4-amino-6-[3-chloro-4-(3-fluoro-benzyloxy)-phenylamino]-pyrimidine-5-carbaldehyde oxime, |
| 88 | (5E)-4-amino-6-[1-(3-fluoro-benzyl)-1H-indol-5-ylamino]-pyrimidine-5-carbaldehyde oxime, |
| 91 | (5E)-4-amino-6-[1-(3-fluoro-benzyl)-1H-indol-5-ylamino]-pyrimidine-5-carbaldehyde O-(3-hydroxy-propyl)-oxime, |
| 93 | (5E)-4-amino-6-[3-chloro-4-(3-fluoro-benzyloxy)-phenylamino]-pyrimidine-5-carbaldehyde O-(2-morpholin-4-yl-ethyl)-oxime, |
| 94 | (5E)-4-amino-6-[3-chloro-4-(3-fluoro-benzyloxy)-phenylamino]-pyrimidine-5-carbaldehyde O-(2-piperidin-1-yl-ethyl)-oxime, |
| 101 | (5E)-4-amino-6-[1-(3-fluoro-benzyl)-1H-indol-5-ylamino]-pyrimidine-5-carbaldehyde O-(2-morpholin-4-yl-ethyl)-oxime, |
| 102 | (5E)-4-amino-6-[1-(3-fluoro-benzyl)-1H-indol-5-ylamino]-pyrimidine-5-carbaldehyde O-(2-piperidin-1-yl-ethyl)-oxime, |
| 118 | 4-amino-6-(4-benzyloxy-3-chloro-phenylamino)-pyrimidine-5-carbonitrile, |
| 125 | 4-amino-6-(1,2,3,4-tetrahydro-naphthalen-1-ylamino)-pyrimidine-5-carbaldehyde O-methyl-oxime, and |
| 128 | 4-amino-6-(6-phenoxy-pyridin-3-ylamino)-pyrimidine-5-carbaldehyde O-methyl-oxime. |

A representative compound of formula (I) includes a compound selected from:

| Cpd | Names |
|---|---|
| 127 | 4-amino-6-[1-(4-methoxy-phenyl)-ethylamino]-pyrimidine-5-carbaldehyde O-methyl-oxime, |
| 130 | 4-amino-6-(1,4-dioxo-1,2,3,4-tetrahydro-phthalazin-5-ylamino)-pyrimidine-5-carbaldehyde O-methyl-oxime, |
| 131 | 4-amino-6-(2-fluoro-5-methyl-phenylamino)-pyrimidine-5-carbaldehyde O-methyl-oxime, |
| 132 | 4-amino-6-(2,4,6-trimethyl-phenylamino)-pyrimidine-5-carbaldehyde O-methyl-oxime, |
| 133 | 4-amino-6-(3-chloro-2-methyl-phenylamino)-pyrimidine-5-carbaldehyde O-methyl-oxime, |
| 134 | 4-amino-6-(3-methylsulfanyl-phenylamino)-pyrimidine-5-carbaldehyde O-methyl-oxime, |
| 135 | 4-amino-6-[3-(1-methoxyimino-ethyl)-phenylamino]-pyrimidine-5-carbaldehyde O-methyl-oxime, |
| 136 | 4-amino-6-(3,5-dimethyl-phenylamino)-pyrimidine-5-carbaldehyde O-methyl-oxime, |
| 137 | N-{4-[6-amino-5-(methoxyimino-methyl)-pyrimidin-4-ylamino]-phenyl}-acetamide, |
| 138 | 4-amino-6-phenylamino-pyrimidine-5-carbaldehyde O-methyl-oxime, |
| 139 | 4-amino-6-(4-morpholin-4-yl-phenylamino)-pyrimidine-5-carbaldehyde O-methyl-oxime, |
| 140 | 4-amino-6-o-tolylamino-pyrimidine-5-carbaldehyde O-methyl-oxime, |
| 141 | 4-amino-6-(3,4-difluoro-phenylamino)-pyrimidine-5-carbaldehyde O-methyl-oxime, |
| 142 | 4-amino-6-(3-fluoro-4-methyl-phenylamino)-pyrimidine-5-carbaldehyde O-methyl-oxime, |
| 143 | 4-amino-6-(3,4-dichloro-phenylamino)-pyrimidine-5-carbaldehyde O-methyl-oxime, |
| 144 | 4-amino-6-(3-chloro-4-methyl-phenylamino)-pyrimidine-5-carbaldehyde O-methyl-oxime, |
| 145 | 4-amino-6-[5-chloro-2-methyl-4-(2-oxo-2-phenyl-ethyl)-phenylamino]-pyrimidine-5-carbaldehyde O-methyl-oxime, |
| 146 | 4-amino-6-(3-ethyl-phenylamino)-pyrimidine-5-carbaldehyde O-methyl-oxime, |
| 147 | 4-amino-6-(4-isopropyl-phenylamino)-pyrimidine-5-carbaldehyde O-methyl-oxime, |
| 148 | 4-amino-6-(1H-indol-5-ylamino)-pyrimidine-5-carbaldehyde O-methyl-oxime, |
| 149 | 4-amino-6-(3-trifluoromethyl-phenylamino)-pyrimidine-5-carbaldehyde O-methyl-oxime, |
| 150 | 4-amino-6-m-tolylamino-pyrimidine-5-carbaldehyde O-methyl-oxime, |
| 151 | 4-amino-6-(4-chloro-phenylamino)-pyrimidine-5-carbaldehyde O-methyl-oxime, |
| 152 | 4-amino-6-(4-chloro-2-methyl-phenylamino)-pyrimidine-5-carbaldehyde O-methyl-oxime, |
| 153 | 4-amino-6-(4-phenylamino-phenylamino)-pyrimidine-5-carbaldehyde O-methyl-oxime, |
| 154 | 4-amino-6-(4-diethylamino-phenylamino)-pyrimidine-5-carbaldehyde O-methyl-oxime, |
| 155 | 4-[6-amino-5-(methoxyimino-methyl)-pyrimidin-4-ylamino]-benzoic acid methyl ester, |
| 156 | 4-amino-6-[4-(methoxyimino-phenyl-methyl)-phenylamino]-pyrimidine-5-carbaldehyde O-methyl-oxime, |
| 157 | 4-(4-acetyl-phenylamino)-6-amino-pyrimidine-5-carbaldehyde O-methyl-oxime, |
| 158 | 4-amino-6-[4-(1-methoxyimino-ethyl)-phenylamino]-pyrimidine-5-carbaldehyde O-methyl-oxime, |
| 159 | {4-[6-amino-5-(methoxyimino-methyl)-pyrimidin-4-ylamino]-phenyl}-acetonitrile, |
| 160 | 4-amino-6-(2-methoxy-4-phenylamino-phenylamino)-pyrimidine-5-carbaldehyde O-methyl-oxime, |

-continued

| Cpd | Names |
|---|---|
| 161 | N-{4-[6-amino-5-(methoxyimino-methyl)-pyrimidin-4-ylamino]-3-methoxy-phenyl}-acetamide, |
| 162 | 4-amino-6-(4-cyclohexyl-phenylamino)-pyrimidine-5-carbaldehyde O-methyl-oxime, |
| 163 | 4-amino-6-(naphthalen-1-ylamino)-pyrimidine-5-carbaldehyde O-methyl-oxime, |
| 164 | 4-amino-6-(4-chloro-naphthalen-1-ylamino)-pyrimidine-5-carbaldehyde O-methyl-oxime, |
| 165 | 4-amino-6-(2,4-difluoro-phenylamino)-pyrimidine-5-carbaldehyde O-methyl-oxime, |
| 166 | 4-amino-6-(2-methylsulfanyl-phenylamino)-pyrimidine-5-carbaldehyde O-methyl-oxime, |
| 167 | 4-amino-6-(3-fluoro-phenylamino)-pyrimidine-5-carbaldehyde O-methyl-oxime, |
| 168 | 4-amino-6-(3,5-dichloro-phenylamino)-pyrimidine-5-carbaldehyde O-methyl-oxime, |
| 169 | 4-amino-6-(3,5-dichloro-phenylamino)-pyrimidine-5-carbaldehyde O-methyl-oxime, |
| 170 | 4-amino-6-(5-chloro-2-methoxy-phenylamino)-pyrimidine-5-carbaldehyde O-methyl-oxime, |
| 171 | 4-amino-6-(5-chloro-2-methyl-phenylamino)-pyrimidine-5-carbaldehyde O-methyl-oxime, |
| 172 | 4-amino-6-(4-fluoro-phenylamino)-pyrimidine-5-carbaldehyde O-methyl-oxime, |
| 173 | 4-amino-6-(biphenyl-4-ylamino)-pyrimidine-5-carbaldehyde O-methyl-oxime, |
| 174 | 4-amino-6-(4-methylsulfanyl-phenylamino)-pyrimidine-5-carbaldehyde O-methyl-oxime, |
| 175 | 4-amino-6-(3,5-dimethoxy-phenylamino)-pyrimidine-5-carbaldehyde O-methyl-oxime, |
| 176 | 4-amino-6-(3,4,5-trimethoxy-phenylamino)-pyrimidine-5-carbaldehyde O-methyl-oxime, |
| 177 | 4-amino-6-(3,4-dimethoxy-phenylamino)-pyrimidine-5-carbaldehyde O-methyl-oxime, |
| 178 | 4-amino-6-(5,6,7,8-tetrahydro-naphthalen-1-ylamino)-pyrimidine-5-carbaldehyde O-methyl-oxime, |
| 179 | 4-[6-amino-5-(methoxyimino-methyl)-pyrimidin-4-ylamino]-N-pyrimidin-2-yl-benzenesulfonamide, |
| 180 | 3-[6-amino-5-(methoxyimino-methyl)-pyrimidin-4-ylamino]-benzoic acid ethyl ester, |
| 181 | {4-[6-amino-5-(methoxyimino-methyl)-pyrimidin-4-ylamino]-benzyl}-phosphonic acid diethyl ester, |
| 182 | 4-amino-6-(4-ethyl-phenylamino)-pyrimidine-5-carbaldehyde O-methyl-oxime, |
| 183 | 4-[6-amino-5-(methoxyimino-methyl)-pyrimidin-4-ylamino]-N-(3,5-dimethyl-pyrazin-2-yl)-benzenesulfonamide, |
| 184 | 4-amino-6-(2-methyl-benzothiazol-5-ylamino)-pyrimidine-5-carbaldehyde O-methyl-oxime, |
| 185 | 4-amino-6-[4-(4-methoxy-phenylamino)-phenylamino]-pyrimidine-5-carbaldehyde O-methyl-oxime, |
| 186 | 4-amino-6-(4-dimethylamino-phenylamino)-pyrimidine-5-carbaldehyde O-methyl-oxime, |
| 187 | 4-[6-amino-5-(methoxyimino-methyl)-pyrimidin-4-ylamino]-N-(2-O-diethylamino-ethyl)-benzamide, |
| 188 | 4-[6-amino-5-(methoxyimino-methyl)-pyrimidin-4-ylamino]-benzoic acid butyl ester, |
| 189 | 4-amino-6-(indan-4-ylamino)-pyrimidine-5-carbaldehyde O-methyl-oxime, |
| 190 | 4-amino-6-(4'-chloro-biphenyl-4-ylamino)-pyrimidine-5-carbaldehyde methyl-oxime, |
| 191 | 4-amino-6-[6-(4-fluoro-phenoxy)-pyridin-3-ylamino]-pyrimidine-5-O-carbaldehyde O-methyl-oxime, |
| 192 | 4'-[6-amino-5-(methoxyimino-methyl)-pyrimidin-4-ylamino]-biphenyl-4-carboxylic acid methyl ester, and |
| 193 | N-(4-benzyloxy-3-chloro-phenyl)-5-[5-(2-morpholin-4-yl-ethyl)-[1,3,4]oxadiazol-2-yl]-pyrimidine-4,6-diamine. |

Synthetic Methods

Representative compounds of the present invention can be synthesized in accordance with the general synthetic schemes described below and are illustrated more particularly in the specific synthetic examples that follow. The general schemes and specific examples are offered by way of illustration; the invention should not be construed as being limited by the chemical reactions and conditions expressed.

Except where indicated, starting materials and intermediates used in the schemes and examples are prepared by known methodologies well within the ordinary skill of persons versed in the art. No attempt has been made to optimize the yields obtained in any of the example reactions. One skilled in the art would also know how to increase such yields through routine variations in materials, solvents, reagents, reaction conditions and the like.

Compounds of the present invention can also be useful as intermediates for conversion to other compounds representative of the present invention via functional group transformations.

DSC analysis was were conducted on a TA Instruments Q100. The calibration standard was indium. A sample (approximately 2 mg) was placed into a TA DSC pan and weight was recorded. Crimped pans were used for analysis and the samples were heated under nitrogen (50 cc/min) at a rate of 10° C./min, up to a final temperature of 250° C. The data were processed using a thermal analyzer (Universal Analyzer 2000, TA Instruments).

The terms used in describing the invention are commonly used and known to those skilled in the art. When used herein, the following abbreviations have the indicated meanings

| Abbreviation | Meaning |
|---|---|
| AcOH | acetic acid |
| Cpd | compound |
| DCM | dichloromethane |
| DMF | N,N-dimethylformamide |
| DMSO | dimethyl sulfoxide |
| EDCI | 1-(3-dimethylaminopropyl)-3-ethyl-carbodiimide hydrochloride |
| EtOAc | ethyl acetate |
| EtOH | ethanol |
| h/hr(s)/min(s) | hour(s)/min(s) |
| LCMS Rt | High Pressure Liquid Chromatography Mass Spectrum Retention Time |
| MeOH | methanol |
| RT/rt/r.t. | room temperature |
| TEA or Et$_3$N | triethylamine |
| THF | tetrahydrofuran |

Scheme A

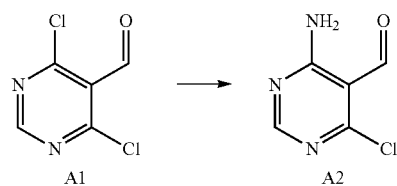

A solution of Compound A1 (in a suitable solvent such as toluene and the like) is reacted with a volume of NH$_3$ gas under suitable conditions to provide a Compound A2.

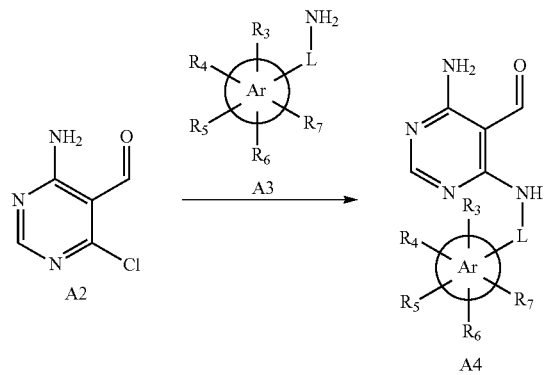

A mixture of Compound A2 (in a suitable solvent such as DMSO and the like) and a reagent (such as triethylamine and the like) is reacted with a Compound A3 to provide a Compound A4.

Alternatively, a mixture of Compound A2 (in a suitable solvent such as 2-methoxy-ethanol and the like) is reacted with Compound A3 in the presence of a catalytic amount of acid (such as aqueous HCl) to provide Compound A4.

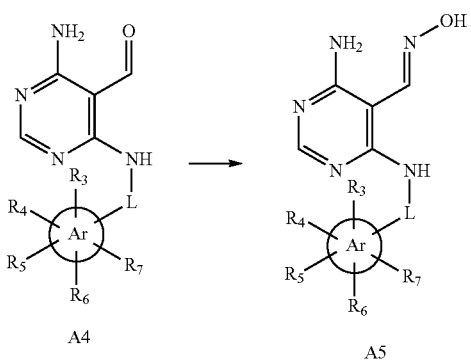

A mixture of Compound A4 (in a suitable solvent such as DMSO and the like) is reacted with NH$_2$OH hydrochloride to provide a Compound A5, representative of a compound of formula (I).

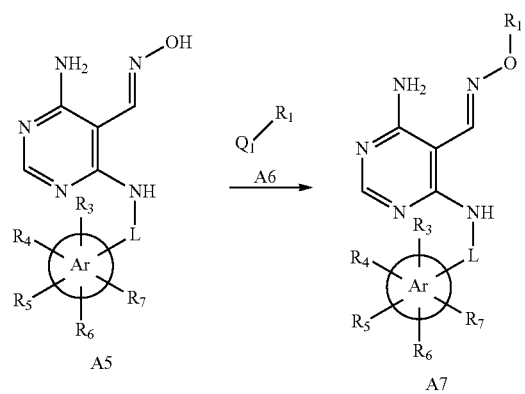

A mixture of Compound A5 (in a suitable solvent such as DMF and the like) and a basic reagent (such as cesium carbonate and the like) is reacted with a Compound A6 (wherein Q$_1$ is a leaving group such as a halogen atom and the like) to provide a Compound A7, representative of a compound of formula (I).

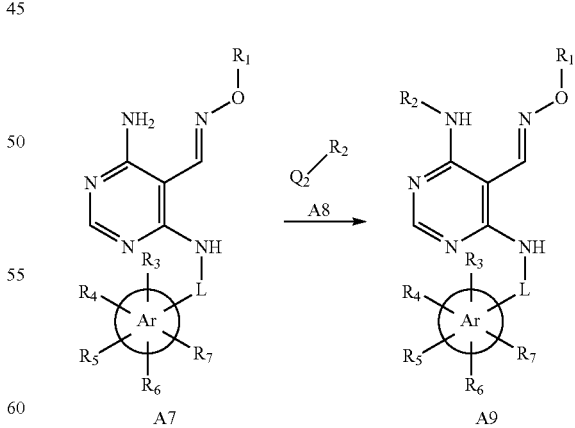

A solution of Compound A7 (in a suitable solvent such as DMF and the like) is reacted with a Compound A8 (wherein Q$_2$ is a leaving group such as a halogen atom and the like) to provide a Compound A9, representative of a compound of formula (I).

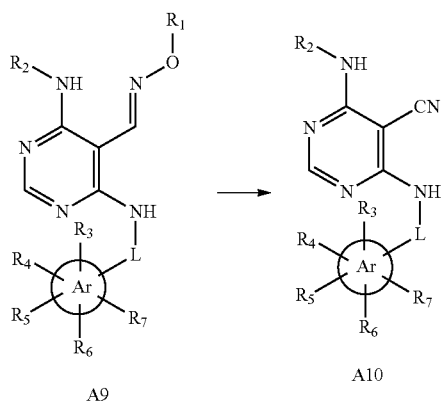

The Compound A9 is metabolized to provide a Compound A10, representative of a compound of formula (I).

A mixture of Compound A13 (in a suitable solvent such as DMSO and the like) and a reagent (such as triethylamine and the like) is reacted with a Compound A3 to provide a Compound A14.

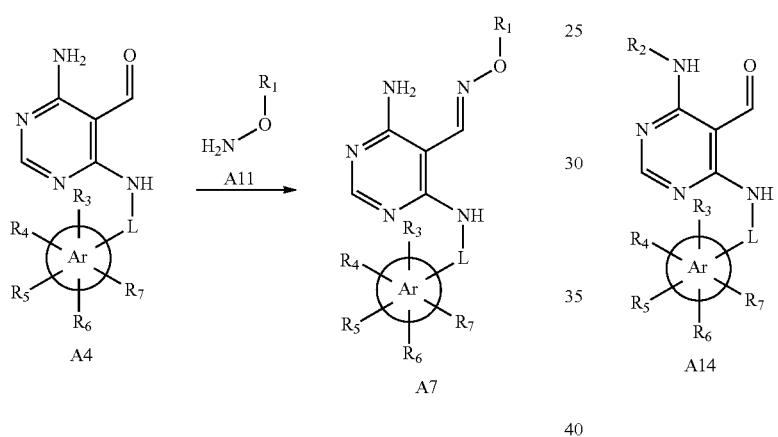

A mixture of Compound A4 (in a suitable solvent such as DMSO and the like) is reacted with Compound A11 to provide a Compound A7, representative of a compound of formula (I).

Alternatively, a mixture of Compound A4 (in a suitable solvent such as 2-methoxy-ethanol and the like) is reacted with a dihydrochloride salt of Compound A11 in the presence of a base (such as NaOH) to provide Compound A7.

A mixture of Compound A14 (in a suitable solvent such as DMSO and the like) is reacted with Compound A11 to provide a Compound A9, representative of a compound of formula (I).

Scheme B

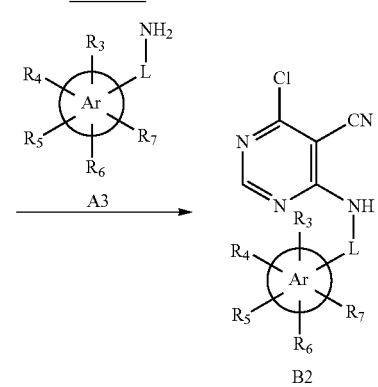

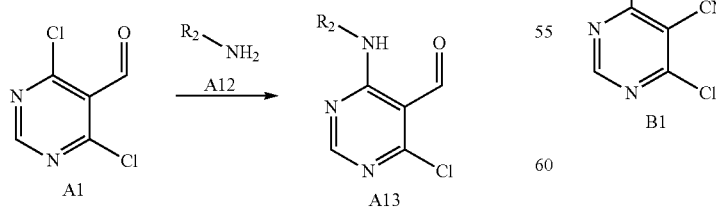

A solution of Compound A1 (in a suitable solvent such as toluene and the like) is reacted with a Compound A12 in a suitable solvent such as THF under suitable conditions to provide a Compound A13.

A mixture of Compound B1 (in a suitable solvent such as THF and the like) and a reagent (such as triethylamine and the like) is reacted with a Compound A3 to provide a Compound B2.

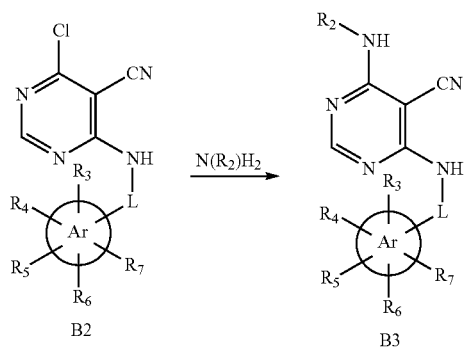

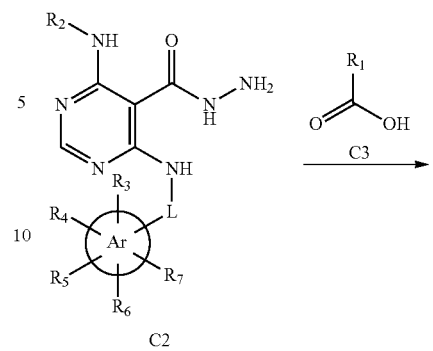

A suspension of Compound B2 in N(R₂)H₂ (in a suitable solvent such as MeOH and the like) is reacted to provide a Compound B3, representative of a compound of formula (I).

Scheme C

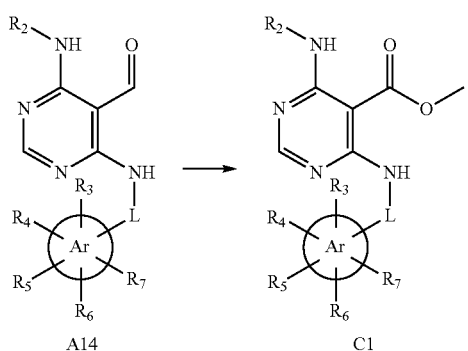

A mixture of Compound A14 (in a suitable solvent such as a mixture of THF and MeOH and the like) is reacted with a reagent mixture (such as a mixture of MnO₂, NaCN, AcOH and the like) to provide a Compound C1.

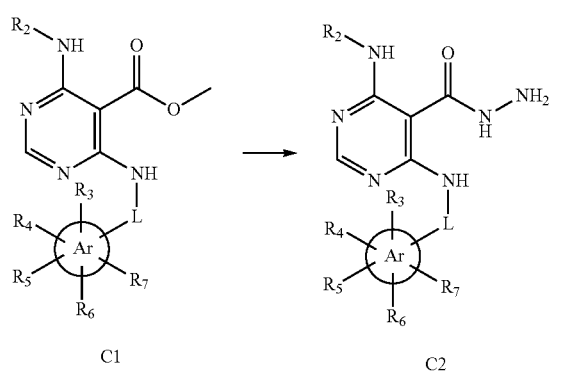

A suspension of Compound C1 (in a solvent such as 100% EtOH and the like) was treated with hydrazine to provide a Compound C2.

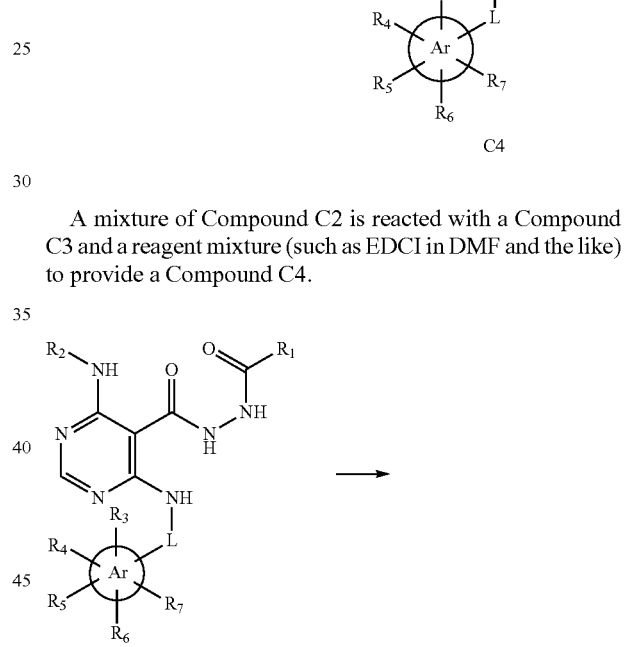

A mixture of Compound C2 is reacted with a Compound C3 and a reagent mixture (such as EDCI in DMF and the like) to provide a Compound C4.

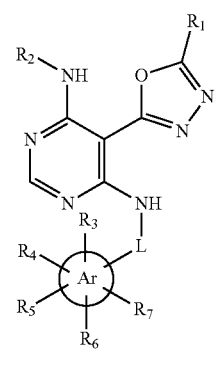

A solution of Compound C4 (in a solvent such as DCM and the like) is reacted with a reagent mixture (such as Et₃N and toluene sulfonyl chloride and the like) to provide a Compound C5, representative of a compound of formula (I).

EXAMPLE 1

(5E)-4-amino-6-(4-benzyloxy-3-chloro-phenylamino)-pyrimidine-5-carbaldehyde O-(2-morpholin-4-yl-ethyl)-oxime (Cpd 78)

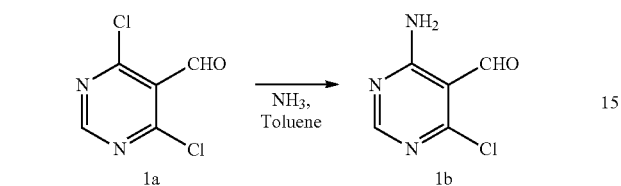

NH$_3$ (g) was blown through a solution of 4,6-dichloro-pyrimidine-5-carbaldehyde Compound 1a (50 g, 282.5 mmol) in toluene (565 mL, 0.5M) for 3 mins using a 12C glass frit, then the mixture was warmed at 60° C. with stirring for 30 min. NH$_3$ (g) was blown through the reaction mixture a second time for 3 min and the reaction was heated for 30 mins. NH$_3$ (g) was blown through the reaction mixture a third time for 3 min and the reaction was heated for a final 20 mins. The reaction mixture was diluted with H$_2$O (1 L), and extracted with EtOAc (1×750 mL, 3×500 mL). The organic extracts were washed with brine (4×) and dried (Na$_2$SO$_4$), then concentrated to afford 4-amino-6-chloro-pyrimidine-5-carbaldehyde Compound 1b (38.5 g, 87%) as a yellow solid. $^1$H NMR (300 MHz, DMSO-d6) δ 10.27 (s, 1H), 8.74 (br s, 1H), 8.58 (br s, 1H), 8.42 (s, 1H).

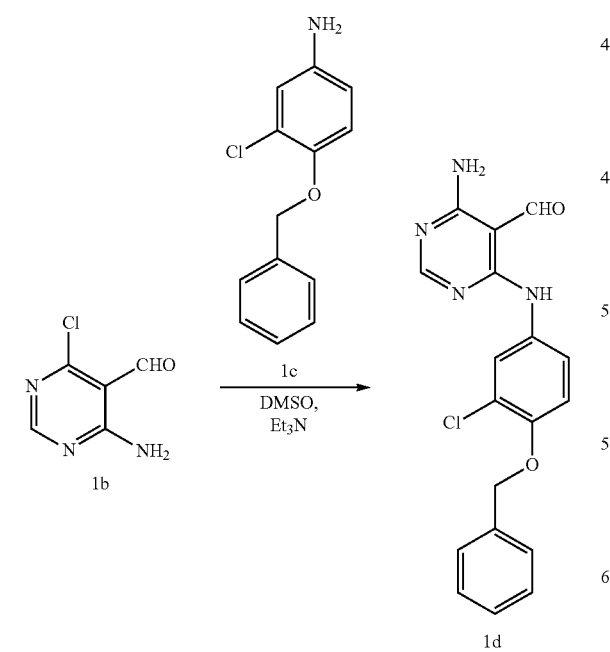

4-benzyloxy-3-chloro-phenylamine Compound 1c (8.9 g, 38 mmol) was added to a solution of Compound 1b (6.0 g, 38 mmol) and Et$_3$N (10.6 mL, 76 mmol) in DMSO (38 mL, 1M). The mixture was warmed at 100° C. for 3 hrs. The reaction mixture was cooled, then diluted with H$_2$O and extracted with EtOAc (3×). The organic extract was washed with H$_2$O (4×), concentrated onto SiO$_2$ (30 g) and purified via column chromatography (Horizon, 65+, 60 to 100% EtOAc/hexanes) to afford 4-amino-6-(4-benzyloxy-3-chloro-phenylamino)-pyrimidine-5-carbaldehyde Compound 1d (8.29 g, 61%) as a yellow solid. $^1$H NMR (400 MHz, CD$_3$OD, warm) δ 10.15 (s, 1H), 8.05 (s, 1H), 7.77 (d, J=2.4 Hz, 1H), 7.48 (d, J=7.6 Hz, 2H), 7.38 (m, 4H), 7.11 (d, J=8.8 Hz, 1H), 5.18, (s, 2H).

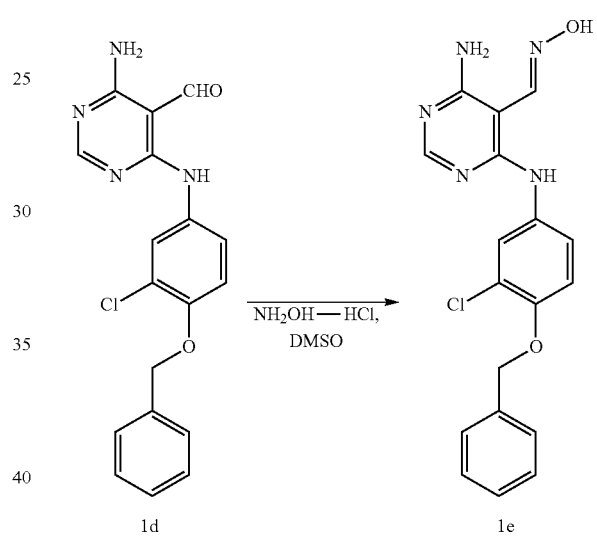

A solution of Compound 1d (3.88 g, 10.9 mmol) and NH$_2$OH hydrochloride (3.02 g, 43.6 mmol) was warmed in DSMO at 90° C. for 4 hours. The reaction mixture was cooled, diluted with H$_2$O and extracted with EtOAc (3×). The combined organic extracts were washed with H$_2$O (4×), then dried (Na$_2$SO$_4$) and concentrated onto SiO$_2$ (12 g). The residue was purified via column chromatography (Horizon 65+, 70 to 100% EtOAc/hexanes) to provide 4-amino-6-(4-benzyloxy-3-chloro-phenylamino)-pyrimidine-5-carbaldehyde oxime Compound 1e (2.65 g (66%) as a yellow solid. $^1$H NMR (300 MHz, DMSO-d6) δ 11.26 (s, 1H), 9.82 (s, 1H), 8.64 (s, 1H), 8.03 (s, 1H), 7.81 (d, J=2.4 Hz, 1H), 7.45 (m, 6H), 7.23 (m, 3H), 5.20 (s, 2H).

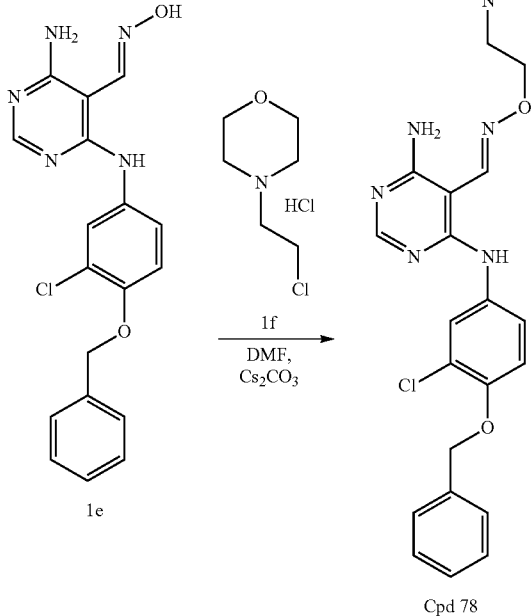

4-(2-chloro-ethyl)-morpholine hydrochloride (1.6 g, 8.9 mmol) was added to a suspension of Compound 1e (3.3 g, 8.9 mmol) and cesium carbonate (8.6 g, 26.7 g) in DMF (90 mL, 0.1 M). The mixture was warmed at 50° C. for 6 hrs. The reaction mixture was cooled, then diluted with $H_2O$ and extracted with EtOAc (3×). The combined organic extracts were washed with $H_2O$ (4×), then dried ($Na_2SO_4$) and concentrated onto $SiO_2$ (12 g). The residue was purified via column chromatography (Horizon 40+M, 0-6% MeOH/DCM) to provide Compound 78 (3.58 g, 83%) as a yellow solid. $^1H$ NMR (300 MHz, DMSO-d6) δ 9.60 (s, 1H), 8.72 (s, 1H), 8.03 (s, 1H), 7.83 (d, J=2.7 Hz, 1H), 7.49-7.39 (m, 6H), 7.28 (s, 2H), 7.18 (d, J=9.0 Hz, 1H), 5.20 (s, 2H), 4.30 (t, J=5.6 Hz, 2H), 3.58 (m, 4H), 2.66 (t, J=5.6 Hz, 2H), 2.47 (m, 4H); MS (ESI) m/z 383 ($MH^+$); DSC Thermogram: single endothermic peak at 175° C. due to melting with onset and peak temperatures of 174.66° C. and 176.28° C., respectively, and an enthalpy of 142.9 J/g.

Compound 78 was further conjugated with monohydrochloride HCl to provide Compound 78 as a monohydrochloride salt. $^1H$ NMR (300 MHz, DMSO-d6) δ 10.78 (br s, 1H), 9.52 (s, 1H), 8.79 (s, 1H), 8.06 (s, 1H), 7.84 (d, J=2.7 Hz, 1H), 7.51-7.19 (m, 9 H), 7.20 (d, J=9 Hz, 1H), 5.22 (s, 2 H), 4.56 (br s, 2 H), 4.03-3.82 (m, 4H), 3.58-3.18 (m, 13H); Anal. Calcd for $C_{24}H_{28}Cl_2N_6O_3$: C, 55.50; H, 5.43; N, 16.18; Cl, 13.65. Found: C, 55.08; H, 5.41; N, 15.94; Cl, 13.17.

Using the procedure of Example 1, other compounds representative of the present invention were prepared:

| Cpd | Name and Data |
|---|---|
| 1 | (5E)-4-amino-6-(3-chloro-4-fluoro-phenylamino)-pyrimidine-5-carbaldehyde O-methyl-oxime<br>$^1H$ NMR (DMSO-d6) δ 9.68 (br, 1H), 8.71 (br, 1H), 8.06 (s, 1H), 7.99 (dd, J = 6.78 and 2.80 Hz, 1H), 7.49 (m, 1H), 7.35 (br, 2H), 7.34 (m, 1H), 3.96 (s, 3H). LC-MS Rt = 1.08 min, m/z 296.3 ($MH^+$) |
| 2 | (5E)-4-amino-6-[1-(3-fluoro-benzyl)-1H-indazol-5-ylamino]-pyrimidine-5-carbaldehyde O-methyl-oxime<br>$^1H$ NMR (DMSO-d6) δ 9.75 (s, 1H), 8.73 (s, 1H), 8.09 (t, J = 0.86 Hz, 1H), 8.06 (d, J = 1.86 Hz, 1H), 8.00 (s, 1H), 7.64 (d, J = 9.07 Hz, 1H), 7.44 (dd, J = 8.88 and 1.93 Hz, 1H), 7.34 (m, 1H), 7.21 (s, 2H), 7.09 (m, 1H), 7.04 (m, 2H), 5.67 (s, 2H), 3.95 (s, 3H). LC-MS Rt = 1.19 min, m/z 392.4 ($MH^+$) |
| 3 | (5E)-4-amino-6-(3-chloro-4-fluoro-benzylamino)-pyrimidine-5-carbaldehyde O-methyl-oxime MS m/z 310.1 ($MH^+$) |
| 4 | (5E)-4-amino-6-[3-chloro-4-(3-fluoro-benzyloxy)-phenylamino)-pyrimidine-5-carbaldehyde O-methyl-oxime<br>$^1H$ NMR (CD$_3$OD) δ 8.56 (s, 1H), 7.96 (s, 1H), 7.68 (d, J = 2.50 Hz, 1H), 7.39 (td, J = 7.98 and 5.58 Hz, 1H), 7.28 (dd, J = 8.85 and 2.61 Hz, 2 H), 7.23 (m, 1H), 7.08 (d, J = 8.92 Hz, 1H), 7.02 (m, 1H), 5.18 (s, 2H), 3.98 (s, 3H). LC-MS Rt = 1.41 min, m/z 402.1 ($MH^+$) |
| 5 | (5E)-4-amino-6-[2-(3-fluoro-benzyl)-2H-indazol-5-ylamino]-pyrimidine-5-carbaldehyde O-methyl-oxime<br>$^1H$ NMR (CDCl$_3$) δ 9.60 (s, 1H), 8.34 (d, J = 0.50 Hz, 1H), 8.18 (s, 1H), 8.03 (dd, J = 1.83 and 0.45 Hz, 1H), 7.91 (br, 1H), 7.71 (dd, J = 9.20 and 0.65 Hz, 1H), 7.31 (m, 1H), 7.23 (m, 1H), 7.02 (dd, J = 7.88 and 1.96 Hz, 2H), 6.96 (m, 1H), 5.72 (br, 2H), 5.58 (s, 2H), 4.03 (s, 3H). LC-MS Rt = 1.12 min, m/z 392.2 ($MH^+$) |
| 6 | (5E)-4-amino-6-[1-(3-fluoro-benzyl)-1H-indazol-5-ylamino]-pyrimidine-5-carbaldehyde O-(2-morpholin-4-yl-2-oxo-ethyl)-oxime<br>$^1H$ NMR (CD$_3$OD) δ 8.73 (s, 1H), 8.13 (d, J = 0.92 Hz, 1H), 8.12 (s, 1H), 7.94 (dd, J = 1.91 and 0.66 Hz, 1H), 7.63 (d, J = 9.0 Hz, 1H), 7.44 (dd, J = 8.92 and 1.97 Hz, 1H), 7.32 (dt, J = 7.98 and 5.75 Hz, 1H), 7.02 (m, 2H), 6.89 (dt, J = 9.66 and 1.79 Hz, 1H), 5.69 (s, 2H), 5.00 (s, 2H), 3.67 (t, J = 4.52 Hz, 2H), 3.60 (m, 4H), 3.53 (t, J = 4.85 Hz, 2H). LC-MS Rt = 1.00 min, m/z 505.1 ($MH^+$) |
| 7 | (5E)-4-amino-6-(3-methoxy-4-phenoxy-phenylamino)-pyrimidine-5-carbaldehyde O-methyl-oxime<br>$^1H$ NMR (CDCl$_3$) δ 9.40 (s, 1H), 8.30 (s, 1H), 8.22 (s, 1H), 7.51 (t, J = 1.24 Hz, 1H), 7.29 (m, 2H), 7.03 (tt, J = 7.31 and 1.11 Hz, 1H), 6.96 (m, 4H), 5.36 (s, 2H), 4.03 (s, 3H), 3.86 (s, 3H). LC-MS Rt = 1.27 min, m/z 366.1 ($MH^+$) |
| 8 | (5E)-4-amino-6-(3-methoxy-4-phenoxy-phenylamino)-pyrimidine-5-carbaldehyde O-(2-morpholin-4-yl-2-oxo-ethyl)-oxime<br>$^1H$ NMR (CDCl$_3$) δ 9.33 (br, 1H), 8.46 (s, 1H), 8.22 (s, 1H), 7.49 (d, J = 2.49 Hz, |

| Cpd | Name and Data |
|---|---|
| | 1H), 7.28 (td, J = 7.44 and 1.23 Hz, 2H), 7.13 (dd, J = 8.68 and 2.46 Hz, 1H), 7.03 (tt, J = 7.34 and 1.07 Hz, 1H), 6.95 (m, 3H), 5.50 (br, 2H), 4.84 (s, 2H), 3.88 (s, 3H), 3.68 (t, J = 4.80 Hz, 2H), 3.64 (4H), 3.53 (t, J = 4.80 Hz, 2H). LC-MS Rt = 1.06 min, m/z 379.2 (MH$^+$) |
| 9 | (5E)-4-amino-6-(4-benzyloxy-3-chloro-phenylamino)-pyrimidine-5-carbaldehyde O-methyl-oxime<br>$^1$H NMR (CDCl$_3$) δ 9.34 (s, 1H), 8.27 (s, 1H), 8.18 (s, 1H), 7.66 (d, J = 2.60 Hz, 1H), 7.46 (m, 2H), 7.32-7.42 (4H), 6.94 (d, J = 8.87 Hz, 1 H), 5.33 (br, 2H), 5.16 (s, 2H), 4.01 (s, 3H). LC-MS Rt = 1.40 min, m/z 384.1 (MH$^+$) |
| 10 | (5E)-4-amino-6-[1-(3-fluoro-benzyl)-1H-indazol-5-ylamino]-pyrimidine-5-carbaldehyde O-ethyl-oxime<br>$^1$H NMR (CDCl$_3$) δ 10.39 (s, 1H), 8.42 (s, 1H), 8.10 (m, 1H), 8.08 (s, 1H), 7.89 (s, 1H), 7.35 (d, J = 1.3 Hz, 1H), 7.24-7.33 (4H), 6.83-7.01 (3H), 5.60 (s, 2H), 4.28 (q, J = 7.06 Hz, 2H), 1.37 (t, J = 7.04 Hz, 3H). LC-MS Rt = 1.27 min, m/z 406.1 (MH$^+$) |
| 11 | (5E)-4-amino-6-[1-(3-fluoro-benzyl)-1H-indazol-5-ylamino]-pyrimidine-5-carbaldehyde O-allyl-oxime<br>$^1$H NMR (CDCl$_3$) δ 9.52 (br, 1H), 8.36 (s, 1H), 8.17 (s, 1H), 8.04 (d, J = 0.88 Hz, 1H), 7.97 (m, 1H), 7.41 (dd, J = 9.05 and 2.1 Hz, 1H), 7.23-7.32 (2H), 6.83-6.98 (3H), 6.06 (m, 1H), 5.58 (s, 2H), 5.45 (br, 2H), 5.39 (dq, J = 17.29 and 1.52 Hz, 1H), 5.31 (m, 1H), 4.69 (dt, J = 5.98 and 1.35 Hz, 2H). LC-MS Rt = 1.32 min, m/z 418.1 (MH$^+$) |
| 12 | (5E)-4-amino-6-[1-(3-fluoro-benzyl)-1H-indazol-5-ylamino]-pyrimidine-5-carbaldehyde O-tert-butyl-oxime<br>$^1$H NMR (CDCl$_3$) δ 8.30 (s, 1H), 8.18 (s, 1H), 8.04 (m, 1H), 8.00 (m, 1H), 7.21-7.36 (4H), 6.84-6.98 (3H), 5.58 (s, 2H), 1.41 (s, 9H). LC-MS Rt = 1.45 min, m/z 434.1 (MH$^+$) |
| 13 | (5E)-4-amino-6-[3-methyl-4-(pyridin-3-yloxy)-phenylamino]-pyrimidine-5-carbaldehyde O-methyl-oxime<br>$^1$H NMR (CDCl$_3$) δ 9.42 (br, 1H), 8.36 (dd, J = 2.81 and 0.60 Hz, 1H), 8.31 (dd, J = 4.41 and 1.60 Hz, 1H), 8.30 (s, 1H), 8.20 (s, 1H), 7.48 (d, J = 2.37 Hz, 1H), 7.40 (dd, J = 8.64 and 2.74 Hz, 1H), 7.23 (ddd, J = 8.39, 4.37, and 0.80 Hz, 1H), 7.17 (ddd, J = 8.40, 2.75, and 1.65 Hz, 1H), 6.93 (d, J = 8.68 Hz, 1H), 5.45 (br, 2H), 4.00 (s, 3H), 2.24 (s, 3H). LC-MS Rt = 0.55 min, m/z 351.1 (MH$^+$) |
| 14 | (5E)-4-amino-6-[(1R)-1-phenyl-ethylamino]-pyrimidine-5-carbaldehyde O-ethyl-oxime<br>$^1$H NMR (CDCl$_3$) δ 8.24 (s, 1H), 8.09 (s, 1H), 7.71 (d, J = 6.85 Hz, 1H), 7.31-7.38 (3H), 7.22-7.28 (2H), 5.45 (m, 1H), 5.29 (br, 2H), 4.18 (q, J = 7.10 Hz, 2H), 1.57 (d, J = 6.85 Hz, 3H), 1.31 (t, J = 7.05 Hz, 3H). LC-MS Rt = 1.19 min, m/z 286.0 (MH$^+$) |
| 15 | (5Z)-4-amino-6-[1-(3-fluoro-benzyl)-1H-indazol-5-ylamino]-pyrimidine-5-carbaldehyde oxime<br>$^1$H NMR (CD$_3$OD) δ 8.54 (s, 1H), 8.05 (d, J = 0.87 Hz, 1H), 7.92 (dd, J = 1.90 and 0.72 Hz, 1H), 7.90 (s, 1H), 7.51 (dt, J = 8.89 and 0.81 Hz, 1H), 7.41 (dd, J = 8.96 and 1.93 Hz, 1H), 7.30 (td, J = 7.94 and 5.84 Hz, 1H), 7.01 (m, 1H), 6.97 (m, 1H), 6.88 (dt, J = 9.79 and 2.27 Hz, 1H), 5.65 (s, 2H). LC-MS Rt = 0.98 min, m/z 378.1 (MH$^+$) |
| 16 | (5E)-4-amino-6-[(1S)-1-phenyl-ethylamino]-pyrimidine-5-carbaldehyde O-ethyl-oxime<br>$^1$H NMR (CDCl$_3$) δ 8.92 (d, J = 7.11 Hz, 1H), 8.42 (s, 1H), 8.02 (s, 1H), 7.28-7.39 (5H), 7.23 (br, 2H), 5.47 (m, 1H), 4.17 (q, J = 7.02 Hz, 2H), 1.61 (d, J = 6.87 Hz, 3H), 1.28 (t, J = 7.04 Hz, 3H). LC-MS Rt = 1.19 min, m/z 286.1 (MH$^+$) |
| 17 | (5E)-4-amino-6-(1H-indol-5-ylamino)-pyrimidine-5-carbaldehyde O-ethyl-oxime<br>$^1$H NMR (CDCl$_3$) δ 9.42 (br, 1H), 8.33 (s, 1H), 8.15 (s, 1H), 7.76 (d, J = 2.03 Hz, 1H), 7.39 (d, J = 8.69 Hz, 1H), 7.24 (m, 2H), 6.55 (m, 1H), 5.65 (br, 2H), 4.26 (q, J = 7.05 Hz, 2H), 1.37 (t, J = 7.08 Hz, 3H). LC-MS Rt = 0.96 min, m/z 297.0 (MH$^+$) |
| 18 | (5E)-4-amino-6-[3-chloro-4-(3-fluoro-benzyloxy)-phenylamino)-pyrimidine-5-carbaldehyde O-ethyl-oxime<br>$^1$H NMR (CDCl$_3$) δ 9.56 (br, 1H), 8.30 (s, 1H), 8.17 (s, 1H), 7.66 (d, J = 2.64 Hz, 1H), 7.34 (m, 2H), 7.21 (m, 2H), 7.02 (td, J = 8.20 and 2.37 Hz, 1H), 6.93 (d, J = 8.81 Hz, 1H), 5.62 (br, 2H), 5.14 (s, 2H), 4.27 (q, J = 7.05 Hz, 2H), 1.37 (t, J = 7.07 Hz, 3H). LC-MS Rt = 1.56 min, m/z 416.1 (MH$^+$) |
| 19 | (5E)-4-amino-6-[1-(3-fluoro-benzyl)-1H-indazol-5-ylamino]-pyrimidine-5-carbaldehyde O-(2-morpholin-4-yl-ethyl)-oxime<br>$^1$H NMR (CD$_3$OD) δ 8.63 (s, 1H), 8.05 (d, J = 0.91 Hz, 1H), 7.92 (m, 2H), 7.50 (m, 1H), 7.42 (dd, J = 8.95 and 1.92 Hz, 1H), 7.30 (m, 1H), 7.00 (m, 2H), 6.87 (m, 1H), 5.65 (s, 2H), 4.38 (t, J = 5.45 Hz, 2H), 3.71 (t, J = 4.65 Hz, 4H), 2.83 (t, J = 5.46 Hz, 2H), 2.64 (t, J = 4.54 Hz, 4H). LC-MS Rt = 0.84 min, m/z 491.2 (MH$^+$) |
| 20 | (5E)-4-amino-6-(indan-5-ylamino)-pyrimidine-5-carbaldehyde O-methyl-oxime<br>$^1$H NMR (CDCl$_3$) δ 9.51 (br, 1H), 8.33 (s, 1H), 8.14 (s, 1H), 7.40 (m, 1H), 7.20 (m, 2H), 6.00 (br, 2H), 4.01 (s, 3H), 2.96 (t, J = 7.79 Hz, 2H), 2.90 (t, J = 7.35 Hz, 2H), 2.10 (m, 2H). LC-MS Rt = 1.15 min, m/z 284.1 (MH$^+$) |
| 21 | (5E)-4-amino-6-(4-difluoromethoxy-phenylamino)-pyrimidine-5-carbaldehyde O-methyl-oxime<br>$^1$H NMR (CDCl$_3$) δ 10.06 (br, 1H), 8.40 (s, 1H), 8.14 (s, 1H), 7.52 (d, J = 8.93 Hz, 2H), 7.16 (d, J = 8.97 Hz, 2H), 6.74 (br, 2H), 6.38 (d, J = 73.68 Hz, 1H), 4.04 (s, 3H). Rt = 1.03 min, m/z 310.1 (MH$^+$) |

| Cpd | Name and Data |
|---|---|
| 22 | (5E)-4-amino-6-(1H-indazol-5-ylamino)-pyrimidine-5-carbaldehyde O-methyl-oxime<br>$^1$H NMR (CDCl$_3$) δ 8.61 (s, 1H), 8.02 (d, J = 0.96 Hz, 1H), 7.94 (s, 1H), 7.92 (dd, J = 1.96 and 0.81 Hz, 1H), 7.53 (dt, J = 8.94 and 0.81 Hz, 1H), 7.42 (dd, J = 8.91 and 1.96 Hz, 1H), 4.00 (s, 3H). LC-MS Rt = 0.60 min, m/z 284.0 (MH$^+$) |
| 23 | (5E)-4-amino-6-(benzo[1,3]dioxol-5-ylamino)-pyrimidine-5-carbaldehyde O-methyl-oxime<br>$^1$H NMR (CDCl$_3$) δ 10.20 (br, 1H), 8.33 (s, 1H), 8.10 (s, 1H), 7.07 (m, 1H), 6.92 (d, J = 3.14 Hz, 1H), 6.82 (br, 2H), 6.81 (d, J = 1.85 Hz, 1H), 6.03 (s, 2H), 4.04 (s, 3H). LC-MS Rt = 0.65 min (22.93%), m/z 288.1 (MH$^+$); Rt = 0.85 min (77.07%), m/z 288.0 (MH$^+$) |
| 24 | (5E)-4-amino-6-(4-phenoxy-phenylamino)-pyrimidine-5-carbaldehyde O-methyl-oxime<br>$^1$H NMR (CDCl$_3$) δ 8.36 (s, 1H), 8.12 (s, 1H), 7.43 (m, 2H), 7.36 (m, 3H), 7.14 (m, 1H), 7.04 (m, 3H), 4.05 (s, 3H). LC-MS Rt = 1.30 min, m/z 336.1 (MH$^+$) |
| 25 | (5E)-4-amino-6-(4-benzyloxy-phenylamino)-pyrimidine-5-carbaldehyde O-methyl-oxime<br>$^1$H NMR (CDCl$_3$) δ 9.31 (br, 1H), 8.31 (s, 1H), 8.15 (s, 1H), 7.28-7.46 (7H), 6.99 (m, 2H), 5.54 (br, 2H), 5.07 (s, 2H), 4.00 (s, 3H). LC-MS Rt = 1.29 min, m/z 350.2 (MH$^+$) |
| 26 | (5E)-4-amino-6-(4-sec-butyl-phenylamino)-pyrimidine-5-carbaldehyde O-methyl-oxime<br>$^1$H NMR (CDCl$_3$) δ 9.72 (s, 1H), 8.33 (s, 1H), 8.16 (s, 1H), 7.43 (d, J = 8.42 Hz, 2H), 7.20 (d, J = 8.44 Hz, 1H), 6.21 (br, 2H), 4.02 (s, 3H), 2.59 (m, 1H), 1.58 (dq, J = 7.28 and 7.25 Hz, 2H), 1.23 (d, J = 6.94 Hz, 3H), 0.83 (t, J = 7.31 Hz, 3H). LC-MS Rt = 1.35 min, m/z 300.2 (MH$^+$) |
| 27 | (5E)-4-amino-6-(4-tert-butyl-phenylamino)-pyrimidine-5-carbaldehyde O-methyl-oxime<br>$^1$H NMR (CDCl$_3$) δ 8.36 (s, 1H), 8.14 (s, 1H), 7.42 (s, 4H), 4.02 (s, 3H), 1.33 (s, 9H). LC-MS Rt = 1.32 min, m/z 300.1 (MH$^+$) |
| 28 | (5E)-4-amino-6-(3-benzyloxy-phenylamino)-pyrimidine-5-carbaldehyde O-methyl-oxime<br>$^1$H NMR (CDCl$_3$) δ 9.73 (br, 1H), 8.32 (s, 1H), 8.16 (s, 1H), 7.24-7.47 (7H), 7.06 (m, 1H), 6.79 (ddd, J = 8.0, 2.33 and 0.65 Hz, 1H), 6.12 (br, 2H), 5.09 (s, 2H), 4.02 (s, 3H). LC-MS Rt = 1.32 min, m/z 350.1 (MH$^+$) |
| 29 | (5E)-4-amino-6-[3-methyl-4-(6-methyl-pyridin-3-yloxy)-phenylamino]-pyrimidine-5-carbaldehyde O-methyl-oxime<br>$^1$H NMR (CDCl$_3$) δ 9.41 (s, 1H), 8.31 (s, 1H), 8.25 (dd, J = 2.59 and 0.75 Hz, 1H), 8.19 (s, 1H), 7.45 (d, J = 2.61 Hz, 1H), 7.35 (dd, J = 8.59 and 2.71 Hz, 1H), 7.12 (dd, J = 8.52 and 2.67 Hz, 1H), 7.09 (t, J = 8.43 Hz, 1H), 6.87 (d, J = 8.62 Hz, 1H), 5.53 (br, 2H), 4.02 (s, 3H), 2.50 (s, 3H), 2.26 (s, 3H). LC-MS Rt = 0.58 min, m/z 365.1 (MH$^+$) |
| 30 | (5E)-4-amino-6-[1-(3-fluoro-benzyl)-1H-indazol-5-ylamino]-pyrimidine-5-carbaldehyde O-isobutyl-oxime<br>$^1$H NMR (CD$_3$OD) δ 8.62 (s, 1H), 8.05 (d, J = 0.97 Hz, 1H), 7.92 (dd, J = 1.91 and 0.78 Hz, 1H), 7.91 (s, 1H), 7.52 (dt, J = 9.01 and 0.83 Hz, 1H), 7.41 (dd, J = 8.98 and 1.95 Hz, 1H), 7.30 (m, 1H), 6.99 (m, 2H), 6.87 (m, 1H), 5.66 (s, 2H), 3.97 (d, J = 6.72 Hz, 2H), 2.05 (m, 1H), 0.99 (d, J = 6.73 Hz, 6H). LC-MS Rt = 1.67 min, m/z 485.1 (MH$^+$) |
| 31 | (5E)-4-amino-6-[1-(3-fluoro-benzyl)-1H-indazol-5-ylamino]-pyrimidine-5-carbaldehyde O-(2-phenoxy-ethyl)-oxime<br>$^1$H NMR (CDCl$_3$) δ 8.47 (s, 1H), 8.10 (m, 1H), 8.05 (s, 1H), 7.85 (m, 1H), 7.21-7.36 (5H), 6.84-7.01 (6H), 5.59 (s, 2H), 4.58 (t, J = 4.42 Hz, 2H), 4.28 (t, J = 4.30 Hz, 2H). LC-MS Rt = 1.47 min, m/z 498.2 (MH$^+$) |
| 32 | (5E)-4-amino-6-[3-chloro-4-(pyridin-2-ylmethoxy)-phenylamino]-pyrimidine-5-carbaldehyde O-methyl-oxime<br>$^1$H NMR (DMSO-d6) δ 9.58 (s, 1H), 8.69 (s, 1H), 8.58 (m, 1H), 8.02 (s, 1H), 7.87 (td, J = 8.21 and 1.72 Hz, 2H), 7.56 (d, J = 7.89 Hz, 1H), 7.37 (m, 2H), 7.27 (br, 2H), 7.17 (d, J = 9.08 Hz, 1H), 5.25 (s, 2H), 3.94 (s, 3H). LC-MS Rt = 0.73 min, m/z 385.1 (MH$^+$) |
| 33 | (5E)-4-amino-6-[1-(3-fluoro-benzyl)-1H-indol-5-ylamino]-pyrimidine-5-carbaldehyde O-ethyl-oxime<br>$^1$H NMR (CDCl$_3$) δ 9.68 (br, 1H), 8.34 (s, 1H), 8.12 (s, 1H), 7.76 (br, 1H), 7.28 (m, 1H), 7.22 (m, 2H), 7.16 (d, J = 3.19 Hz, 1H), 6.96 (dt, J = 8.74 and 2.75 Hz, 1H), 6.89 (m, 1H), 6.77 (dt, J = 9.55 and 2.27 Hz, 1H), 6.56 (d, J = 3.13 Hz, 1H), 6.11 (br, 2H), 5.32 (s, 2H), 4.26 (q, J = 7.09 Hz, 2H), 1.36 (t, J = 7.06 Hz, 3H). LC-MS Rt = 1.44 min, m/z 405.2 (MH$^+$) |
| 34 | (5E)-4-amino-6-[1-(3-fluoro-benzyl)-1H-indol-5-ylamino]-pyrimidine-5-carbaldehyde O-methyl-oxime<br>$^1$H NMR (CD$_3$OD) δ 8.59 (s, 1H), 7.85 (s, 1H), 7.64 (dd, J = 2.02 and 0.57 Hz, 1H), 6.91-6.98 (3H), 7.11 (dd, J = 8.74 and 2.01 Hz, 1H), 6.93 (m, 2H), 6.78 (dt, J = 9.95 and 2.18 Hz, 1H), 6.51 (dd, J = 3.16 and 0.82 Hz, 1H), 5.41 (s, 2H), 3.96 (s, 3H). LC-MS Rt = 1.34 min, m/z 391.1 (MH$^+$) |
| 35 | (5E)-4-amino-6-[2,2-difluoro-2-(6-methyl-pyridin-2-yl)-ethylamino]-pyrimidine-5-carbaldehyde O-methyl-oxime<br>$^1$H NMR (CD$_3$OD) δ 8.41 (s, 1H), 7.85 (s, 1H), 7.79 (t, J = 7.81 Hz, 1H), 7.49 (t, J = 7.79 Hz, 1H), 7.35 (d, J = 7.74 Hz, 1H), 4.44 (t, J = 13.98 Hz, 2H), 3.81 (s, 3H), |

| Cpd | Name and Data |
|---|---|
| | 2.56 (s, 3H). LC-MS Rt = 0.59 min (32.36%), m/z 323.2 (MH$^+$); Rt = 0.88 min (67.64%), m/z 323.2 (MH$^+$) |
| 36 | (5E)-4-amino-6-(3-bromo-phenylamino)-pyrimidine-5-carbaldehyde O-methyl-oxime<br>$^1$H NMR (CDCl$_3$) δ 8.31 (br, 1H), 8.17 (s, 1H), 7.78 (m, 1H), 7.34-7.44 (3H), 4.07 (s, 3H). LC-MS Rt = 1.07 min, m/z 322.0 (MH$^+$). |
| 37 | (5E)-4-amino-6-(4-benzyloxy-3-chloro-phenylamino)-pyrimidine-5-carbaldehyde O-ethyl-oxime<br>$^1$H NMR (CDCl$_3$) δ 9.59 (br, 1H), 8.30 (s, 1 H), 8.16 (s, 1 H), 7.65 (d, J = 2.64 Hz, 1H), 7.30-7.48 (6H), 6.95 (d, J = 8.87 Hz, 1H), 5.73 (br, 2H), 5.16 (s, 2H), 4.27 (q, J = 7.05 Hz, 2 H), 1.37 (t, J = 7.06 Hz, 3H). LC-MS Rt = 1.49 min, m/z 398.1 (MH$^+$) |
| 38 | (5E)-4-amino-6-[3-chloro-4-(pyridin-3-yloxy)-phenylamino]-pyrimidine-5-carbaldehyde O-methyl-oxime<br>$^1$H NMR (CDCl$_3$) δ 10.14 (br, 1H), 8.41 (s, 1H), 8.38 (m, 2H), 8.19 (s, 1H), 7.81 (d, J = 2.79 Hz, 1H), 7.42 (dd, J = 8.97 and 2.63 Hz, 1H), 7.29 (m, 2H), 7.07 (d, J = 8.84 Hz, 1H), 6.68 (br, 2H), 4.06 (s, 3H). LC-MS Rt = 0.55 min, m/z 371.0 (MH$^+$) |
| 44 | (5E)-4-amino-6-[1-(3-fluoro-benzyl)-1H-indazol-5-ylamino]-pyrimidine-5-carbaldehyde O-(4-methoxy-benzyl)-oxime<br>$^1$H NMR (CD$_3$OD) δ 8.60 (s, 1H), 8.05 (d, J = 0.96 Hz, 1H), 7.89 (s, 1H), 7.76 (m, 1H), 7.47 (d, J = 8.93 Hz, 1H), 7.22-7.36 (4H), 6.94-7.03 (3H), 6.85 (m, 2H), 5.66 (s, 2H), 5.11 (s, 2H), 3.68 (s, 3H). LC-MS Rt = 1.41 min, m/z 498.1 (MH$^+$) |
| 45 | (5E)-4-amino-6-[1-(3-fluoro-benzyl)-1H-indazol-5-ylamino]-pyrimidine-5-carbaldehyde O-(2-methoxy-benzyl)-oxime<br>$^1$H NMR (CD$_3$OD) δ 8.60 (s, 1H), 8.05 (d, J = 0.92 Hz, 1H), 7.89 (s, 1H), 7.80 (dd, J = 1.94 and 0.73 Hz, 1H), 7.49 (d, J = 8.97 Hz, 1H), 7.37 (dd, J = 7.43 and 2.09 Hz, 1H), 7.29 (m, 3H), 6.94-7.03 (3H), 6.88 (m, 2H), 5.66 (s, 2H), 5.22 (s, 2H), 3.77 (s, 3H). LC-MS Rt = 1.46 min, m/z 498.0 (MH$^+$) |
| 46 | (5E)-4-amino-6-[1-(3-fluoro-benzyl)-1H-indazol-5-ylamino]-pyrimidine-5-carbaldehyde O-benzyl-oxime<br>$^1$H NMR (CD$_3$OD) δ 8.64 (s, 1H), 8.04 (d, J = 0.88 Hz, 1H), 7.90 (s, 1H), 7.77 (m, 1H), 7.41-7.47 (3H), 7.27-7.36 (4H), 7.22 (dd, J = 8.96 and 1.96 Hz, 1H), 6.95-7.02 (2H), 6.87 (dt, J = 9.58 and 2.01 Hz, 1H), 5.65 (s, 2H), 5.19 (s, 2H). LC-MS Rt = 1.42 min, m/z 468.1 (MH$^+$). |
| 47 | (5E)-4-amino-6-[1-(3-fluoro-benzyl)-1H-indazol-5-ylamino]-pyrimidine-5-carbaldehyde O-isopropyl-oxime<br>$^1$H NMR (CD$_3$OD) δ 8.57 (s, 1H), 8.05 (d, J = 0.88 Hz, 1H), 7.94 (dd, J = 1.92 and 0.82 Hz, 1H), 7.92 (s, 1H), 7.51 (d, J = 8.92 Hz, 1H), 7.42 (dd, J = 8.99 and 1.95 Hz, 1H), 7.30 (td, J = 7.98 and 5.73 Hz, 1H), 6.94-7.02 (2H), 6.87 (dt, J = 9.66 and 2.01 Hz, 1H), 5.65 (s, 2H), 4.46 (m, 1H), 1.32 (d, J = 6.24 Hz, 6H). LC-MS Rt = 1.34 min, m/z 420.2 (MH$^+$) |
| 48 | (5E)-4-amino-6-(1-benzyl-1H-indazol-5-ylamino)-pyrimidine-5-carbaldehyde O-methyl-oxime<br>$^1$H NMR (CD$_3$OD) δ 8.60 (s, 1H), 8.03 (d, J = 0.91 Hz, 1H), 7.92 (d, J = 0.77 Hz, 1H), 7.91 (s, 1H), 7.50 (dt, J = 8.96 and 0.74 Hz, 1H), 7.40 (dd, J = 8.93 and 1.91 Hz, 1H), 7.16-7.32 (5H), 5.64 (s, 2H), 3.98 (s, 3H). LC-MS Rt = 1.12 min, m/z 374.1 (MH$^+$) |
| 49 | (5E)-4-amino-6-(1-benzyl-1H-indazol-5-ylamino)-pyrimidine-5-carbaldehyde O-ethyl-oxime<br>$^1$H NMR (CD$_3$OD) δ 8.59 (s, 1H), 8.03 (d, J = 0.89 Hz, 1H), 7.93 (dd, J = 1.90 and 0.73 Hz, 1H), 7.91 (s, 1H), 7.51 (dt, J = 9.01 and 0.78 Hz, 1H), 7.40 (dd, J = 8.94 and 1.94 Hz, 1H), 7.16-7.32 (5H), 5.64 (s, 2H), 4.23 (q, J = 7.07 Hz, 2H), 1.34 (t, J = 7.04 Hz, 3H). LC-MS Rt = 1.21 min, m/z 388.1 (MH$^+$) |
| 50 | 3-{5-[6-amino-(5E)-5-(methoxyimino-methyl)-pyrimidin-4-ylamino]-indazol-1-ylmethyl}-benzonitrile<br>$^1$H NMR (CD$_3$OD) δ 8.60 (s, 1H), 8.07 (d, J = 0.91 Hz, 1H), 7.93 (dd, J = 1.92 and 0.71 Hz, 1H), 7.92 (s, 1H), 7.63 (td, J = 5.39 and 1.81 Hz, 1H), 7.54 (dt, J = 8.90 and 0.86 Hz, 1H), 7.53 (s, 1H), 7.48 (m, 2H), 7.44 (dd, J = 8.95 and 1.94 Hz, 1H), 5.71 (s, 2H), 3.98 (s, 3H). LC-MS Rt = 1.08 min, m/z 399.2 (MH$^+$) |
| 51 | 3-{5-[6-amino-(5E)-5-(ethoxyimino-methyl)-pyrimidin-4-ylamino]-indazol-1-ylmethyl}-benzonitrile<br>$^1$H NMR (CD$_3$OD) δ 8.60 (s, 1H), 8.07 (d, J = 0.91 Hz, 1H), 7.94 (dd, J = 1.92 and 0.73 Hz, 1H), 7.92 (s, 1H), 7.62 (td, J = 5.25 and 1.61 Hz, 1H), 7.54 (dt, J = 8.97 and 0.86 Hz, 1H), 7.53 (m, 1H), 7.48 (m, 2H), 7.43 (dd, J = 8.95 and 1.96 Hz, 1H), 5.70 (s, 2H), 4.24 (q, J = 7.07 Hz, 2H), 1.34 (t, J = 7.08 Hz, 3H). LC-MS Rt = 1.16 min, m/z 413.3 (MH$^+$) |
| 52 | (5E)-4-amino-6-(2-benzyl-2H-indazol-5-ylamino)-pyrimidine-5-carbaldehyde O-ethyl-oxime<br>$^1$H NMR (CD$_3$OD) δ 8.59 (s, 1H), 8.22 (d, J = 0.73 Hz, 1H), 7.95 (s, 1H), 7.93 (dd, J = 1.98 and 0.76 Hz, 1H), 7.58 (dt, J = 9.21 and 0.85 Hz, 1H), 7.27-7.37 (6H), 5.62 (s, 2H), 4.24 (q, J = 7.10 Hz, 2H), 1.35 (t, J = 7.05 Hz, 3H). LC-MS Rt = 1.16 min, m/z 388.2 (MH$^+$) |
| 54 | (5E)-4-amino-6-[1-(3-chloro-benzyl)-1H-indazol-5-ylamino]-pyrimidine-5-carbaldehyde O-methyl-oxime<br>$^1$H NMR (300 Hz, CDCl$_3$) δ 9.88 (bs, 1H), 8.44 (bs, 1H), 8.13 (s, 1H), 8.06 (s, 1H), 7.93 (s, 1H), 7.39-7.05 (m, 6H), 6.37 (bs, 1H), 5.57 (s, 2H), 4.02 (s, 3H);); LC/MS (m/z) (MH$^+$) 408.1 (calculated for C$_{20}$H$_{18}$ClN$_7$O, 407.86) |

| Cpd | Name and Data |
|---|---|
| 55 | (5E)-4-amino-6-[1-(3-chloro-benzyl)-1H-indazol-5-ylamino]-pyrimidine-5-carbaldehyde O-ethyl-oxime<br>$^1$H NMR (300 Hz, CDCl$_3$) δ 9.63 (bs, 1H), 8.36 (s, 1H), 8.16 (s, 1H), 8.04 (s, 1H), 7.96 (m, 1H), 7.43-7.04 (m, 6H), 5.68 (bs, 1H), 5.30 (s, 2H), 4.26 (q, J = 7.05 Hz, 2H), 1.37 (t, J = 7.05 Hz, 3H); LC/MS (m/z) (MH$^+$) 422.1 (calculated for C$_{21}$H$_{20}$ClN$_7$O, 421.88) |
| 56 | (5E)-4-amino-6-[1-(3-methoxy-benzyl)-1H-indazol-5-ylamino]-pyrimidine-5-carbaldehyde O-methyl-oxime<br>$^1$H NMR (300 Hz, CDCl$_3$) δ 9.89 (bs, 1H), 8.43 (s, 1H), 8.12 (s, 1H), 8.04 (s, 1H), 7.91 (bs, 1H), 7.36-7.19 (m, 2H), 6.82-6.6.44 (m, 2H), 5.57 (s, 2H), 4.02 (s, 3H), 3.74 (s, 3H); LC/MS (m/z) (MH$^+$) 404.2 (calculated for C$_{21}$H$_{21}$N$_7$O$_2$, 403.44) |
| 57 | (5E)-4-amino-6-[1-(3-methoxy-benzyl)-1H-indazol-5-ylamino]-pyrimidine-5-carbaldehyde O-ethyl-oxime<br>$^1$H NMR (300 Hz, CDCl$_3$) δ 10.45 (bs, 1H), 8.40 (s, 1H), 8.069 (s, 1H), 8.067 (s, 1H), 7.85 (s, 1H), 7.55 (bs, 1H), 7.36-7.27 (m, 3H), 6.74 (m, 3H), 5.58 (s, 2H), 4.28 (q, J = 7.08 Hz, 2H), 3.75 (s, 3H), 1.37 (t, J = 7.08 Hz, 3H); LC/MS (m/z) (MH$^+$) 418.2 (calculated for C$_{22}$H$_{23}$N$_7$O$_2$, 417.46) |
| 58 | (5E)-4-amino-6-[2-(3-fluoro-benzyl)-1H-benzoimidazol-5-ylamino]-pyrimidine-5-carbaldehyde O-ethyl-oxime<br>$^1$H NMR (CD$_3$OD) δ 8.64 (s, 1H), 8.13 (s, 1H), 8.11 (d, J = 1.83 Hz, 1H), 7.68 (d, J = 8.77 Hz, 1H), 7.49 (dd, J = 8.82 and 1.86 Hz, 1H), 7.43 (m, 1H), 7.07-7.24 (3H), 4.52 (s, 2H), 4.30 (q, J = 7.10 Hz, 2H), 1.36 (t, J = 7.07 Hz, 3H). LC-MS Rt = 0.28 min (68.74%), m/z 406.0 (MH$^+$); Rt = 0.76 min (31.26%), m/z 406.2 (MH$^+$) |
| 59 | (5E)-4-amino-6-(3-chloro-phenylamino)-pyrimidine-5-carbaldehyde O-methyl-oxime<br>$^1$H NMR (CDCl$_3$) δ 9.82 (br, 1H), 8.28 (s, 1H), 8.21 (s, 1H), 7.41 (m, 1H), 7.30 (m, 1H), 7.13 (m, 1H), 5.96 (br, 2H), 4.05 (s, 3H). LC-MS Rt = 0.56 min (51.88%), m/z 278.0 (MH$^+$); Rt = 1.02 min (48.12%), m/z 278.1 (MH$^+$) |
| 60 | (5E)-4-amino-6-[2-(3-fluoro-benzyl)-1H-benzoimidazol-5-ylamino]-pyrimidine-5-carbaldehyde O-methyl-oxime<br>$^1$H NMR (CD$_3$OD) δ 8.59 (s, 1H), 7.94 (s, 1H), 7.83 (dd, J = 1.99 and 0.54 Hz, 1H), 7.50 (dd, J = 8.59 and 0.53 Hz, 1H), 7.34 (dt, J = 6.09 and 7.96 Hz, 1H), 7.23 (dd, J = 8.60 and 2.01 Hz, 1H), 7.14 (dt, J = 7.60 and 0.75 Hz, 1H), 7.06 (dt, J = 9.98 and 1.94 Hz, 1H), 6.99 (td, J = 8.84 and 2.87 Hz, 1H), 4.27 (s, 2H), 3.99 (s, 3H). LC-MS Rt = 0.55 min, m/z 392.1 (MH$^+$) |
| 61 | (5E)-4-amino-6-[4-(3-fluoro-benzyloxy)-3-methoxy-phenylamino]-pyrimidine-5-carbaldehyde O-methyl-oxime<br>$^1$H NMR (300 Hz, CDCl$_3$) δ 9.32 (bs, 1H), 8.32 (s, 1H), 8.16 (s, 1H), 7.36-7.02 (m, 4H), 6.91-6.82 (m, 3H), 5.62 (bs, 1H), 5.13 (s, 2H), 3.998 (s, 3H), 3.91 (s, 3H); LC/MS (m/z) (MH$^+$) 398.1 (calculated for C$_{20}$H$_{20}$FN$_5$O$_3$, 397.40) |
| 62 | (5E)-4-amino-6-[4-(3-fluoro-benzyloxy)-3-methoxy-phenylamino]-pyrimidine-5-carbaldehyde O-ethyl-oxime<br>$^1$H NMR (300 Hz, CDCl$_3$) δ 9.51 (bs, 1H), 8.32 (s, 1H), 8.15 (s, 1H), 7.36-7.16 (m. 4H), 7.02-6.82 (m, 3H), 5.80 (bs, 1H), 5.13 (s, 2H), 4.25 (q, J = 7.06 Hz, 2H), 3.91 (s, 3H), 1.36 (t, J = 7.06 Hz, 3H);); LC/MS (m/z) (MH$^+$) 412.2 (calculated for C$_{21}$H$_{22}$FN$_5$O$_3$, 411.43) |
| 63 | (5E)-4-amino-6-(3-chloro-4-methoxy-phenylamino)-pyrimidine-5-carbaldehyde O-methyl-oxime<br>$^1$H NMR (CDCl$_3$) δ 9.32 (br, 1H), 8.28 (s, 1H), 8.18 (s, 1H), 7.61 (d, J = 2.63 Hz, 1H), 7.39 (dd, J = 8.85 and 2.63 Hz, 1H), 6.93 (d, J = 8.86 Hz, 1H), 5.39 (br, 2H), 4.02 (s, 3H), 3.90 (s, 3H). LC-MS Rt = 1.00 min, m/z 308.1 (MH$^+$) |
| 64 | (5E)-4-amino-6-(3-chloro-4-morpholin-4-yl-phenylamino)-pyrimidine-5-carbaldehyde O-methyl-oxime<br>$^1$H NMR (CDCl$_3$) δ 9.43 (br, 1H), 8.28 (s, 1H), 8.19 (s, 1H), 7.66 (d, J = 2.51 Hz, 1H), 7.41 (dd, J = 8.71 and 2.66 Hz, 1H), 7.04 (d, J = 8.68 Hz, 1H), 5.45 (br, 2H), 4.02 (s, 3H), 3.88 (t, J = 4.59 Hz, 4H), 3.04 (t, J = 4.55 Hz, 4H). LC-MS Rt = 1.02 min, m/z 363.1 (MH$^+$) |
| 65 | (5E)-4-amino-6-[1-(3-fluoro-benzyl)-1H-indazol-5-ylamino]-pyrimidine-5-carbaldehyde O-phenyl-oxime<br>$^1$H NMR (CDCl$_3$) δ 8.70 (s, 1H), 8.21 (s, 1H), 8.04 (s, 1H), 7.99 (s, 1H), 6.81-7.44 (10H), 5.58 (s, 2H). LC-MS Rt = 1.44 min, m/z 454.2 (MH$^+$) |
| 66 | (5E)-4-amino-6-[1-(4-fluoro-benzyl)-1H-indazol-5-ylamino]-pyrimidine-5-carbaldehyde O-methyl-oxime<br>$^1$H NMR (300 Hz, CDCl$_3$) δ 9.64 (bs, 1H), 8.38 (s, 1H), 8.14 (s, 1H), 8.02 (s, 1H), 7.93 (s, 1H), 7.42-7.16 (m, 4H), 7.01-6.95 (m, 2H), 5.92 (bs, 2H), 5.56 (s, 2H), 4.01 (s, 3H); LC/MS (m/z) (MH$^+$) 392.2 (calculated for C$_{20}$H$_{18}$FN$_7$O, 391.40) |
| 67 | (5E)-4-amino-6-[1-(4-fluoro-benzyl)-1H-indazol-5-ylamino]-pyrimidine-5-carbaldehyde O-ethyl-oxime<br>$^1$H NMR (300 Hz, CDCl$_3$) δ 9.73 (bs, 1H), 8.37 (s, 1H), 8.15 (s, 1H), 8.02 (s, 1H), 7.93 (s, 1H), 7.41-7.16 (m, 4H), 7.01-6.95 (m, 2H), 5.94 (bs, 1H), 5.56 (s, 2H), 4.25 (q, J = 7.06 Hz, 2H), 1.36 (t, J = 7.06 Hz, 3H); LC/MS (m/z) (MH$^+$) 406.2 (calculated for C$_{21}$H$_{20}$FN$_7$O, 405.43) |
| 68 | (5E)-4-amino-6-[1-(3-fluoro-benzyl)-1H-indazol-5-ylamino]-pyrimidine-5-carbaldehyde O-(2-methoxy-ethyl)-oxime<br>$^1$H NMR (CD$_3$OD) δ 8.60 (s. 1H), 8.05 (d, J = 0.89 Hz, 1H), 7.93 (dd, J = 1.91 and 0.75 Hz, 1H), 7.92 (s, 1H), 7.51 (dt, J = 8.97 and 0.76 Hz, 1H), 7.43 (dd, J = 8.94 and 1.93 Hz, 1H), 7.30 (td, J = 7.97 and 5.95 Hz, 1H), 7.01 (m, 1H), 6.96 (m, 1H), |

| Cpd | Name and Data |
|---|---|
| | 6.87 (dt, J = 9.70 and 1.71 Hz, 1H), 5.65 (s, 1H), 4.32 (t, J = 4.49 Hz, 2H), 3.71 (t, J = 4.60 Hz, 2H), 3.35 (s, 3H). LC-MS Rt = 1.13 min, m/z 436.2 (MH$^+$) |
| 69 | (5Z)-4-amino-6-[1-(3-fluoro-benzyl)-1H-indazol-5-ylamino]-pyrimidine-5-carbaldehyde O-(3-hydroxy-propyl)-oxime<br>$^1$H NMR (CD$_3$OD) δ 8.62 (s, 1H), 8.05 (d, J = 0.89 Hz, 1H), 7.93 (dd, J = 1.91 and 0.75 Hz, 1H), 7.91 (s, 1H), 7.46 (m, 2H), 7.30 (m, 1H), 7.01 (m, 1H), 6.87-6.96 (2H), 5.65 (s, 2H), 4.28 (t, J = 6.48 Hz, 2H), 3.69 (t, J = 6.35 Hz, 2H), 1.94 (m, 2H). LC-MS Rt = 0.55 min, m/z 436.3 (MH$^+$) |
| 70 | (5E)-4-amino-6-[1-(3-fluoro-benzyl)-1H-indazol-5-ylamino]-pyrimidine-5-carbaldehyde O-(3-dimethylamino-propyl)-oxime<br>$^1$H NMR (CDCl$_3$) δ 9.38 (br, 1H), 8.33 (s, 1H), 8.18 (s, 1H), 8.03 (d, J = 0.73 Hz, 1H), 7.97 (d, J = 1.92 Hz, 1H), 7.42 (dd, J = 8.87 and 1.91 Hz, 1H), 7.23-7.37 (2H), 6.91-6.98 (2H), 6.86 (m, 1H), 5.58 (s, 2H), 5.21 (br, 2H), 4.26 (t, J = 6.51 Hz, 2H), 2.41 (t, J = 7.05 Hz, 2H), 2.24 (s, 6H), 1.92 (m, 2H). LC-MS Rt = 0.29 min (37.41%), m/z 463.2 (MH$^+$); Rt = 0.76 min (62.59%), m/z 463.2 (MH$^+$) |
| 71 | (5E)-4-amino-6-(4-benzyloxy-3-chloro-phenylamino)-pyrimidine-5-carbaldehyde O-(2-methoxy-ethyl)-oxime<br>$^1$H NMR (CD$_3$OD) δ 8.56 (s, 1H), 7.95 (s, 1H), 7.66 (d, J = 2.58 Hz, 1H), 7.47 (m, 2H), 7.28-7.40 (4H), 7.08 (d, J = 8.89 Hz, 1H), 5.16 (s, 2H), 4.32 (t, J = 4.45 Hz, 2H), 3.71 (t, J = 4.58 Hz, 2H), 3.36 (s, 3H). LC-MS Rt = 1.36 min, m/z 428.1 (MH$^+$) |
| 72 | (5E)-4-amino-6-[2-(3-fluoro-phenyl)-benzofuran-5-ylamino]-pyrimidine-5-carbaldehyde O-methyl-oxime<br>$^1$H NMR (300 Hz, CDCl$_3$) δ 9.80 (bs, 1H), 8.44 (s, 1H), 8.15 (s, 1H), 7.82 (d, J = 2.16 Hz, 1H), 7.64-7.26 (m, 5H), 7.09-7.03 (m, 2H), 6.24 (bs, 1H), 4.03 (s, 3H); LC/MS (m/z) (MH$^+$) 378.2 (calculated for C$_{20}$H$_{16}$FN$_5$O$_2$, 377.37) |
| 73 | (5E)-4-amino-6-(2-benzyl-benzofuran-5-ylamino)-pyrimidine-5-carbaldehyde O-methyl-oxime<br>$^1$H NMR (300 Hz, CDCl$_3$) δ 9.35 (bs, 1H), 8.33 (s, 1H), 8.14 (s, 1H), 7.69 (d, J = 2.12 Hz, 1H), 7.38-7.21 (m, 8H), 5.55 (bs, 1H), 4.10 (s, 2H), 3.99 (s, 3H); LC/MS (m/z) (MH$^+$) 374.1 (calculated for C$_{21}$H$_{19}$N$_5$O$_2$, 373.41) |
| 74 | (5E)-4-amino-6-[1-(3-fluoro-benzyl)-2,3-dihydro-1H-indol-5-ylamino]-pyrimidine-5-carbaldehyde O-methyl-oxime<br>$^1$H NMR (CDCl$_3$) δ 9.07 (s, 1H), 8.29 (s, 1H), 8.13 (s, 1H), 7.29 (td, J = 7.55 and 5.49 Hz, 1H), 7.24 (m, 1H), 7.14 (d, J = 8.01 Hz, 1H), 7.09 (dd, J = 9.89 and 2.23 Hz, 1H), 7.04 (dd, J = 8.71 and 2.05 Hz, 1H), 6.96 (td, J = 8.11 and 2.65 Hz, 1H), 6.42 (d, J = 8.31 Hz, 1H), 5.42 (br, 2H), 4.23 (s, 2H), 3.98 (s, 3H), 3.36 (t, J = 8.19 Hz, 2H), 3.01 (t, J = 8.29 Hz, 2H); LC-MS Rt = 1.48 min, m/z 393.3 (MH$^+$) |
| 75 | (5E)-4-amino-6-[3-chloro-4-(3-fluoro-benzyloxy)-phenylamino]-pyrimidine-5-carbaldehyde O-(3-hydroxy-propyl)-oxime<br>$^1$H NMR (300 Hz, CDCl$_3$) δ 8.56 (s, 1H), 7.96 (s, 1H), 7.70 (d, J = 2.55 Hz, 1H), 7.01-7.00 (m, 6H), 5.17 (s, 2H), 4.29 (t, J = 6.35 Hz, 2H), 3.70 (d, J = 6.35 Hz, 2H), 1.96 (m, 2H); LC/MS (m/z) 446.2 (MH$^+$) (calculated for C$_{21}$H$_{21}$ClFN$_5$O$_3$, 445.87). |
| 76 | (5E)-4-amino-6-(4-benzyloxy-3-chloro-phenylamino)-pyrimidine-5-carbaldehyde O-(3-hydroxy-propyl)-oxime<br>$^1$H NMR (400 MHz, CD$_3$OD) δ 8.56 (s, 1H), 7.97 (s, 1H), 7.67 (d, j = 2.5, 1H), 7.46 (d, j = 7.1, 2H), 7.38-7.25 (m, 4H), 7.06 (d, j = 8.9, 1H), 5.15 (s, 2H), 4.28 (t, j = 12.5, 2H), 3.70 (t, j = 12.7, 2H), 1.97-1.94 (m, 2H); MS (ESI) m/z 427, 428 (MH$^+$), 426 (MH–) |
| 77 | (5E)-4-amino-6-(4-benzyloxy-3-chloro-phenylamino)-pyrimidine-5-carbaldehyde oxime<br>$^1$H NMR (300 MHz, CD$_3$OD) δ 8.52 (s, 1H), 7.96 (s, 1H), 7.66 (d, J = 2.4 Hz, 1H), 7.50-7.29 (m, 6H), 7.10 (d, J = 9 Hz, 1H), 5.17 (s, 2H); MS (ESI) m/z 370 (MH$^+$) |
| 79 | (5E)-4-amino-6-[3-chloro-4-(3-fluoro-benzyloxy)-phenylamino]-pyrimidine-5-carbaldehyde oxime<br>$^1$H NMR (300 MHz, CD$_3$OD) δ 8.51 (s, 1H), 7.95 (s, 1H), 7.66 (d, J = 2.4 Hz, 1H), 7.40-7.04 (m, 7H), 5.17 (s, 2H) |
| 80 | (5E)-4-amino-6-(4-chloro-2-fluoro-phenylamino)-pyrimidine-5-carbaldehyde O-methyl-oxime MS m/z 296.1 (MH$^+$) |
| 81 | (5Z)-4-amino-6-(4-chloro-2-fluoro-phenylamino)-pyrimidine-5-carbaldehyde O-methyl-oxime MS m/z 296.1 (MH$^+$) |
| 82 | (5E)-4-amino-6-(4-bromo-2-fluoro-phenylamino)-pyrimidine-5-carbaldehyde O-methyl-oxime MS m/z 340 (MH$^+$) |
| 83 | (5Z)-4-amino-6-(4-bromo-2-fluoro-phenylamino)-pyrimidine-5-carbaldehyde O-methyl-oxime MS m/z 340 (MH$^+$) |
| 84 | (5E)-4-amino-6-[1-(3-fluoro-benzyl)-1H-indazol-5-ylamino]-pyrimidine-5-carbaldehyde oxime<br>$^1$H NMR (300 MHz, DMSO-d6) δ 11.22 (s, 1H), 9.92 (s, 1H), 8.65 (s, 1H), 8.09 (s, 1H), 8.04 (d, J = 1.8 Hz, 1H), 7.97 (s, 1H), 7.65 (d, J = 9.0 Hz, 1H), 7.44-7.36 (m, 2H), 7.11-7.03 (m, 5H), 5.66 (s, 2H); MS (ESI) m/z 376 (MH$^+$) |
| 85 | (5E)-4-amino-6-[1-(3-fluoro-benzyl)-1H-indazol-5-ylamino]-pyrimidine-5-carbaldehyde O-(3-hydroxy-propyl)-oxime<br>$^1$H NMR (300 MHz, CDCl$_3$) δ 9.40 (s, 1H), 8.34 (s, 1H), 8.18 (s, 1H), 8.04 (s, 1H), 7.94 (s, 1H), 7.40-7.25 (m, 2H), 6.98-6.84 (m, 3H), 5.58 (s, 2H), 5.33 (br s, 2H), 4.37 (t, J = 5.7 Hz, 2H), 3.83 (t, J = 12.3 Hz, 2H), 2.04 (m, 2H); MS (ESI) m/z 434 (MH$^+$) |

-continued

| Cpd | Name and Data |
|---|---|
| 86 | (5E)-4-(4-bromo-2-fluoro-phenylamino)-6-methoxyamino-pyrimidine-5-carbaldehyde O-methyl-oxime MS m/z 370 (MH⁺) |
| 87 | (5E)-4-amino-6-[1-(3-fluoro-benzyl)-1H-indazol-5-ylamino]-pyrimidine-5-carbaldehyde O-(3-morpholin-4-yl-propyl)-oxime<br>$^1$H NMR (300 MHz, CDCl$_3$) δ 9.37 (s, 1H), 8.34 (s, 1H), 8.17 (s, 1H), 8.03 (s, 1H), 7.96 (s, 1H), 7.42 (dd, J = 9.0, 1.8 Hz, 1H), 7.30-7.24 (m, #H), 6.97-6.83 (m, 3H), 5.57 (s, 2H), 5.34 (s, 2H), 4.26 (t, J = 6.3 Hz, 2H), 3.72 (m, 4H), 2.52 (m, 6H), 1.95 (m, 2H); MS (ESI) m/z 505 (MH⁺) |
| 88 | (5E)-4-amino-6-[1-(3-fluoro-benzyl)-1H-indol-5-ylamino]-pyrimidine-5-carbaldehyde oxime<br>$^1$H NMR (300 MHz, DMSO-d6) δ 11.18 (s, 1H), 9.89 (s, 1H), 8.65 (s, 1H), 7.95 (s, 1H), 7.81 (d, J = 1.5 Hz, 1H), 7.52 (d, J = 3.0 Hz, 1H), 7.42-7.02 (m, 7H), 6.48 (d, J = 2.7 Hz, 1H), 5.44 (s, 2H); MS (ESI) m/z 377 (MH⁺) |
| 89 | (5E)-4-amino-6-(4-chloro-2-fluoro-5-hydroxy-phenylamino)-pyrimidine-5-carbaldehyde O-methyl-oxime MS m/z 312.1 (MH⁺) |
| 90 | (5Z)-4-amino-6-(4-chloro-2-fluoro-5-hydroxy-phenylamino)-pyrimidine-5-carbaldehyde O-methyl-oxime MS m/z 312.1 (MH⁺) |
| 91 | (5E)-4-amino-6-[1-(3-fluoro-benzyl)-1H-indol-5-ylamino]-pyrimidine-5-carbaldehyde O-(3-hydroxy-propyl)-oxime<br>$^1$H NMR (300 MHz, DMSO-d6) δ 9.74 (s, 1H), 8.74 (s, 1H), 7.98 (s, 1H), 7.86 (d, J = 1.8 Hz, 1H), 7.53 (d, J = 3.3 Hz, 1H), 7.38-7.34 (m, 2H), 7.20-7.00 (m, 6H), 6.49 (d, J = 3.0 Hz, 1H), 5.78 (s, 2H), 4.56 (t, J = 5.1 Hz, 1H), 4.24 (t, J = 6.3 Hz, 2H), 3.55 (m, 2H), 1.86 (m, 2H); MS (ESI) m/z 435 (MH⁺) |
| 92 | (5E)-4-amino-6-[1-(3-fluoro-benzyl)-1H-indazol-5-ylamino]-pyrimidine-5-carbaldehyde O-(3-piperidin-1-yl-propyl)-oxime<br>$^1$H NMR (300 MHz, CD$_3$OD) δ 8.62 (s, 1H), 8.05 (s, 1H), 7.92 (s, 1H), 7.52 (m, 2H), 7.40 (m, 1H), 7.02-6.85 (m, 3H), 5.65 (s, 2H), 4.23 (t, J = 6.3 Hz, 2H), 2.60 (m, 6H), 2.00 (m, 2H), 1.61 (m, 4H), 1.47 (m, 2H); MS (ESI) m/z 503 (MH⁺) |
| 93 | (5E)-4-amino-6-[3-chloro-4-(3-fluoro-benzyloxy)-phenylamino]-pyrimidine-5-carbaldehyde O-(2-morpholin-4-yl-ethyl)-oxime<br>$^1$H NMR (300 MHz, CD$_3$OD) δ 8.59 (s, 1H), 7.98 (s, 1H), 7.68 (d, J = 2.7 Hz, 1H), 7.42-7.26 (m, 4H), 7.10-7.06 (m, 2H), 5.20 (s, 2H), 4.38 (t, J = 5.7 Hz, 2H), 3.71 (t, J = 4.8 Hz, 4H), 2.78 (t, J = 5.7 Hz, 2H), 2.59 (t, J = 4.5 Hz, 4H); MS (ESI) m/z 499 (MH⁺) |
| 94 | (5E)-4-amino-6-[3-chloro-4-(3-fluoro-benzyloxy)-phenylamino]-pyrimidine-5-carbaldehyde O-(2-piperidin-1-yl-ethyl)-oxime<br>$^1$H NMR (300 MHz, DMSO-d6) δ 9.63 (s, 1H), 8.72 (s, 2H), 8.03 (s, 1H), 7.85 (d, J = 3.0 Hz, 1H), 7.49-7.17 (m, 7H), 5.23 (s, 3H), 4.27 (t, J = 6.0 Hz, 2H), 2.61 (t, J = 5.4 Hz, 2H), 2.50 (m, 4H), 1.51-1.37 (m, 6H); MS (ESI) m/z 499 (MH⁺) |
| 95 | (5E)-4-amino-6-(4-benzyloxy-3-chloro-phenylamino)-pyrimidine-5-carbaldehyde O-(2-piperidin-1-yl-ethyl)-oxime<br>$^1$H NMR (300 MHz, DMSO-d6) δ 9.63 (s, 1H), 8.72 (s, 1H), 8.03 (s, 1H), 7.85 (d, J = 3.0 Hz, 1H), 7.50-7.18 (m, 9H), 5.21 (s, 2H), 4.28 (t, J = 6.0 Hz, 2H), 2.61 (t, J = 6.0 Hz, 2H), 2.39 (m, 4H), 1.49 (m, 4H), 1.39 (m, 2H); MS (ESI) m/z 481 (MH⁺) |
| 96 | (5E)-4-amino-6-[1-(3-fluoro-benzyl)-1H-indazol-5-ylamino]-pyrimidine-5-carbaldehyde O-(2-piperidin-1-yl-ethyl)-oxime<br>$^1$H NMR (400 MHz, DMSO-d6) δ 9.78 (s, 1H), 8.74 (s, 1H), 8.08 (d, j = 302, 2H), 7.99 (s, 1H), 7.64 (d, j = 9.0, 1H), 7.44-7.32 (m, 2H), 7.19 (s, 2H), 7.11-7.01 (m, 3H), 5.67 (s, 2H), 4.27 (t, j = 11.6, 2H), 2.61 (t, j = 11.5, 2H), 2.49-2.39 (m, 4H), 1.50-1.45 (m, 4H), 1.35 (d, j = 5.0, 2H) |
| 97 | (5E)-4-amino-6-[3-chloro-4-(3,5-difluoro-benzyloxy)-phenylamino]-pyrimidine-5-carbaldehyde O-methyl-oxime<br>$^1$H NMR (300 MHz, DMSO-d6) δ 9.60 (s, 1H), 8.71 (s, 1H), 8.04 (s, 1H), 7.88 (d, J = 2.7 Hz, 1H), 7.42 (dd, J = 9.3, 2.7 Hz, 1H), 7.30-7.16 (m, 6H), 5.25 (s, 2H), 3.98 (s, 3H); MS (ESI) m/z 420 (MH⁺) |
| 98 | (5E)-4-amino-6-[3-chloro-4-(3,5-difluoro-benzyloxy)-phenylamino]-pyrimidine-5-carbaldehyde oxime<br>$^1$H NMR (300 MHz, DMSO-d6) δ 11.25 (s, 1H), 9.81 (s, 1H), 8.62 (s, 1H), 8.01 (s, 1H), 7.82 (d, J = 2.4 Hz, 1H), 7.42 (dd, J = 9.0, 2.7 Hz, 1H), 7.23-7.17 (m, 6H), 5.23 (s, 2H); MS (ESI) m/z 406 (MH⁺) |
| 99 | (5E)-4-amino-6-[3-chloro-4-(3,5-difluoro-benzyloxy)-phenylamino]-pyrimidine-5-carbaldehyde O-(2-morpholin-4-yl-ethyl)-oxime<br>$^1$H NMR (300 MHz, DMSO-d6) δ 9.61 (s, 1H), 8.73 (s, 1H), 8.04 (s, 1H), 7.87 (d, J = 2.7 Hz, 1H), 7.42 (dd, J = 8.7, 2.7 Hz, 1H), 7.29-7.16 (m, 6H), 5.24 (s, 2H), 4.30 (t, J = 5.7 Hz, 2H), 3.58 (m, 4H), 2.66 (t, J = 5.7 Hz, 2H), 2.45 (m, 4H); MS (ESI) m/z 519 (MH⁺) |
| 100 | (5E)-4-amino-6-[(1S)-1-phenyl-ethylamino]-pyrimidine-5-carbaldehyde oxime MS m/z 258.1 (MH⁺) |
| 101 | (5E)-4-amino-6-[1-(3-fluoro-benzyl)-1H-indol-5-ylamino]-pyrimidine-5-carbaldehyde O-(2-morpholin-4-yl-ethyl)-oxime<br>$^1$H NMR (400 MHz, DMSO-d6) δ 9.72 (s, 1H), 8.73 (s, 1H), 7.95 (s, 1H), 7.83 (d, j = 1.7, 1H), 7.50 (d, j = 3.0, 1H), 7.38-7.32 (m, 2H), 7.18-6.97 (m, 6H), 6.46 (d, j = 2.9, 1H), 5.43 (s, 2H), 4.27 t, j = 11.3, 2H), 3.55 (m, j = 9.0, 4H), 2.65 (t, j = 11.3, 2H), 2.50-2.44 (m, 4H); MS (ESI) m/z 490 (MH⁺), 488 (MH−) |
| 102 | (5E)-4-amino-6-[1-(3-fluoro-benzyl)-1H-indol-5-ylamino]-pyrimidine-5-carbaldehyde O-(2-piperidin-1-yl-ethyl)-oxime<br>$^1$H NMR (400 MHz, CD$_3$OD) δ 8.61-8.59 (m, 1H), 7.86-7.83 (m, 1H), 7.64-7.62 (m, 1H), 7.32-7.25 (m, 3H), 7.12-7.08 (m, 1H), 6.96-6.94 (m, 2H), 6.77 (d, j = 9.3, |

| Cpd | Name and Data |
|---|---|
| | 1H), 6.51-6.48 (m, 1H), 5.41-5.38 (m, 2H), 4.35-4.31 m, 2H), 2.77-2.74 (m, 2H), 2.53 (s, 1H), 1.59 (s, 4H), 1.45 (s, 2H); MS (ESI) m/z 488 (MH+), 486 (MH−) |
| 103 | (5E)-4-amino-6-[(1S)-1-phenyl-ethylamino]-pyrimidine-5-carbaldehyde O-(2-morpholin-4-yl-ethyl)-oxime MS m/z 371.2 (MH+) |
| 104 | N-{4-[6-amino-(5E)-5-(methoxyimino-methyl)-pyrimidin-4-ylamino]-phenyl}-benzamide MS m/z 363.2 (MH+) |
| 105 | N-{4-[6-amino-(5E)-5-(hydroxyimino-methyl)-pyrimidin-4-ylamino]-phenyl}-benzamide MS m/z 349.1 (MH+) |
| 106 | (5E)-4-amino-6-[(1S)-1-phenyl-ethylamino]-pyrimidine-5-carbaldehyde O-(2-piperidin-1-yl-ethyl)-oxime MS m/z 369.2 (MH+) |
| 107 | N-(4-{6-amino-(5E)-5-[(2-morpholin-4-yl-ethoxyimino)-methyl]-pyrimidin-4-ylamino}-phenyl)-benzamide MS m/z 462.2 (MH+) |
| 108 | (5E)-4-amino-6-(3-chloro-4-fluoro-phenylamino)-pyrimidine-5-carbaldehyde O-(2-morpholin-4-yl-ethyl)-oxime<br>$^1$H NMR (400 MHz, CD$_3$OD) δ 8.58 (d, j = 2.6, 1H), 8.00 (d, j = 2.2, 1H), 7.82-7.80 (m, 1H), 7.40-7.36 (m, 1H), 7.20-7.16 (m, 1H), 4.37 (t, j = 12.1, 2H), 3.71-3.69 (m, 4H), 2.77 (t, j = 11.1, 2H), 2.58 (d, j = 4.8, 4H); MS (ESI) m/z 394, 395 (MH+) 396 |
| 109 | (5E)-4-amino-6-(4-phenoxy-phenylamino)-pyrimidine-5-carbaldehyde O-(2-morpholin-4-yl-ethyl)-oxime<br>$^1$H NMR (400 MHz, DMSO-d6) δ 8.12 (s, 1H), 7.42-7.34 (m, 4H), 7.13-7.05 (m, 6H), 4.02 (t, j = 13.3, 2H), 3.50 (d, j = 4.0, 4H), 2.52-2.50 (m, 2H), 2.33 (s, 4H) |
| 110 | N-{5-[6-amino-(5E)-5-(methoxyimino-methyl)-pyrimidin-4-ylamino]-pyrimidin-2-yl}-benzamide MS m/z 365.1 (MH+) |
| 111 | (5E)-4-amino-6-(4-phenoxy-phenylamino)-pyrimidine-5-carbaldehyde oxime MS m/z 322.1 (MH+) |
| 112 | (5E)-4-amino-6-(4-benzyloxy-3-chloro-phenylamino)-pyrimidine-5-carbaldehyde O-(3-morpholin-4-yl-propyl)-oxime<br>$^1$H NMR (400 MHz, CD$_3$OD) δ 8.56 (s, 1H), 7.95 (s, 1H), 7.66 (d, j = 2.5, 1H), 7.46 (d, j = 7.1, 2H), 7.38-7.26 (m, 4H), 7.06 (d, j = 28.9, 1H), 5.15 (s, 1H), 4.23 (t, j = 12.5, 2H), 3.67 (t, j = 9.6, 4H), 2.53-2.46 (m, 6H), 2.00-1.90 (m, 2H); MS (ESI) m/z 497 (MH+) |
| 113 | methanesulfonic acid (5E)-3-[4-amino-6-(4-benzyloxy-3-chloro-phenylamino)-pyrimidin-5-ylmethyleneaminooxy]-propyl ester<br>$^1$H NMR (400 MHz, CD$_3$OD) δ 8.58 (s, 1H), 7.95 (s, 1H), 7.67 (d, j = 2.4, 1H), 7.47-7.45 (m, 2H), 7.38-7.23 (m, 4H), 7.07-7.04 (m, 1H), 5.14 (s, 2H), 4.38 (t, j = 12.4, 2H), 4.30 (t, j = 12.2, 2H), 3.07 (s, 3H), 2.18-2.15 (m, 2H) |
| 114 | (5E)-4-amino-6-(4-benzyloxy-3-chloro-phenylamino)-pyrimidine-5-carbaldehyde O-pyridin-2-ylmethyl-oxime<br>$^1$H NMR (400 MHz, CD$_3$OD) δ 8.66 (s, 1H), 8.52-8.49 (m, 1H), 7.92 (s, 1H), 7.85-7.80 (m, 1H), 7.58-7.55 (m, 1H), 7.49-7.42 (m, 3H), 7.40-7.28 (m, 4H), 7.16-7.12 (m, 1H), 7.05-7.01 (m, 1H), 5.28 (s, 2H), 5.16 (s, 2H) |
| 115 | (5E)-4-amino-6-(4-benzyloxy-3-chloro-phenylamino)-pyrimidine-5-carbaldehyde O-[3-(2-methoxy-ethylamino)-propyl]-oxime<br>$^1$H NMR (400 MHz, CD$_3$OD) δ 8.56 (s, 1H), 7.95 (s, 1H), 7.66 (d, j = 2.4, 1H), 7.46 (d, j = 7.6, 2H), 7.38-7.24 (m, 4H), 7.05 (d, j = 8.9, 1H), 5.14 (s, 2H), 4.25 (t, j = 12.3, 2H), 3.49-3.47 (m, 2H), 3.31-3.29 (m, 3H), 2.80-2.76 (m, 4H), 1.99-1.92 (m, 2H); MS (ESI) m/z 512, 485 (MH+), 483 (MH−) |
| 116 | (5E)-4-amino-6-(4-benzyloxy-3-chloro-phenylamino)-pyrimidine-5-carbaldehyde O-[3-(4-hydroxy-piperidin-1-yl)-propyl]-oxime<br>$^1$H NMR (400 MHz, CD$_3$OD) δ 8.55 (s, 1H), 7.95 (s, 1H), 7.66 (d, j = 2.4, 1H), 7.47-7.25 (m, 6H), 7.05 (d, j = 8.9, 1H), 5.14 (s, 2H), 4.21 (t, j = 12.0, 2H), 3.62 (s, 1H), 2.84-2.81 (m, 2H), 2.54-2.50 (m, 2H), 2.22-2.18 (m, 2H), 1.98-1.91 (m, 2H), 1.87-1.83 (m, 2H), 1.60-1.51 (m, 2H); MS (ESI) m/z 511, 512 (MH+), 513, 509, 510 (MH−) |
| 117 | (5E)-4-[4-amino-6-(4-benzyloxy-3-chloro-phenylamino)-pyrimidin-5-ylmethyleneaminooxymethyl]-piperidine-1-carboxylic acid tert-butyl ester<br>$^1$H NMR (400 MHz, CD$_3$OD) δ 8.57 (s, 1H), 7.95 (s, 1H), 7.65 (d, j = 2.6, 1H), 7.48-7.45 (m, 2H), 7.39-7.35 (m, 2H), 7.34-7.23 (m, 2H), 7.09-7.05 (m, 1H), 5.15 (s, 2H), 4.06 (d, j = 6.4, 4H), 2.82-2.75 (m, 2H), 1.81-1.74 (m, 2H), 1.44 (s, 9H), 1.30-1.17 (m, 2H); MS (ESI) m/z 567 (MH+), 565 (MH−) |
| 119 | N-benzo[1,3]dioxol-5-ylmethyl-5-[(benzo[1,3]dioxol-5-ylmethylimino)-methyl]-pyrimidine-4,6-diamine MS m/z 406 (MH+) |
| 120 | 4-amino-6-(4-methoxy-phenylamino)-pyrimidine-5-carbaldehyde O-methyl-oxime MS m/z 274 (MH+) |
| 121 | 4-amino-6-[(benzo[1,3]dioxol-5-ylmethyl)-amino]-pyrimidine-5-carbaldehyde O-methyl-oxime MS m/z 302 (MH+) |
| 122 | 4-amino-6-(3,4-dimethoxy-benzylamino)-pyrimidine-5-carbaldehyde O-methyl-oxime MS m/z 318 (MH+) |
| 123 | 4-amino-6-(4-phenoxy-benzylamino)-pyrimidine-5-carbaldehyde O-methyl-oxime MS m/z 350 (MH+) |
| 124 | 4-amino-6-(indan-1-ylamino)-pyrimidine-5-carbaldehyde O-methyl-oxime MS m/z 284 (MH+) |
| 125 | 4-amino-6-(1,2,3,4-tetrahydro-naphthalen-1-ylamino)-pyrimidine-5-carbaldehyde O-methyl-oxime MS m/z 298 (MH+) |
| 126 | 4-amino-6-[1-(4-chloro-phenyl)-ethylamino]-pyrimidine-5-carbaldehyde O-methyl-oxime MS m/z 306 (MH+) |

| Cpd | Name and Data |
|---|---|
| 127 | 4-amino-6-[1-(4-methoxy-phenyl)-ethylamino]-pyrimidine-5-carbaldehyde O-methyl-oxime MS m/z 302 (MH$^+$) |
| 128 | 4-amino-6-(6-phenoxy-pyridin-3-ylamino)-pyrimidine-5-carbaldehyde O-methyl-oxime MS m/z 337 (MH$^+$) |
| 129 | 4-amino-6-(6-morpholin-4-yl-pyridin-3-ylamino)-pyrimidine-5-carbaldehyde O-methyl-oxime MS m/z 330 (MH$^+$) |
| 130 | 4-amino-6-(1,4-dioxo-1,2,3,4-tetrahydro-phthalazin-5-ylamino)-pyrimidine-5-carbaldehyde O-methyl-oxime MS m/z 328 (MH$^+$) |
| 131 | 4-amino-6-(2-fluoro-5-methyl-phenylamino)-pyrimidine-5-carbaldehyde O-methyl-oxime MS m/z 276 (MH$^+$) |
| 132 | 4-amino-6-(2,4,6-trimethyl-phenylamino)-pyrimidine-5-carbaldehyde O-methyl-oxime MS m/z 286 (MH$^+$) |
| 133 | 4-amino-6-(3-chloro-2-methyl-phenylamino)-pyrimidine-5-carbaldehyde O-methyl-oxime MS m/z 292 (MH$^+$) |
| 134 | 4-amino-6-(3-methylsulfanyl-phenylamino)-pyrimidine-5-carbaldehyde O-methyl-oxime MS m/z 290 (MH$^+$) |
| 135 | 4-amino-6-[3-(1-methoxyimino-ethyl)-phenylamino]-pyrimidine-5-carbaldehyde O-methyl-oxime MS m/z 315 (MH$^+$) |
| 136 | 4-amino-6-(3,5-dimethyl-phenylamino)-pyrimidine-5-carbaldehyde O-methyl-oxime MS m/z 272 (MH$^+$) |
| 137 | N-{4-[6-amino-5-(methoxyimino-methyl)-pyrimidin-4-ylamino]-phenyl}-acetamide MS m/z 301 (MH$^+$) |
| 138 | 4-amino-6-phenylamino-pyrimidine-5-carbaldehyde O-methyl-oxime MS m/z 244 (MH$^+$) |
| 139 | 4-amino-6-(4-morpholin-4-yl-phenylamino)-pyrimidine-5-carbaldehyde O-methyl-oxime MS m/z 329 (MH$^+$) |
| 140 | 4-amino-6-o-tolylamino-pyrimidine-5-carbaldehyde O-methyl-oxime MS m/z 258 (MH$^+$) |
| 141 | 4-amino-6-(3,4-difluoro-phenylamino)-pyrimidine-5-carbaldehyde O-methyl-oxime MS m/z 280 (MH$^+$) |
| 142 | 4-amino-6-(3-fluoro-4-methyl-phenylamino)-pyrimidine-5-carbaldehyde O-methyl-oxime MS m/z 276 (MH$^+$) |
| 143 | 4-amino-6-(3,4-dichloro-phenylamino)-pyrimidine-5-carbaldehyde O-methyl-oxime MS m/z 312 (MH$^+$) |
| 144 | 4-amino-6-(3-chloro-4-methyl-phenylamino)-pyrimidine-5-carbaldehyde O-methyl-oxime MS m/z 292 (MH$^+$) |
| 145 | 4-amino-6-[5-chloro-2-methyl-4-(2-oxo-2-phenyl-ethyl)-phenylamino]-pyrimidine-5-carbaldehyde O-methyl-oxime MS m/z 410 (MH$^+$) |
| 146 | 4-amino-6-(3-ethyl-phenylamino)-pyrimidine-5-carbaldehyde O-methyl-oxime MS m/z 272 (MH$^+$) |
| 147 | 4-amino-6-(4-isopropyl-phenylamino)-pyrimidine-5-carbaldehyde O-methyl-oxime MS m/z 286 (MH$^+$) |
| 148 | 4-amino-6-(1H-indol-5-ylamino)-pyrimidine-5-carbaldehyde O-methyl-oxime MS m/z 283 (MH$^+$) |
| 149 | 4-amino-6-(3-trifluoromethyl-phenylamino)-pyrimidine-5-carbaldehyde O-methyl-oxime MS m/z 312 (MH$^+$) |
| 150 | 4-amino-6-m-tolylamino-pyrimidine-5-carbaldehyde O-methyl-oxime MS m/z 258 (MH$^+$) |
| 151 | 4-amino-6-(4-chloro-phenylamino)-pyrimidine-5-carbaldehyde O-methyl-oxime MS m/z 278 (MH$^+$) |
| 152 | 4-amino-6-(4-chloro-2-methyl-phenylamino)-pyrimidine-5-carbaldehyde O-methyl-oxime MS m/z 292 (MH$^+$) |
| 153 | 4-amino-6-(4-phenylamino-phenylamino)-pyrimidine-5-carbaldehyde O-methyl-oxime MS m/z 335 (MH$^+$) |
| 154 | 4-amino-6-(4-diethylamino-phenylamino)-pyrimidine-5-carbaldehyde O-methyl-oxime MS m/z 315 (MH$^+$) |
| 155 | 4-[6-amino-5-(methoxyimino-methyl)-pyrimidin-4-ylamino]-benzoic acid methyl ester MS m/z 302 (MH$^+$) |
| 156 | 4-amino-6-[4-(methoxyimino-phenyl-methyl)-phenylamino]-pyrimidine-5-carbaldehyde O-methyl-oxime MS m/z 377 (MH$^+$) |
| 157 | 4-(4-acetyl-phenylamino)-6-amino-pyrimidine-5-carbaldehyde O-methyl-oxime MS m/z 286 (MH$^+$) |
| 158 | 4-amino-6-[4-(1-methoxyimino-ethyl)-phenylamino]-pyrimidine-5-carbaldehyde O-methyl-oxime MS m/z 315 (MH$^+$) |
| 159 | {4-[6-amino-5-(methoxyimino-methyl)-pyrimidin-4-ylamino]-phenyl}-acetonitrile MS m/z 283 (MH$^+$) |
| 160 | 4-amino-6-(2-methoxy-4-phenylamino-phenylamino)-pyrimidine-5-carbaldehyde O-methyl-oxime MS m/z 365 (MH$^+$) |
| 161 | N-{4-[6-amino-5-(methoxyimino-methyl)-pyrimidin-4-ylamino]-3-methoxy-phenyl}-acetamide MS m/z 331 (MH$^+$) |
| 162 | 4-amino-6-(4-cyclohexyl-phenylamino)-pyrimidine-5-carbaldehyde O-methyl-oxime MS m/z 326 (MH$^+$) |
| 163 | 4-amino-6-(naphthalen-1-ylamino)-pyrimidine-5-carbaldehyde O-methyl-oxime MS m/z 294 (MH$^+$) |
| 164 | 4-amino-6-(4-chloro-naphthalen-1-ylamino)-pyrimidine-5-carbaldehyde O-methyl-oxime MS m/z 328 (MH$^+$) |
| 165 | 4-amino-6-(2,4-difluoro-phenylamino)-pyrimidine-5-carbaldehyde O-methyl-oxime MS m/z 280 (MH$^+$) |

-continued

| Cpd | Name and Data |
|---|---|
| 166 | 4-amino-6-(2-methylsulfanyl-phenylamino)-pyrimidine-5-carbaldehyde O-methyl-oxime MS m/z 290 (MH$^+$) |
| 167 | 4-amino-6-(3-fluoro-phenylamino)-pyrimidine-5-carbaldehyde O-methyl-oxime MS m/z 262 (MH$^+$) |
| 168 | 4-amino-6-(3,5-dichloro-phenylamino)-pyrimidine-5-carbaldehyde O-methyl-oxime MS m/z 276 (MH$^+$) |
| 169 | 4-amino-6-(3,5-dichloro-phenylamino)-pyrimidine-5-carbaldehyde O-methyl-oxime MS m/z 312 (MH$^+$) |
| 170 | 4-amino-6-(5-chloro-2-methoxy-phenylamino)-pyrimidine-5-carbaldehyde O-methyl-oxime MS m/z 308 (MH$^+$) |
| 171 | 4-amino-6-(5-chloro-2-methyl-phenylamino)-pyrimidine-5-carbaldehyde O-methyl-oxime MS m/z 292 (MH$^+$) |
| 172 | 4-amino-6-(4-fluoro-phenylamino)-pyrimidine-5-carbaldehyde O-methyl-oxime MS m/z 262 (MH$^+$) |
| 173 | 4-amino-6-(biphenyl-4-ylamino)-pyrimidine-5-carbaldehyde O-methyl-oxime MS m/z 320 (MH$^+$) |
| 174 | 4-amino-6-(4-methylsulfanyl-phenylamino)-pyrimidine-5-carbaldehyde O-methyl-oxime MS m/z 290 (MH$^+$) |
| 175 | 4-amino-6-(3,5-dimethoxy-phenylamino)-pyrimidine-5-carbaldehyde O-methyl-oxime MS m/z 304 (MH$^+$) |
| 176 | 4-amino-6-(3,4,5-trimethoxy-phenylamino)-pyrimidine-5-carbaldehyde O-methyl-oxime MS m/z 334 (MH$^+$) |
| 177 | 4-amino-6-(3,4-dimethoxy-phenylamino)-pyrimidine-5-carbaldehyde O-methyl-oxime MS m/z 304 (MH$^+$) |
| 178 | 4-amino-6-(5,6,7,8-tetrahydro-naphthalen-1-ylamino)-pyrimidine-5-carbaldehyde O-methyl-oxime MS m/z 298 (MH$^+$) |
| 179 | 4-[6-amino-5-(methoxyimino-methyl)-pyrimidin-4-ylamino]-N-pyrimidin-2-yl-benzenesulfonamide MS m/z 401 (MH$^+$) |
| 180 | 3-[6-amino-5-(methoxyimino-methyl)-pyrimidin-4-ylamino]-benzoic acid ethyl ester MS m/z 316 (MH$^+$) |
| 181 | {4-[6-amino-5-(methoxyimino-methyl)-pyrimidin-4-ylamino]-benzyl}-phosphonic acid diethyl ester MS m/z 394 (MH$^+$) |
| 182 | 4-amino-6-(4-ethyl-phenylamino)-pyrimidine-5-carbaldehyde O-methyl-oxime MS m/z 272 (MH$^+$) |
| 183 | 4-[6-amino-5-(methoxyimino-methyl)-pyrimidin-4-ylamino]-N-(3,5-dimethyl-pyrazin-2-yl)-benzenesulfonamide MS m/z 429 (MH$^+$) |
| 184 | 4-amino-6-(2-methyl-benzothiazol-5-ylamino)-pyrimidine-5-carbaldehyde O-methyl-oxime MS m/z 315 (MH$^+$) |
| 185 | 4-amino-6-[4-(4-methoxy-phenylamino)-phenylamino]-pyrimidine-5-carbaldehyde O-methyl-oxime MS m/z 365 (MH$^+$) |
| 186 | 4-amino-6-(4-dimethylamino-phenylamino)-pyrimidine-5-carbaldehyde O-methyl-oxime MS m/z 287 (MH$^+$) |
| 187 | 4-[6-amino-5-(methoxyimino-methyl)-pyrimidin-4-ylamino]-N-(2-diethylamino-ethyl)-benzamide MS m/z 386 (MH$^+$) |
| 188 | 4-[6-amino-5-(methoxyimino-methyl)-pyrimidin-4-ylamino]-benzoic acid butyl ester MS m/z 344 (MH$^+$) |
| 189 | 4-amino-6-(indan-4-ylamino)-pyrimidine-5-carbaldehyde O-methyl-oxime MS m/z 284 (MH$^+$) |
| 190 | 4-amino-6-(4'-chloro-biphenyl-4-ylamino)-pyrimidine-5-carbaldehyde O-methyl-oxime MS m/z 354 (MH$^+$) |
| 191 | 4-amino-6-[6-(4-fluoro-phenoxy)-pyridin-3-ylamino]-pyrimidine-5-carbaldehyde O-methyl-oxime MS m/z 355 (MH$^+$) |
| 192 | 4'-[6-amino-5-(methoxyimino-methyl)-pyrimidin-4-ylamino]-biphenyl-4-carboxylic acid methyl ester MS m/z 378 (MH$^+$) |

EXAMPLE 2

4-amino-6-(4-benzyloxy-3-chloro-phenylamino)-pyrimidine-5-carbonitrile (Cpd 118)

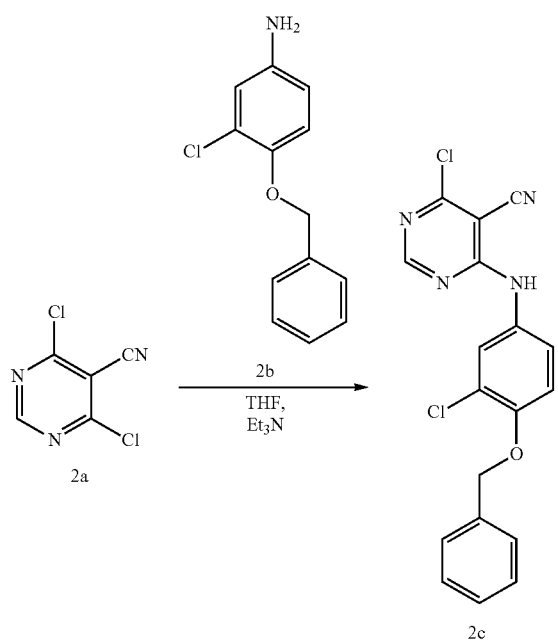 [SMILES: N#Cc1c(Cl)ncnc1Cl ; Nc1ccc(OCc2ccccc2)c(Cl)c1 ; N#Cc1c(Cl)ncnc1Nc1ccc(OCc2ccccc2)c(Cl)c1]

A solution of 4,6-dichloro-pyrimidine-5-carbonitrile Compound 2a (82 mg, 0.47 mmol), Et$_3$N (0.13 mL, 0.94 mmol) and 4-benzyloxy-3-chloro-phenylamine Compound 2b (110 mg, 0.47 mmol) in THF (4.7 mL) was stirred at 25° C. for 3 hours. The reaction mixture was diluted with EtOAc (50 mL), washed with water (1×50 mL) and concentrated to afford 4-(4-benzyloxy-3-chloro-phenylamino)-6-chloro-pyrimidine-5-carbonitrile Compound 2c (175 mg, 100%) as an off-white solid; $^1$H NMR (300 MHz, CD$_3$OD) δ 8.42 (s, 1H), 7.63 (s, 1H), 7.52-7.40 (m, 7H), 7.12 (m, 1H), 5.22 (s, 2H), 5.19 (s, 2); MS (ESI) m/z: 373 (MH$^+$).

A suspension of Compound 2c (10 mg, 0.027 mmol) in 2M NH$_3$ in MeOH (0.26 mL) was warmed at reflux for 1 hour. The reaction mixture was cooled and concentrated. The resulting residue was dissolved in EtOAc (25 mL) and washed with water (15 mL). The organic layer was dried using Na$_2$SO$_4$ and concentrated to afford Compound 118 (5 mg, 50%) as a yellow solid. $^1$H NMR (400 MHz, CD$_3$OD) δ 8.05 (s, 1H), 7.57 (s, 1H), 7.48 (d, J=7.2 Hz, 2H), 7.37-7.29 (m, 4H), 7.11 (d, J=8.8 Hz, 1H), 5.19 (s, 2).

Using the procedure of Example 2, other compounds representative of the present invention may be prepared:

| Name |
| --- |
| 4-amino-6-[3-chloro-4-(3-fluoro-benzyloxy)-phenylamino]-pyrimidine-5-carbonitrile |
| 4-amino-6-[2-(3-fluoro-benzyl)-1H-benzoimidazol-5-ylamino]-pyrimidine-5-carbonitrile |
| 4-amino-6-[1-(3-fluoro-benzyl)-1H-indol-5-ylamino]-pyrimidine-5-carbonitrile |
| 4-amino-6-(4-phenoxy-phenylamino)-pyrimidine-5-carbonitrile |
| 4-amino-6-(3-chloro-4-fluoro-phenylamino)-pyrimidine-5-carbonitrile |

EXAMPLE 3

4-[3-Chloro-4-(3-fluoro-benzyloxy)-phenylamino]-6-methylamino-pyrimidine-5-carbaldehyde O-methyl-oxime (Compound 39)

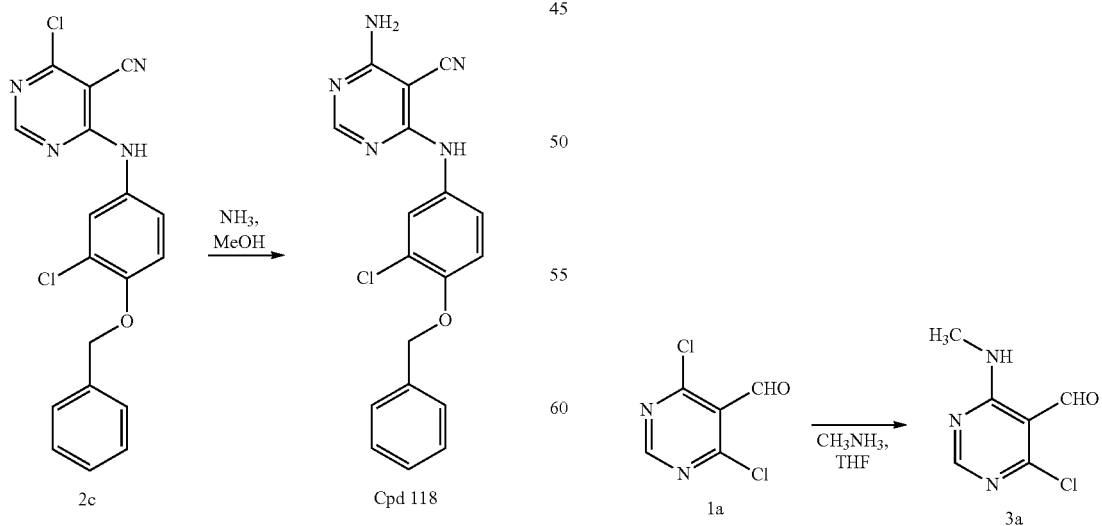

A solution of 4,6-dichloro-pyrimidine-5-carbaldehyde Compound 1a (100 mg, 0.57 mmol) in CHCl$_3$ (1 mL) was treated with methylamine (0.31 mL, 0.63 mmol, 2.0 M in THF) at RT under air. After 1 h the solvent was removed in vacuo and the product, 4-chloro-6-methylamino-pyrimidine-5-carbaldehyde Compound 3a was used in the next step without further purification. LC/MS (m/z) [M+1]$^+$ 172 (calculated for C$_6$H$_6$ClN$_3$O, 171.58).

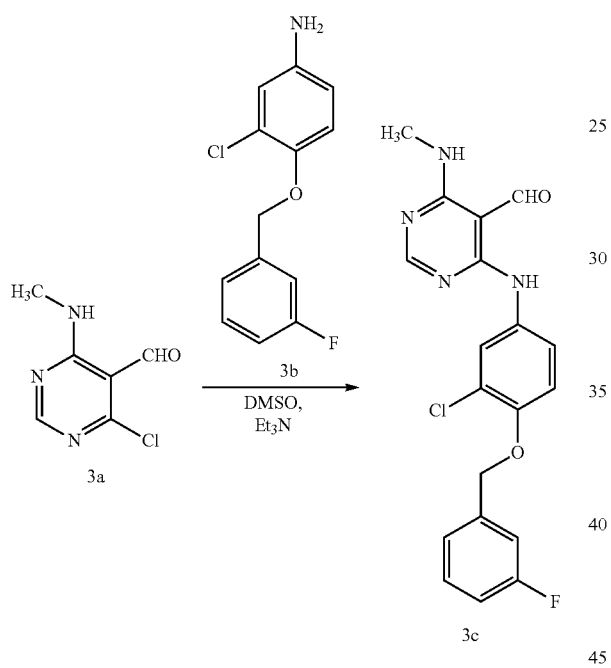

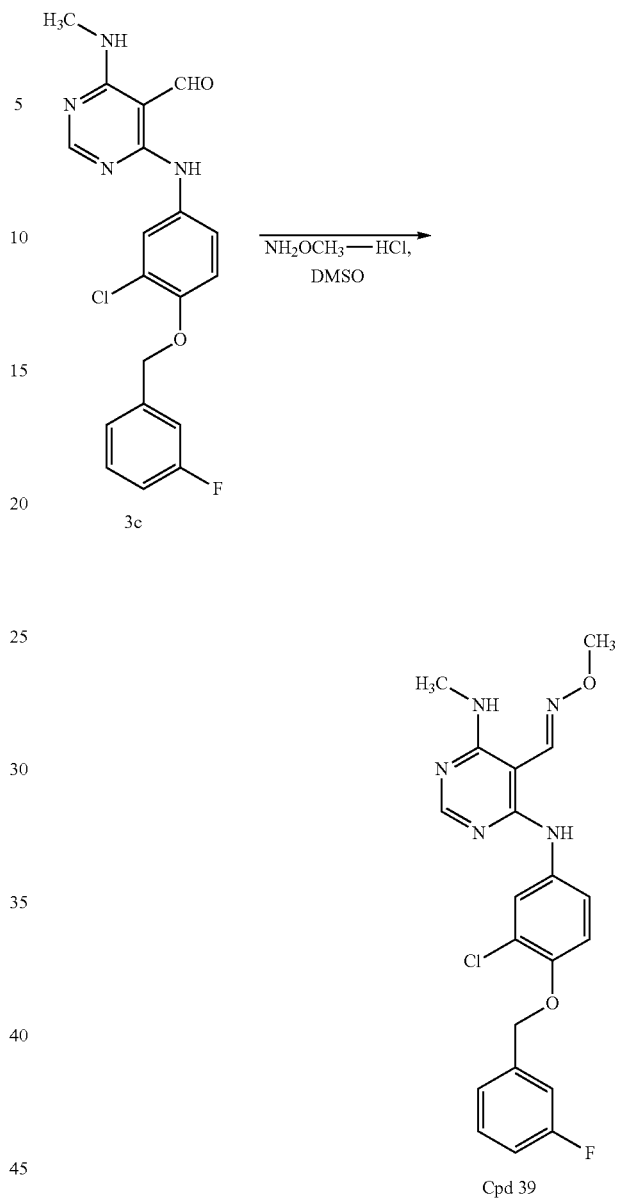

Crude 4-chloro-6-methylamino-pyrimidine-5-carbaldehyde Compound 3a was dissolved into DMSO (1 mL) and treated with 3-chloro-4-(3-fluoro-benzyloxy)-phenylamine Compound 3b (157 mg, 0.63 mmol). The resulting solution was heated to 90° C. for 2 h 40 min. Conversion of starting materials to 4-[3-chloro-4-(3-fluoro-benzyloxy)-phenylamino]-6-methylamino-pyrimidine-5-carbaldehyde Compound 3c was verified by LC/MS; (m/z) [M+1]$^+$387 (calculated for C$_{19}$H$_{16}$ClFN$_4$O$_2$, 386.81). The reaction solution was carried on directly to the next step without workup.

The reaction solution of Compound 3c was removed from the heating block, then methoxylamine hydrochloride (142 mg, 1.7 mmol) was added and heating resumed at 90° C. for 1 h. The crude reaction was cooled to RT, partitioned between EtOAc (30 mL) and H$_2$O (20 mL), the organic phase was dried over Na$_2$SO$_4$, then concentrated in vacuo. Purification on the Chromatotron radial, thin-layer chromatograph (http://www.chromatotron.com/chromatotron/specs.html) (1 mm, 20% EtOAc/CH$_2$Cl$_2$) afforded the product 4-[3-chloro-4-(3-fluoro-benzyloxy)-phenylamino]-6-methylamino-pyrimidine-5-carbaldehyde O-methyl-oxime Compound 39 as a yellow oil (4.7 mg, 0.01 mmol). $^1$H NMR (300 Hz, CDCl$_3$) δ 8.99 (bs, 1H), 8.31 (bs, 1H), 8.26 (s, 1H), 7.54 (d, J=2.5 Hz, 1H), 7.38-7.17 (m, 4H), 7.04-6.90 (m, 2H), 5.13 (s, 2H), 3.97 (s, 3H), 3.13 (d, J=4.9 Hz, 3H); LC/MS (m/z) [M+1]$^+$ 416.1 (calculated for C$_{20}$H$_{19}$ClFN$_5$O$_2$, 415.85).

Using the procedure of Example 3, other compounds representative of the present invention were prepared:

| Cpd | Name and Data |
|---|---|
| 40 | (5E)-4-ethylamino-6-[1-(3-fluoro-benzyl)-1H-indazol-5-ylamino]-pyrimidine-5-carbaldehyde O-methyl-oxime<br>$^1$H NMR (300 Hz, CDCl$_3$) δ 8.97 (bs, 1H), 8.23 (s, 1H), 8.21 (bs, 1H), 8.02 (s, 1H), 7.83 (s, 1H), 7.37-7.23 (m, 4H), 6.97-6.95 (m, 2H), 6.86-6.81 (m, 1H), 5.58 (s, 2H), 3.95 (s, 3H), 3.63-3.59 (m, 2H), 1.29 (t, J = 7.2 Hz, 3H); LC/MS (m/z) (MH$^+$) 420.1 (calculated for C$_{22}$H$_{22}$FN$_7$O, 419.46) |
| 41 | (5E)-4-ethylamino-6-[1-(3-fluoro-benzyl)-1H-indazol-5-ylamino]-pyrimidine-5-carbaldehyde O-ethyl-oxime<br>$^1$H NMR (300 Hz, CDCl$_3$) δ 9.07 (bs, 1H), 8.24 (s, 1H), 8.22 (bs, 1H), 8.02 (s, 1H), 7.83 (s, 1H), 7.34-7.23 (m, 4H), 6.97-6.95 (m, 2H), 6.86-6.82 (m, 1H), 5.58 (s, 2H), 4.19 (q, J = 7.05, 2H), 3.64-3.57 (m, 2H), 1.33-1.27 (m, 6H); LC/MS (m/z) (MH$^+$) 434.2 (calculated for C$_{23}$H$_{24}$FN$_7$O, 433.48) |
| 42 | (5E)-4-[3-chloro-4-(3-fluoro-benzyloxy)-phenylamino]-6-ethylamino-pyrimidine-5-carbaldehyde O-methyl-oxime<br>$^1$H NMR (300 Hz, CDCl$_3$) δ 8.86 (bs, 1H), 8.24 (s, 2H), 7.56 (d, J = 2.61 Hz, 1H), 7.39-7.37 (m, 4H), 7.17-7.03 (m, 1H), 6.93-6.90 (m, 1H), 6.44 (bs, 1H), 5.13 (s, 2H), 3.98 (s, 3H), 3.59 (m, 2H), 1.28 (t, J = 7.23 Hz, 3H); LC/MS (m/z) (MH$^+$) 430.1 (calculated for C$_{21}$H$_{21}$ClFN$_5$O$_2$, 429.88) |
| 43 | (5E)-4-[3-chloro-4-(3-fluoro-benzyloxy)-phenylamino]-6-ethylamino-pyrimidine-5-carbaldehyde O-ethyl-oxime<br>$^1$H NMR (300 Hz, CDCl$_3$) δ 8.75 (bs, 1H), 8.25 (s, 1H), 8.24 (s, 1H), 7.59 (d, J = 2.57 Hz, 1H), 7.35-7.18 (m, 4H), 7.04-6.98 (m, 1H), 6.91-6.88 (m, 1H), 6.18 (bs, 1H), 5.12 (s, 2H), 4.23 (q, J = 7.05 Hz, 2H), 3.56 (m, 2H), 1.35 (t, J = 7.05 Hz, 3H), 1.26 (t, J = 7.14 Hz, 3H); LC/MS (m/z) (MH$^+$) 444.1 (calculated for C$_{22}$H$_{23}$ClFN$_5$O$_2$, 443.90) |
| 53 | (5E)-4-[1-(3-fluoro-benzyl)-1H-indazol-5-ylamino]-6-methylamino-pyrimidine-5-carbaldehyde O-methyl-oxime<br>$^1$H NMR (300 Hz, CDCl$_3$) δ 8.65 (bs, 1H), 8.31 (s, 1H), 8.26 (s, 1H), 8.01 (s, 1H), 7.85 (d, J = 1.74 Hz, 1H), 7.39-7.22 (m, 3H), 6.97-6.94 (m, 2H), 6.41-6.37 (m, 1H), 5.57 (s, 2H), 3.97 (s, 3H), 3.09 (d, J = 4.80 Hz, 3H); LC/MS (m/z) (MH$^+$) 406.1 (calculated for C$_{21}$H$_{20}$FN$_7$O, 405.43) |

EXAMPLE 4

(5E)-4-amino-6-(4-benzyloxy-3-chloro-phenylamino)-pyrimidine-5-carbaldehyde O-(2-morpholin-4-yl-ethyl)-oxime (Cpd 78)

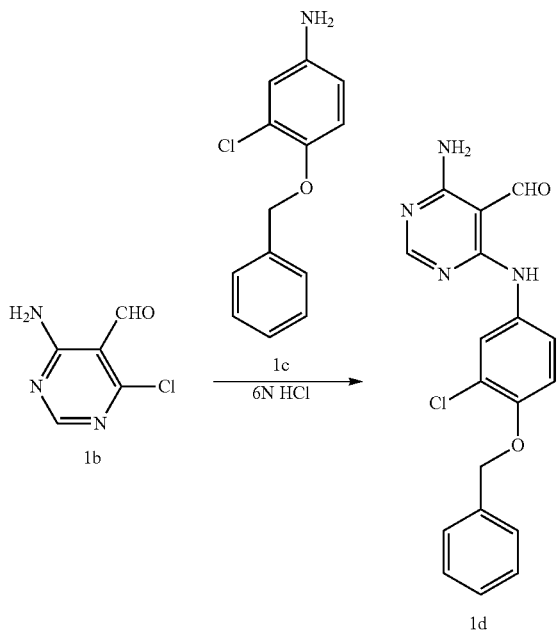

To a 100 L reactor equipped with nitrogen sweep, thermocouple and condensers was added 2-methoxy-ethanol (66.5 kg), 4-amino-6-chloro-pyrimidine-5-carbaldehyde Compound 1b (5.98 kg), 4-benzyloxy-3-chloro-phenylamine Compound 1c (5.98 kg), 6N HCl (1.54 kg) and purified water (0.55 kg). The reactor wall was rinsed with 2-methoxy-ethanol (0.5 kg). The slurry was heated to about 40° C. and aged for 15 minutes. A second addition of Compound 1c (3.09 kg) was made and the reaction mixture was aged for an additional 15 minutes. The slurry solution then crystallized. A third addition of Compound 1c (3.08 kg) was made and the reaction mixture was aged for 15 minutes. The slurry was heated to about 65° C. until HPLC analysis showed the reaction was complete, thus providing 4-amino-6-(4-benzyloxy-3-chloro-phenylamino)-pyrimidine-5-carbaldehyde Compound 1d which was used in the next step as an unisolated intermediate.

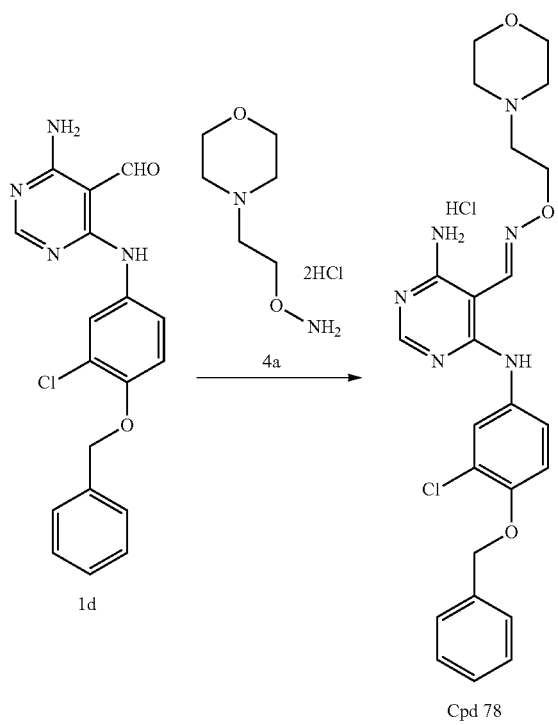 [SMILES: Nc1ncnc(Nc2ccc(OCc3ccccc3)c(Cl)c2)c1C=O ; NOCCN1CCOCC1 ; "2HCl" ; Nc1ncnc(Nc2ccc(OCc3ccccc3)c(Cl)c2)c1/C=N/OCCN1CCOCC1 ; Cl]

The slurry containing Compound 1d was cooled to between about 20-25° C., then O-(2-morpholin-4-yl-ethyl)-hydroxylamine dihydrochloride Compound 4a (9.37 kg) and 6.0N NaOH solution (12.1 L) was added. The suspension was heated to reflux between about 105° C. to about 115° C. and the distillate (between about 38.5 to about 43.5 kg) was collected. The slurry was cooled to between about 20° C. to about 25° C., then 2-methoxy-ethanol (18.5 kg) and purified water (19.1 kg) was added. The resulting slurry was stirred for 0.5 h, then filtered on an 18" polypropylene filter lined with polypropylene cloth. The filter cake was washed thrice with a mixture (1:1 v/v) of 2-methoxy-ethanol (15.1 kg) and water (13.9 kg). The wet cake was dried on the filter for at least 30 minutes then transferred to polypropylene drying trays, weighed and covered with polypropylene tray covers. The product was dried to a constant weight at between about 55° C. to about 60° C. under vacuum with a nitrogen bleed to provide Compound 78 (13.79 kg, 81% yield) as a yellow powder. 98.9 HPLC Area %, 99.6 HPLC wt. % vs. standard.

Compound 78 (11.00 kg), 1-propanol (44.2 kg) and water (55.0 kg) was added to a 100 L reactor equipped with nitrogen sweep, thermocouple, and condensers. The resulting suspension was heated until a solution was achieved (at about 70° C.). The solution was cooled to between about 60° C. to about 65° C. and the contents were polish filtered to another 100 L reactor using a 145-175 micron filter. The solution was cooled to about 10° C. over a period of about 3.5 hours and then aged for about one hour. The suspension was filtered on an 18" polypropylene filter lined with polypropylene cloth and the resulting cake was washed twice each with a 1:1 (v/v) mixture of 1-propanol/water (19.8 kg). The filter cake was dried with nitrogen for at least 30 minutes on the filter and then transferred to polypropylene drying trays, weighed and covered with polypropylene tray covers. The product was dried to a constant weight at between about 55° C. to about 60° C. under vacuum with a nitrogen bleed to provide the mono hydrochloride salt of Compound 78 (9.60 kg, 87% yield) as a light yellow powder. 99.0 HPLC Area %, 99.8 HPLC wt. % vs. standard.

The present invention is further directed to a method for selectively coupling an aniline compound with a chlorinated pyrimidine aldehyde compound.

The first step of the foregoing Example 4 is representative of this method whereby an aniline compound reacts with a chlorinated pyrimidine aldehyde compound at the chloro substituted carbon atom instead of at the aldehyde. This coupling is induced by using a catalytic amount of acid. Acids that may be used in the present method include, and are not limited to, aqueous HCl. Solvents that may be used in the present method include, and are not limited to, 2-methoxy-ethanol.

EXAMPLE 5

N-(4-benzyloxy-3-chloro-phenyl)-5-[5-(2-morpholin-4-yl-ethyl)-[1,3,4]oxadiazol-2-yl]-pyrimidine-4,6-diamine (Cpd 193)

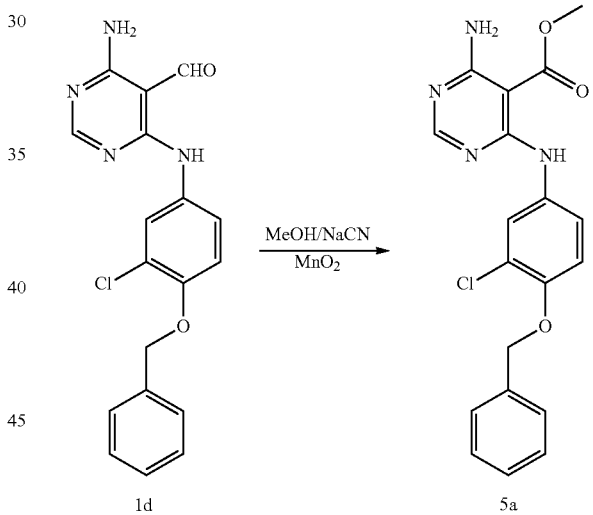

4-amino-6-(4-benzyloxy-3-chloro-phenylamino)-pyrimidine-5-carbaldehyde Compound 1d (5.0 g, 14.1 mmol) in THF/MeOH (1/1, 125 mL) was treated with $MnO_2$ (7.4 g, 84.5 mmol), NaCN (2.1 g, 42.3 mmol), AcOH (2.4 mL, 42.3 mmol) and the reaction mixture was warmed at reflux for 24 h. The mixture was cooled to rt and filtered through Celite. The filtrate was diluted with $H_2O$ (200 mL) and then extracted with a (1/1) mixture of EtOAc/THF (3×100 mL). The resulting organic extracts were dried ($Na_2SO_4$), and concentrated to afford 4-amino-6-(4-benzyloxy-3-chloro-phenylamino)-pyrimidine-5-carboxylic acid hydrazide Compound 5a (4.33 g, 80%) as a yellow solid. $^1$H NMR (300 MHz, DMSO-d6) δ 10.26 (s, 1H), 8.05 (s, 1H), 7.86 (d, J=2.4 Hz, 1H), 7.64 (br s, 2 H), 7.51-7.35 (m, 7H), 7.20 (d, J=8.7 Hz, 1H), 5.22 (s, 2H), 3.89 (s, 3H).

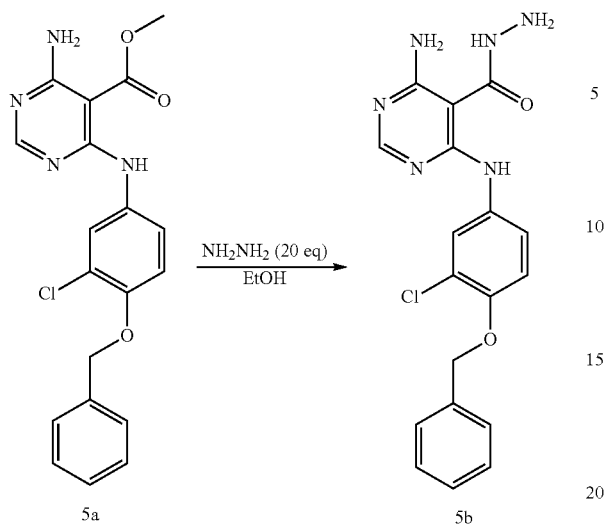

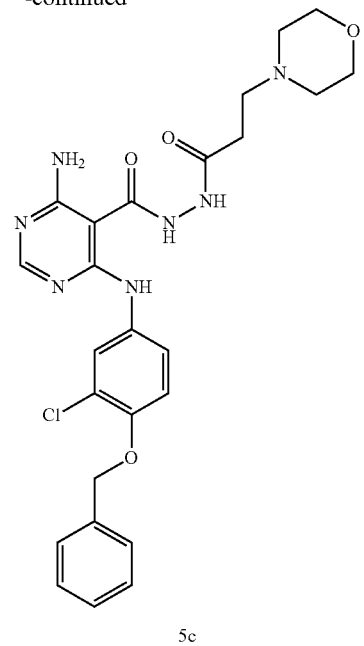

A suspension of Compound 5a (4.3 g, 11.2 mmol) in 100% EtOH (110 mL) was treated with hydrazine (6.8 mL, 224 mol) and warmed at reflux for 24 h. The reaction mixture was concentrated onto $SiO_2$ (15 g). The residue was purified via column chromatography (Horizon 65+M, 0-10% MeOH/DCM) to provide 4-amino-6-(4-benzyloxy-3-chloro-phenylamino)-pyrimidine-5-carboxylic acid hydrazide Compound 5b (2.50 g, 58%) as a yellow solid. $^1$H NMR (300 MHz, $CD_3OD$) δ 7.96 (s, 1H), 7.61 (d, J=2.0 Hz, 1H), 7.64-7.22 (m, 6H), 7.04 (d, J=8.7 Hz, 1H), 5.22 (s, 2H); MS m/z 385.0 ($MH^+$).

A mixture of Compound 5b (6.8 mg, 0.018 mmol), 3-morpholin-4-yl-propionic acid hydrochloride (3.8 mg, 0.019 mmol) and EDCI (10.2 mg, 0.053 mmol) in DMF (0.17 mL) was stirred at rt for 12 h. The reaction was diluted with $H_2O$ (20 mL) and extracted with EtOAc (3×10 mL). The combined organic extracts were dried ($Na_2SO_4$) and concentrated to afford 4-amino-6-(4-benzyloxy-3-chloro-phenylamino)-pyrimidine-5-carboxylic acid N'-(3-morpholin-4-yl-propionyl)-hydrazide Compound 5c (8.3 mg, 88%) as a yellow solid. $^1$H NMR (400 MHz, $CD_3OD$) δ 8.03 (s, 1H), 7.76 (d, J=1.2 Hz, 1H), 7.47-7.30 (m, 6H), 7.05 (d, J=6.4 Hz, 1H), 5.15 (s, 2H), 2.76 (m, 2H), 2.56 (m, 6H), 1.29 (br s, 6H); MS m/z 526.5 ($MH^+$).

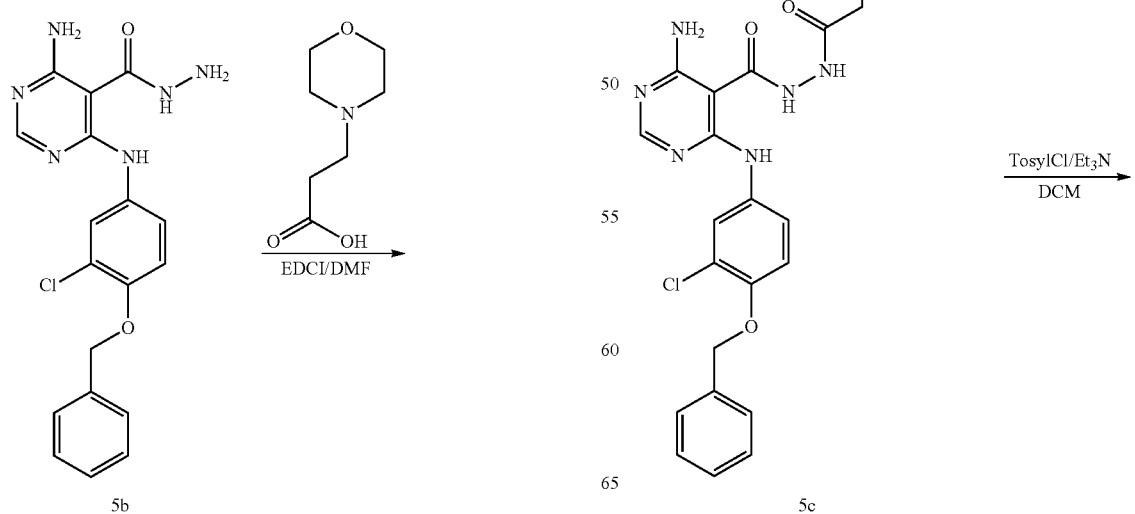

-continued

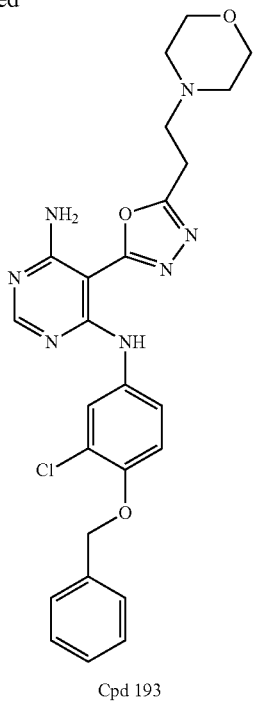

Cpd 193

A solution of Compound 5c (6.2 mg, 0.012 mmol) in DCM (0.20 mL) was treated with Et$_3$N (3.3 μL), then toluene sulfonyl chloride (2.4 mg, 0.012 mmol) was added and the resulting solution was stirred at rt for 3 h. The reaction was loaded directly onto a SiO$_2$ column (Horizon 12+M, 0-5% MeOH/DCM) to afford Compound 193 (5.0 mg, 85%) as a white solid. $^1$H NMR (400 MHz, CD$_3$OD) δ 8.09 (s, 1H), 7.75 (d, J=2.7 Hz, 1H), 7.47-7.32 (m, 6H), 7.13 (d, J=9.0 Hz, 1H), 5.17 (s, 2H), 3.67 (m, 4H), 3.29 (t, J=1.5 Hz, 2H), 2.87 (t, J=6.9 Hz, 2H), 2.55 (m, 4H); MS m/z 508.2 (MH$^+$).

BIOLOGICAL EXAMPLES

The ability of the compounds for treating, preventing or ameliorating a chronic or acute kinase mediated disease, disorder or condition was determined using the following procedures.

Example 1

EGFR Kinase Assay

The EGFR kinase used was a fusion of Glutathione-S-Transferase (GST) and a PCR amplified intracellular portion of EGFR (NM_005228). The intracellular portion of EGFR started at nucleotide 2189 (corresponding to amino acid 667) and ended at the termination codon. The portion was PCR amplified with primers that added the lambda attB sequences to each end, recombined into an entry vector, then into a GST destination vector (as described in Gateway Technologies Manual by Invitrogen Corporation, Carlsbad, Calif.).

The destination vector was recombined in the DH10BAC strain of bacteria to produce a bacmid. The bacmid was transfected into Sf 9 cells and the supernatant containing the baculovirus was collected. The GSTEGFR protein was purified using large cultures of Sf 9 cells infected with stock virus. After an appropriate period of time, the cells were collected and lysed. The GSTEGFR was then purified from the lysate on Glutathione-Sepharose columns (as described by Amersham Biosciences, Buckinghamshire, United Kingdom).

The EGFR substrate was prepared by biotinylating polyGluTyr (128 mg) (Sigma™, St. Louis, Mo.) in a 1×PBS buffer incubated together with a 12-fold molar excess of Sulfo-NHS-LC-Biotin on ice for at least 2 hrs. The free biotin was separated from the biotinylated polyGluTyr on a gel filtration column.

A mixture of a 10× kinase buffer (500 mM Tris at pH 8.0, 100 mM Magnesium Chloride and 1 mM Sodium Vanadate), DTT (1 mM final from 500 mM stock), ATP (5 μM final from 10 mM stock), biotinylated polyGluTyr (10 μg/μL stock), γ-$^{33}$PATP (10 μCi/μL stock) and water was added to each well (90 μL/well) of a Streptavidin Flashplate (Perkin Elmer, Wellesley, Mass.).

Test compound in 100% DMSO (2 μL) was added to the appropriate wells. Diluted GSTEGFR (1:300 dilution in 50 mM Tris at pH 8.0 and 0.1% bovine serum albumin) (10 μL) was added to the wells to initiate the reactions.

The plates were incubated at 30° C. for 1 hr with shaking. The reacted contents were removed and the plates were sequentially washed three times with a 1×PBS stop buffer (300 μL without Magnesium and Calcium) and 100 mM EDTA. After the final wash, the same stop buffer (200 μL) was added to the wells. The plates were then sealed and read on the TopCount scintillation counter.

Test compounds were assayed in triplicate at 16 concentrations at half-log dilutions starting at 200 μM. A maximum and minimum signal for the assay was determined on each plate. The percent inhibition of a test compound was calculated according to the formula $$\left[\frac{(\text{max signal} - \text{test compound})}{(\text{max signal} - \text{min signal})}\right](100) = \% \text{ inhibition}$$

For a series of test concentrations, the IC$_{50}$ was derived by graphing percent inhibition against the log of the concentrations tested for a given compound. The EGFR IC$_{50}$ results are shown in Table 1. Values shown as % indicate % inhibition at a test concentration of 2 μM.

TABLE 1

| Cpd | EGFR IC$_{50}$ (μM) |
|---|---|
| 1 | 0.07 |
| 2 | 0.008 |
| 3 | 1.1 |
| 4 | 0.01 |
| 5 | 0.5 |
| 7 | 0.05 |
| 9 | 0.02 |
| 10 | 0.005 |
| 11 | 0.008 |
| 12 | 0.04 |
| 13 | 0.2 |
| 14 | 0.1 |
| 16 | 0.01 |
| 17 | 0.02 |
| 18 | 0.03 |
| 19 | 0.02 |
| 20 | 1.2 |
| 21 | 1.5 |
| 22 | 0.3 |
| 23 | 1.9 |
| 24 | 0.09 |
| 25 | 0.03 |
| 28 | 0.9 |

TABLE 1-continued

EGFR IC$_{50}$ (μM)

| Cpd | IC$_{50}$ |
|---|---|
| 29 | 0.2 |
| 30 | 0.03 |
| 31 | 0.02 |
| 32 | 0.01 |
| 33 | 0.02 |
| 34 | 0.01 |
| 36 | 0.02 |
| 37 | 0.02 |
| 38 | 0.1 |
| 41 | 0.4 |
| 42 | 7.8 |
| 43 | 1.4 |
| 44 | 0.07 |
| 45 | 0.05 |
| 46 | 0.02 |
| 47 | 0.01 |
| 48 | 0.04 |
| 49 | 0.03 |
| 50 | 0.02 |
| 51 | 0.04 |
| 54 | 0.02 |
| 55 | 0.04 |
| 56 | 0.3 |
| 57 | 0.2 |
| 58 | 0.03 |
| 59 | 0.05 |
| 60 | 0.05 |
| 61 | 0.2 |
| 62 | 0.2 |
| 63 | 1.2 |
| 65 | 0.04 |
| 66 | 0.1 |
| 67 | 0.1 |
| 68 | 0.01 |
| 69 | 0.01 |
| 70 | 0.02 |
| 71 | 0.01 |
| 74 | 0.06 |
| 75 | 0.008 |
| 76 | 0.01 |
| 77 | 0.02 |
| 78 | 0.02 |
| 79 | 0.008 |
| 80 | 0.3 |
| 82 | 0.2 |
| 84 | 0.01 |
| 85 | 0.02 |
| 87 | 0.03 |
| 88 | 0.009 |
| 91 | 0.007 |
| 92 | 0.05 |
| 93 | 0.02 |
| 94 | 0.02 |
| 95 | 0.05 |
| 96 | 0.06 |
| 97 | 0.03 |
| 98 | 0.02 |
| 99 | 0.07 |
| 100 | 0.02 |
| 102 | 0.04 |
| 108 | 0.2 |
| 111 | 0.1 |
| 112 | 0.02 |
| 118 | 0.03 |
| 120 | 15% |
| 122 | 6% |
| 123 | 7% |
| 124 | 26% |
| 125 | 42% |
| 128 | 45% |
| 129 | 1% |

Example 2

HER-2 Kinase Assay

The HER-2 kinase used was purified at Proqinase (Freiburg, Germany) from a construct that consisted of a fusion of GST (Glutathione-S-Transferase), HIS6-Thrombin and the nucleotides encoding amino acids 679 to 1255 of HER-2 (Accession Number M11730).

A mixture of a 10× kinase reaction buffer (600 mM Hepes at pH 7.5, 30 mM Magnesium Chloride, 0.03 mM Sodium Vanadate and 500 μg/mL PEG 20,000), DTT (1.2 mM final from a 10 mM stock), ATP (1 μM from a 10 mM stock), biotinylated polyGluTyr (1.5 ng/4 final from stock of 1 μg/μL) prepared by Upstate Biotechnologies, Lake Placid, N.Y.), Manganese Chloride (3 mM final from a 1 M stock), γ-$^{33}$P-ATP (10 μCi/μL stock) and water (70 μL/well) was added to each well of a Streptavidin Flashplate (Cat. # SMP103, NEN, Boston, Mass.).

Test compound stock (1 μL) was added to the appropriate wells. Diluted GSTHER2 kinase (6.7 ng/μL diluted into 50 mM Tris-HCl at pH 8.0 and 0.1% bovine serum albumin) (30 μL) was added (total volume of 200 ng/well) to initiate the reactions.

The reaction plates were incubated at 30° C. for 1 hr. The reaction was terminated by aspirating the reaction mixture from the plate wells and washing the wells three times with a 1×PBS stop buffer (300 μL) and 100 mM EDTA. After the final wash, the same stop buffer (200 μL) was again added to the wells. The plates were then sealed and read on the Top-Count scintillation counter.

Test compounds were assayed in triplicate at 8 concentrations at one-log dilutions starting at 100 μM. A maximum and minimum signal for the assay was determined on each plate. The percent inhibition of a test compound was calculated according to the formula:

$$\left[\frac{(\text{max signal} - \text{test compound})}{(\text{max signal} - \text{min signal})}\right](100) = \%\ \text{inhibition}$$

For a series of test concentrations, the IC$_{50}$ was derived by graphing percent inhibition against the log of the concentrations tested for a given compound. The Her-2 IC$_{50}$ values are shown in Table 2. Values shown as % indicate % inhibition at a test concentration of 1 μM.

TABLE 2

HER2 IC$_{50}$ (μM)

| Cpd | IC$_{50}$ |
|---|---|
| 1 | 0.2 |
| 2 | 0.01 |
| 3 | 5.2 |
| 4 | 0.02 |
| 5 | 3.7 |
| 6 | 0.1 |
| 7 | 0.1 |
| 8 | 0.7 |
| 9 | 0.2 |
| 10 | 0.007 |
| 11 | 0.01 |
| 12 | 0.05 |
| 13 | 0.1 |
| 14 | 3.1 |
| 15 | 100 |
| 16 | 0.01 |
| 17 | 0.6 |
| 18 | 0.04 |

TABLE 2-continued

HER2 IC$_{50}$ (µM)

| Cpd | IC$_{50}$ |
|---|---|
| 19 | 0.05 |
| 20 | 14.1 |
| 21 | 5.3 |
| 22 | 4.1 |
| 23 | 28.5 |
| 24 | 0.2 |
| 25 | 0.3 |
| 26 | 100 |
| 27 | 100 |
| 28 | 5.5 |
| 29 | 0.2 |
| 30 | 0.2 |
| 31 | 0.3 |
| 32 | 0.09 |
| 33 | 0.1 |
| 34 | 0.03 |
| 35 | 100 |
| 36 | 0.6 |
| 37 | 0.09 |
| 38 | 0.05 |
| 39 | 14.8 |
| 40 | 10.6 |
| 41 | 3.6 |
| 42 | 100 |
| 43 | 10.4 |
| 44 | 1.6 |
| 45 | 0.4 |
| 46 | 0.1 |
| 47 | 0.03 |
| 48 | 0.02 |
| 49 | 0.01 |
| 50 | 0.04 |
| 51 | 0.04 |
| 52 | 4.5 |
| 53 | 10.0 |
| 54 | 0.03 |
| 55 | 0.03 |
| 60 | 0.08 |
| 63 | 1.0 |
| 64 | 100 |
| 65 | 0.2 |
| 66 | 0.2 |
| 67 | 0.2 |
| 68 | 0.006 |
| 69 | 0.004 |
| 70 | 0.02 |
| 71 | 0.05 |
| 72 | 100 |
| 73 | 2.9 |
| 74 | 0.3 |
| 75 | 0.009 |
| 76 | 0.03 |
| 77 | 0.1 |
| 78 | 0.06 |
| 79 | 0.01 |
| 80 | 100 |
| 81 | 100 |
| 82 | 100 |
| 83 | 100 |
| 84 | 0.04 |
| 85 | 0.02 |
| 86 | 100 |
| 87 | 0.07 |
| 88 | 0.02 |
| 89 | 10.0 |
| 90 | 100 |
| 91 | 0.03 |
| 92 | 0.03 |
| 93 | 0.008 |
| 94 | 0.04 |
| 95 | 0.2 |
| 96 | 0.1 |
| 97 | 1.0 |
| 98 | 0.1 |
| 99 | 0.2 |
| 100 | 10.0 |
| 101 | 0.06 |
| 102 | 0.14 |
| 103 | 100 |
| 104 | 100 |
| 105 | 100 |
| 106 | 100 |
| 107 | 10.0 |
| 108 | 1.1 |
| 109 | 100 |
| 110 | 10.0 |
| 111 | 0.3 |
| 118 | 0.1 |
| 119 | >10 |
| 120 | 7.923 |
| 121 | >10 |
| 122 | >100 |
| 123 | >100 |
| 124 | 2.46 |
| 125 | 25% |
| 128 | 1.822 |
| 129 | >100 |

Example 3

In Vitro Cell Proliferation Inhibition Assays

The ability of a test compound to inhibit unregulated in vitro cell proliferation may be determined by measuring incorporation of $^{14}$C-labelled thymidine into newly synthesized DNA within cell lines derived from carcinomas originating from several tissues. Accordingly, the effect of a test compound on proliferation of cells with a variety of phenotypes may be determined.

Carcinoma cell lines used include the HeLa cervical adenocarcinoma from the American Type Culture Collection (ATCC Cat. #CCL2), SK-OV-3 ovarian carcinoma (ATCC Cat. #HTB-77), MCF-7 breast carcinoma (ATCC Cat. # HTB-22), BT474 breast carcinoma (ATCC Cat. #HTB-20), SKBR3 breast carcinoma (ATCC Cat. #HTB-30), A431 epidermoid carcinoma (ATCC Cat. #CRL-1555) and NCI-N87 gastric carcinoma (ATCC Cat. #CRL-5822).

The carcinoma cells are trypsinized and counted. The cells (3000-8000 count) are added to each well of a 96-well CytoStar tissue culture treated scintillating microplate (Amersham #RPNQ0160) in complete medium (100 µL) and the plate is then incubated in complete medium for 24 hrs at 37° C. in an inert atmosphere containing 5% $CO_2$.

Test compound (1 µL) in 100% DMSO is added to the plate test-wells with DMSO only added to control-wells. The plate is incubated in complete medium for a second 24 hr period at 37° C. in an atmosphere containing 5% $CO_2$.

An aliquot of a solution of Methyl $^{14}$C-thymidine (56 mC/mmol) (NEN #NEC568 or Amersham #CFA532) and complete medium (20 µL to provide 0.2 µCi/well) is then added to each well and the plate is incubated for a third 24 hr period at 37° C. in an atmosphere containing 5% $CO_2$.

The plate contents are then discarded, the plate is washed twice with PBS (200 µL) and then PBS (200 µL) is added to each well. The plate is sealed and the degree of methyl $^{14}$C-thymidine incorporation is quantified on a Packard Top Count.

Cell proliferation of the Hela cell line was measured using the ATP-Lite method as described in the ATP Lite Kit (Perkin-Elmer Kit Number 6106941) or the $C^{14}$ method as described above. Cell proliferation of the other cell lines was measured using the $C^{14}$ method.

The IC$_{50}$ values for the compounds tested in various cell lines are shown in Tables 3 and 4. The term "NT" means that the compound indicated was not tested in a particular cell line. The lack of such testing is not intended to imply a belief that the compound is not otherwise active in a particular cell line or any other cell line not tested.

TABLE 3

HeLa IC$_{50}$ (μM)

| Cpd | IC$_{50}$ |
|---|---|
| 9 | 35.0 |
| 19 | 10.0 |
| 34 | 3.5 |
| 46 | 100 |
| 60 | 10.0 |
| 70 | 10.0 |
| 75 | 40.1 |
| 76 | 59.4 |
| 77 | 10.0 |
| 78 | 19.6 |
| 79 | 100 |
| 80 | 100 |
| 81 | 10.0 |
| 82 | 100 |
| 83 | 3.6 |
| 84 | 4.9 |
| 85 | 15.6 |
| 86 | 100 |
| 87 | 4.9 |
| 88 | 10.9 |
| 89 | 10.0 |
| 90 | 10.0 |
| 91 | 9.4 |
| 92 | 4.7 |
| 93 | 22.1 |
| 94 | 6.1 |
| 95 | 12.1 |
| 96 | 14.7 |
| 97 | 100 |
| 98 | 100 |
| 99 | 100 |
| 100 | 10.0 |
| 101 | 25.1 |
| 102 | 1.4 |
| 103 | 10.0 |
| 104 | 10.0 |
| 105 | 100 |
| 106 | 10.0 |
| 107 | 100 |
| 108 | 10.0 |
| 109 | 100 |
| 110 | 33.1 |
| 118 | 100 |

TABLE 4

IC$_{50}$ (μM)

| Cpd | SK-OV-3 | MCF-7 | BT474 | SKBR3 | N87 | A431 |
|---|---|---|---|---|---|---|
| 9 | 100 | 86.6 | NT | NT | 0.7 | NT |
| 19 | 19.1 | 2.5 | 0.03 | 0.1 | 0.04 | 1.1 |
| 34 | 3.2 | 3.8 | NT | NT | 0.2 | NT |
| 46 | NT | NT | 0.1 | 0.3 | 10.0 | 100 |
| 60 | 10.0 | 10.0 | NT | NT | 0.6 | NT |
| 70 | NT | NT | 0.1 | 0.4 | 0.3 | 14.2 |
| 75 | 10.0 | 30.7 | NT | NT | 0.001 | NT |
| 76 | 24.1 | 10.0 | 0.2 | 0.3 | 0.3 | 1.8 |
| 78 | 100 | 100 | 0.06 | 0.2 | 0.2 | 0.8 |
| 87 | NT | NT | 0.3 | 0.5 | 0.3 | 3.6 |
| 91 | 5.4 | 10.0 | 0.2 | 0.3 | 0.2 | 1.3 |
| 92 | NT | NT | 0.2 | 0.4 | 0.2 | 3.1 |
| 93 | 100 | 100 | 0.04 | 0.02 | 0.07 | 0.6 |
| 94 | 1.0 | 1.0 | 0.5 | 0.5 | 0.4 | NT |
| 95 | 2.4 | 1.0 | 10.0 | 10.0 | 1.1 | 100 |
| 96 | 15.3 | 2.1 | 0.2 | 0.4 | 0.2 | 0.8 |
| 99 | NT | NT | 10.0 | 100 | 100 | 100 |
| 101 | NT | NT | 0.05 | 0.06 | 0.03 | 0.009 |
| 102 | NT | NT | 0.9 | 0.7 | 0.2 | 0.001 |
| 118 | NT | NT | 100 | 100 | 100 | 100 |

Example 4

N87 Human Tumor Xenograft Model

The N87 gastric carcinoma cell line overexpresses HER-2 as a result of gene amplification and forms tumors in nude mice (Kasprzyk P G, Song S U, Di Fiore P P, King C R, Therapy of an animal model of human gastric cancer using a combination of anti-erbB-2 monoclonal antibodies, *Cancer Res.*, 1992, 52, 2771-2776).

Female nu/nu mice (Charles River; 8 to 9 weeks of age) were implanted subcutaneously with from $3\times10^6$ to $5\times10^6$ N87 gastric carcinoma cells (obtained from the American Type Culture Collection, ATCC Cat. #CRL-5822) in the flank. Animals were weighed twice weekly during the study and examined frequently.

Tumor size was monitored twice weekly and then daily as the neoplasms reached the target weight range (about 75 mg). Animals were pair-matched when tumors were in the 62 to 126 mg range (group mean tumor size: 70 to 74 mg). Estimated tumor weight was calculated using the formula:

$$\text{Tumor Weight} = \frac{(\text{width}^2)(\text{length})}{2}$$

A test compound was orally administered daily in the test treatment group after the tumor reached the target weight. For treatment group 1, the test compound was administered once daily for 35 days. For treatment group 2, the test compound was administered once daily for 30 days. For treatment group 3, each dose of test compound was administered once daily for 30 days. For treatment group 4, each dose of test compound was administered once daily for 36 days. For treatment group 5-10, the test compound was administered once daily for 30 days.

Tumor weight was measured daily for subjects (n=8) in the test group and the matched subjects (n=8) in the vehicle-treated group.

The tumor growth inhibition (in percent) was calculated on the last day of the study using the formula:

$$\text{Tumor Growth Inhibition} = X\ 100\% \frac{\left(\begin{array}{c}\text{mean tumor weight}\\\text{vehicle group}\end{array}\right) - \left(\begin{array}{c}\text{mean tumor weight}\\\text{test group}\end{array}\right)}{\text{mean tumor weight vehicle group}}$$

The results for the study are shown in Table 5. Statistical significance was evaluated by comparing the vehicle group to the test group using a two tailed Students t test. The term "NC" means that the P value for the treatment group indicated was not calculated. The lack of such calculation is not intended to imply a belief that the activity of the compound is not otherwise statistically significant in this particular cell line or in any other cell line not tested.

TABLE 5

N87 Tumor Growth Inhibition

| Treatment Group | Cpd | Dose (mg/kg) | TGI | P value |
|---|---|---|---|---|
| 1 | 78 | 100 | 71.0% | 0.006 |
| 2 | 78 | 100 | 69.4% | 0.003 |
| 3 | 78 | 100 | 59.56% | 0.044 |
| 3 | 78 | 50 | 50.56% | 0.025 |
| 3 | 78 | 25 | 41.29% | 0.023 |
| 4 | 78 | 100 | 49.3% | 0.007 |
| 4 | 78 | 50 | 33.9% | 0.02 |
| 4 | 78 | 25 | 6.5% | 0.04 |
| 5 | 93 | 100 | 59.9% | NC |
| 6 | 94 | 100 | 47.1% | NC |
| 7 | 101 | 100 | 66% | NC |
| 8 | 112 | 100 | 48.6% | NC |
| 9 | 114 | 100 | 47% | NC |
| 10 | 115 | 100 | 50.2% | NC |

Example 5

A431 Human Tumor Xenograft Model

The A431 epidermoid carcinoma cell line overexpresses EGFR, activating signaling pathways responsible for driving the proliferation, invasion and survival of cancer cells and forming tumors in nude mice (Giard D J, Aaronson S A, Todaro G J, Arnstein P, Kersey J H, Dosik H, Parks W P, In vitro cultivation of human tumors: establishment of cell lines derived from a series of solid tumors, *J. Natl. Cancer Inst.*, 1973, 51, 1417-1423; and, Kawamoto T, Sato J D, Le A, Polikoff J, Sato G H, Mendelsohn J, Growth stimulation of A431 cells by epidermal growth factor: identification of high-affinity receptors for epidermal growth factor by an anti-receptor monoclonal antibody, *Proc. Natl. Acad. Sci. USA*, 1983, 80, 1337-1341).

Female nu/nu mice (Charles River; 8 to 9 weeks of age) were implanted subcutaneously in the flank with $4 \times 10^6$ A431 epidermoid carcinoma cells (obtained from the American Type Culture Collection, ATCC Cat. #CRL-1555). Animals were weighed twice weekly during the study and examined frequently.

Tumor size was monitored twice weekly and then daily as the neoplasms reached the target weight range (about 75 mg). Animals were pair-matched when tumors were in the 62 to 126 mg range (group mean tumor size: 70 to 74 mg). Estimated tumor weight was calculated using the formula of Example 4.

A test compound was orally administered daily in the test treatment group after the tumor reached the target weight. For treatment groups 1 and 2, each dose of test compound was administered once daily for 25 days. For treatment group 3, each dose of test compound was administered twice daily for 25 days. For treatment group 4, the test compound was administered twice daily for 30 days. For treatment group 5-10, the test compound was administered once daily for 30 days.

Using the formula of Example 4, tumor weight was measured daily for subjects (n=8) in the test group and the matched subjects (n=8) in the vehicle-treated group. Using the formula of Example 4, tumor growth inhibition (in percent) was calculated on the last day of the study.

The results for the study are shown in Table 6. Statistical significance was evaluated by comparing the vehicle group to the test group using a two tailed Students t test. The term "NC" means that the P value for the treatment group indicated was not calculated. The lack of such calculation is not intended to imply a belief that the activity of the compound is not otherwise statistically significant in this particular cell line or in any other cell line not tested.

TABLE 6

A431 Tumor Growth Inhibition

| Treatment Group | Cpd | Dose (mg/kg) | TGI | P value |
|---|---|---|---|---|
| 1 | 78 | 100 | 66.8% | 0.025 |
| 1 | 78 | 30 | 10.6% | 0.553 |
| 2 | 78 | 100 | 34.6% | 0.216 |
| 2 | 78 | 50 | 14.3% | 0.571 |
| 3 | 78 | 100 | 51.1% | 0.038 |
| 3 | 78 | 50 | 45.12% | 0.106 |
| 4 | 78 | 100 | 52% | 0.048 |
| 5 | 93 | 100 | 64.0% | NC |
| 6 | 94 | 100 | 66% | NC |
| 7 | 101 | 100 | 51% | NC |
| 8 | 112 | 100 | 33% | NC |
| 9 | 114 | 100 | -3% | NC |
| 10 | 115 | 100 | 4% | NC |

Example 6

BT474 Human Tumor Xenograft Model

The BT474 human tumor cell line overexpresses HER-2 and forms tumors in immunocompromised mice (Rabindran S K, Discafani C M, Rosfjord E C, Baxter M, Floyd M B, Golas J, Hallett W A, Johnson B D, Nilakantan R, Overbeek E, Reich M F, Shen R, Shi X, Tsou H R, Wang Y F and Wissner A, Antitumor Activity of HKI-272, an Orally Active, Irreversible Inhibitor of the HER-2 Tyrosine Kinase, *Cancer Res.*, 2004, 64, 3958-3965).

Immunocompromised CB.17 SCID female mice were subcutaneously implanted in the hindflank with 1 $mm^3$ BT474 breast carcinoma tumor fragments. Animals were weighed twice weekly during the study and examined frequently.

Tumor size was monitored twice weekly and then daily as the neoplasms reached the target weight range (about 75 mg). Animals were pair-matched when tumors were in the 62 to 126 mg range (group mean tumor size: 70 to 74 mg). Estimated tumor weight was calculated using the formula of Example 4.

A test compound was orally administered daily in the test treatment group after the tumor reached the target weight. For treatment group 1, each dose of test compound was administered once daily for 25 days. For treatment groups 2 and 3, each dose of test compound was administered twice daily for 30 days.

Using the formula of Example 4, tumor weight was measured daily for subjects (n=15 for group 1, n=10 for groups 2 and 3) in the test groups and the matched subjects (n=8) in the vehicle-treated group. Using the formula of Example 4, tumor growth inhibition (in percent) was calculated on the last day of the study.

The results for the study are shown in Table 7. Statistical significance was evaluated by comparing the vehicle group to the test group using a two tailed Students t test.

TABLE 7

BT474 Tumor Growth Inhibition

| Treatment Group | Cpd | Dose (mg/kg) | TGI | P value |
|---|---|---|---|---|
| 1 | 78 | 50 | 27% | 0.100 |
| 2 | 78 | 100 | 52% | 0.004 |
| 3 | 78 | 200 | 62% | 0.035 |

Example 7

Blood-Brain Barrier Penetration

The blood-brain barrier penetration of Compound 78 was examined in male Sprague Dawley rats following i.v. (3 mg/kg) or oral (10 mg/kg) administration.

The i.v. formulation consisted of a 1 mg/mL dose in vehicle (10% solutol in D5W at pH 3) with plasma samples drawn at 0.25 hours, 0.5 hours and 1 hour after administration.

The oral (p.o) formulation consisted of a 1 mg/mL dose in vehicle (0.5% methylcellulose) with plasma samples drawn at 0.5 hours, 1 hour and 2 hours after administration.

The plasma samples (0.5 ml) were collected and centrifuged (2000 rpm, 3 min), then stored at −60° C. until LC-MS/MS analysis. Brain samples were collected immediately after the last blood sample collection. The samples were rinsed with 0.9% NaCl, patted dry, then weighed and placed in Falcon 14 mL polypropylene round-bottom tubes containing 3 mL methanol. The methanolic mixtures were homogenized with an OMNI TH115 homogenizer then centrifuged for 10 minutes at 7,000 rpm. The supernatant was removed and stored frozen in 15 mL polyethylene tubes at −60° C. until LC-MS/MS analysis.

TABLE 8

Concentration in Plasma (ng/mL) and Brain (ng/g)

| Administration | Mean ± SEM | Brain/Plasma Ratio |
|---|---|---|
| p.o. 60 min (plasma) | 73.6 ± 16.4 | 1.2 |
| p.o. 120 min (brain) | 46.1 ± 17.4 | |
| p.o. 120 min (brain) | 51.16 ± 13.71 | |
| i.v. 60 min (plasma) | 124.1 ± 5.5 | 2.5 |
| i.v. 60 min (brain) | 306.9 ± 55 | |

While the foregoing specification teaches the principles of the present invention, with examples provided for the purpose of illustration, it will be understood that the practice of the invention encompasses all of the usual variations, adaptations and modifications as come within the scope of the following claims and their equivalents.

Throughout this application, various publications are cited. These publications are hereby incorporated by reference in their entirety into this application to describe more fully the state of the art to which this invention pertains.

What is claimed is:
1. A compound of Formula (I)

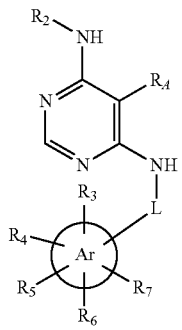

or a salt, stereoisomer, or tautomer thereof, wherein
L is a bond, $C_{1-6}$alkyl or halo-$C_{1-6}$alkyl;
Ar is aryl, heteroaryl, benzofused-heterocyclyl or benzofused-$C_{3-12}$cycloalkyl;
$R_A$ is —CH=N—O—$R_1$ or cyano or an $R_1$ substituted oxadiazole;
$R_1$ is hydrogen, $C_{1-8}$alkyl, $C_{1-8}$alkenyl, $C_{1-8}$alkoxy, $C_{1-8}$alkoxy-$C_{1-8}$alkyl, hydroxy-$C_{1-8}$alkyl, hydroxy-$C_{1-8}$alkoxy, amino-$C_{1-8\ l\ alkyl}$, $C_{1-8}$alkyl-amino-$C_{1-8}$alkyl, $C_{1-8}$alkoxy-$C_{1-8}$alkyl-amino-$C_{1-8}$alkyl, $C_{1-8}$alkyl-sulfonyl-$C_{1-8}$alkyl, $C_{1-8}$alkyl-sulfonyloxy-$C_{1-8}$alkyl, aryl, aryl-$C_{1-8}$alkyl, aryloxy-$C_{1-8}$alkyl, heterocyclyl-$C_{1-8}$alkyl, heterocyclyl-carbonyl-$C_{1-8}$alkyl, benzofused-heterocyclyl-$C_{1-8}$alkyl or heteroaryl-$C_{1-8}$alkyl,
wherein aryl-$C_{1-8}$alkyl is optionally substituted on aryl with one, two, three, four or five substituents that are each hydroxy, $C_{1-8}$alkyl, $C_{1-8}$alkoxy, amino, $C_{1-8}$alkyl-amino or $C_{1-8}$alkoxycarbonyl, and
wherein heterocyclyl-$C_{1-8}$alkyl is optionally substituted on heterocyclyl with one, two, three or four substituents that are each hydroxy, $C_{1-8}$alkyl, $C_{1-8}$alkoxy, amino, $C_{1-8}$alkyl-amino or $C_{1-8}$alkoxycarbonyl;
$R_2$ is hydrogen, $C_{1-8}$alkyl or $C_{1-8}$alkoxy; and
$R_3$, $R_4$, $R_5$, $R_6$ and $R_7$ is each hydrogen, halogen, hydroxy, $C_{1-8}$alkyl, $C_{1-8}$alkoxy, $C_{1-8}$alkoxy-$C_{1-8}$alkyl, hydroxy-$C_{1-8}$alkyl, halo-$C_{1-8}$alkyl, hydroxy-$C_{1-8}$alkoxy, halo-$C_{1-8}$alkoxy, cyano-$C_{1-8}$alkyl, amino, $C_{1-8}$alkyl-amino, amino-$C_{1-8}$alkyl, $C_{1-8}$alkyl-amino-$C_{1-8}$alkyl, $C_{1-8}$alkyl-amino-$C_{1-8}$alkyl-amino-carbonyl, $C_{1-8}$alkoxy-imino-$C_{1-8}$alkyl, $C_{1-8}$alkoxy-imino-(aryl)$C_{1-8}$alkyl, carboxy, $C_{1-8}$acyl, $C_{1-8}$acyl-amino, $C_{1-8}$alkoxycarbonyl, thio-$C_{1-8}$ alkyl, substituted phosphonic acid, $C_{3-12}$cycloalkyl, aryl, aryloxy, aryl-amino, aryl-$C_{1-8}$alkyl, aryl-$C_{1-8}$ alkoxy, aryl-carbonyl-$C_{1-8}$alkyl, aryl-amido, heteroaryl, heteroaryloxy, heteroaryl-$C_{1-8}$alkoxy, heteroaryl-amino-sulfonyl, benzofused-heterocyclyl or heterocyclyl,
wherein phosphonic acid is substituted on the phosphorous atom with two substituents that are each hydroxy or $C_{1-8}$alkoxy,
wherein aryl, aryloxy, aryl-amino, aryl-$C_{1-8}$alkyl and aryl-$C_{1-8}$alkoxy are each optionally substituted on aryl with one, two, three, four or five substituents that are each cyano, halogen, hydroxy, $C_{1-8}$alkyl, $C_{1-8}$alkoxy, amino, $C_{1-8}$alkyl-amino, amino-$C_{1-8}$alkyl, $C_{1-8}$alkyl-amino-$C_{1-8}$alkyl or $C_{1-8}$alkoxycarbonyl,
wherein benzofused-heterocyclyl is optionally substituted on the heterocyclyl portion with one or two oxo substituents, and wherein heteroaryl, heteroaryl-amino-sulfonyl and heteroaryloxy is each optionally substituted on heteroaryl with one, two, three, four or five substituents that are each $C_{1-8}$alkyl, amino-$C_{1-8}$alkyl, $C_{1-8}$alkyl-amino-$C_{1-8}$alkyl, carboxy, $C_{1-8}$acyl or $C_{1-8}$alkoxycarbonyl.

2. A compound of Formula (II):

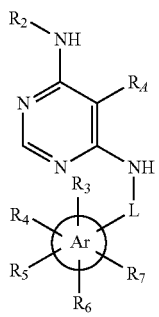

or a salt, stereoisomer, or tautomer thereof, wherein

L is a bond, $C_{1-6}$alkyl or halo-$C_{1-6}$alkyl;

Ar is aryl, heteroaryl, benzofused-heterocyclyl or benzofused-$C_{3-12}$cycloalkyl, wherein the benzene ring portion of the benzofused ring system is attached to the L variable;

$R_4$ is —CH=N—O—$R_1$ or cyano;

$R_1$ is hydrogen, $C_{1-8}$alkyl, $C_{1-8}$alkenyl, $C_{1-8}$alkoxy, $C_{1-8}$alkoxy-$C_{1-8}$alkyl, hydroxy-$C_{1-8}$alkyl, hydroxy-$C_{1-8}$alkoxy, amino-$C_{1-8}$alkyl, $C_{1-8}$alkyl-amino-$C_{1-8}$alkyl, $C_{1-8}$alkoxy-$C_{1-8}$alkyl-amino-$C_{1-8}$alkyl, $C_{1-8}$alkyl-sulfonyl-$C_{1-8}$alkyl, $C_{1-8}$alkyl-sulfonyloxy-$C_{1-8}$alkyl, aryl, aryl-$C_{1-8}$alkyl, aryloxy-$C_{1-8}$alkyl, heterocyclyl-$C_{1-8}$alkyl, heterocyclyl-carbonyl-$C_{1-8}$alkyl or heteroaryl-$C_{1-8}$alkyl, wherein aryl-$C_{1-8}$alkyl is optionally substituted on aryl with one, two, three, four or five substituents that are each hydroxy, $C_{1-8}$alkyl, $C_{1-8}$alkoxy, amino, $C_{1-8}$alkyl-amino or $C_{1-8}$alkoxycarbonyl, and wherein heterocyclyl-$C_{1-8}$alkyl is optionally substituted on heterocyclyl with one, two, three or four substituents that are each hydroxy, $C_{1-8}$alkyl, $C_{1-8}$alkoxy, amino, $C_{1-8}$alkyl-amino or $C_{1-8}$alkoxycarbonyl;

$R_2$ is hydrogen, $C_{1-8}$alkyl or $C_{1-8}$alkoxy; and $R_3$, $R_4$, $R_5$, $R_6$ and $R_7$ is each hydrogen, halogen, hydroxy, $C_{1-8}$alkyl, $C_{1-8}$alkoxy, $C_{1-8}$alkoxy-$C_{1-8}$alkyl, hydroxy-$C_{1-8}$alkyl, halo-$C_{1-8}$alkyl, hydroxy-$C_{1-8}$alkoxy, halo-$C_{1-8}$alkoxy, amino, $C_{1-8}$alkyl-amino, amino-$C_{1-8}$alkyl, $C_{1-8}$alkyl-amino-$C_{1-8}$alkyl, carboxy, $C_{1-8}$acyl, $C_{1-8}$alkoxycarbonyl, $C_{3-12}$cycloalkyl, aryl, aryloxy, aryl-$C_{1-8}$alkyl, aryl-$C_{1-8}$alkoxy, aryl-amido, heteroaryl, heteroaryloxy, heteroaryl-$C_{1-8}$alkoxy or heterocyclyl, wherein aryl, aryloxy, aryl-$C_{1-8}$alkyl and aryl-$C_{1-8}$alkoxy is each optionally substituted on aryl with one, two, three, four or five substituents that are each cyano, halogen, hydroxy, $C_{1-8}$alkyl, $C_{1-8}$alkoxy, amino, $C_{1-8}$alkyl-amino, amino-$C_{1-8}$alkyl, $C_{1-8}$alkyl-amino-$C_{1-8}$alkyl or $C_{1-8}$alkoxycarbonyl, and wherein heteroaryl and heteroaryloxy is each optionally substituted on heteroaryl with one, two, three, four or five substituents that are each $C_{1-8}$alkyl, amino-$C_{1-8}$alkyl, $C_{1-8}$alkyl-amino-$C_{1-8}$alkyl, carboxy, $C_{1-8}$acyl or $C_{1-8}$alkoxycarbonyl.

3. A compound of formula (Ic):

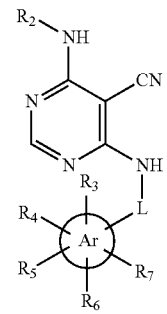

or a salt, stereoisomer, or tautomer thereof, wherein

L is a bond, $C_{1-6}$alkyl or halo-$C_{1-6}$alkyl;

Ar is aryl, heteroaryl, benzofused-heterocyclyl or benzofused-$C_{3-12}$cycloalkyl;

$R_2$ is hydrogen, $C_{1-8}$alkyl or $C_{1-8}$alkoxy; and $R_3$, $R_4$, $R_5$, $R_6$ and $R_7$ is each hydrogen, halogen, hydroxy, $C_{1-8}$alkyl, $C_{1-8}$alkoxy, $C_{1-8}$alkoxy-$C_{1-8}$alkyl, hydroxy-$C_{1-8}$alkyl, halo-$C_{1-8}$alkyl, hydroxy-$C_{1-8}$alkoxy, halo-$C_{1-8}$alkoxy, cyano-$C_{1-8}$alkyl, amino, $C_{1-8}$alkyl-amino, amino-$C_{1-8}$alkyl, $C_{1-8}$alkyl-amino-$C_{1-8}$alkyl, $C_{1-8}$alkyl-amino-$C_{1-8}$alkyl-amino-carbonyl, $C_{1-8}$alkoxy-imino-$C_{1-8}$alkyl, $C_{1-8}$alkoxy-imino-(aryl)$C_{1-8}$alkyl, carboxy, $C_{1-8}$acyl, $C_{1-8}$acyl-amino, $C_{1-8}C_{1-8}$alkoxycarbonyl, thio-$C_{1-8}$alkyl, substituted phosphonic acid, $C_{3-12}$cycloalkyl, aryl, aryloxy, aryl-amino, aryl-$C_{1-8}$alkyl, aryl-$C_{1-8}$alkoxy, aryl-carbonyl-$C_{1-8}$alkyl, aryl-amido, heteroaryl, heteroaryloxy, heteroaryl-$C_{1-8}$alkoxy, heteroaryl-amino-sulfonyl, benzofused-heterocyclyl or heterocyclyl, wherein phosphonic acid is substituted on the phosphorous atom with two substituents that are each hydroxy or $C_{1-8}$alkoxy, wherein aryl, aryloxy, aryl-amino, aryl-$C_{1-8}$alkyl and aryl-$C_{1-8}$alkoxy is each optionally substituted on aryl with one, two, three, four or five substituents that are each cyano, halogen, hydroxy, $C_{1-8}$alkyl, $C_{1-8}$alkoxy, amino, $C_{1-8}$alkyl-amino, amino-$C_{1-8}$alkyl, $C_{1-8}$alkyl-amino-$C_{1-8}$alkyl or $C_{1-8}$alkoxycarbonyl, wherein benzofused-heterocyclyl is optionally substituted on the heterocyclyl portion with one or two oxo substituents, and wherein heteroaryl, heteroaryl-amino-sulfonyl and heteroaryloxy is each optionally substituted on heteroaryl with one, two, three, four or five substituents that are each $C_{1-8}$alkyl, amino-$C_{1-8}$alkyl, $C_{1-8}$alkyl-amino-$C_{1-8}$alkyl, carboxy, $C_{1-8}$acyl or $C_{1-8}$alkoxycarbonyl.

wherein heteroaryl-amino-sulfonyl and heteroaryloxy is each optionally substituted on heteroaryl with one or two $C_{1-8}$alkyl substituents.

4. A compound of formula (Id):

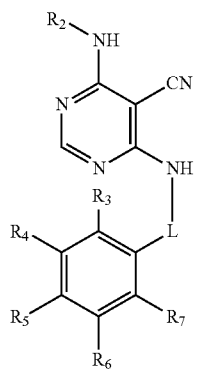

or a salt, stereoisomer, or tautomer thereof, wherein
L is a bond, $C_{1-6}$alkyl or halo-$C_{1-6}$alkyl;
$R_2$ is hydrogen, $C_{1-8}$alkyl or $C_{1-8}$alkoxy; and
$R_3$, $R_4$, $R_5$, $R_6$ and $R_7$ is each hydrogen, halogen, hydroxy, $C_{1-8}$alkyl, $C_{1-8}$alkoxy, $C_{1-8}$alkoxy-$C_{1-8}$alkyl, hydroxy-$C_{1-8}$alkyl, halo-$C_{1-8}$alkyl, hydroxy-$C_{1-8}$alkoxy, halo-$C_{1-8}$alkoxy, cyano-$C_{1-8}$alkyl, amino, $C_{1-8}$alkyl-amino, amino-$C_{1-8}$alkyl, $C_{1-8}$alkyl-amino-$C_{1-8}$alkyl, $C_{1-8}$alkyl-amino-$C_{1-8}$alkyl-amino-carbonyl, $C_{1-8}$alkoxy-imino-$C_{1-8}$alkyl, $C_{1-8}$alkoxy-imino-(aryl)$C_{1-8}$alkyl, carboxy, $C_{1-8}$acyl, $C_{1-8}$acyl-amino, $C_{1-8}C_{1-8}$alkoxycarbonyl, thio-$C_{1-8}$alkyl, substituted phosphonic acid, $C_{3-12}$cycloalkyl, aryl, aryloxy, aryl-amino, aryl-$C_{1-8}$alkyl, aryl-$C_{1-8}$alkoxy, aryl-carbonyl-$C_{1-8}$alkyl, aryl-amido, heteroaryl, heteroaryloxy, heteroaryl-$C_{1-8}$alkoxy, heteroaryl-amino-sulfonyl, benzofused-heterocyclyl or heterocyclyl,
wherein phosphonic acid is substituted on the phosphorous atom with two substituents that are each hydroxy or $C_{1-8}$alkoxy,
wherein aryl, aryl-amino, aryloxy, aryl-$C_{1-8}$alkyl and aryl-$C_{1-8}$alkoxy is each optionally substituted on aryl with one, two, three, four or five substituents that are each cyano, halogen, hydroxy, $C_{1-8}$alkyl, $C_{1-8}$alkoxy, amino, $C_{1-8}$alkyl-amino, amino-$C_{1-8}$alkyl, $C_{1-8}$alkyl-amino-$C_{1-8}$alkyl or $C_{1-8}$alkoxycarbonyl,
wherein benzofused-heterocyclyl is optionally substituted on the heterocyclyl portion with one or two oxo substituents, and
wherein heteroaryl, heteroaryl-amino-sulfonyl and heteroaryloxy is each optionally substituted on heteroaryl with one, two, three, four or five substituents that are each $C_{1-8}$alkyl, amino-$C_{1-8}$alkyl, $C_{1-8}$alkyl-amino-$C_{1-8}$alkyl, carboxy, $C_{1-8}$acyl or $C_{1-8}$alkoxycarbonyl.

5. A pharmaceutical composition comprising a pharmaceutical acceptable excipient and an effective amount of a compound of claim 1.

6. The pharmaceutical composition of claim 5 wherein the effective amount of the compound is in a range of from about 0.001 mg/kg to about 300 mg/kg of body weight per day.

7. A process for preparing a pharmaceutical composition comprising the step of admixing a compound of claim 1 and a pharmaceutically acceptable carrier.

8. A method of treating rheumatoid arthritis in a subject in need thereof comprising administering to the subject an effective amount of a compound of claim 1.

9. A method of treating breast cancer in a subject in need thereof comprising administering to the subject an effective amount of a compound of claim 1.

10. The method of claim 8 further comprising administering the compound in combination with at least one other therapeutic agent for treating or ameliorating rheumatoid arthritis.

11. A process for preparing a compound of claim 1 comprising the steps of:
a. reacting a compound of Formula A4 with $NH_2OH$ hydrochloride to provide a compound of Formula A5:

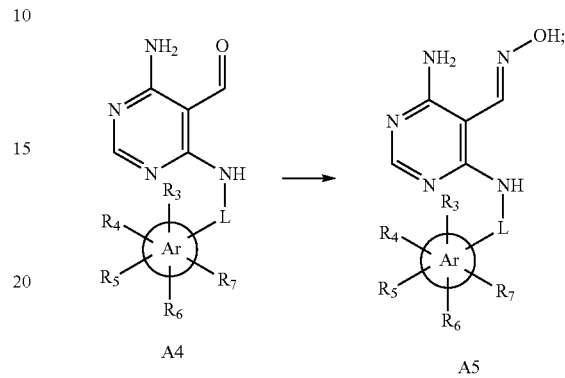

b. reacting a mixture of the compound of Formula A5 and a basic reagent with a compound of Formula A6 (wherein Q1 is a halogen leaving group) to provide a compound of Formula A7:

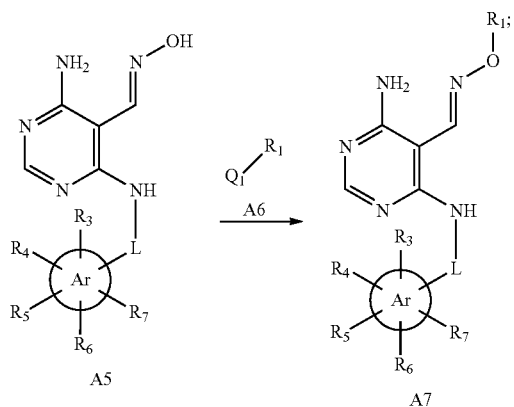

c. reacting the compound of Formula A7 with a compound of Formula A8 (wherein Q2 is a halogen leaving group) to provide a compound of Formula A9:

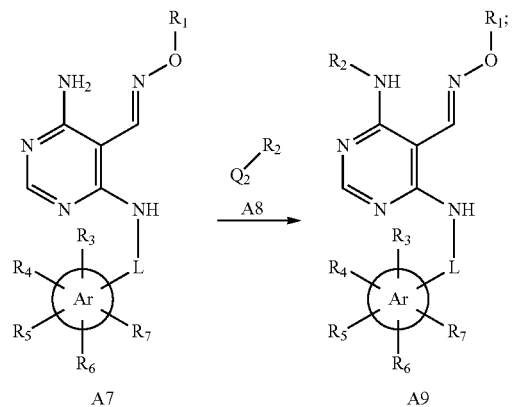

and d. converting the compound of Formula A9 to provide a compound of Formula A10:

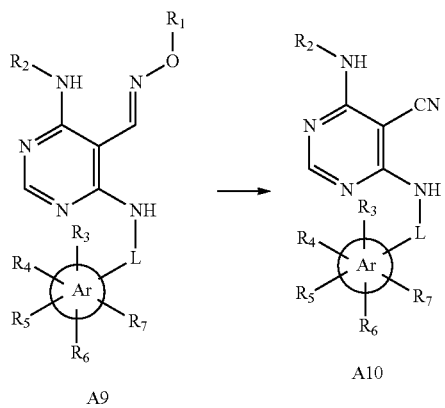

wherein
L is a bond, $C_{1-6}$alkyl or halo-$C_{1-6}$alkyl;
Ar is aryl, heteroaryl, benzofused-heterocyclyl or benzofused-$C_{3-12}$cycloalkyl;
$R_A$ is —CH=N—O—$R_1$ or cyano or an $R_1$ substituted oxadiazole;
$R_1$ is hydrogen, $C_{1-8}$alkyl, $C_{1-8}$alkenyl, $C_{1-8}$alkoxy, $C_{1-8}$alkoxy-$C_{1-8}$alkyl, hydroxy-$C_{1-8}$alkyl, hydroxy-$C_{1-8}$alkoxy, amino-$C_{1-8}$alkyl, $C_{1-8}$alkyl-amino-$C_{1-8}$alkyl, $C_{1-8}$alkoxy-$C_{1-8}$alkyl-amino-$C_{1-8}$alkyl, $C_{1-8}$alkyl-sulfonyl-$C_{1-8}$alkyl, $C_{1-8}$alkyl-sulfonyloxy-$C_{1-8}$alkyl, aryl, aryl-$C_{1-8}$alkyl, aryloxy-$C_{1-8}$alkyl, heterocyclyl-$C_{1-8}$alkyl, heterocyclyl-carbonyl-$C_{1-8}$alkyl, benzofused-heterocyclyl-$C_{1-8}$alkyl or heteroaryl-$C_{1-8}$alkyl,
wherein aryl-$C_{1-8}$alkyl is optionally substituted on aryl with one, two, three, four or five substituents that are each hydroxy, $C_{1-8}$alkyl, $C_{1-8}$alkoxy, amino, $C_{1-8}$alkyl-amino or $C_{1-8}$alkoxycarbonyl, and
wherein heterocyclyl-$C_{1-8}$alkyl is optionally substituted on heterocyclyl with one, two, three or four substituents that are each hydroxy, $C_{1-8}$alkyl, $C_{1-8}$alkoxy, amino, $C_{1-8}$alkyl-amino or $C_{1-8}$alkoxycarbonyl;
$R_2$ is hydrogen, $C_{1-8}$alkyl or $C_{1-8}$alkoxy; and
$R_3$, $R_4$, $R_5$, $R_6$ and $R_7$ is each hydrogen, halogen, $C_{1-8}$alkyl, $C_{1-8}$alkoxy, $C_{1-8}$alkoxy-$C_{1-8}$alkyl, halo-$C_{1-8}$alkyl, halo-$C_{1-8}$alkoxy, $C_{1-8}$alkoxy-imino-$C_{1-8}$alkyl, $C_{1-8}$alkoxy-imino-(aryl)$C_{1-8}$alkyl, substituted phosphonic acid, $C_{3-12}$cycloalkyl, aryl, aryloxy, aryl-$C_{1-8}$alkyl, aryl-$C_{1-8}$alkoxy, heteroaryl, heteroaryloxy, heteroaryl-$C_{1-8}$alkoxy, benzofused-heterocyclyl or heterocyclyl,
wherein phosphonic acid is substituted on the phosphorous atom with two substituents that are each hydroxy or $C_{1-8}$alkoxy,
wherein aryl, aryloxy, aryl-$C_{1-8}$alkyl and aryl-$C_{1-8}$alkoxy are each optionally substituted on aryl with one, two, three, four or five substituents that are each cyano, halogen, $C_{1-8}$alkyl, or $C_{1-8}$alkoxy,
wherein benzofused-heterocyclyl is optionally substituted on the heterocyclyl portion with one or two oxo substituents, and
wherein heteroaryl and heteroaryloxy is each optionally substituted on heteroaryl with one, two, three, four or five substituents that are each $C_{1-8}$alkyl.

12. A process for preparing a compound of claim 1 comprising the step of converting a compound of Formula C4 to a compound of Formula C5:

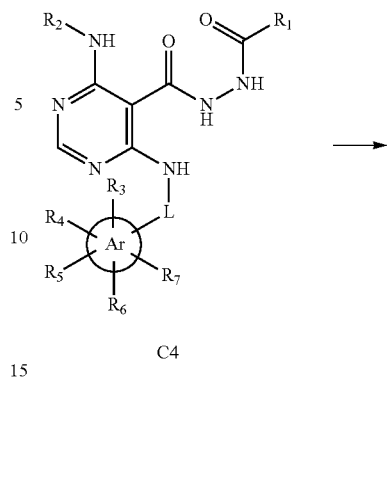

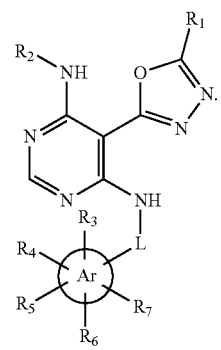

wherein
L is a bond, $C_{1-6}$alkyl or halo-$C_{1-6}$alkyl;
Ar is aryl, heteroaryl, benzofused-heterocyclyl or benzofused-$C_{3-12}$cycloalkyl;
$R_A$ is —CH=N—O—$R_1$ or cyano or an $R_1$ substituted oxadiazole;
$R_1$ is hydrogen, $C_{1-8}$alkyl, $C_{1-8}$alkenyl, $C_{1-8}$alkoxy, $C_{1-8}$alkoxy-$C_{1-8}$alkyl, hydroxy-$C_{1-8}$alkyl, hydroxy-$C_{1-8}$alkoxy, amino-$C_{1-8}$alkyl, $C_{1-8}$alkyl-amino-$C_{1-8}$alkyl, $C_{1-8}$alkoxy-$C_{1-8}$alkyl-amino-$C_{1-8}$alkyl, $C_{1-8}$alkyl-sulfonyl-$C_{1-8}$alkyl, $C_{1-8}$alkyl-sulfonyloxy-$C_{1-8}$alkyl, aryl, aryl-$C_{1-8}$alkyl, aryloxy-$C_{1-8}$alkyl, heterocyclyl-$C_{1-8}$alkyl, heterocyclyl-carbonyl-$C_{1-8}$alkyl, benzofused-heterocyclyl-$C_{1-8}$alkyl or heteroaryl-$C_{1-8}$alkyl,
wherein aryl-$C_{1-8}$alkyl is optionally substituted on aryl with one, two, three, four or five substituents that are each hydroxy, $C_{1-8}$alkyl, $C_{1-8}$alkoxy, amino, $C_{1-8}$alkyl-amino or $C_{1-8}$alkoxycarbonyl, and
wherein heterocyclyl-$C_{1-8}$alkyl is optionally substituted on heterocyclyl with one, two, three or four substituents that are each hydroxy, $C_{1-8}$alkyl, $C_{1-8}$alkoxy, amino, $C_{1-8}$alkyl-amino or $C_{1-8}$alkoxycarbonyl;
$R_2$ is hydrogen, $C_{1-8}$alkyl or $C_{1-8}$alkoxy; and
$R_3$, $R_4$, $R_5$, $R_6$ and $R_7$ is each hydrogen, halogen, $C_{1-8}$alkyl, $C_{1-8}$alkoxy, $C_{1-8}$alkoxy-$C_{1-8}$alkyl, halo-$C_{1-8}$alkyl, halo-$C_{1-8}$alkoxy, cyano-$C_{1-8}$alkyl, $C_{1-8}$alkoxy-imino-$C_{1-8}$alkyl, $C_{1-8}$alkoxy-imino-(aryl)$C_{1-8}$alkyl, $C_{1-8}$alkoxycarbonyl, thio-$C_{1-8}$alkyl, substituted phosphonic acid, $C_{3-12}$cycloalkyl, aryl, aryloxy, aryl-$C_{1-8}$alkyl, aryl-$C_{1-8}$alkoxy, heteroaryl, heteroaryloxy, heteroaryl-$C_{1-8}$alkoxy, benzofused-heterocyclyl or heterocyclyl,
wherein phosphonic acid is substituted on the phosphorous atom with two substituents that are each hydroxy or $C_{1-8}$alkoxy,
wherein aryl, aryloxy, aryl-$C_{1-8}$alkyl and aryl-$C_{1-8}$alkoxy are each optionally substituted on aryl with one, two, three, four or five substituents that are each cyano, halogen, $C_{1-8}$alkyl, or $C_{1-8}$alkoxy,
wherein benzofused-heterocyclyl is optionally substituted on the heterocyclyl portion with one or two oxo substituents, and
wherein heteroaryl and heteroaryloxy is each optionally substituted on heteroaryl with one, two, three, four or five substituents that are each $C_{1-8}$alkyl.

13. The method of claim 9 further comprising administering the compound as an adjunct to chemotherapy and radiation therapy.

* * * * *